(12) United States Patent
O'Hagan et al.

(10) Patent No.: US 9,517,263 B2
(45) Date of Patent: Dec. 13, 2016

(54) BENZONAPHTHYRIDINE-CONTAINING VACCINES

(75) Inventors: Derek O'Hagan, Winchester, MA (US); Manmohan Singh, Lexington, MA (US); Siddhartha Jain, Cambridge, MA (US); Sushma Kommareddy, Waltham, MA (US)

(73) Assignee: GlaxoSmithKline Biologicals SA, Rixensart (BE)

( * ) Notice: Subject to any disclaimer, the term of this patent is extended or adjusted under 35 U.S.C. 154(b) by 663 days.

(21) Appl. No.: 13/377,511

(22) PCT Filed: Jun. 10, 2010

(86) PCT No.: PCT/US2010/038216
§ 371 (c)(1),
(2), (4) Date: Mar. 26, 2012

(87) PCT Pub. No.: WO2010/144734
PCT Pub. Date: Dec. 16, 2010

(65) Prior Publication Data
US 2012/0263753 A1    Oct. 18, 2012

Related U.S. Application Data

(60) Provisional application No. 61/185,954, filed on Jun. 10, 2009.

(51) Int. Cl.
*A61K 39/02* (2006.01)
*C07D 471/00* (2006.01)
*A61K 39/39* (2006.01)
*A61K 39/00* (2006.01)
*A61K 39/12* (2006.01)

(52) U.S. Cl.
CPC ...... *A61K 39/39* (2013.01); *A61K 2039/55511* (2013.01); *A61K 2039/6093* (2013.01)

(58) Field of Classification Search
USPC ..... 514/292; 546/81; 424/204.1, 280, 277.1, 424/280.1, 234.1, 265.1
See application file for complete search history.

(56) References Cited

FOREIGN PATENT DOCUMENTS

| EP | 0208621 A1 | 1/1987 |
|---|---|---|
| WO | 2004/098509 A2 | 11/2004 |
| WO | 2007/109813 A1 | 9/2007 |
| WO | 2009/111337 A1 | 9/2009 |
| WO | 2010/009277 A2 | 1/2010 |

*Primary Examiner* — Shirley V Gembeh
(74) *Attorney, Agent, or Firm* — Helen Lee; Virginia Campen

(57) ABSTRACT

The invention provides, inter alia, immunogenic compositions that comprise (a) a first antigen, (b) polymeric particles and (c) a benzonaphthyridine compound, which compositions elicits an immune response when administered to a vertebrate subject. The invention also provides, inter alia, methods of producing immunogenic compositions and methods for using immunogenic compositions (e.g., for treatment), among other benefits.

41 Claims, 7 Drawing Sheets

BENZONAPHTHYRIDINE-CONTAINING VACCINES

RELATED APPLICATION

This application is a U.S. national stage application of PCT/US2010/038216, filed on Jun. 10, 2010, which claims priority from U.S. provisional application 61/185,954, filed Jun. 10, 2009, which are incorporated by reference herein in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 303822017800SEQLIST.TXT, date recorded: Oct. 7, 2016, size: 19 KB).

FIELD OF THE INVENTION

The present invention relates, inter alia, to immunogenic compositions and to agents that enhance the immune response to one or more selected antigens.

BACKGROUND OF THE INVENTION

The emergence of subunit vaccines created by recombinant DNA technology has intensified the need for safe and effective adjuvant-containing compositions. Subunit vaccines, while offering significant advantages over traditional live and killed vaccines in terms of safety and cost of production, generally present isolated polypeptides or mixtures of isolated polypeptides to the immune system, which have limited immunogenicity as compared to, for example, whole viruses, bacteria and other microorganisms. As a result, these vaccines generally benefit from adjuvants with immunostimulatory capabilities, which help them to reach their full potential in treating disease.

Traditional live vaccines, on the other hand, commonly do not require adjuvants. Moreover, killed vaccines are generally more immunogenic than subunit vaccines and commonly do not require adjuvants. Nonetheless, these vaccines, like subunit vaccines, can also benefit from adjuvants with immunostimulatory capabilities.

SUMMARY OF THE INVENTION

The present invention provides immunogenic compositions that comprise (a) a first antigen, (b) polymeric particles and (c) a benzonaphthyridine compound.

In certain embodiments of the immunogenic compositions provided herein, the benzonaphthyridine compound is a compound having the structure of Formula (VI), or a pharmaceutically acceptable salt thereof:

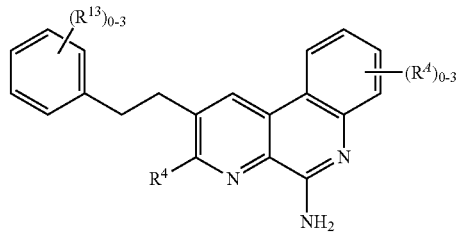

Formula (VI)

wherein:
$R^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of $R^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

$R^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of $R^7$ are each optionally substituted with 1 to 3 $R^{13}$ groups;

each $R^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of $R^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each $R^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each $R^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of $R^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, $^-$OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;

or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^{10}$, -LC(O)R$^8$, —OLC(O)R$^8$, -LC(O)OR$^8$, -LC(O)R$^{10}$, -LOC(O)R$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;

each R$^A$ is independently selected from —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$; or two adjacent R$^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In other embodiments of the immunogenic compositions provided herein, the benzonaphthyridine compound is a compound having the structure of Formula (VII), or a pharmaceutically acceptable salt thereof:

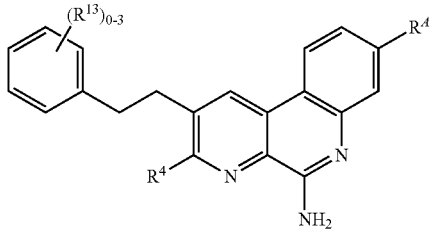

Formula (VII)

wherein:

R$^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

R$^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of R$^7$ are each optionally substituted with 1 to 3 R$^{13}$ groups;

each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each $R^9$ is independently selected from H, —C(O)$R^8$, —C(O)O$R^8$, —C(O)$R^{10}$, —C(O)O$R^{10}$, —S(O)$_2R^{10}$, —C$_1$-C$_6$ alkyl, C$_1$-C$_6$ heteroalkyl and C$_3$-C$_6$ cycloalkyl, or each $R^9$ is independently a C$_1$-C$_6$alkyl that together with N they are attached to form a C$_3$-C$_8$heterocycloalkyl, wherein the C$_3$-C$_8$ heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of $R^9$ are each optionally substituted with 1 to 3 substituents independently selected from —CN, $R^{11}$, —O$R^{11}$, —S$R^{11}$, —C(O)$R^{11}$, —OC(O)$R^{11}$, —C(O)O$R^{11}$, —N$R^{11}R^{12}$, —C(O)N$R^{11}R^{12}$, —C(O)N$R^{11}$OH, —S(O)$_2R^{11}$, —S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$;

each $R^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —$R^8$, —O$R^8$, -L$R^9$, -LO$R^9$, —N($R^9$)$_2$, —N$R^9$C(O)$R^8$, —N$R^9$CO$_2R^8$, —CO$_2R^8$, —C(O)$R^8$ and —C(O)N($R^9$)$_2$;

$R^{11}$ and $R^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of $R^{11}$ and $R^{12}$ are each optionally substituted with 1 to 3 substituents independently selected from halogen, —CN, $R^8$, —O$R^8$, —C(O)$R^8$, ⁻OC(O)$R^8$, —C(O)O$R^8$, —N($R^9$)$_2$, —N$R^8$C(O)$R^8$, —N$R^8$C(O)O$R^8$, —C(O)N($R^9$)$_2$, C$_3$-C$_8$heterocycloalkyl, —S(O)$_2R^8$, —S(O)$_2$N($R^9$)$_2$, —N$R^9$S(O)$_2R^8$, C$_1$-C$_6$haloalkyl and C$_1$-C$_6$haloalkoxy;

or $R^{11}$ and $R^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each $R^{13}$ is independently selected from halogen, —CN, -L$R^9$, -LO$R^9$, —OL$R^9$, -L$R^{10}$, -LO$R^{10}$, —OL$R^{10}$, -L$R^8$, -LO$R^8$, —OL$R^8$, -LS$R^8$, -LS$R^{10}$, -LC(O)$R^8$, —OLC(O)$R^8$, -LC(O)O$R^8$, -LC(O)$R^{10}$, -LOC(O)O$R^8$, -LC(O)N$R^9R^{11}$, -LC(O)N$R^9R^8$, -LN($R^9$)$_2$, -LN$R^9R^8$, -LN$R^9R^{10}$, -LC(O)N($R^9$)$_2$, -LS(O)$_2R^8$, -LS(O)$R^8$, -LC(O)N$R^8$OH, -LN$R^9$C(O)$R^8$, -LN$R^9$C(O)O$R^8$, -LS(O)$_2$N($R^9$)$_2$, —OLS(O)$_2$N($R^9$)$_2$, -LN$R^9$S(O)$_2R^8$, -LC(O)N$R^9$LN($R^9$)$_2$, -LP(O)(O$R^8$)$_2$, -LOP(O)(O$R^8$)$_2$, -LP(O)(O$R^{10}$)$_2$ and —OLP(O)(O$R^{10}$)$_2$;

each $R^4$ is independently selected from —$R^8$, —$R^7$, —O$R^7$, —O$R^8$, —$R^{10}$, —O$R^{10}$, —S$R^8$, —NO$_2$, —CN, —N($R^9$)$_2$, —N$R^9$C(O)$R^8$, —N$R^9$C(S)$R^8$, —N$R^9$C(O)N($R^9$)$_2$, —N$R^9$C(S)N($R^9$)$_2$, —N$R^9$CO$_2R^8$, —N$R^9$N$R^9$C(O)$R^8$, —N$R^9$N$R^9$C(O)N($R^9$)$_2$, —N$R^9$N$R^9$CO$_2R^8$, —C(O)C(O)$R^8$, —C(O)CH$_2$C(O)$R^8$, —CO$_2R^8$, —(CH$_2$)$_n$CO$_2R^8$, —C(O)$R^8$, —C(S)$R^8$, —C(O)N($R^9$)$_2$, —C(S)N($R^9$)$_2$, —OC(O)N($R^9$)$_2$, —OC(O)$R^8$, —C(O)N(O$R^8$)$R^8$, —C(NO$R^8$)$R^8$, —S(O)$_2R^8$, —S(O)$_3R^8$, —SO$_2$N($R^9$)$_2$, —S(O)$R^8$, —N$R^9$SO$_2$N($R^9$)$_2$, —N$R^9$SO$_2R^8$, —P(O)(O$R^8$)$_2$, —OP(O)(O$R^8$)$_2$, —P(O)(O$R^{10}$)$_2$, —OP(O)(O$R^{10}$)$_2$, —N(O$R^8$)$R^8$, —CH═CHCO$_2R^8$, —C(═NH)—N($R^9$)$_2$, and —(CH$_2$)$_n$NHC(O)$R^8$;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain embodiments of the benzonaphthyridine compounds of the immunogenic compositions provided herein, each $R^{13}$ is selected from -L$R^9$, -LO$R^9$, —OL$R^9$, -L$R^{10}$, -LO$R^{10}$, —OL$R^{10}$, -L$R^8$, -LO$R^8$, —OL$R^8$, -LS$R^8$, -LS$R^{10}$, -LC(O)$R^8$, —OLC(O)$R^8$, -LC(O)O$R^8$, -LC(O)$R^{10}$, -LOC(O)O$R^8$, -LC(O)N$R^9R^{11}$, -LC(O)N$R^9R^8$, -LN($R^9$)$_2$, -LN$R^9R^8$, -LN$R^9R^{10}$, -LC(O)N($R^9$)$_2$, -LS(O)$_2R^8$, -LS(O)$R^8$, -LC(O)N$R^8$OH, -LN$R^9$C(O)$R^8$, -LN$R^9$C(O)O$R^8$, -LS(O)$_2$N($R^9$)$_2$, —OLS(O)$_2$N($R^9$)$_2$, -LN$R^9$S(O)$_2R^8$, -LC(O)N$R^9$LN($R^9$)$_2$, -LP(O)(O$R^8$)$_2$, -LOP(O)(O$R^8$)$_2$, -LP(O)(O$R^{10}$)$_2$ and —OLP(O)(O$R^{10}$)$_2$, and each $R^4$ is independently selected from —$R^7$, —O$R^7$, —$R^8$, —O$R^8$, —$R^{10}$, —O$R^{10}$, —S$R^8$, —N($R^9$)$_2$, —S(O)$_2R^8$, —S(O)$_3R^8$, —SO$_2$N($R^9$)$_2$, —S(O)$R^8$, —N$R^9$SO$_2$N($R^9$)$_2$, —CH═CHCO$_2R^8$, (CH$_2$)$_n$CO$_2R^8$, —N$R^9$SO$_2R^8$, —P(O)(O$R^8$)$_2$, —OP(O)(O$R^8$)$_2$, —P(O)(O$R^{10}$)$_2$, and —OP(O)(O$R^{10}$)$_2$.

In certain embodiments of the benzonaphthyridine compounds of the immunogenic compositions provided herein, each L is independently selected from a —(O(CH$_2$)$_m$)$_t$—, and C$_1$-C$_6$alkyl, wherein the C$_1$-C$_6$alkyl of L is optionally substituted with 1 to 4 substituents independently selected from halogen, —$R^8$, —O$R^8$, —N($R^9$)$_2$, —P(O)(O$R^8$)$_2$, —OP(O)(O$R^8$)$_2$, —P(O)(O$R^{10}$)$_2$, and —OP(O)(O$R^{10}$)$_2$.

In certain embodiments of the benzonaphthyridine compounds of the immunogenic compositions provided herein, $R^A$ is H or C$_1$-C$_6$alkyl.

In certain embodiments of the benzonaphthyridine compounds of the immunogenic compositions provided herein, $R^A$ is H, —CH$_3$ or —CH$_2$CH$_3$; and each $R^{13}$ is independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$ and C$_2$-C$_6$ alkyl substituted with 1-3 substituents selected from —OH, —CH$_3$, —COOH, —COOCH$_3$, cyclopropyl, —O(CH$_2$)$_{2-4}$—COOH, —O(CH$_2$)$_{2-4}$(PO$_3$H$_2$), and —COOCH$_2$CH$_3$.

In certain embodiments of the benzonaphthyridine compounds of the immunogenic compositions provided herein, each $R^8$ is independently selected from H, —CH($R^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of $R^8$ are each optionally substituted with 1 to 3 substituents independently selected from —CN, $R^{11}$, —O$R^{11}$, —S$R^{11}$, —C(O)$R^{11}$, —OC(O)$R^{11}$, —C(O)N($R^9$)$_2$, —C(O)O$R^{11}$, —N$R^9$C(O)$R^{11}$, —N$R^9R^{10}$, —N$R^{11}R^{12}$, —N($R^9$)$_2$, —O$R^9$, —O$R^{10}$, —C(O)N$R^{11}R^{12}$, —C(O)N$R^{11}$OH, —S(O)$_2R^{11}$, —S(O)$R^{11}$, —S(O)$_2$N$R^{11}R^{12}$, —N$R^{11}$S(O)$_2R^{11}$, —P(O)(O$R^{11}$)$_2$, and —OP(O)(O$R^{11}$)$_2$.

In certain embodiments of the benzonaphthyridine compounds of the immunogenic compositions provided herein, $R^8$ is H or C$_1$-C$_6$alkyl.

In certain embodiments of the benzonaphthyridine compounds of the immunogenic compositions provided herein, $R^9$ is H or C$_1$-C$_6$alkyl.

In certain embodiments of the benzonaphthyridine compounds of the immunogenic compositions provided herein, $R^4$ is H or —$CH_3$.

In certain embodiments of the benzonaphthyridine compounds of the immunogenic compositions provided herein, $R^4$ is H.

In other embodiments of the immunogenic compositions provided herein, the benzonaphthyridine compound is a compound having the structure of Formula (VIII), or a pharmaceutically acceptable salt thereof:

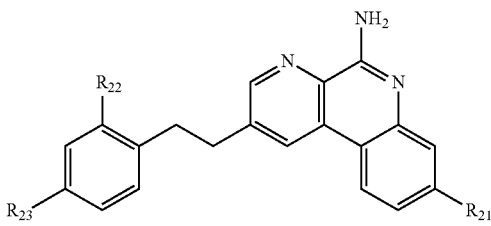

Formula (VIII)

wherein:
$R^{21}$ is H, $C_1$-$C_6$alkyl, —$C(R^{25})_2OH$, -$L^{21}R^{25}$, -$L^{21}R^{26}$, -$L^2R^{25}$, -$L^{22}R^{26}$, —$OL^{22}R^{25}$, or —$OL^{22}R^{26}$;
$L^{21}$ is —C(O)— or —O—;
$L^{22}$ is $C_1$-$C_6$alkylene, $C_2$-$C_6$alkenylene, arylene, heteroarylene or —$((CR^{24}R^{24})_pO)_q(CH_2)_p$—, wherein the $C_1$-$C_6$alkylene and $C_2$-$C_6$alkenylene of $L^{22}$ are optionally substituted with 1 to 4 fluoro groups;
each $L^{23}$ is independently selected from $C_1$-$C_6$alkylene and —$((CR^{24}R^{24})_pO)_q(CH_2)_p$—, wherein the $C_1$-$C_6$alkylene of $L^{23}$ is optionally substituted with 1 to 4 fluoro groups;
$L^{24}$ is arylene or heteroarylene;
$R^{22}$ is H or $C_1$-$C_6$alkyl;
$R^{23}$ is selected from $C_1$-$C_4$alkyl, -$L^{23}R^{25}$, -$L^{21}R^{25}$, -$L^{23}R^{27}$, -$L^{23}L^{24}L^3R^{27}$, -$L^{23}L^{24}R^{25}$, -$L^{23}L^{24}L^{23}R^{25}$, —$OL^{23}R^{25}$, —$OL^{23}R^{27}$, —$OL^{23}L^{24}R^{27}$, —$OL^{23}L^{24}L^{23}R^{27}$, —$OR^{28}$, —$OL^{23}L^{24}R^{25}$, —$OL^{23}L^{24}L^{23}R^{25}$ and —$C(R^{25})_2OH$;
each $R^{24}$ is independently selected from H and fluoro;
$R^{25}$ is —$P(O)(OR^{29})_2$;
$R^{26}$ is —$CF_2P(O)(OR^{29})_2$ or —$C(O)OR^{30}$;
$R^{27}$ is —$CF_2P(O)(OR^{29})_2$ or —$C(O)OR^{30}$;
$R^{28}$ is H or $C_1$-$C_4$alkyl;
each $R^{29}$ is independently selected from H and $C_1$-$C_6$alkyl;
$R^{30}$ is H or $C_1$-$C_4$alkyl;
each p is independently selected from 1, 2, 3, 4, 5 and 6, and
q is 1, 2, 3 or 4;
with the proviso that when $R^{23}$ is $C_1$-$C_4$ alkyl or —$OR^{28}$, then $R^{21}$ is —$C(R^{25})_2OH$, -$L^{21}R^{25}$, -$L^{21}R^{26}$, -$L^{22}R^{25}$, -$L^{22}R^{26}$, —$OL^{22}R^{25}$, or —$OL^{22}R^{26}$, wherein $R^{26}$ is —$CF_2P(O)(OR^{29})_2$ and $R^{27}$ is —$CF_2P(O)(OR^{29})_2$.

In certain embodiments of the compounds of Formula (VIII), $R^{21}$ is $C_1$-$C_6$ alkyl, in other embodiments $R^{21}$ is a methyl. In certain embodiments, $R^{21}$ is H. In other embodiments, $R^{21}$ is —$C(R^{25})_2OH$, -$L_{21}R^{25}$, -$L^{21}R^{26}$, -$L^{22}R^{25}$, -$L^{22}R^{26}$, —$OL^{22}R^{25}$, or —$OL^{22}R^{26}$.

In certain embodiments of the compounds of Formula (VIII), when $R^{21}$ —$C(R^{25})_2OH$, -$L^{21}R^{25}$, -$L^{21}R^{26}$, -$L^{22}R^{25}$, -$L^{22}R^{26}$, —$OL^{22}R^{25}$, or —$OL^{22}R^{26}$, then $R^{23}$ is —$OR^{28}$ or $C_1$-$C_6$ alkyl. In certain embodiments, $R^{21}$ is —$C(R^{25})_2OH$, -$L_{21}R^{25}$, -$L^{21}R^{26}$, -$L^{22}R^{25}$, -$L^{22}R^{26}$, —$OL^{22}R^{25}$, or —$OL^{22}R^{26}$, and $R^{23}$ is —OMe.

In some embodiments of the compounds of Formula (VIII), $R^{22}$ is $C_1$-$C_6$alkyl. In certain embodiments, $R^{22}$ is methyl.

In some embodiments of the compounds of Formula (VIII), $R^{23}$ is selected from $C_1$-$C_4$ alkyl, -$L^{23}R^{25}$, -$L^{21}R^{25}$, -$L^{23}R^{27}$, -$L^{23}L^{24}L^{23}R^{27}$, -$L^{23}L^{24}R^{25}$, and -$L^{23}L^{24}L^{23}R^{25}$. In alternative embodiments, $R^{23}$ is selected from —$OL^{23}R^{25}$, —$OL^{23}R^{27}$, —$OL^{23}L^{24}R^{27}$, —$OL^{23}L^{24}L^3R^{27}$, —$OR^{28}$, —$OL^{23}L^{24}R^{25}$, —$OL^{23}L^{24}L^{23}R^{25}$ and —$C(R^{25})_2OH$. In certain embodiments, $R^{23}$ is —$OL^{23}R^{25}$, wherein —$OL^{23}R^{25}$ is a group of the formula —$O(CH_2)_{1-5}P(O)(OR)_2$. In other embodiments, $R^{23}$ is —$OL^{23}R^{25}$, wherein —$OL^{23}R^{25}$ is a group of the formula —$O(CH_2)_{1-5}CF_2P(O)(OR)_2$.

Where more than one $R^{29}$ is present, as in compounds comprising a —$P(O)(OR^{29})_2$, moiety, the $R^{29}$ groups are the same or are different. In certain embodiments of such compounds of Formula (VIII), $R^{29}$ is H at each occurrence. In other embodiments, at least one $R^{29}$ is H and the other $R^{29}$ is $C_1$-$C_6$alkyl. In other embodiments, at least one $R^{29}$ is H and the other $R^{29}$ is methyl. In other embodiments, at least one $R^{29}$ is H and the other $R^{29}$ is ethyl. In other embodiments of such compounds of Formula (VIII), each $R^{29}$ is $C_1$-$C_6$alkyl and in certain embodiments, $R^{29}$ is methyl or ethyl, or a combination thereof.

In certain embodiments of the compounds of Formula (VIII), $L^{22}$ and/or $L^{23}$ is a group of the formula —$((CR^{24}R^{24})_pO)_q(CH_2)_p$—, and in certain embodiments, this group is of the formula —$(CH_2CH_2O)_{1-3}(CH_2)_{1-3}$—.

In certain embodiments of the compounds of Formula (VIII), $L^{22}$ is $C_1$-$C_6$ alkylene, while in other embodiments $L^{22}$ is $C_1$-$C_6$ alkylene substituted with one to four fluoro groups. In certain embodiments of such compounds of Formula (VIII), $L^{22}$ is of the formula $(CH_2)_{0-5}CF_2$, wherein the fluoro-substituted carbon is not directly attached to the phenyl ring of Formula I. In certain embodiments of the compounds of Formula (VIII), $L^{22}$ is $C_2$-$C_6$ alkenylene, while in other embodiments $L^{22}$ is $C_2$-$C_6$ alkenylene substituted with one to four fluoro groups.

In certain embodiments of the compounds of Formula (VIII), $L^{23}$ is $C_1$-$C_6$ alkylene while in other embodiments $L^{23}$ is $C_1$-$C_6$ alkylene substituted with one to four fluoro groups. In certain embodiments of such compounds of Formula (VIII), $L^{23}$ is of the formula $(CH_2)_{0-5}CF_2$, wherein the fluoro-substituted carbon is not directly attached to the phenyl ring of Formula I.

In certain embodiments of the compounds of Formula (VIII), $L^2$ is arylene or heteroarylene. In some of these embodiments, $L^2$ is phenylene, such as 1,3-disubstituted phenylene or 1,4-disubstituted phenylene.

In certain embodiments of such compounds of Formula (VIII), $R^{21}$ is $C_1$-$C_6$alkyl; $R^{22}$ is $C_1$-$C_6$alkyl; $R^{23}$ is —$OL^{23}R^{25}$ or —$OL^{23}R^{27}$; $R^{25}$ is —$P(O)(OR^{29})_2$; $R^{27}$ is —$CF_2P(O)(OR^{29})_2$, and $L^{23}$ is $C_1$-$C_6$alkylene.

In certain embodiments of such compounds of Formula (VIII), $R^{21}$ is $C_1$-$C_6$alkyl; $R^{22}$ is $C_1$-$C_6$alkyl; $R^{23}$ or —$OL^{23}R^{25}$ or —$OL^{23}R^{27}$; $R^{25}$ is —$P(O)(OR^{29})_2$; $R^{27}$ is —$CF^2P(O)(OR^{29})_2$; $L^{23}$ is —$((CR^{24}R^{24})_pO)_q(CH_2)_p$—; $R^{24}$ is H; q is 1 or 2, and p is 2.

In certain embodiments of such compounds of Formula (VIII), $R^{21}$ is -$L^{22}R^{26}$; $R^{22}$ is $C_1$-$C_6$alkyl; $R^{23}$ is —$OL^{23}R^{25}$ or —$OL^{23}R^{27}$; $R^{25}$ is —$P(O)(OR^{29})_2$; $R^{26}$ is —$C(O)OR^{30}$; $R^{27}$ is —$CF_2P(O)(OR^{29})_2$; $L^{22}$ is $C_1$-$C_6$alkylene, and $L^{23}$ is $C_1$-$C_6$alkylene.

In certain embodiments of such compounds of Formula (VIII), $R^{21}$ is $-L^{22}R^{26}$; $R^{22}$ is $C_1$-$C_6$alkyl; $R23^3$ is $-OL^{23}R^{25}$ or $-OL^{23}R^{27}$; $R^5$ is $-P(O)(OR^{29})_2$; $R^{26}$ is $-C(O)OR^{30}$; $R^{27}$ is $-CF_2P(O)(OR^{29})_2$, $L^{22}$ is $C_1$-$C_6$alkylene; $L^{23}$ is $-((CR^{24}R^{24})_pO)_q(CH_2)_p-$; $R^{24}$ is H; q is 1 or 2, and p is 2.

In certain embodiments of such compounds of Formula (VIII), $R^{21}$ is $-C(R^{25})_2OH$, $-L^{21}R^{25}$, $L^{22}R^{25}$ or $-L^{21}R^{26}$; $R^{22}$ is $C_1$-$C_6$alkyl; $R^{23}$ is $-OR^{28}$; $R^{28}$ is $C_1$-$C_6$alkyl; $R^{25}$ is $-P(O)(OR^{29})_2$; $R^{26}$ is $-CF_2P(O)(OR^{29})_2$, $L^{21}$ is $-C(O)-$, and $L^{22}$ is $C_1$-$C_6$alkylene or $C_2$-$C_6$alkenylene, each optionally substituted with 1 to 4 fluoro groups.

In certain embodiments of such compounds of Formula (VIII), $R^{21}$ is $C_1$-$C_6$alkyl; $R^{22}$ is $C_1$-$C_6$alkyl; $R^{23}$ is $-OL^{23}L^{24}R^{25}-OL^{23}L^{24}L^{23}R^{25}$, or $-OL^{23}L^{24}L^{23}R^{27}$; $R^{25}$ is $-P(O)(OR^{29})_2$; $R^{27}$ is $-CF_2P(O)(OR^{29})_2$; each $L^{23}$ is independently a $C_1$-$C_6$alkylene, and $L^{24}$ is phenylene.

In certain embodiments of such compounds of Formula (VIII), $R^{21}$ is $C_1$-$C_6$alkyl; $R^{22}$ is $C_1$-$C_6$alkyl; $R^{23}$ is $-C(R^{25})_2OH$ or $-L^{21}R^{25}$; $R^{25}$ is $-P(O)(OR^{29})_2$, and $L^{21}$ is $-C(O)-$ or $-O-$.

In certain embodiments of the immunogenic compositions provided herein, the benzonaphthyridine compounds is selected from:

2-(4-(2-(5-amino-8-methylbenzo[f][1,7]naphthyridin-2-yl)ethyl)-3-methylphenyl)propan-2-ol;
2-(4-methoxy-2-methylphenethyl)-8-methylbenzo[f][1,7]naphthyridin-5-amine;
2-(2,4-dimethylphenethyl)benzo[f][1,7]naphthyridin-5-amine;
ethyl 4-(2-(5-amino-8-methylbenzo[f][1,7]naphthyridin-2-yl)ethyl)-3-methylbenzoate;
2-(4-(dimethylamino)phenethyl)-8-methylbenzo[f][1,7]naphthyridin-5-amine, 2-(4-methoxyphenethyl)-8-methylbenzo[f][1,7]naphthyridin-5-amine, 4-(4-(2-(5-amino-8-methylbenzo[f][1,7]naphthyridin-2-yl)ethyl)-3-methylphenoxy)-1,1-difluorobutylphosphonic acid; 3-(5-amino-2-(4-(4,4-difluoro-4-phosphonobutoxy)-2-methylphenethyl)benzo[f][1,7]naphthyridin-8-yl)propanoic acid; 3-(5-amino-2-(4-(2-(3,3-difluoro-3-phosphonopropoxy)ethoxy)-2-methylphenethyl)benzo[f][1,7]naphthyridin-8-yl)propanoic acid; 3-(5-amino-2-(2-methyl-4-(2-(2-phosphonoethoxy)ethoxy)phenethyl)benzo[f][1,7]naphthyridin-8-yl)propanoic acid; 4-(2-(5-amino-8-methylbenzo[f][1,7]naphthyridin-2-yl)ethyl)-3-methylphenyl dihydrogen phosphate; (4-(2-(5-amino-8-methylbenzo[f][1,7]naphthyridin-2-yl)ethyl)-3-methylphenoxy)methylphosphonic acid; 5-(4-(2-(5-amino-8-methylbenzo[f][1,7]naphthyridin-2-yl)ethyl)-3-methylphenoxy)-1,1-difluoropentylphosphonic acid; 4-(4-(2-(5-amino-8-methylbenzo[f][1,7]naphthyridin-2-yl)ethyl)-3-methylphenoxy)-1,1-difluorobutylphosphonic acid; 3-(2-(4-(2-(5-amino-8-methylbenzo[f][1,7]naphthyridin-2-yl)ethyl)-3-methylphenoxy)ethoxy)-1,1-difluoropropylphosphonic acid; 2-(4-((4-(2-(5-amino-8-methylbenzo[f][1,7]naphthyridin-2-yl)ethyl)-3-methylphenoxy)methyl)phenyl)-1,1-difluoroethylphosphonic acid; 2-(5-amino-2-(4-methoxy-2-methylphenethyl)benzo[f][1,7]naphthyridin-8-yl)-1,1-difluoro-2-oxoethylphosphonic acid; (E)-2-(5-amino-2-(4-methoxy-2-methylphenethyl)benzo[f][1,7]naphthyridin-8-yl)vinylphosphonic acid; 2-(5-amino-2-(4-methoxy-2-methylphenethyl)benzo[f][1,7]naphthyridin-8-yl)ethylphosphonic acid; (E)-2-(5-amino-2-(4-methoxy-2-methylphenethyl)benzo[f][1,7]naphthyridin-8-yl)-1-fluorovinylphosphonic acid; 3-((4-(2-(5-amino-8-methylbenzo[f][1,7]naphthyridin-2-yl)ethyl)-3-methylphenoxy)methyl)phenylphosphonic acid; 5-amino-2-(4-methoxy-2-methylphenethyl)benzo[f][1,7]naphthyridine-8-carbonylphosphonic acid; 3-(5-amino-2-(2-methyl-4-(3-phosphonopropoxy)phenethyl)benzo[f][1,7]naphthyridin-8-yl)propanoic acid; (4-(2-(5-amino-8-methylbenzo[f][1,7]naphthyridin-2-yl)ethyl)-3-methylphenyl)(hydroxy)methylenediphosphonic acid; 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid; (5-amino-2-(4-methoxy-2-methylphenethyl)benzo[f][1,7]naphthyridin-8-yl)(hydroxy)methylenediphosphonic acid; 3-(5-amino-2-(2-methyl-4-(2-(2-phosphonoethoxy)ethoxy)phenethyl)benzo[f][1,7]naphthyridin-8-yl)propanoic acid; 2-(4-(2-(5-amino-8-methylbenzo[f][1,7]naphthyridin-2-yl)ethyl)-3-methylphenoxy)ethylphosphonic acid; 6-(4-(2-(5-amino-8-methylbenzo[f][1,7]naphthyridin-2-yl)ethyl)-3-methylphenoxy)hexylphosphonic acid; 6-(4-(2-(5-amino-8-methylbenzo[f][1,7]naphthyridin-2-yl)ethyl)-3-methylphenoxy)-1,1-difluorohexylphosphonic acid; 4-((4-(2-(5-amino-8-methylbenzo[f][1,7]naphthyridin-2-yl)ethyl)-3-methylphenoxy)methyl)benzylphosphonic acid, 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid, and 2-(2-(2-(4-(2-(5-amino-8-methylbenzo[f][1,7]naphthyridin-2-yl)ethyl)-3-methylphenoxy)ethoxy)ethoxy)ethylphosphonic acid.

In some embodiments, the present invention provides pharmaceutical compositions comprising immunogenic compositions of the present invention.

In some embodiments, the present invention provides injectable vaccine compositions comprising immunogenic compositions in accordance with the present invention.

In some embodiments, the present invention provides methods for eliciting immune responses in a vertebrate subject comprising administering to the vertebrate subject an effective amount of an immunogenic composition in accordance with the present invention.

In some embodiments, the present invention provides methods for eliciting a cytotoxic-T lymphocyte (CTL) response in a vertebrate subject comprising administering to the vertebrate subject an effective amount of an immunogenic composition of the present invention.

In some embodiments, the present invention provides methods of eliciting an antibody-mediated immune response in a vertebrate subject comprising administering an effective amount of an immunogenic composition of the present invention to the vertebrate subject.

In some embodiments, the present invention provides methods of making immunogenic compositions such as those described herein.

These and other embodiments of the present invention will readily occur to those of ordinary skill in the art in view of the disclosure herein.

DETAILED DESCRIPTION OF THE INVENTION

Figure 1:
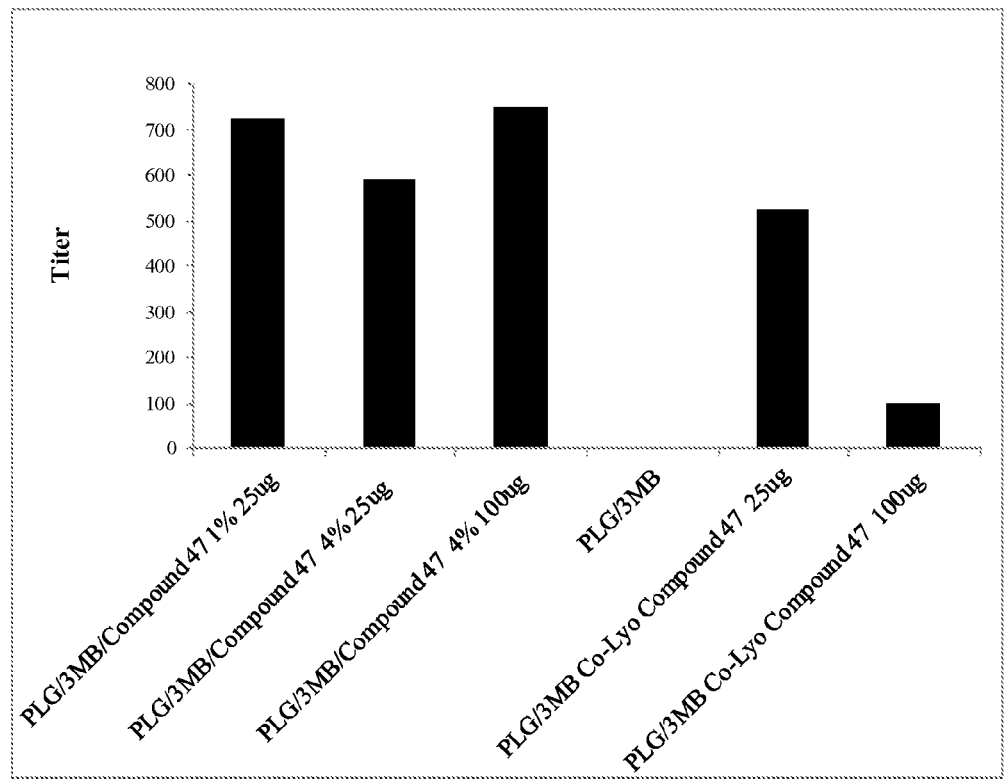
FIGS. 1 and 2 illustrate titer results of a bactericidal assay against the MenB strain NZ98 at 2 weeks and 8 weeks post $2^{nd}$ immunization, respectively, for various formulations in accordance with the invention.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th ed. (Easton, Pa.: Mack Publishing Company, 1990); *Methods In Enzymology* (S. Colowick and N. Kaplan, eds., Academic Press, Inc.); Weir, D. M., *Handbook of Experimental Immunology*, Vols. I-IV, 5th ed. (Blackwell Publishers, 1996); Sambrook, J. et al., *Molecular Cloning: A Laboratory Manual*, 3rd ed. (Cold Spring Harbor Laboratory Press, 2001); Ausubel, F. M. et al., *Short Protocols In Molecular Biology*, 5th ed. (Current Protocols, 2002); *Handbook of Surface and Colloidal Chemistry* (Birdi, K. S., ed, CRC Press, 2003) and *Seymour/Carraher's Polymer Chemistry*, 5th ed. (Marcel Dekker Inc., 2007).

A. DEFINITIONS

As used herein, the singular forms "a," "an" and "the" include plural references unless the content clearly dictates otherwise.

The term "about", as used here, refers to +/−10% of a value.

The term "alkenyl," as used herein, refers to a partially unsaturated branched or straight chain hydrocarbon having at least one carbon-carbon double bond. Atoms oriented about the double bond are in either the cis (Z) or trans (E) conformation. An alkenyl group can be optionally substituted. As used herein, the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. If not otherwise specified, an alkenyl group generally is a $C_2$-$C_6$ alkenyl. Non-limiting examples of alkenyl groups, as used herein, include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. An alkenylene group can be optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. If not otherwise specified, an alkenylene group generally is a $C_1$-$C_6$ alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, iso-propyl, n-butyl, isobutyl, sec-butyl, t-butyl, n-pentyl, iso-pentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. If not otherwise specified, an alkylene group generally is a $C_1$-$C_6$ alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkynyl," as used herein, refers to a partially unsaturated branched or straight chain hydrocarbon having at least one carbon-carbon triple bond. An alkynyl group can be optionally substituted. As used herein, the terms "$C_2$-$C_3$alkynyl", "$C_2$-$C_4$ alkynyl", "$C_2$-$C_5$alkynyl", "$C_2$-$C_6$alkynyl", "$C_2$-$C_7$alkynyl", and "$C_2$-$C_8$alkynyl" refer to an alkynyl group containing at least 2, and at most 3, 4, 5, 6, 7 or 8 carbon atoms, respectively. If not otherwise specified, an alkynyl group generally is a $C_2$-$C_6$ alkynyl. Non-limiting examples of alkynyl groups, as used herein, include ethynyl, propynyl, butynyl, pentynyl, hexynyl, heptynyl, octynyl, nonynyl, decynyl and the like.

The term "alkynylene," as used herein, refers to a partially unsaturated branched or straight chain divalent hydrocarbon radical derived from an alkynyl group. An alkynylene group can be optionally substituted. As used herein, the terms "$C_2$-$C_3$alkynylene", "$C_2$-$C_4$alkynylene", "$C_2$-$C_5$alkynylene", "$C_2$-$C_6$alkynylene", "$C_2$-$C_7$alkynylene", and "$C_2$-$C_8$alkynylene" refer to an alkynylene group containing at least 2, and at most 3, 4, 5, 6, 7 or 8 carbon atoms respectively. If not otherwise specified, an alkynylene group generally is a $C_2$-$C_6$ alkynylene. Non-limiting examples of alkynylene groups as used herein include, ethynylene, propynylene, butynylene, pentynylene, hexynylene, heptynylene, octynylene, nonynylene, decynylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. An aryl group can be optionally substituted. Non-limiting examples of aryl groups, as used herein, include phenyl, naphthyl, fluorenyl, indenyl, azulenyl, anthracenyl and the like.

The term "arylene," as used means a divalent radical derived from an aryl group. An arylene group can be optionally substituted.

The term "cyano," as used herein, refers to a —CN group.

The term "cycloalkyl," as used herein, refers to a saturated or partially unsaturated, monocyclic, fused bicyclic, fused tricyclic or bridged polycyclic ring assembly. As used herein, the terms "$C_3$-$C_5$ cycloalkyl", "$C_3$-$C_6$ cycloalkyl", "$C_3$-$C_7$ cycloalkyl", "$C_3$-$C_8$ cycloalkyl, "$C_3$-$C_9$ cycloalkyl and "$C_3$-$C_{10}$ cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. A cycloalkyl group can be optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The terms "haloalkynyl" or "halo-substituted alkynyl," as used herein, refers to an alkynyl group as defined above, substituted with one or more halogen groups, wherein the halogen groups are the same or different. A haloalkynyl group can be optionally substituted. Non-limiting examples of such branched or straight chained haloalkynyl groups, as used herein, include ethynyl, propynyl, butynyl, pentynyl, hexynyl, heptynyl, octynyl, nonynyl, decynyl, and the like substituted with one or more halogen groups, wherein the halogen groups are the same or different.

The term "haloalkoxy," as used herein, refers to an alkoxy group as defined herein, substituted with one or more halogen groups, wherein the halogen groups are the same or different. A haloalkoxy group can be optionally substituted. Non-limiting examples of such branched or straight chained haloalkynyl groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like, substituted with one or more halogen groups, wherein the halogen groups are the same or different.

The term "heteroalkyl," as used herein, refers to an alkyl group as defined herein wherein one or more carbon atoms are independently replaced by one or more of oxygen, sulfur, nitrogen, or combinations thereof.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. A heteroaryl group may contain one or more substituents. A heteroaryl group can be optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heterocycloalkyl," as used herein, refers to a cycloalkyl, as defined herein, wherein one or more of the ring carbons are replaced by a moiety selected from —O—, —N═, —NR—, —C(O)—, —S—, —S(O)— or —S(O)$_2$—, wherein R is hydrogen, $C_1$-$C_4$alkyl or a nitrogen protecting group, with the proviso that the ring of said group does not contain two adjacent O or S atoms. A heterocycloalkyl group can be optionally substituted. Non-limiting examples of heterocycloalkyl groups, as used herein, include morpholino, pyrrolidinyl, pyrrolidinyl-2-one, piperazinyl, piperidinyl, piperidinylone, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

As used here, the term "injectable composition", or variants thereof, refers to pharmaceutically acceptable compositions suitable for injection into a vertebrate subject, which compositions are typically sterile, pyrogen-free, and possess specific pH and isotonicity values suitable for injection.

The term "isocyanato," as used herein, refers to a —N═C═O group.

The term "isothiocyanato," as used herein, refers to a —N═C═S group

The term "mercaptyl," as used herein, refers to an (alkyl) S— group.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, ═O, ═N—OH, ═N—OR, ═N—R, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$NR$_2$, —NRS(O)$_2$NR$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example ═O is a suitable substituent for an alkyl group but not for an aryl group.

By "pharmaceutically acceptable" or "pharmacologically acceptable" is meant a material which is not biologically or otherwise undesirable, e.g., the material may be administered to an individual without causing any unduly undesirable biological effects or interacting in an unduly deleterious manner with any of the components of the composition in which it is contained.

By "physiological pH" or a "pH in the physiological range" is meant a pH in the range of approximately 6.5 to 8.0 inclusive, more typically in the range of approximately 7.2 to 7.6 inclusive.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, "treatment" refers to any of (i) the prevention of a condition (e.g., a disease or disorder) in question (e.g. cancer or a pathogenic infection, as in a traditional vaccine), (ii) the reduction or elimination of symptoms associated with the condition in question, and (iii) the substantial or complete elimination of the condition in question. Treatment may be effected prophylactically (prior to arrival of the condition in question) or therapeutically (following arrival of the same).

The terms "effective amount" or "pharmaceutically effective amount" of an immunogenic composition of the present invention refer herein to a sufficient amount of the immunogenic composition for the treatment or diagnosis of a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

As used herein, the term "particle" refers to a particle of about 10 nm or less to about 150 µm in diameter, for example, ranging from 10 nm to 25 nm to 50 nm to 100 nm to 250 nm to 500 nm to 1 µm to 2.5 µm to 5 µm to 10 µm to 25 µm to 50 µm to 100 µm. The term "particle' as used herein thus includes "nanoparticle," which is defined herein as a particle having a diameter less than 1000 nm, and "microparticle," which is defined herein as a particle having a diameter ranging from 1 µm to 1000 µm. In some embodiments, the polymeric particles described herein can be generally spherical. In some embodiments, the polymeric particles described herein can be of irregular geometry.

The particles within the compositions of the present invention typically have a size distribution in which the Z average and/or the D(v,0.5) value ranges from 50 nm to 5 µm, for example, ranging from 50 nm to 100 nm to 200 nm to 250 nm to 300 nm to 400 nm to 500 nm to 750 nm to 1 µm to 2.5 µm to 5 µm to 10 µm. In some embodiments, the particles within the compositions of the present invention have a size distribution in which the D(v,0.9) value lies within this range.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy in some embodiments), volume-based size parameters may be measured. For instance, the D(v,0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value. Similarly, the D(v,0.9) is a size parameter whose value is defined as the point where 90% (volume basis) of the particles in the composition have a size that is less than the D(v,0.9) value, and 10% of the particles in the composition have a size that is greater than the D(v,0.9) value.

As used herein, a "polymeric particle" refers to a particle that comprises one or more types of polymer. Polymeric particles for use herein are typically formed from polymers that are at least partially biodegradable.

Polymeric particles may aggregate into larger masses under some circumstances (e.g., upon lyophilization). The polymeric particle will generally be of a diameter that permits parenteral or mucosal administration without occluding needles and capillaries.

The term "polypeptide" refers to a polymer of amino acid residues and is not limited to a minimum length of the product. Thus, full length proteins, peptides, oligopeptides, dimers, multimers, and the like, are included within the definition.

A "polypeptide-containing species" is a molecule, at least a portion of which is a polypeptide. Examples include polypeptides, proteins including glycoproteins, metalloproteins and lipoproteins, polysaccharide antigens conjugated to carrier proteins, and so forth. Proteins for use herein include full-length proteins and fragments thereof. In certain embodiments, modifications to the native sequence, such as deletions, additions and substitutions (generally conservative in nature), are employed.

The term "fragment" as used herein refers to a physically contiguous portion of the primary structure of a biomolecule. In the case of proteins, a fragment may be defined by a contiguous portion of the amino acid sequence of that protein and may be at least 3-5 amino acids, at least 6-10 amino acids, at least 11-15 amino acids, at least 16-24 amino acids, at least 25-30 amino acids, and at least 30-45 amino acids. In the case of polynucleotide, a fragment is defined by a contiguous portion of the nucleic acid sequence of that polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

A "polynucleotide" is a nucleic acid polymer. A polynucleotide can include as few as 5, 6, 7 or 8 nucleotides. Furthermore, a "polynucleotide" can include both double- and single-stranded sequences and refers to, but is not limited to, cDNA from viral, procaryotic or eukaryotic mRNA, genomic RNA and DNA sequences from viral (e.g. RNA and DNA viruses and retroviruses), prokaryotic or eukaryotic organisms, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

A "polynucleotide-containing species" is a molecule, at least a portion of which is a polynucleotide. Examples include RNA vector constructs, DNA vector constructs and so forth.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

As used herein the term "isolated" refers to a chemical species such as a polynucleotide, a polypeptide, and an antibody, etc. that is in an environment different from that in which the chemical species naturally occurs. A chemical species which is isolated is generally substantially purified. Methods of isolating cells are also well known to those skilled in the art.

A "purified" protein is a protein which is produced (e.g., recombinantly or synthetically) or isolated from its natural host, such that the amount of protein present in a composition is substantially higher than that present in a crude preparation. In general, a purified protein will be at least about 50% homogeneous, more preferably at least about 80%, about 85%, about 90%, about 95%, about 97%, about 98%, about 99%, or more, homogeneous.

As used herein, an "immunological response" or "immune response" is the development in a subject of a humoral and/or a cellular immune response to the immunogenic species.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be used as immunogenic species in various embodiments of the invention) include the following: TLR1 (bacterial lipoproteins from *Mycobacteria, Neisseria*), TLR2 (zymosan yeast particles, peptidoglycan, lipoproteins, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, *Nature Medicine*, 11, S63-S68 (2005), K. S. Rosenthal and D. H. Zimmerman, *Clinical and Vaccine Immunology*, 13(8), 821-829 (2006), and the references cited therein.

For purposes of the present invention, a humoral immune response refers to an immune response mediated by antibody molecules, while a cellular immune response is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "antigen" refers to a molecule containing one or more epitopes (either linear, conformational or both) that elicit an immunological response. The term may be used interchangeably with the term "immunogen." An "epitope" is that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids. The term "antigen" denotes both subunit antigens, i.e., antigens which are separate and discrete from a whole organism or cell with which the antigen is associated in nature, as well as killed, attenuated or inactivated bacteria, viruses, fungi, parasites or other microbes or tumor cells. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

Thus, for purposes of the present invention, antigens can be derived from any of the various viruses, bacteria, parasites, fungi and other microbes, as well as any of the various tumor antigens. Antigens also include nucleic acids which express an antigen or antigenic determinant in vivo. As a few specific examples, antigens may be proteins from or derived from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV, including members of the various genetic subtypes of HIV isolates $HIV_{IIIb}$, $HIV_{SF2}$, $HIV_{LAV}$, $HIV_{LAI}$, $HW_{MN}$, $HIV-1_{CM235}$, $HIV-1_{US4}$, HIV-2; proteins derived from simian immunodeficiency virus (SIV); and proteins derived from Neisseria meningitidis (A, B, C, Y), Hemophilus influenza type B (HIB), Helicobacter pylori; human serum albumin and ovalbumin, among many others.

An immunogenic composition which contains an antigen in accordance with the present invention displays "enhanced immunogenicity" when it possesses a greater capacity to elicit an immune response than the immune response elicited by an equivalent amount of the antigen administered using a different delivery system, e.g., wherein the antigen is administered as a soluble protein. Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the antigen composition and antigen controls to animals and comparing antibody titers and/or cellular-mediated immunity against the two using standard assays described herein.

The term "adjuvant" or "immunological adjuvant" refers to any substance that assists or modifies the action of an antigen in the immune system. Adjuvants can potentiate humoral and/or cellular immunity.

The term "excipient" refers to any essentially accessory substance that may be present in the finished dosage form. For example, the term "excipient" includes vehicles, binders, disintegrants, fillers (diluents), suspending/dispersing agents, and so forth.

As used herein, the phrase "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

The compound names provided herein were obtained using ChemDraw Ultra 10.0 (CambridgeSoft®) or JChem version 5.0.3 (ChemAxonk).

B. GENERAL

The present invention provides immunogenic compositions comprising (a) a first antigen, (b) a polymeric particles comprising one or more types of polymers and (c) a benzonaphthyridine compound.

In some embodiments, the first antigen is a killed or live (e.g., attenuated or inactivated) pathogenic organism. In some embodiments, the first antigen is a polypeptide-containing antigen (e.g., full-length proteins, protein fragments, etc.). In some embodiments, the first antigen is a polysaccharide-containing antigen (e.g., a capsular polysaccharide, a polysaccharide-protein protein conjugate, etc.). In some embodiments, the first antigen is a polynucleotide-containing antigen (e.g., a polynucleotide that is linked to a regulatory sequence which controls expression of the polynucleotide, etc.).

Immunogenic compositions in accordance with the invention can also be used in methods for eliciting an immune response, for example, a cytotoxic-T lymphocyte (CTL) response, an antibody-mediated immune response, or both, in a vertebrate subject, which comprise administering to the vertebrate subject the immunogenic composition.

In some embodiments, the immunogenic compositions of the invention are used in an injectable vaccine to treat, for example, a pathogen or tumor.

Immunogenic compositions in accordance with the invention can also be prepared in various other forms.

The present invention also provides kits for preparing immunogenic compositions. The kits may also comprise, for example, a first container comprising an antigen and a second container comprising polymeric particles and a benzonaphthyridine compound. The kits also may comprise, for example, a first container comprising an antigen, a second container comprising polymeric particles, and a third container comprising a benzonaphthyridine compound.

In some embodiments, the immunogenic compositions of the invention can further comprise one or more supplemental components.

In some embodiments, the compositions further comprise a second antigen. Like the first antigen, the second antigen may be, for example, a killed or live pathogenic organism, a polypeptide-containing antigen, a polysaccharide-containing antigen, a polynucleotide-containing antigen, and so forth. In some embodiments, the immunogenic compositions of the invention can further comprise 2, 3, 4 or more antigens.

C. BENZONAPHTHYRIDINE COMPOUNDS

"Benzonaphthyridine compounds" used in the invention include compounds having the structure of Formula (I), and pharmaceutically acceptable salts, solvates, N-oxides, prodrugs and isomers thereof.

"Benzonaphthyridine compounds" used in the invention include compounds, pharmaceutically acceptable salts, pharmaceutically acceptable solvates (e.g. hydrates), the N-oxide derivatives, prodrug derivatives, protected derivatives, individual isomers and mixture of isomers thereof, having the structure of Formula (I):

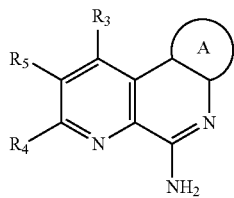

Formula (I)

wherein:
  $R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —C(O)$R^8$, —OC(O)$R^8$, —C(O)$OR^8$, —N($R^9$)$_2$, —C(O)N($R^9$)$_2$, —S(O)$_2R^8$, —S(O)$_2$N($R^9$)$_2$ and —$NR^9$S(O)$_2R^8$;

$R^4$ and $R^5$ are each independently selected from H, halogen, —C(O)$OR^7$, —C(O)$R^7$, —C(O)N($R^{11}R^{12}$), —N($R^{11}R^{12}$), —N($R^9$)$_2$, —NHN($R^9$)$_2$, —$SR^7$, —(CH$_2$)$_n$$OR^7$, —(CH$_2$)$_n$$R^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —NO$_2$, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —S(O)$_2R^8$, —S(O)$R^8$, —S(O)$_2$N($R^9$)$_2$, and —$NR^9$S(O)$_2R^8$;
    or $R^3$ and $R^4$, or $R^4$ and $R^5$, when present on adjacent ring atoms, can optionally be linked together to form a 5-6 membered ring, wherein the 5-6 membered ring is optionally substituted with $R^7$;
    each L is independently selected from a bond, —(O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —N($R^9$)$_2$, —P(O)($OR^8$)$_2$, —OP(O)($OR^8$)$_2$, —P(O)($OR^{10}$)$_2$, and —OP(O)($OR^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;
  each $R^8$ is independently selected from H, —CH($R^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)N($R^9$)$_2$, —C(O)$OR^{11}$, —$NR^9$C(O)$R^{11}$, —$NR^9R^{10}$, —$NR^{11}R^{12}$, —N($R^9$)$_2$, —$OR^9$, —$OR^{10}$, —C(O)$NR^{11}R^{12}$, —C(O)$NR^{11}$OH, —S(O)$_2R^{11}$, —S(O)$R^{11}$, —S(O)$_2NR^{11}R^{12}$, —$NR^{11}$S(O)$_2R^{11}$, —P(O)($OR^{11}$)$_2$ and —OP(O)($OR^{11}$)$_2$;
  each $R^9$ is independently selected from H, —C(O)$R^8$, —C(O)$OR^8$, —C(O)$R^{10}$, —C(O)$OR^{10}$, —S(O)$_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —C(O)$R^{11}$, —OC(O)$R^{11}$, —C(O)$OR^{11}$, —$NR^{11}R^{12}$, —C(O)$NR^{11}R^{12}$, —C(O)$NR^{11}$OH, —S(O)$_2R^{11}$, —S(O)$R^{11}$, —S(O)$_2NR^{11}R^{12}$, —$NR^{11}$S(O)$_2R^{11}$, —P(O)($OR^{11}$)$_2$, and —OP(O)($OR^{11}$)$_2$;
  each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —N($R^9$)$_2$, —$NR^9$C(O)$R^8$, —$NR^9$CO$_2R^8$, —CO$_2R^8$, —C(O)$R^8$ and —C(O)N($R^9$)$_2$;
  $R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —C(O)$R^8$, ⁻OC(O)$R^8$, —C(O)$OR^8$, —N($R^9$)$_2$, —$NR^8$C(O)$R^8$, —$NR^8$C(O)$OR^8$, —C(O)N($R^9$)$_2$, $C_3$-$C_8$heterocycloalkyl, —S(O)$_2R^8$, —S(O)$_2$N($R^9$)$_2$, —$NR^9$S(O)$_2R^8$, $C_1$-$C_6$haloalkyl and $C_1$-$C_6$haloalkoxy; or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;
  each $R^{13}$ is independently selected from halogen, —CN, -$LR^9$, -$LOR^9$, —$OLR^9$, -$LR^{10}$, -$LOR^{10}$, —$OLR^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -L=NOH, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;

Ring A is an aryl or a heteroaryl, wherein the aryl and heteroaryl groups of Ring A are optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$; or two adjacent R$^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain embodiments of compounds of Formulas (I), ring A is selected from phenyl, naphthyl, fluorenyl, indenyl, azulenyl and anthracenyl, each of which is optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$.

In other embodiments of compounds of Formulas (I), Ring A is phenyl or naphthyl, each of which is optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$.

In certain embodiments of compounds of Formulas (I), ring A is selected from benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl, each of which is optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$.

In other embodiments of compounds of Formulas (I), Ring A is selected from pyridyl, benzo[1,3]dioxole, thienyl, benzothienyl, benzofuranyl, or indolyl, each of which is optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$.

In certain embodiments of compounds of Formulas (I), Ring A is selected from phenyl, thienyl, and pyridyl, and in other embodiments such phenyl, thienyl, and pyridyl groups are optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$.

In certain embodiments of compounds of Formulas (I), Ring A is a phenyl optionally substituted with 1 to 3 R$^A$ groups, wherein each R$^A$ is independently selected from halogen, —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)

N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸.

In certain embodiments of compounds of Formulas (I), Ring A is a pyridyl optionally substituted with 1 to 3 $R^A$ groups, wherein each $R^A$ is independently selected from halogen, —R⁸, —R⁷, —OR⁷, —OR⁸, —R¹⁰, —OR¹⁰, —SR⁸, —NO₂, —CN, —N(R⁹)₂, —NR⁹C(O)R⁸, —NR⁹C(S)R⁸, —NR⁹C(O)N(R⁹)₂, —NR⁹C(S)N(R⁹)₂, —NR⁹CO₂R⁸, —NR⁹NR⁹C(O)R⁸, —NR⁹NR⁹C(O)N(R⁹)₂, —NR⁹NR⁹CO₂R⁸, —C(O)C(O)R⁸, —C(O)CH₂C(O)R⁸, —CO₂R⁸, —(CH₂)ₙCO₂R⁸, —C(O)R⁸, —C(S)R⁸, —C(O)N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸.

In certain embodiments compounds of Formula (I), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (II), Formula (II)

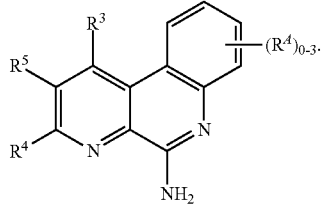

wherein:
  $R^3$ is H, halogen, C₁-C₆alkyl, C₂-C₈alkene, C₂-C₈alkyne, C₁-C₆heteroalkyl, C₁-C₆haloalkyl, C₁-C₆alkoxy, C₁-C₆haloalkoxy, aryl, heteroaryl, C₃-C₈cycloalkyl, and C₃-C₈heterocycloalkyl, wherein the C₁-C₆alkyl, C₁-C₆heteroalkyl, C₁-C₆haloalkyl, C₁-C₆alkoxy, C₁-C₆haloalkoxy, C₃-C₈cycloalkyl, or C₃-C₈heterocycloalkyl groups of $R^3$ are each optionally substituted with 1 to 3 substituents independently selected from halogen, —CN, —R⁷, —OR⁸, —C(O)R⁸, —OC(O)R⁸, —C(O)OR⁸, —N(R⁹)₂, —C(O)N(R⁹)₂, —S(O)₂R⁸, —S(O)₂N(R⁹)₂ and —NR⁹S(O)₂R⁸;
  $R^4$ and $R^5$ are each independently selected from H, halogen, —C(O)OR⁷, —C(O)R⁷, —C(O)N(R¹¹R¹²), —N(R¹¹R¹²), —N(R⁹)₂, —NHN(R⁹)₂, —SR⁷, —(CH₂)ₙOR⁷, —(CH₂)ₙR⁷, -LR⁸, -LR¹⁰, —OLR⁸, —OLR¹⁰, C₁-C₆alkyl, C₁-C₆heteroalkyl, C₁-C₆haloalkyl, C₂-C₈alkene, C₂-C₈alkyne, C₁-C₆alkoxy, C₁-C₆haloalkoxy, aryl, heteroaryl, C₃-C₈cycloalkyl, and C₃-C₈heterocycloalkyl, wherein the C₁-C₆alkyl, C₁-C₆heteroalkyl, C₁-C₆haloalkyl, C₂-C₈alkene, C₂-C₈alkyne, C₁-C₆alkoxy, C₁-C₆haloalkoxy, aryl, heteroaryl, C₃-C₈cycloalkyl, and C₃-C₈heterocycloalkyl groups of $R^4$ and $R^5$ are each optionally substituted with 1 to 3 substituents independently selected from halogen, —CN, —NO₂, —R⁷, —OR⁸, —C(O)R⁸, —OC(O)R⁸, —C(O)OR⁸, —N(R⁹)₂, —P(O)(OR⁸)₂, —OP(O)(OR⁸)₂, —P(O)(OR¹⁰)₂, —OP(O)(OR¹⁰)₂, —C(O)N(R⁹)₂, —S(O)₂R⁸, —S(O)R⁸, —S(O)₂N(R⁹)₂, and —NR⁹S(O)₂R⁸;
  or $R^3$ and $R^4$, or $R^4$ and $R^5$, when present on adjacent ring atoms, can optionally be linked together to form a 5-6 membered ring, wherein the 5-6 membered ring is optionally substituted with $R^7$;
  each L is independently selected from a bond, —(O(CH₂)ₘ)ₜ—, C₁-C₆alkyl, C₂-C₆alkenylene and C₂-C₆alkynylene, wherein the C₁-C₆alkyl, C₂-C₆alkenylene and C₂-C₆alkynylene of L are each optionally substituted with 1 to 4 substituents independently selected from halogen, —R⁸, —OR⁸, —N(R⁹)₂, —P(O)(OR⁸)₂, —OP(O)(OR⁸)₂, —P(O)(OR¹⁰)₂, and —OP(O)(OR¹⁰)₂;
  $R^7$ is selected from H, C₁-C₆alkyl, aryl, heteroaryl, C₃-C₈cycloalkyl, C₁-C₆heteroalkyl, C₁-C₆haloalkyl, C₂-C₈alkene, C₂-C₈alkyne, C₁-C₆alkoxy, C₁-C₆haloalkoxy, and C₃-C₈heterocycloalkyl, wherein the C₁-C₆alkyl, aryl, heteroaryl, C₃-C₈cycloalkyl, C₁-C₆heteroalkyl, C₁-C₆haloalkyl, C₂-C₈alkene, C₂-C₈alkyne, C₁-C₆alkoxy, C₁-C₆haloalkoxy, and C₃-C₈heterocycloalkyl groups of $R^7$ are each optionally substituted with 1 to 3 $R^{13}$ groups, and each $R^{13}$ is independently selected from halogen, —CN, -LR⁹, -LOR⁹, —OLR⁹, -LR¹⁰, -LOR¹⁰, —OLR¹⁰, -LR⁸, -LOR⁸, —OLR⁸, -LSR⁸, -LSR¹⁰, -LC(O)R⁸, —OLC(O)R⁸, -LC(O)OR⁸, -LC(O)R¹⁰, -LOC(O)OR⁸, -LC(O)NR⁹R¹¹, -LC(O)NR⁹R⁸, -LN(R⁹)₂, -LNR⁹R⁸, -LNR⁹R¹⁰, -LC(O)N(R⁹)₂, -LS(O)₂R⁸, -LS(O)R⁸, -LC(O)NR⁸OH, -LNR⁹C(O)R⁸, -LNR⁹C(O)OR⁸, -LS(O)₂N(R⁹)₂, —OLS(O)₂N(R⁹)₂, -LNR⁹S(O)₂R⁸, -LC(O)NR⁹LN(R⁹)₂, -LP(O)(OR⁸)₂, -LOP(O)(OR⁸)₂, -LP(O)(OR¹⁰)₂ and —OLP(O)(OR¹⁰)₂;
  each $R^8$ is independently selected from H, —CH(R¹⁰)₂, C₁-C₈alkyl, C₂-C₈alkene, C₂-C₈alkyne, C₁-C₆haloalkyl, C₁-C₆alkoxy, C₁-C₆heteroalkyl, C₃-C₈cycloalkyl, C₂-C₈heterocycloalkyl, C₁-C₆hydroxyalkyl and C₁-C₆haloalkoxy, wherein the C₁-C₈alkyl, C₂-C₈alkene, C₂-C₈alkyne, C₁-C₆heteroalkyl, C₁-C₆haloalkyl, C₁-C₆alkoxy, C₃-C₈cycloalkyl, C₂-C₈heterocycloalkyl, C₁-C₆hydroxyalkyl and C₁-C₆haloalkoxy groups of $R^8$ are each optionally substituted with 1 to 3 substituents independently selected from —CN, R¹¹, —OR¹¹, —SR¹¹, —C(O)R¹¹, —OC(O)R¹¹, —C(O)N(R⁹)₂, —C(O)OR¹¹, —NR⁹C(O)R¹¹, —NR⁹R¹⁰, —NR¹¹R¹², —N(R⁹)₂, —OR⁹, —OR¹⁰, —C(O)NR¹¹R¹², —C(O)NR¹¹OH, —S(O)₂R¹¹, —S(O)R¹¹, —S(O)₂NR¹¹R¹², NR¹¹S(O)₂R¹¹, —P(O)(OR¹¹)₂, and —OP(O)(OR¹¹)₂;
  each $R^9$ is independently selected from H, —C(O)R⁸, —C(O)OR⁸, —C(O)R¹⁰, —C(O)OR¹⁰, —S(O)₂R¹⁰, —C₁-C₆ alkyl, C₁-C₆ heteroalkyl and C₃-C₆ cycloalkyl, or each $R^9$ is independently a C₁-C₆alkyl that together with N they are attached to form a C₃-C₈heterocycloalkyl, wherein the C₃-C₈heterocycloalkyl ring optionally contains an additional heteroatom selected from N, O and S, and wherein the C₁-C₆ alkyl, C₁-C₆ heteroalkyl, C₃-C₆ cycloalkyl, or C₃-C₈heterocycloalkyl groups of $R^9$ are each optionally substituted with 1 to 3 substituents independently selected from —CN, R¹¹, —OR¹¹, —SR¹¹, —C(O)R¹¹, —OC(O)R¹¹, —C(O)OR¹¹, —NR¹¹R¹², —C(O)NR¹¹R¹², —C(O)NR¹¹OH, —S(O)₂R¹¹, —S(O)R¹¹, —S(O)₂NR¹¹R¹², —NR¹¹S(O)₂R¹¹, —P(O)(OR¹¹)₂, and —OP(O)(OR¹¹)₂;
  each $R^{10}$ is independently selected from aryl, C₃-C₈cycloalkyl, C₃-C₈heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, ⁻$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, $C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —C(=NH)—$N(R^9)_2$, and —$(CH_2)_nNHC(O)R^8$; or two adjacent $R^A$ substituents form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain embodiments compounds of Formula (I) or Formula (II), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (III),

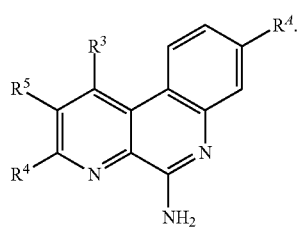

Formula (III)

In certain embodiments compounds of Formula (I)-(III), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (IV),

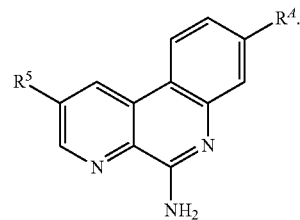

Formula (IV)

In certain embodiments of compounds of Formulas (I)-(IV), $R^4$ and $R^5$, when present, are independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, - $LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ and $R^5$ are each optionally substituted with 1 to 3 substituents independently selected from halogen, —CN, =O, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$, and wherein the aryl and heteroaryl groups of $R^4$ and $R^5$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$Si(R^8)_3$, —$S(O)_2R^8$, —$S(O)R^8$, —$S(O)_2N(R^9)_2$, and —$NR^9S(O)_2R^8$.

In certain embodiments compounds of Formula (I) or Formula (II), pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (V),

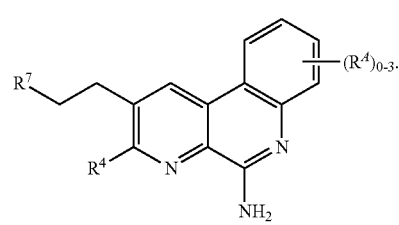

Formula (V)

In certain embodiments of compounds of Formulas (V), $R^4$ is selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ are each optionally substituted with 1 to 3 substituents independently selected from halogen, —CN, =O, —$NO_2$, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$, and wherein the aryl and heteroaryl groups of $R^4$ are each optionally substituted with 1 to 3 substituents independently selected from halogen, —CN, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$.

In certain embodiments of compounds of Formulas (I)-(V), $R^7$ is selected from H, $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups and each $R^{13}$ is independently selected from halogen —CN, =O, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -LN($R^9$)$_2$, -$LNR^9R^8$, -$LNR^9R^{10}$, -LC(O)N($R^9$)$_2$, -LS(O)$_2R^8$, -LS(O)$R^8$, -LC(O)$NR^8$OH, -$LNR^9$C(O)$R^8$, -$LNR^9$C(O)$OR^8$, -LC(=N—$OR^8$)$R^8$, -LC(=NH)—$NHOR^8$, —NHC(=NH)$NH_2$, -LS(O)$_2$N($R^9$)$_2$, —OLS(O)$_2$N($R^9$)$_2$, -$LNR^9$S(O)$_2R^8$, -LC(O)$NR^9$LN($R^9$)$_2$, -LP(O)($OR^8$)$_2$, -LOP(O)($OR^8$)$_2$, -LP(O)($OR^{10}$)$_2$ and —OLP(O)($OR^{10}$)$_2$.

In certain embodiments of compounds of Formulas (I)-(V), $R^7$ is an aryl or heteroaryl group optionally substituted with 1 to 3 $R^{13}$ groups and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -LC(O)$R^8$, —OLC(O)$R^8$, -LC(O)$OR^8$, -LC(O)$R^{10}$, -LOC(O)$OR^8$, -LC(O)$NR^9R^{11}$, -LC(O)$NR^9R^8$, -LN($R^9$)$_2$, -$LNR^9R^8$, -$LNR^9R^{10}$, -LC(O)N($R^9$)$_2$, -LS(O)$_2R^8$, -LS(O)$R^8$, -LC(O)$NR^8$OH, -$LNR^9$C(O)$R^8$, -$LNR^9$C(O)$OR^8$, -LC(=N—$OR^8$)$R^8$, -LC(=NH)—$NHOR^8$, —NHC(=NH)$NH_2$, -LS(O)$_2$N($R^9$)$_2$, —OLS(O)$_2$N($R^9$)$_2$, -$LNR^9$S(O)$_2R^8$, -LC(O)$NR^9$LN($R^9$)$_2$, -LP(O)($OR^8$)$_2$, -LOP(O)($OR^8$)$_2$, -LP(O)($OR^{10}$)$_2$ and —OLP(O)($OR^{10}$)$_2$.

In certain embodiments of compounds of Formulas (I)-(V), $R^7$ is selected from H, $C_1$-$C_6$alkyl, $C_3$-$C_8$cycloalkyl, and $C_3$-$C_8$heterocycloalkyl, and the $C_1$-$C_6$alkyl, $C_3$-$C_8$cycloalkyl, and $C_3$-$C_8$heterocycloalkyl groups are each optionally substituted with 1-3 $R^{13}$ groups and each $R^{13}$ is independently selected from halogen, $C_1$-$C_6$haloalkyl, =O, $LR^8$, $LR^9$, $OLR^8$ and -$LOR^8$.

In certain embodiments of compounds of Formulas (I)-(V), $R^7$ is an aryl or heteroaryl group optionally substituted with 1-3 $R^{13}$ groups.

In certain embodiments of compounds of Formulas (I)-(V), each $R^{13}$ is independently selected from halogen, $C_1$-$C_6$haloalkyl, $LR^8$, $OLR^8$, $LR^9$, $OLR^9$, $LR^{10}$, $OLR^{10}$ and -$LOR^8$.

In certain embodiments compounds of Formula (I), Formula (II) or Formula (V), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (XV),

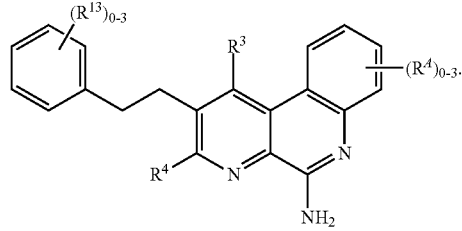

Formula (VI)

In certain embodiments compounds of Formulas (I)-(VI), or pharmaceutically acceptable salts, pharmaceutically acceptable solvates (e.g. hydrates), the N-oxide derivatives, prodrug derivatives, protected derivatives, individual isomers and mixture of isomers thereof, have a structure of Formula (VII),

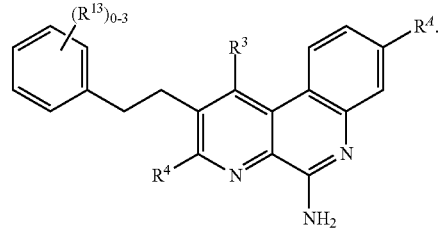

Formula (VII)

In certain embodiments of compounds of Formulas (I)-(VII), $R^3$ is H.

In certain embodiments of compounds of Formula (VI) and Formula (VII), $R^3$ is H and $R^4$ is selected from H, halogen, —C(O)$OR^7$, —C(O)$R^7$, —C(O)N($R^{11}R^{12}$), —N($R^{11}R^{12}$), —N($R^9$)$_2$, —NHN($R^9$)$_2$, —$SR^7$, —($CH_2$)$_nOR^7$, —($CH_2$)$_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, $C_3$-$C_8$cycloalkyl, or $C_3$-$C_8$heterocycloalkyl groups of $R^4$ are each optionally substituted with 1 to 3 substituents independently selected from halogen, —CN, =O, —$NO_2$, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$, and wherein the aryl and heteroaryl groups of $R^4$ are each optionally substituted with 1 to 3 substituents independently selected from halogen, —CN, —$R^7$, —$OR^8$, —C(O)$R^8$, —OC(O)$R^8$, —C(O)$OR^8$, —N($R^9$)$_2$, —P(O)($OR^8$)$_2$, —OP(O)($OR^8$)$_2$, —P(O)($OR^{10}$)$_2$, —OP(O)($OR^{10}$)$_2$, —C(O)N($R^9$)$_2$, —Si($R^8$)$_3$, —S(O)$_2R^8$, —S(O)$R^8$, —S(O)$_2$N($R^9$)$_2$, and —$NR^9$S(O)$_2R^8$.

In certain embodiments of compounds of Formulas (I)-(VII), $R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups.

In certain embodiments of compounds of Formulas (I)-(VII), each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)R^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LP(O)(OR^8)_2$, -$LC(O)NR^9LN(R^9)_2$, -$LOP(O)(OR^8)_2$, -$LP(O)(OR^{10})_2$ and —$OLP(O)(OR^{10})_2$; and each L is independently selected from a bond, —$O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments of compounds of Formulas (I)-(VII), each $R^{13}$ is independently selected from halogen, $C_1$-$C_6$haloalkyl, $LR^{10}$, $LOR^{10}$, $LR^8$, -$LOR^8$, $LR^9$, $OLR^9$, -$LSR^8$, $LSR^{10}$, -$LC(O)OR^8$, -$LN(R^9)_2$, -$LC(O)N(R^9)_2$, -$LS(O)_2R^8$, -$LS(O)R^8$, $LP(O)(OR^8)_2$, —$OLP(O)(OR^8)_2$, -$LP(O)(OR^{10})_2$ and—$OLP(O)(OR^{10})_2$.

In certain embodiments of compounds of Formulas (I)-(VII), each $R^{13}$ is independently selected from halogen, $C_1$-$C_6$haloalkyl, $LR^8$, $OLR^8$, $LR^9$, $OLR^9$, $LR^{10}$, $OLR^{10}$ and -$LOR^8$.

In certain embodiments of compounds of Formulas (I)-(VII), each L is independently selected from a bond, —(O(CH_2)_m)_t—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments of compounds of Formulas (I)-(VII), each L is independently selected from a bond, —(O(CH_2)_m)_t— and $C_1$-$C_6$alkyl, wherein the $C_1$-$C_6$alkyl of L is optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$.

In certain embodiments of compounds of Formulas (I)-(VII), $R^4$ is selected from H, halogen and $C_1$-$C_6$alkyl, wherein the $C_1$-$C_6$alkyl of $R^4$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^B$, —$S(O)_2N(R^9)_2$, and —$NR^9S(O)_2R^8$.

In certain embodiments of compounds of Formulas (I)-(VII), each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$.

In certain embodiments of compounds of Formulas (I)-(VII), each $R^9$ is independently selected from H, —$C(O)R^8$, —$C(O)OR^8$, —$C(O)R^{10}$, —$C(O)OR^{10}$, —$S(O)_2R^{10}$, $C_1$-$C_6$alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)_2NR^{11}R^{12}$, —$NR^{11}S(O)_2R^{11}$, —$P(O)(OR^{11})_2$, and —$OP(O)(OR^{11})_2$.

In certain embodiments of compounds of Formulas (I)-(VII), each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$.

In certain embodiments of compounds of Formulas (I)-(VII), $R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy, or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S.

In certain embodiments of compounds of Formulas (I)-(VII), each $R^4$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH=CHCO_2R^8$, —$C(=NH)-N(R^9)_2$, and —$(CH_2)_nNHC(O)R^8$.

In certain embodiments of compounds of Formulas (I)-(VII), each $R^{13}$ is selected from -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)R^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$; and each $R^4$ is independently selected from —R$^7$, —OR$^7$, —R$^8$, —OR$^8$, —R$^{10}$, —OR$^{10}$, —SR$^8$, —N(R$^9$)$_2$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —CH=CHCO$_2$R$^8$, (CH$_2$)$_n$CO$_2$R$^8$, —NR$^9$SO$_2$R$^8$, —P(O)(OR$^8$)$_2$, —OP(O)(OR$^8$)$_2$, —P(O)(OR$^{10}$)$_2$, and —OP(O)(OR$^{10}$)$_2$.

In certain embodiments of compounds of Formulas (I)-(VII), each L is independently selected from a —(O(CH$_2$)$_m$)$_t$—, and C$_1$-C$_6$alkyl, wherein the C$_1$-C$_6$alkyl of L is optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$.

In certain embodiments of compounds of Formulas (I)-(VII), R$^4$ is H or C$_1$-C$_6$alkyl.

In certain embodiments of compounds of Formulas (I)-(VII), R$^4$ is H, —CH$_3$ or —CH$_2$CH$_3$; and each R$^{13}$ is independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$ and C$_2$-C$_6$ alkyl substituted with 1-3 substituents selected from —OH, —CH$_3$, —COOH, —COOCH$_3$, cyclopropyl, —O(CH$_2$)$_{2-4}$—COOH, —O(CH$_2$)$_{2-4}$(PO$_3$H$_2$), and —COOCH$_2$CH$_3$.

In certain embodiments of compounds of Formulas (I)-(VII), each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$.

In certain embodiments of compounds of Formulas (I)-(VII), each R$^8$ is independently selected from H, —CH(R$^{10}$)$_2$ or C$_1$-C$_8$alkyl, wherein the C$_1$-C$_8$alkyl of R$^8$ is optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$.

In certain embodiments of compounds of Formulas (I)-(VII), R$^8$ is H, C$_1$-C$_6$alkyl or C$_1$-C$_6$haloalkyl. In certain embodiments of compounds of Formulas (I)-(VII), R$^9$ is H or C$_1$-C$_6$alkyl. In certain embodiments of compounds of Formulas (I)-(VII), R$^4$ is H or —CH$_3$. In certain embodiments of compounds of Formulas (I)-(VII), R$^4$ is H.

In certain embodiments of compounds of Formulas (I)-(VII), n is, independently at each occurrence, 0, 1, 2 or 3. In certain embodiments of compounds of Formulas (I)-(VII), each m is independently selected from 1, 2 or 3 and in certain embodiments of compounds of Formulas (I)-(VII), t is 1, 2, 3, 4 or 5.

In certain embodiments of compounds of Formulas (I)-(VII), R$^4$, R$^{4'}$ and R$^{13}$ are independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —O(CH$_2$)$^{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$, C$_2$-C$_6$ alkyl substituted with 1-3 substituents selected from —OH, —CH$_3$, cyclopropyl, —O(CH$_2$)$_{2-4}$—COOH, —O(CH$_2$)$_{2-4}$(PO$_3$H$_2$), —COOH, COOCH$_3$, and —COOCH$_2$CH$_3$.

In certain embodiments of compounds of Formula (I)-Formula (VII), R$^7$ is a phenyl ring substituted with one to three R$^{13}$ groups. In other embodiments of compounds of Formulas (I)-(VII), R$^7$ is a phenyl ring substituted with two R$^{13}$ groups, and the R$^{13}$ groups are selected from the group consisting of —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, —CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$, C$_2$-C$_6$ alkyl substituted with 1-3 substituents selected from —OH, —CH$_3$, cyclopropyl, —O(CH$_2$)$_{2-4}$—COOH, —O(CH$_2$)$_{2-4}$(PO$_3$H$_2$), —COOH, —COOCH$_3$, and —COOCH$_2$CH$_3$.

In certain embodiments of the compounds of Formula (I)-(VII), the compound is selected from: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; 2-(2,4-dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine, and 2-(4-methoxyphenethyl)-8-methylbenzo[f][1,7]naphthyridin-5-amine.

In certain embodiments the compound of Formulas (I) is 3-chloro-2-methylbenzo[f][1,7]naphthyridin-5-amine; 2-methylbenzo[f][1,7]naphthyridin-5-amine; 2-(ethoxymethyl)benzo[f][1,7]naphthyridin-5-amine; (E)-2-(2-cyclopropylvinyl)benzo[f][1,7]naphthyridin-5-amine; (E)-2-(pent-1-enyl)benzo[f][1,7]naphthyridin-5-amine; 4-(5-aminobenzo[f][1,7]naphthyridin-2-yl)-2-methylbut-3-yn-2-ol; 2-pentylbenzo[f][1,7]naphthyridin-5-amine; (E)-2-(prop-1-enyl)benzo[f][1,7]naphthyridin-5-amine; (E)-2-(3-phenylprop-1-enyl)benzo[f][1,7]naphthyridin-5-amine; 2-(2-cyclopropylethyl)benzo[f][1,7]naphthyridin-5-amine; 4-(5-aminobenzo[f][1,7]naphthyridin-2-yl)-2-methylbutan-2-ol; 2-propylbenzo[f][1,7]naphthyridin-5-amine; (E)-2-(3-phenylpropyl)benzo[f][1,7]naphthyridin-5-amine; 2-ethylbenzo[f][1,7]naphthyridin-5-amine; 2-(2-methylprop-1-enyl)benzo[f][1,7]naphthyridin-5-amine; 2-isobutylbenzo[f][1,7]naphthyridin-5-amine; (E)-2-(2,4-difluorostyryl)benzo[f][1,7]naphthyridin-5-amine; (E)-2-(hex-1-enyl)benzo[f][1,7]naphthyridin-5-amine; (E)-2-(2-cyclohexylvinyl)benzo[f][1,7]naphthyridin-5-amine; E)-2-(3-(trifluoromethyl)styryl)benzo[f][1,7]naphthyridin-5-amine; (E)-2-(3-methoxystyryl)benzo[f][1,7]naphthyridin-5-amine; 8-methyl-2-vinylbenzo[f][1,7]naphthyridin-5-amine; (E)-8-methyl-2-styrylbenzo[f][1,7]naphthyridin-5-amine; 2-(2-cyclohexylethyl)benzo[f][1,7]naphthyridin-5-amine; 2-fluorobenzo[f][1,7]naphthyridin-5-amine; 2-(3-(trifluoromethyl)phenethyl)benzo[f][1,7]naphthyridin-5-amine; 2-(2,4-difluorophenethyl)benzo[f][1,7]naphthyridin-5-amine; 2-(3-methoxyphenethyl)benzo[f][1,7]naphthyridin-5-amine; 2-hexylbenzo[f][1,7]naphthyridin-5-amine; 2-ethyl-8-methylbenzo[f][1,7]naphthyridin-5-amine; 8-methylbenzo[f][1,7]naphthyridin-5-amine; 8-methyl-2-phenylbenzo[f][1,7]naphthyridin-5-amine; methyl 5-aminobenzo[f][1,7]naphthyridine-3-carboxylate; 5-amino-N-methylbenzo[f][1,7]naphthyridine-3-carboxamide; (5-aminobenzo[f][1,7]naphthyridin-3-yl)methanol;

8-phenylbenzo[f][1,7]naphthyridin-5-amine; 3-(ethoxymethyl)benzo[f][1,7]naphthyridin-5-amine; benzo[f][1,7]naphthyridine-3,5-diamine; benzo[f][1,7]naphthyridine-5-amine; methyl 5-aminobenzo[f][1,7]naphthyridine-8-carboxylate; 5-aminobenzo[f][1,7]naphthyridine-8-carboxylic acid; ethyl 5-aminobenzo[f][1,7]naphthyridine-8-carboxylate; (5-aminobenzo[f][1,7]naphthyridin-8-yl)methanol; 5-aminobenzo[f][1,7]naphthyridine-3-carboxylic acid; 5-aminobenzo[f][1,7]naphthyridine-3-carbaldehyde; 2-(o-tolylethynyl)benzo[f][1,7]naphthyridin-5-amine; 2-(m-tolylethynyl)benzo[f][1,7]naphthyridin-5-amine; 2-(p-tolylethynyl)benzo[f][1,7]naphthyridin-5-amine; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 3-chloro-2-(ethoxymethyl)benzo[f][1,7]naphthyridin-5-amine; 9-chlorobenzo[f][1,7]naphthyridin-5-amine; 8-chlorobenzo[f][1,7]naphthyridin-5-amine; 9-methylbenzo[f][1,7]naphthyridin-5-amine; 10-methylbenzo[f][1,7]naphthyridin-5-amine; ethyl 5-aminobenzo[f][1,7]naphthyridine-9-carboxylate; 5-aminobenzo[f][1,7]naphthyridine-9-carboxylic acid; 8-methoxybenzo[f][1,7]naphthyridin-5-amine; 7-fluorobenzo[f][1,7]naphthyridin-5-amine; 8-(methylsulfonyl)benzo[f][1,7]naphthyridin-5-amine; 8-(trifluoromethyl)benzo[f][1,7]naphthyridin-5-amine; 8-fluorobenzo[f][1,7]naphthyridin-5-amine; 3-methoxybenzo[f][1,7]naphthyridin-5-amine; 3-butoxybenzo[f][1,7]naphthyridin-5-amine; 3-(benzyloxy)benzo[f][1,7]naphthyridin-5-amine; 3-methylbenzo[f][1,7]naphthyridin-5-amine; 3-chlorobenzo[f][1,7]naphthyridin-5-amine; $N^3,N^3$-dimethylbenzo[f][1,7]naphthyridine-3,5-diamine; $N^3$-butylbenzo[f][1,7]naphthyridine-3,5-diamine; 3-vinylbenzo[f][1,7]naphthyridin-5-amine; 3-ethylbenzo[f][1,7]naphthyridin-5-amine; 3-fluorobenzo[f][1,7]naphthyridin-5-amine; 2-(trifluoromethyl)benzo[f][1,7]naphthyridin-5-amine; 2-methoxybenzo[f][1,7]naphthyridin-5-amine; 2-(benzyloxy)benzo[f][1,7]naphthyridin-5-amine; 2-vinylbenzo[f][1,7]naphthyridin-5-amine; 2-phenylbenzo[f][1,7]naphthyridin-5-amine; (E)-2-styrylbenzo[f][1,7]naphthyridin-5-amine; 2-phenethylbenzo[f][1,7]naphthyridin-5-amine; (E)-2-(3-methoxyprop-1-enyl)benzo[f][1,7]naphthyridin-5-amine; 2-(3-methoxypropyl)benzo[f][1,7]naphthyridin-5-amine; 2-(prop-1-en-2-yl)benzo[f][1,7]naphthyridin-5-amine; 2-isopropylbenzo[f][1,7]naphthyridin-5-amine; 1-methylbenzo[f][1,7]naphthyridin-5-amine; pyrido[3,2-f][1,7]naphthyridin-6-amine; 8-methyl-2-(naphthalen-2-ylethynyl)benzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 8-methyl-2-(naphthalen-1-ylethynyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(trifluoromethyl)benzo[f][1,7]naphthyridin-5-amine; 2-tert-butoxybenzo[f][1,7]naphthyridin-5-amine; 5-aminobenzo[f][1,7]naphthyridin-2-ol; 2-((4-butylphenyl)ethynyl)benzo[f][1,7]naphthyridin-5-amine; 2-(4-butylphenethyl)benzo[f][1,7]naphthyridin-5-amine; 2-(2-(6-methoxynaphthalen-2-yl)ethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]naphthyridin-5-amine; 2-(4-heptylphenethyl)-8-methylbenzo[f][1,7]naphthyridin-5-amine; (Z)-2-(2-(biphenyl-4-yl)vinyl)-8-methylbenzo[f][1,7]naphthyridin-5-amine; 2-(4-isobutoxyphenethyl)-8-methylbenzo[f][1,7]naphthyridin-5-amine; 2-(4-(2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 2-(4-(2-(tert-butyldimethylsilyloxy)ethoxy)phenethyl)-8-methylbenzo[f][1,7]naphthyridin-5-amine; 2-(4-butoxy-2-methylphenethyl)-N-butyl-8-methylbenzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 2-(4-(2-(tert-butyldimethylsilyloxy)ethoxy)-2-methylphenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; diethyl 3-(2-(4-(2-(2-hydroxyethoxy)ethoxy)-2-methylphenethyl)-8-methylbenzo[f][1,7]naphthyridin-5-ylamino)propylphosphonate; (E)-N-(4-(2-(5-aminobenzo[f][1,7]naphthyridin-2-yl)vinyl)phenyl)acetamide; N-(4-(2-(5-amino-8-methylbenzo[f][1,7]naphthyridin-2-yl)ethyl)phenyl)acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 4-(2-(5-amino-8-methylbenzo[f][1,7]naphthyridin-2-yl)ethyl)-3-methylbenzonitrile; 4-(2-(5-amino-8-methylbenzo[f][1,7]naphthyridin-2-yl)ethyl)-N-(2-aminoethyl)-3-methylbenzamide; 2-(4-(2-(5-amino-3-chloro-8-methylbenzo[f][1,7]naphthyridin-2-yl)ethyl)-3-methylbenzamido)acetic acid; (S)-2-(4-(2-(5-amino-3-chloro-8-methylbenzo[f][1,7]naphthyridin-2-yl)ethyl)-3-methylbenzamido)-4-methylpentanoic acid; 4-(2-(5-amino-3-chloro-8-methylbenzo[f][1,7]naphthyridin-2-yl)ethyl)-N-(2-(dimethylamino)ethyl)-N,3-dimethylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; 2-phenethylbenzo[f][1,7]

naphthyridin-5-amine; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 2-(4-cyclobutoxyphenethyl)-8-methylbenzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 8-bromo-3-methoxybenzo[f][1,7]naphthyridin-5-amine; 2-((tert-butyldimethylsilyl)ethynyl)benzo[f][1,7]naphthyridin-5-amine; 2-((2-fluorophenyl)ethynyl)benzo[f][1,7]naphthyridin-5-amine; 2-((3-fluorophenyl)ethynyl)benzo[f][1,7]naphthyridin-5-amine; 2-((4-fluorophenyl)ethynyl)benzo[f][1,7]naphthyridin-5-amine; 2-(thiophen-3-ylethynyl)benzo[f][1,7]naphthyridin-5-amine; 2-ethynylbenzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; ethyl 5-aminobenzo[f][1,7]naphthyridine-2-carboxylate; ethyl 5-amino-8-methylbenzo[f][1,7]naphthyridine-2-carboxylate; (5-aminobenzo[f][1,7]naphthyridin-2-yl)methanol; 2-(3,4-dimethylphenethyl)benzo[f][1,7]naphthyridin-5-amine; 1-chloro-8-methylbenzo[f][1,7]naphthyridin-5-amine; 8-methyl-1-(3-phenylpropyl)benzo[f][1,7]naphthyridin-5-amine; (Z)-2-(2-(benzo[d][1,3]dioxol-5-yl)vinyl)-8-methylbenzo[f][1,7]naphthyridin-5-amine; (Z)-2-(4-methoxy-2-methylstyryl)-8-methylbenzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 8-methyl-2-(1-phenylvinyl)benzo[f][1,7]naphthyridin-5-amine; 8-methyl-2-(4-phenylbutyl)benzo[f][1,7]naphthyridin-5-amine; 8-methyl-2-(1-phenylethyl)benzo[f][1,7]naphthyridin-5-amine; 2-(2-(benzofuran-5-yl)ethyl)-8-methylbenzo[f][1,7]naphthyridin-5-amine; (Z)-2-(2-ethoxyvinyl)-8-methylbenzo[f][1,7]naphthyridin-5-amine; 2-(2-ethoxyethyl)-8-methylbenzo[f][1,7]naphthyridin-5-amine; 2-(chloromethyl)-8-methylbenzo[f][1,7]naphthyridin-5-amine; 8-methyl-2-(2-nitroethyl)benzo[f][1,7]naphthyridin-5-amine; diethyl 2-((5-amino-8-methylbenzo[f][1,7]naphthyridin-2-yl)methyl)malonate; 2-(isopropylsulfonyl)-8-methylbenzo[f][1,7]naphthyridin-5-amine; 2-((methoxymethoxy)methyl)-8-methylbenzo[f][1,7]naphthyridin-5-amine; 8-methyl-2-((methylamino)methyl)benzo[f][1,7]naphthyridin-5-amine; tert-butyl 5-amino-8-methylbenzo[f][1,7]naphthyridin-2-ylcarbamate; 8-methyl-2-((phenylamino)methyl)benzo[f][1,7]naphthyridin-5-amine; 2-(aminomethyl)-8-methylbenzo[f][1,7]naphthyridin-5-amine; 8-methyl-2-(pyrrolidin-1-ylmethyl)benzo[f][1,7]naphthyridin-5-amine; $N^2$-(2,4-dimethoxybenzyl)-8-methylbenzo[f][1,7]naphthyridine-2,5-diamine; $N^2,N^2,8$-trimethylbenzo[f][1,7]naphthyridine-2,5-diamine; $N^2,8$-dimethylbenzo[f][1,7]naphthyridine-2,5-diamine; 8-methyl-2-(pyrrolidin-1-yl)benzo[f][1,7]naphthyridin-5-amine; 2-(5-amino-8-methylbenzo[f][1,7]naphthyridin-2-yl)-1-phenylethanol; 2-(2-aminoethyl)-8-methylbenzo[f][1,7]naphthyridin-5-amine; 2-hydrazinyl-8-methylbenzo[f][1,7]naphthyridin-5-amine; 1-(5-amino-8-methylbenzo[f][1,7]naphthyridin-2-yl)-2-methylpropan-2-ol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 3-methyldibenzo[b,f][1,7]naphthyridin-6-amine; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-ethyl 3-(5-amino-2-(4-methoxy-2-methylphenethyl)benzo[f][1,7]naphthyridin-8-yl)acrylate; $N^3,N^5$-dibutylbenzo[f][1,7]naphthyridine-3,5-diamine; 8-(prop-1-en-2-yl)benzo[f][1,7]naphthyridin-5-amine; 5-aminobenzo[f][1,7]naphthyridine-8-carbonitrile; (E)-8-(3-methylbut-1-enyl)benzo[f][1,7]naphthyridin-5-amine; 8-(2-methylprop-1-enyl)benzo[f][1,7]naphthyridin-5-amine; (E)-8-(pent-1-enyl)benzo[f][1,7]naphthyridin-5-amine; (E)-8-styrylbenzo[f][1,7]naphthyridin-5-amine; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; methyl 5-amino-2-(4-methoxyphenethyl)benzo[f][1,7]naphthyridine-8-carboxylate; 8-nitrobenzo[f][1,7]naphthyridin-5-amine; 3-chloro-8-methylbenzo[f][1,7]naphthyridin-5-amine; methyl 5-amino-3-chlorobenzo[f][1,7]naphthyridine-8-carboxylate; methyl 5-amino-3-fluorobenzo[f][1,7]naphthyridine-8-carboxylate; 3-chloro-8-nitrobenzo[f][1,7]naphthyridin-5-amine; (5-amino-3-chlorobenzo[f][1,7]naphthyridin-8-yl)methanol; (5-amino-2-phenethylbenzo[f][1,7]naphthyridin-8-yl)methanol; 4-(2-(5-amino-8-fluorobenzo[f][1,7]naphthyridin-2-yl)ethyl)benzaldehyde; 2-(4-(2-(5-amino-8-fluorobenzo[f][1,7]naphthyridin-2-yl)ethyl)benzylamino)ethanol; 3-(4-(2-(5-amino-8-fluorobenzo[f][1,7]naphthyridin-2-yl)ethyl)benzylamino)propan-1-ol; 8-fluoro-2-(4-((2-methoxyethylamino)methyl)phenethyl)benzo[f][1,7]naphthyridin-5-amine; 8-((tert-butyldimethylsilyloxy)methyl)-2-(4-methoxy-2-methylphenethyl)benzo[f][1,7]naphthyridin-5-amine; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 8-methyl-2-(2-(1-methyl-1H-imidazol-5-yl)ethyl)benzo[f][1,7]naphthyridin-5-amine;

4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-ethyl 3-(5-amino-2-(4-methoxy-2-methylphenethyl)benzo[f][1,7]naphthyridin-8-yl)acrylate; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; (5-aminobenzo[f][1,7]naphthyridin-8-yl)methanol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-phenethylbenzo[f][1,7]naphthyridin-8-yl)methanol; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; N-(4-(2-(5-amino-8-methylbenzo[f][1,7]naphthyridin-2-yl)ethyl)phenyl)acetamide; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3- methylbenzamide; (4-(2-(5-amino-8-methylbenzo[f][1,7]naphthyridin-2-yl)ethyl)-3-methylphenyl)(4-ethylpiperazin-1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-amino-8-methylbenzo[f][1,7]naphthyridin-2-yl)ethyl)-N-(2-aminoethyl)-3-methylbenzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 24442-(5-aminobenzo[f][1,7]naphthyridin-2-yl)ethyl)-3-methylphenoxy)ethanol; 2-(4-(2-(5-aminobenzo[f][1,7]naphthyridin-2-yl)ethyl)-3-methylphenoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol; and 2-(4-(2-aminopropan-2-yl)phenethyl)-8-methylbenzo[f][1,7]naphthyridin-5-amine.

In certain embodiments the compound of Formulas (I) 2-methylbenzo[f][1,7]naphthyridin-5-amine; 2-propylbenzo[f][1,7]naphthyridin-5-amine; 2-ethylbenzo[f][1,7]naphthyridin-5-amine; 2-(3-methoxyphenethyl)benzo[f][1,7]naphthyridin-5-amine; 8-methylbenzo[f][1,7]naphthyridin-5-amine, 8-methyl-2-phenethylbenzo[f][1,7]naphthyridin-5-amine; methyl-5-aminobenzo[f][1,7]naphthyridine-3-carboxylate; (5-aminobenzo[f][1,7]naphthyridin-3-yl)methanol; benzo[f][1,7]naphthyridin-5-amine; (5-aminobenzo[f][1,7]naphthyridin-8-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine, 8-chlorobenzo[f][1,7]naphthyridin-5-amine; ethyl 5-aminobenzo[f][1,7]naphthyridine-9-carboxylate; 8-methoxybenzo[f][1,7]naphthyridin-5-amine; 8-(trifluoromethyl) benzo[f][1,7]naphthyridin-5-amine; 8-fluorobenzo[f][1,7] naphthyridin-5-amine; 3-methylbenzo[f][1,7]naphthyridin-5-amine; 3-fluorobenzo[f][1,7]naphthyridin-5-amine; 2-phenethylbenzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7] naphthyridin-5-amine; 4-(2-(5-amino-8-methylbenzo[f][1, 7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7] naphthyridin-5-amine; (3-(2-(5-amino-8-methylbenzo[f][1, 7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7] naphthyridin-5-amine; 2-(4-propylphenethyl)benzo[f][1,7] naphthyridin-5-amine; 2-(4-(trifluoromethyl)phenethyl) benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7] naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7] naphthyridin-5-amine; 2-(4-heptylphenethyl)-8-methyl-benzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f] [1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f] [1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1, 7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7] naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl) benzo[f][1,7]naphthyridin-5-amine; N-(4-(2-(5-amino-8-methylbenzo[f][1,7]naphthyridin-2-yl)ethyl)phenyl) acetamide; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl) ethyl)-3-methylbenzonitrile; 4-(2-(5-amino-8-methylbenzo [f][1,7]naphthyridin-2-yl)ethyl)-N-(2-aminoethyl)-3-methylbenzamide; 8-methyl-2-(2-methyl-4-(1H-tetrazol-5-yl) phenethyl)benzo[f][1,7]naphthyridin-5-amine; methyl 2-(4-(2-(5-amino-8-methylbenzo[f][1,7]naphthyridin-2-yl) ethyl)-3-methylbenzamido)-4-methylpentanoate; methyl 2-(4-(2-(5-amino-8-methylbenzo[f][1,7]naphthyridin-2-yl) ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f] [1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7] naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7] naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f] [1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-di-amine; 2-(5-amino-8-methylbenzo[f][1,7]naphthyridin-2-yl)-1-phenylethanol; 2-(5-amino-8-methylbenzo[f][1,7] naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7] naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f] [1,7]naphthyridin-2-yl)ethyl)pyridin-3-ol 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7] naphthyridin-2-yl)ethyl)-3-methylphenyl)acrylic acid; (E)-ethyl 3-(5-amino-2-(4-methoxy-2-methylphenethyl)benzo [f][1,7]naphthyridin-8-yl)acrylate; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; (5-amino-2-phenethylbenzo[f][1,7]naphthyridin-8-yl)methanol; (5-amino-2-(4-methoxy-2-methylphenethyl)benzo[f][1,7]naphthyridin-8-yl)methanol; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f] [1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5- amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid; 8-methyl-2-(4-(1-(phenylamino)ethyl)phenethyl)benzo[f][1,7]naphthyridin-5-amine; 2-ethyl-8-methylbenzo[f][1,7]naphthyridin-5-amine; (5-amino-8-methylbenzo[f][1,7]naphthyridin-2-yl)methanol; 8-methyl-2-propylbenzo[f][1,7]naphthyridin-5-amine; 2-(2-(1H-indol-5-yl)ethyl)-8-methylbenzo[f][1,7]naphthyridin-5-amine; 2-(4-ethoxyphenethyl)-8-methylbenzo[f][1,7]naphthyridin-5-amine; 8-methyl-2-(4-phenoxyphenethyl)benzo[f][1,7]naphthyridin-5-amine; 2-(2,4-dimethylphenethyl)benzo[f][1,7]naphthyridin-5-amine; 2-(2,4-dimethylphenethyl)-8-methylbenzo[f][1,7]naphthyridin-5-amine; 2-(4-methoxy-2-methylphenethyl)-8-methylbenzo[f][1,7]naphthyridin-5-amine; 4-(2-(5-amino-8-methylbenzo[f][1,7]naphthyridin-2-yl)ethyl)-3-methylphenol; 2-(2-(2,3-dihydrobenzofuran-5-yl)ethyl)-8-methylbenzo[f][1,7]naphthyridin-5-amine; 2-(5-amino-8-methylbenzo[f][1,7]naphthyridin-2-yl)ethanol; 3-methyl-9-phenyl-9,10-dihydrobenzo[f]furo[2,3-b][1,7]naphthyridin-6-amine; 8-methylbenzo[f][1,7]naphthyridine-2,5-diamine; 1-(5-amino-8-methylbenzo[f][1,7]naphthyridin-2-yl)propan-2-ol; 2-(5-amino-8-methylbenzo[f][1,7]naphthyridin-2-yl)acetonitrile; N-(5-amino-8-methylbenzo[f][1,7]naphthyridin-2-yl)acetamide; 2-(5-amino-8-methylbenzo[f][1,7]naphthyridin-2-yl)-1-(2,4-dimethylphenyl)ethanol; 2-(2-(6-methoxy-4-methylpyridin-3-yl)ethyl)-8-methylbenzo[f][1,7]naphthyridin-5-amine; 4-(4-(2-(5-amino-8-methylbenzo[f][1,7]naphthyridin-2-yl)ethyl)phenyl)butan-1-ol; methyl 3-(4-(2-(5-amino-8-methylbenzo[f][1,7]naphthyridin-2-yl)ethyl)phenyl)propanoate; 3-(4-(2-(5-amino-8-methylbenzo[f][1,7]naphthyridin-2-yl)ethyl)phenyl)propan-1-ol; 4-(4-(2-(5-amino-8-methylbenzo[f][1,7]naphthyridin-2-yl)ethyl)phenyl)-2-methylbutan-2-ol; 2-(4-(aminomethyl)phenethyl)-8-methylbenzo[f][1,7]naphthyridin-5-amine; (E)-ethyl 3-(4-(2-(5-amino-8-methylbenzo[f][1,7]naphthyridin-2-yl)ethyl)-3-methylphenyl)acrylate; ethyl 3-(4-(2-(5-amino-8-methylbenzo[f][1,7]naphthyridin-2-yl)ethyl)-3-methylphenyl)propanoate; 2-(4-(2-(5-amino-8-methylbenzo[f][1,7]naphthyridin-2-yl)ethyl)-3-methylbenzyl)propane-1,3-diol; 3-(4-(2-(5-amino-8-methylbenzo[f][1,7]naphthyridin-2-yl)ethyl)-3-methylphenyl)propanoic acid; 5-amino-2-(4-methoxy-2-methylphenethyl)benzo[f][1,7]naphthyridine-8-carbaldehyde; ethyl 4-(2-(5-amino-8-methylbenzo[f][1,7]naphthyridin-2-yl)ethyl)benzoate; 8-methyl-2-(4-methylphenethyl)benzo[f][1,7]naphthyridin-5-amine; 2-(4-(2-(5-amino-8-methylbenzo[f][1,7]naphthyridin-2-yl)ethyl)phenyl)propan-2-ol; (4-(2-(5-amino-8-methylbenzo[f][1,7]naphthyridin-2-yl)ethyl)phenyl)methanol; ethyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-3-methylbenzoic acid; (4-(2-(5-amino-8-methylbenzo[f][1,7]naphthyridin-2-yl)ethyl)-3-methylphenyl)methanol; 8-methyl-2-(2,4,6-trimethylphenethyl)benzo[f][1,7]naphthyridin-5-amine; 2-(4-(2-(5-amino-8-methylbenzo[f][1,7]naphthyridin-2-yl)ethyl)-3-methylphenyl)propan-2-ol; 8-methyl-2-(4-propoxyphenethyl)benzo[f][1,7]naphthyridin-5-amine; (E)-3-(5-amino-2-(4-methoxy-2-methylphenethyl)benzo[f][1,7]naphthyridin-8-yl)acrylic acid; ethyl 3-(5-amino-2-(4-methoxy-2-methylphenethyl)benzo[f][1,7]naphthyridin-8-yl)propanoate; 3-(5-amino-2-(4-methoxy-2-methylphenethyl)benzo[f][1,7]naphthyridin-8-yl)propanoic acid; 3-(5-amino-2-(4-methoxy-2-methylphenethyl)benzo[f][1,7]naphthyridin-8-yl)propan-1-ol; 5-aminobenzo[f][1,7]naphthyridin-8-ol; 5-aminobenzo[f][1,7]naphthyridine-8-carbaldehyde; 1-(5-aminobenzo[f][1,7]naphthyridin-8-yl)ethanol; 1-(5-aminobenzo[f][1,7]naphthyridin-8-yl)ethanone; 8-isopropylbenzo[f][1,7]naphthyridin-5-amine; 8-vinylbenzo[f][1,7]naphthyridin-5-amine; 8-ethylbenzo[f][1,7]naphthyridin-5-amine; 8-(methoxymethyl)benzo[f][1,7]naphthyridin-5-amine; (5-amino-2-(4-methoxyphenethyl)benzo[f][1,7]naphthyridin-8-yl)methanol; benzo[f][1,7]naphthyridine-5,8-diamine; 8-(aminomethyl)benzo[f][1,7]naphthyridin-5-amine; 3-fluoro-8-methylbenzo[f][1,7]naphthyridin-5-amine; (5-amino-3-fluorobenzo[f][1,7]naphthyridin-8-yl)methanol; 3-chlorobenzo[f][1,7]naphthyridine-5,8-diamine; 3-fluorobenzo[f][1,7]naphthyridine-5,8-diamine; 8-isobutylbenzo[f][1,7]naphthyridin-5-amine; (E)-8-(prop-1-enyl)benzo[f][1,7]naphthyridin-5-amine; 8-propylbenzo[f][1,7]naphthyridin-5-amine; 8-(2-cyclopropylethyl)benzo[f][1,7]naphthyridin-5-amine; 8-phenethylbenzo[f][1,7]naphthyridin-5-amine; (5-amino-2-(4-bromophenethyl)benzo[f][1,7]naphthyridin-8-yl)methanol; 2-(4-methoxy-2-methylphenethyl)-8-pentylbenzo[f][1,7]naphthyridin-5-amine; 8-(2-cyclopropylethyl)-2-(4-methoxy-2-methylphenethyl)benzo[f][1,7]naphthyridin-5-amine; (5-amino-2-(2,4,6-trimethylphenethyl)benzo[f][1,7]naphthyridin-8-yl)methanol; (5-amino-2-(4-propoxyphenethyl)benzo[f][1,7]naphthyridin-8-yl)methanol; (2-(2-(1H-indol-5-yl)ethyl)-5-aminobenzo[f][1,7]naphthyridin-8-yl)methanol; methyl 4-(2-(5-amino-8-methylbenzo[f][1,7]naphthyridin-2-yl)ethyl)-3-methylbenzoate; 4-(2-(5-amino-8-methylbenzo[f][1,7]naphthyridin-2-yl)ethyl)-N,3-dimethylbenzamide; N-(2-acetamidoethyl)-4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N-(2-(dimethylamino)ethyl)-N,3-dimethylbenzamide; 2-(4-methoxyphenethyl)benzo[f][1,7]naphthyridin-5-amine; 2-(4-methoxy-2-methylphenethyl)benzo[f][1,7]naphthyridin-5-amine; 4-(2-(5-amino-8-methylbenzo[f][1,7]naphthyridin-2-yl)ethyl)-3-methylbenzamide; 4-(2-(5-amino-8-methylbenzo[f][1,7]naphthyridin-2-yl)ethyl)-N,N,3-trimethylbenzamide; 4-(2-(5-amino-8-methylbenzo[f][1,7]naphthyridin-2-yl)ethyl)-N-(2-hydroxyethyl)-3-methylbenzamide; 4-(2-(5-amino-8-methylbenzo[f][1,7]naphthyridin-2-yl)ethyl)-N-(2-(dimethylamino)ethyl)-3-methylbenzamide; (4-(2-(5-amino-8-methylbenzo[f][1,7]naphthyridin-2-yl)ethyl)-3-methylphenyl)(pyrrolidin-1-yl)methanone; 4-(2-(5-amino-8-methylbenzo[f][1,7]naphthyridin-2-yl)ethyl)-N-(2-(diethylamino)ethyl)-3-methylbenzamide; (4-(2-(5-amino-8-methylbenzo[f][1,7]naphthyridin-2-yl)ethyl)-3-methylphenyl)(4-ethylpiperazin- 1-yl)methanone; (4-(2-(5-amino-8-methylbenzo[f][1,7]naphthyridin-2-yl)ethyl)-3-methylphenyl)(piperazin-1-yl)methanone; 4-(2-(5-amino-8-methylbenzo[f][1,7]naphthyridin-2-yl)ethyl)-3-methyl-N-(2-(pyrrolidin-1-yl)ethyl)benzamide; 4-(2-(5-aminobenzo[f][1,7]naphthyridin-2-yl)ethyl)-N-(2-(dimethylamino)ethyl)-N,3-dimethylbenzamide; 4-(2-(5-amino-8-methylbenzo[f][1,7]naphthyridin-2-yl)ethyl)-N-(2-(dimethylamino)ethyl)-N-methylbenzamide; 2-(4-(2-(5-aminobenzo[f][1,7]naphthyridin-2-yl)ethyl)-3-methylphenyl)propan-2-ol; 2-(4-butoxyphenethyl)-8-methylbenzo[f][1,7]naphthyridin-5-amine; 2-(2-(biphenyl-4-yl)ethyl)-8-methylbenzo[f][1,7]naphthyridin-5-amine; 2-((1,3-dihydroisobenzofuran-1-yl)methyl)-8-methylbenzo[f][1,7]naphthyridin-5-amine; 8-methyl-2-(4-(2-methylallyloxy)phenethyl)benzo[f][1,7]naphthyridin-5-amine; 2-(4-(isopentyloxy)phenethyl)-8-methylbenzo[f][1,7]naphthyridin-5-amine; 4-(2-(5-amino-8-methylbenzo[f][1,7]naphthyridin-2-yl)ethyl)phenyl propyl carbonate; ethyl 5-(4-(2-(5-amino-8-methylbenzo[f][1,7]naphthyridin-2-yl)ethyl)phenoxy)pentanoate; 2-(4-(cyclopentyloxy)phenethyl)-8-methylbenzo[f][1,7]naphthyridin-5-amine; 2-(4-(cyclobutylmethoxy)phenethyl)-8-methylbenzo[f][1,7]naphthyridin-5-amine; 8-methyl-2-(4-(2-morpholinoethoxy)phenethyl)benzo[f][1,7]naphthyridin-5-amine; 2-(4-(2-(5-amino-8-methylbenzo[f][1,7]naphthyridin-2-yl)ethyl)phenoxy)-1-phenylethanone; 5-(4-(2-(5-amino-8-methylbenzo[f][1,7]naphthyridin-2-yl)ethyl)phenoxy)pentanoic acid; 2-(4-(2-(5-amino-8-methylbenzo[f][1,7]naphthyridin-2-yl)ethyl)phenoxy)ethanol; 2-(4-(2-(5-amino-8-methylbenzo[f][1,7]naphthyridin-2-yl)ethyl)phenoxy)-N,N-dimethylacetamide; 8-methyl-2-(2-methyl-4-(2-morpholinoethoxy)phenethyl)benzo[f][1,7]naphthyridin-5-amine; 2-(2-(4-(2-(5-amino-8-methylbenzo[f][1,7]naphthyridin-2-yl)ethyl)-3-methylphenoxy)ethoxy)ethanol; diethyl 3-(4-(2-(5-amino-8-methylbenzo[f][1,7]naphthyridin-2-yl)ethyl)-3-methylphenoxy)propylphosphonate; 3-(4-(2-(5-amino-8-methylbenzo[f][1,7]naphthyridin-2-yl)ethyl)-3-methylphenoxy)propylphosphonic acid; 2-(4-butoxy-2-methylphenethyl)-8-methylbenzo[f][1,7]naphthyridin-5-amine; 2-(4-(2-(5-aminobenzo[f][1,7]naphthyridin-2-yl)ethyl)-3-methylphenoxy)ethanol; 2-(2-(4-(2-(5-aminobenzo[f][1,7]naphthyridin-2-yl)ethyl)-3-methylphenoxy)ethoxy)ethanol; ethyl 5-(4-(2-(5-amino-8-methylbenzo[f][1,7]naphthyridin-2-yl)ethyl)-3-methylphenoxy)pentanoate; 5-(4-(2-(5-amino-8-methylbenzo[f][1,7]naphthyridin-2-yl)ethyl)-3-methylphenoxy)pentanoic acid; 2-(4-(2-(5-amino-8-methylbenzo[f][1,7]naphthyridin-2-yl)ethyl)-3-methylphenoxy)ethanol; 4-(2-(5-amino-8-methylbenzo[f][1,7]naphthyridin-2-yl)ethyl)phenyl ethyl carbonate; methyl 4-(4-(2-(5-amino-8-methylbenzo[f][1,7]naphthyridin-2-yl)ethyl)phenoxy)butanoate; 4-(4-(2-(5-amino-8-methylbenzo[f][1,7]naphthyridin-2-yl)ethyl)phenoxy)butanoic acid; 4-(4-(2-(5-amino-8-methylbenzo[f][1,7]naphthyridin-2-yl)ethyl)-3-methylphenoxy)butanoic acid; 2-(4-(isopentyloxy)-2-methylphenethyl)-8-methylbenzo[f][1,7]naphthyridin-5-amine; 4-(2-(5-amino-8-methylbenzo[f][1,7]naphthyridin-2-yl)ethyl)phenyl hexyl carbonate; 2-(2,4,6-trimethylphenethyl)benzo[f][1,7]naphthyridin-5-amine; (5-amino-2-(2,4-dimethylphenethyl)benzo[f][1,7]naphthyridin-8-yl)methanol; diethyl 3-(2-(4-(2-(5-amino-8-methylbenzo[f][1,7]naphthyridin-2-yl)ethyl)-3-methylphenoxy)ethoxy)propylphosphonate; diethyl 3-(2-(2-(4-(2-(5-amino-8-methylbenzo[f][1,7]naphthyridin-2-yl)ethyl)-3-methylphenoxy)ethoxy)propylphosphonate; 4-(2-(5-amino-8-methylbenzo[f][1,7]naphthyridin-2-yl)ethyl)-3-methylphenyl dimethylsulfamate; (5-amino-2-(4-(dimethylamino)phenethyl)benzo[f][1,7]naphthyridin-8-yl)methanol; 2-(4-(dimethylamino)phenethyl)-8-methylbenzo[f][1,7]naphthyridin-5-amine; 4-(2-(5-amino-8-methylbenzo[f][1,7]naphthyridin-2-yl)ethyl)phenol; 1-(4-(2-(5-amino-8-methylbenzo[f][1,7]naphthyridin-2-yl)ethyl)phenyl)ethanone; 2-(4-((dimethylamino)methyl)phenethyl)-8-methylbenzo[f][1,7]naphthyridin-5-amine; 2-(4-(1-(dimethylamino)ethyl)phenethyl)-8-methylbenzo[f][1,7]naphthyridin-5-amine; 1-(4-(2-(5-amino-8-methylbenzo[f][1,7]naphthyridin-2-yl)ethyl)phenyl)ethanone oxime; 8-methyl-2-(4-((methylamino)methyl)phenethyl)benzo[f][1,7]naphthyridin-5-amine; (4-(2-(5-amino-8-methylbenzo[f][1,7]naphthyridin-2-yl)ethyl)benzylamino)ethanol; 8-methyl-2-(4-(pyrrolidin-1-ylmethyl)phenethyl)benzo[f][1,7]naphthyridin-5-amine; 2-(3,4-dimethoxyphenethyl)-8-methylbenzo[f][1,7]naphthyridin-5-amine; 2-(1-(4-(2-(5-amino-8-methylbenzo[f][1,7]naphthyridin-2-yl)ethyl)phenyl)ethylamino)ethanol; 1-(4-(2-(5-amino-8-methylbenzo[f][1,7]naphthyridin-2-yl)ethyl)phenyl)ethanol; 8-methyl-2-(4-(oxazol-5-yl)phenethyl)benzo[f][1,7]naphthyridin-5-amine; 3-(1-(4-(2-(5-amino-8-methylbenzo[f][1,7]naphthyridin-2-yl)ethyl)phenyl)ethylamino)propanenitrile; (2R)-2-(1-(4-(2-(5-amino-8-methylbenzo[f][1,7]naphthyridin-2-yl)ethyl)phenyl)ethylamino)propan-1-ol; 8-methyl-2-(4-(1-(piperazin-1-yl)ethyl)phenethyl)benzo[f][1,7]naphthyridin-5-amine; ((2S)-1-(1-(4-(2-(5-amino-8-methylbenzo[f][1,7]naphthyridin-2-yl)ethyl)phenyl)ethyl)pyrrolidin-2-yl)methanol; $N^1$-(1-(4-(2-(5-amino-8-methylbenzo[f][1,7]naphthyridin-2-yl)ethyl)phenyl)ethyl)-$N^2$,$N^2$-dimethylethane-1,2-diamine; 3-(1-(4-(2-(5-amino-8-methylbenzo[f][1,7]naphthyridin-2-yl)ethyl)phenyl)ethylamino)propanoic acid; 8-methyl-2-(4-(1-(4-methylpiperazin-1-yl)ethyl)phenethyl)benzo[f][1,7]naphthyridin-5-amine; $N^2$-(1-(4-(2-(5-amino-8-methylbenzo[f][1,7]naphthyridin-2-yl)ethyl)phenyl)ethyl)-$N^1$,$N^1$-dimethylpropane-1,2-diamine; 8-methyl-2-(4-(1-(2-(pyridin-4-yl)ethylamino)ethyl)phenethyl)benzo[f][1,7]naphthyridin-5-amine; $N^1$-(1-(4-(2-(5-amino-8-methylbenzo[f][1,7]naphthyridin-2-yl)ethyl)phenyl)ethyl)-$N^2$,$N^2$-diethylethane-1,2-diamine; 2-(4-(dimethylamino)-2-methylphenethyl)-8-methylbenzo[f][1,7]naphthyridin-5-amine; 1-(1-(4-(2-(5-amino-8-methylbenzo[f][1,7]naphthyridin-2-yl)ethyl)phenyl)ethyl)pyrrolidine-3-carboxylic acid; 4-(1-(4-(2-(5-amino-8-methylbenzo[f][1,7]naphthyridin-2-yl)ethyl)phenyl)ethylamino)phenol; 1-(1-(4-(2-(5-amino-8-methylbenzo[f][1,7]naphthyridin-2 yl)ethyl)phenyl)ethyl)pyrrolidin-3-ol, and 2-(4-(2-aminopropan-2-yl)phenethyl)-8-methylbenzo[f][1,7]naphthyridin-5-amine.

Other "Benzonaphthyridine compounds" used in the invention include compounds, pharmaceutically acceptable salts, pharmaceutically acceptable solvates (e.g. hydrates), the N-oxide derivatives, prodrug derivatives, protected derivatives, individual isomers and mixture of isomers thereof, having the structure of Formula (VIII):

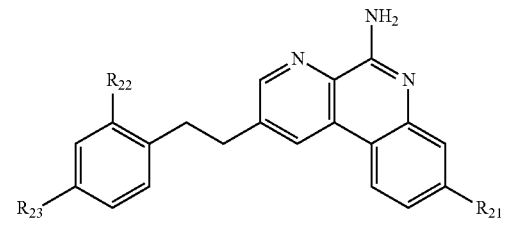

Formula (VIII)

wherein:
$R^{21}$ is H, $C_1$-$C_6$alkyl, —C($R^{25}$)$_2$OH, -$L^{21}R^{25}$, -$L^{21}R^{26}$, -$L^2R^{25}$, -$L^{22}R^{26}$, —O$L^{22}R^{25}$, or —O$L^{22}R^{26}$;
$L^{21}$ is —C(O)— or —O—;
$L^{22}$ is $C_1$-$C_6$alkylene, $C_2$-$C_6$alkenylene, arylene, heteroarylene or —((C$R^{24}R^{24}$)$_p$O)$_q$(CH$_2$)$_p$—, wherein the $C_1$-$C_6$alkylene and $C_2$-$C_6$alkenylene of $L^{22}$ are optionally substituted with 1 to 4 fluoro groups;
each $L^{23}$ is independently selected from $C_1$-$C_6$alkylene and —((C$R^{24}R^{24}$)$_p$O)$_q$(CH$_2$)$_p$—, wherein the $C_1$-$C_6$alkylene of $L^{23}$ is optionally substituted with 1 to 4 fluoro groups;
$L^{24}$ is arylene or heteroarylene;
$R^{22}$ is H or $C_1$-$C_6$alkyl;
$R^{23}$ is selected from $C_1$-$C_4$alkyl, -$L^{23}R^{25}$, -$L^{21}R^{25}$, -$L^{23}R^{27}$, -$L^{23}L^{24}L^3R^{27}$, -$L^{23}L^{24}R^{25}$, -$L^{23}L^{24}L^{23}R^{25}$, —O$L^{23}R^{25}$, —O$L^{23}R^{27}$, —O$L^{23}L^{24}R^{27}$, —O$L^{23}L^{24}L^{23}R^{27}$, —O$R^{28}$, —O$L^{23}L^{24}R^{25}$, —O$L^{23}L^{24}L^{23}R^{25}$ and —C($R^{25}$)$_2$OH;
each $R^{24}$ is independently selected from H and fluoro;
$R^{25}$ is —P(O)(O$R^{29}$)$_2$,
$R^{26}$ is —CF$_2$P(O)(O$R^{29}$)$_2$ or —C(O)O$R^{30}$;
$R^{27}$ is —CF$_2$P(O)(O$R^{29}$)$_2$ or —C(O)O$R^{30}$;
$R^{28}$ is H or $C_1$-$C_4$alkyl;
each $R^{29}$ is independently selected from H and $C_1$-$C_6$alkyl;
$R^{30}$ is H or $C_1$-$C_4$alkyl;
each p is independently selected from 1, 2, 3, 4, 5 and 6, and
q is 1, 2, 3 or 4;
with the proviso that when $R^{23}$ is $C_1$-$C_4$ alkyl or —O$R^{28}$, then $R^{21}$ is —C($R^{25}$)$_2$OH, -$L^{21}R^{25}$, -$L^{21}R^{26}$, -$L^{22}R^{25}$, -$L^{22}R^{25}$, or —O$L^{22}R^{26}$, wherein $R^{26}$ is —CF$_2$P(O)(O$R^{29}$)$_2$ and $R^{27}$ is —CF$_2$P(O)(O$R^{29}$)$_2$.

In certain embodiments of the compounds of Formula (VIII), $R^{21}$ is $C_1$-$C_6$ alkyl, in other embodiments $R^{21}$ is a methyl. In certain embodiments, $R^{21}$ is H. In other embodiments, $R^{21}$ is —C($R^{25}$)$_2$OH, -$L^{21}R^{25}$, -$L^{21}R^{26}$, -$L^{22}R^{25}$, -$L^{22}R^{26}$, —O$L^{22}R^{25}$, or —O$L^{22}R^{26}$.

In certain embodiments of the compounds of Formula (VIII), when $R^{21}$ —C($R^{25}$)$_2$OH, -$L^{21}R^{25}$, -$L^{21}R^{26}$, -$L^{22}R^{25}$, -$L^{22}R^{26}$, —O$L^{22}R^{25}$, or —O$L^{22}R^{26}$, then $R^{23}$ is —O$R^{28}$ or $C_1$-$C_6$ alkyl. In certain embodiments, $R^{21}$ is —C($R^{25}$)$_2$OH, -$L^{21}R^{25}$, -$L^{21}R^{26}$, -$L^{22}R^{25}$, -$L^{22}R^{26}$, —O$L^{22}R^{25}$, or —O$L^{22}R^{26}$, and $R^{23}$ is —OMe.

In some embodiments of the compounds of Formula (VIII), $R^{22}$ is $C_1$-$C_6$alkyl. In certain embodiments, $R^{22}$ is methyl.

In some embodiments of the compounds of Formula (VIII), $R^{23}$ is selected from $C_1$-$C_4$ alkyl, -$L^{23}R^{25}$, -$L^{21}R^{25}$, -$L^{23}R^{27}$, -$L^{23}L^{24}L^{23}R^{27}$, -$L^{23}L^{24}R^{25}$, and -$L^{23}L^{24}L^{23}R^{25}$. In alternative embodiments, $R^{23}$ is selected from —O$L^{23}R^{25}$, —O$L^{23}R^{27}$, —O$L^{23}L^{24}R^{27}$, —O$L^{23}L^{24}L^3R^{27}$, —O$R^{28}$, —O$L^{23}L^{24}R^{25}$, —O$L^{23}L^{24}L^{23}R^{25}$ and —C($R^{25}$)$_2$OH. In certain embodiments, $R^{23}$ is —O$L^{23}R^{25}$, wherein —O$L^{23}R^{25}$ is a group of the formula —O(CH$_2$)$_{1-5}$P(O)(OR)$_2$. In other embodiments, $R^{23}$ is —O$L^{23}R^{25}$, wherein —O$L^{23}R^{25}$ is a group of the formula —O(CH$_2$)$_{1-5}$CF$_2$P(O)(OR)$_2$.

Where more than one $R^{29}$ is present, as in compounds comprising a —P(O)(O$R^{29}$)$_2$, moiety, the $R^{29}$ groups are the same or are different. In certain embodiments of such compounds of Formula (VIII), $R^{29}$ is H at each occurrence. In other embodiments, at least one $R^{29}$ is H and the other $R^{29}$ is $C_1$-$C_6$alkyl. In other embodiments, at least one $R^{29}$ is H and the other $R^{29}$ is methyl. In other embodiments, at least one $R^{29}$ is H and the other $R^{29}$ is ethyl. In other embodiments of such compounds of Formula (VIII), each $R^{29}$ is $C_1$-$C_6$alkyl and in certain embodiments, $R^{29}$ is methyl or ethyl, or a combination thereof.

In certain embodiments of the compounds of Formula (VIII), $L^{22}$ and/or $L^{23}$ is a group of the formula —((C$R^{24}R^{24}$)$_p$O)$_q$(CH$_2$)$_p$—, and in certain embodiments, this group is of the formula —(CH$_2$CH$_2$O)$_{1-3}$(CH$_2$)$_{1-3}$—.

In certain embodiments of the compounds of Formula (VIII), $L^{22}$ is $C_1$-$C_6$ alkylene, while in other embodiments $L^{22}$ is $C_1$-$C_6$ alkylene substituted with one to four fluoro groups. In certain embodiments of such compounds of Formula (VIII), $L^{22}$ is of the formula (CH$_2$)$_{0-5}$CF$_2$, wherein the fluoro-substituted carbon is not directly attached to the phenyl ring of Formula I. In certain embodiments of the compounds of Formula (VIII), $L^{22}$ is $C_2$-$C_6$ alkenylene, while in other embodiments $L^{22}$ is $C_2$-$C_6$ alkenylene substituted with one to four fluoro groups.

In certain embodiments of the compounds of Formula (VIII), $L^{23}$ is $C_1$-$C_6$ alkylene while in other embodiments $L^{23}$ is $C_1$-$C_6$ alkylene substituted with one to four fluoro groups. In certain embodiments of such compounds of Formula (VIII), $L^{23}$ is of the formula (CH$_2$)$_{0-5}$CF$_2$, wherein the fluoro-substituted carbon is not directly attached to the phenyl ring of Formula I.

In certain embodiments of the compounds of Formula (VIII), $L^2$ is arylene or heteroarylene. In some of these embodiments, $L^2$ is phenylene, such as 1,3-disubstituted phenylene or 1,4-disubstituted phenylene.

In certain embodiments of such compounds of Formula (VIII), $R^{21}$ is $C_1$-$C_6$alkyl; $R^{22}$ is $C_1$-$C_6$alkyl; $R^{23}$ is —O$L^{23}R^{25}$ or —O$L^{23}R^{22}$; $R^{25}$ is —P(O)(O$R^{29}$)$_2$; $R^{27}$ is —CF$_2$P(O)(O$R^{29}$)$_2$, and $L^{23}$ is $C_1$-$C_6$alkylene.

In certain embodiments of such compounds of Formula (VIII), $R^{21}$ is $C_1$-$C_6$alkyl; $R^{22}$ is $C_1$-$C_6$alkyl; $R^{23}$ is —O$L^{23}R^{25}$ or —O$L^{23}R^{27}$; $R^{25}$ is —P(O)(O$R^{29}$)$_2$; $R^{27}$ is —CF$_2$P(O)(O$R^{29}$)$^2$; $L^{23}$ is —((C$R^{24}R^{24}$)$_p$O)$_q$(CH$_2$)$_p$—; $R^{24}$ is H; q is 1 or 2, and p is 2.

In certain embodiments of such compounds of Formula (VIII), $R^{21}$ is -$L^{22}R^{26}$; $R^{22}$ is $C_1$-$C_6$alkyl; $R^{23}$ is —O$L^{23}R^{25}$ or —O$L^{23}R^{27}$; $R^{25}$ is —P(O)(O$R^{29}$)$_2$, $R^{26}$ is —C(O)O$R^{30}$; $R^{27}$ is —CF$_2$P(O)(O$R^{29}$)$_2$; $L^{22}$ is $C_1$-$C_6$alkylene, and $L^{23}$ is $C_1$-$C_6$alkylene.

In certain embodiments of such compounds of Formula (VIII), $R^{21}$ is -$L^{22}R^{26}$; $R^{22}$ is $C_1$-$C_6$alkyl; R23$^3$ is —O$L^{23}R^{25}$ or —O$L^{23}R^{27}$; $R^5$ is —P(O)(O$R^{29}$)$_2$; $R^{26}$ is —C(O)O$R^{30}$; $R^{27}$ is —CF$_2$P(O)(O$R^{29}$)$_2$, $L^{22}$ is $C_1$-$C_6$alkylene; $L^{23}$ is —((C$R^{24}R^{24}$)$_p$O)$_q$(CH$_2$)$_p$—; $R^{24}$ is H; q is 1 or 2, and p is 2.

In certain embodiments of such compounds of Formula (VIII), $R^{21}$ is —C($R^{25}$)$_2$OH, -$L^{21}R^{25}$, -$L^{22}R^{25}$ or -$L^{21}R^{26}$; $R^{22}$ is $C_1$-$C_6$alkyl; $R^{23}$ is —O$R^{28}$; $R^{28}$ is $C_1$-$C_6$alkyl; $R^{25}$ is —P(O)(O$R^{29}$)$_2$; $R^{26}$ is —CF$_2$P(O)(O$R^{29}$)$_2$; $L^{21}$ is —C(O)—, and $L^{22}$ is $C_1$-$C_6$alkylene or $C_2$-$C_6$alkenylene, each optionally substituted with 1 to 4 fluoro groups.

In certain embodiments of such compounds of Formula (VIII), $R^{21}$ is $C_1$-$C_6$alkyl; $R^{22}$ is $C_1$-$C_6$alkyl; $R^{23}$ is —O$L^{23}L^{24}R^{25}$—$L^{23}L^{24}L^{23}R^{25}$, or —O$L^{23}8R^{27}$; $R^{25}$ is —P(O)(O$R^{29}$)$_2$; $R^{27}$ is —CF$_2$P(O)(O$R^{29}$)$_2$; each $L^{23}$ is independently a $C_1$-$C_6$alkylene, and $L^{24}$ is phenylene.

In certain embodiments of such compounds of Formula (VIII), $R^{21}$ is $C_1$-$C_6$alkyl; $R^{22}$ is $C_1$-$C_6$alkyl; $R^{23}$ is —C($R^{25}$)$_2$OH or -$L^{21}R^{25}$; $R^{25}$ is —P(O)(O$R^{29}$)$_2$, and $L^{21}$ is —C(O)— or —O—.

In certain embodiments of the compounds of Formula (VIII), the compound is selected from:
4-(4-(2-(5-amino-8-methylbenzo[f][1,7]naphthyridin-2-yl)ethyl)-3-methylphenoxy)-1,1-difluorobutylphosphonic acid; 3-(5-amino-2-(4-(4,4-difluoro-4-phosphonobutoxy)-2-methylphenethyl)benzo[f][1,7]naphthyridin-8-yl)propanoic acid; 3-(5-amino-2-(4-(2-(3,3-difluoro-3-phosphonopropoxy)ethoxy)-2-methylphenethyl)benzo[f][1,7]naphthyridin-8-yl)propanoic acid; 3-(5-amino-2-(2-methyl-4-(2-(2-(2-phosphonoethoxy)ethoxy)ethoxy)phenethyl)benzo[f][1,7]naphthyridin-8-yl)propanoic acid; 4-(2-(5-amino-8-methylbenzo[f][1,7]naphthyridin-2-yl)ethyl)-3-methylphenyl dihydrogen phosphate; (4-(2-(5-amino-8-methylbenzo[f][1,7]naphthyridin-2-yl)ethyl)-3-methylphenoxy)methylphosphonic acid; 5-(4-(2-(5-amino-8-methylbenzo[f][1,7]naphthyridin-2-yl)ethyl)-3-methylphenoxy)-1,1-difluoropentylphosphonic acid; 4-(4-(2-(5-amino-8-methylbenzo[f][1,7]naphthyridin-2-yl)ethyl)-3-methylphenoxy)-1,1-difluorobutylphosphonic acid; 3-(2-(4-(2-(5-amino-8-methylbenzo[f][1,7]naphthyridin-2-yl)ethyl)-3-methylphenoxy)ethoxy)-1,1-difluoropropylphosphonic acid; 2-(4-((4-(2-(5-amino-8-methylbenzo[f][1,7]naphthyridin-2-yl)ethyl)-3-methylphenoxy)methyl)phenyl)-1,1-difluoroethylphosphonic acid; 2-(5-amino-2-(4-methoxy-2-methylphenethyl)benzo[f][1,7]naphthyridin-8-yl)-1,1-difluoro-2-oxoethylphosphonic acid; (E)-2-(5-amino-2-(4-methoxy-2-methylphenethyl)benzo[f][1,7]naphthyridin-8-yl)vinylphosphonic acid; 2-(5-amino-2-(4-methoxy-2-methylphenethyl)benzo[f][1,7]naphthyridin-8-yl)ethylphosphonic acid; (E)-2-(5-amino-2-(4-methoxy-2-methylphenethyl)benzo[f][1,7]naphthyridin-8-yl)-1-fluorovinylphosphonic acid; 3-((4-(2-(5-amino-8-methylbenzo[f][1,7]naphthyridin-2-yl)ethyl)-3-methylphenoxy)methyl)phenylphosphonic acid; 5-amino-2-(4-methoxy-2-methylphenethyl)benzo[f][1,7]naphthyridine-8-carbonylphosphonic acid; 3-(5-amino-2-(2-methyl-4-(3-phosphonopropoxy)phenethyl)benzo[f][1,7]naphthyridin-8-yl)propanoic acid; (4-(2-(5-amino-8-methylbenzo[f][1,7]naphthyridin-2-yl)ethyl)-3-methylphenyl)(hydroxy)methylenediphosphonic acid; 3-(5-amino-2-(4-(2-(2-(3,3-difluoro-3-phosphonopropoxy)ethoxy)-2-methylphenethyl)benzo[f][1,7]naphthyridin-8-yl)propanoic acid; (5-amino-2-(4-methoxy-2-methylphenethyl)benzo[f][1,7]naphthyridin-8-yl)(hydroxy)methylenediphosphonic acid; 3-(5-amino-2-(2-methyl-4-(2-(2-phosphonoethoxy)ethoxy)phenethyl)benzo[f][1,7]naphthyridin-8-yl)propanoic acid; 2-(4-(2-(5-amino-8-methylbenzo[f][1,7]naphthyridin-2-yl)ethyl)-3-methylphenoxy)ethylphosphonic acid; 6-(4-(2-(5-amino-8-methylbenzo[f][1,7]naphthyridin-2-yl)ethyl)-3-methylphenoxy)hexylphosphonic acid; 6-(4-(2-(5-amino-8-methylbenzo[f][1,7]naphthyridin-2-yl)ethyl)-3-methylphenoxy)-1,1-difluorohexylphosphonic acid; 4-((4-(2-(5-amino-8-methylbenzo[f][1,7]naphthyridin-2-yl)ethyl)-3-methylphenoxy)methyl)benzylphosphonic acid, 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid, and 2-(2-(2-(4-(2-(5-amino-8-methylbenzo[f][1,7]naphthyridin-2-yl)ethyl)-3-methylphenoxy)ethoxy)ethoxy)ethylphosphonic acid.

The compounds of Formula (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds provided herein and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Benzonaphthyridine compounds used in the invention are also described in U.S. Provisional Application No. 61/033,139, U.S. Provisional Application No. 61/148,336, and International Publication No. WO 2009/111337, which references are incorporated herein in their entirety by reference.

In a particular embodiment, a particularly preferred benzonaphthyridine compound, pharmaceutically acceptable salt, pharmaceutically acceptable solvate, N-oxide derivative, prodrug derivative, protected derivative, individual isomer or mixture of isomers thereof, for use in the invention has the structure (also referred to herein as Compound 47):

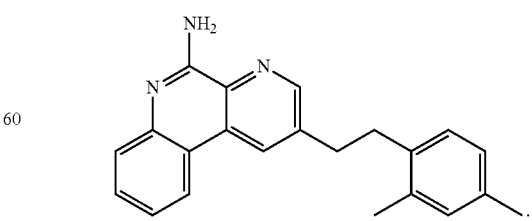

In other embodiments, the benzonaphthyridine compound is selected from a compound set forth in Table A.

TABLE A

| Compound Number | Structure | Physical Data NMR and/or MS (m/z) [M + H] | Human TLR7 EC50 (nM) HEK293 |
|---|---|---|---|
| 1A | 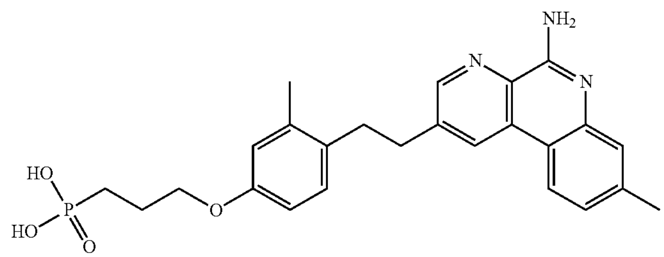 [SMILES: Cc1ccc2c(c1)nc(N)c1ncc(CCc3ccc(OCCCP(=O)(O)O)cc3C)cc12] | 466.2 | 226 |
| 2A | 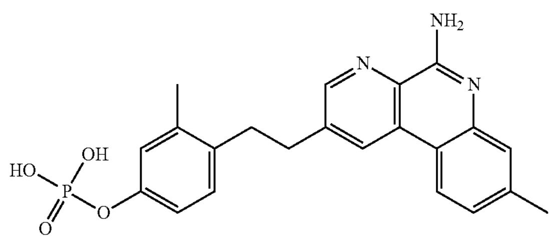 [SMILES: Cc1ccc2c(c1)nc(N)c1ncc(CCc3ccc(OP(=O)(O)O)cc3C)cc12] | 424.0 | 315 |
| 3A | 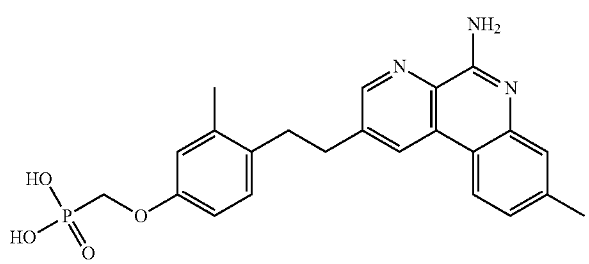 [SMILES: Cc1ccc2c(c1)nc(N)c1ncc(CCc3ccc(OCP(=O)(O)O)cc3C)cc12] | 438.0 | 3170 |
| 4A | 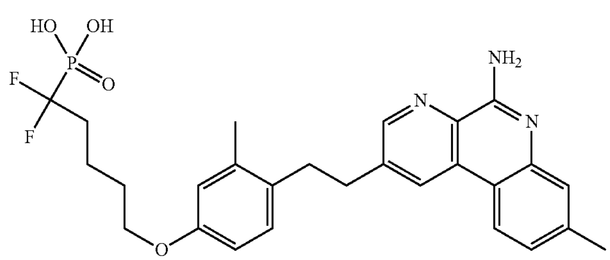 [SMILES: Cc1ccc2c(c1)nc(N)c1ncc(CCc3ccc(OCCCCC(F)(F)P(=O)(O)O)cc3C)cc12] | 530.2 | 559 |
| 5A | 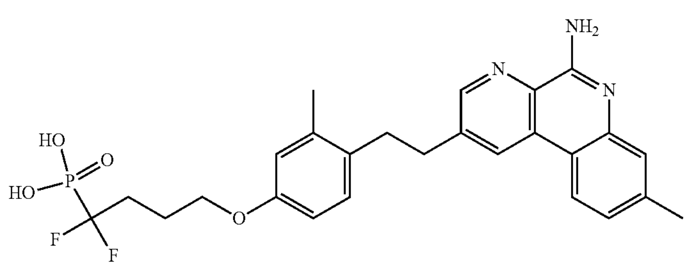 [SMILES: Cc1ccc2c(c1)nc(N)c1ncc(CCc3ccc(OCCCC(F)(F)P(=O)(O)O)cc3C)cc12] | 516.2 | 308 |

TABLE A-continued

| Compound Number | Structure | Physical Data NMR and/or MS (m/z) [M + H] | Human TLR7 EC50 (nM) HEK293 |
|---|---|---|---|
| 6A | 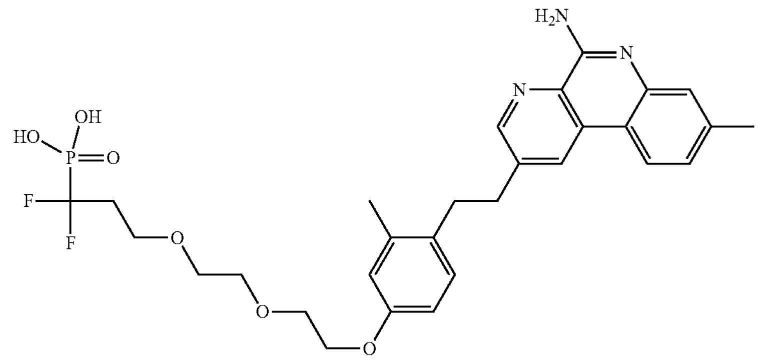 [SMILES: Cc1ccc2c(c1)nc(N)c1ncc(CCc3ccc(OCCOCCOCCC(F)(F)P(=O)(O)O)cc3C)cc12] | 590.2 | 1640 |
| 7A | 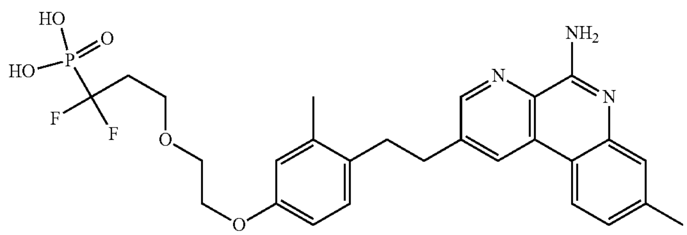 [SMILES: Cc1ccc2c(c1)nc(N)c1ncc(CCc3ccc(OCCOCCC(F)(F)P(=O)(O)O)cc3C)cc12] | 546.3 | 1010 |
| 8A | 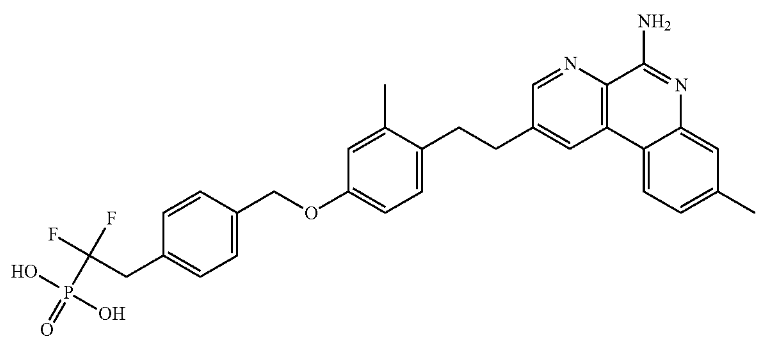 [SMILES: Cc1ccc2c(c1)nc(N)c1ncc(CCc3ccc(OCc4ccc(CC(F)(F)P(=O)(O)O)cc4)cc3C)cc12] | 578.2 | 375 |
| 9A | 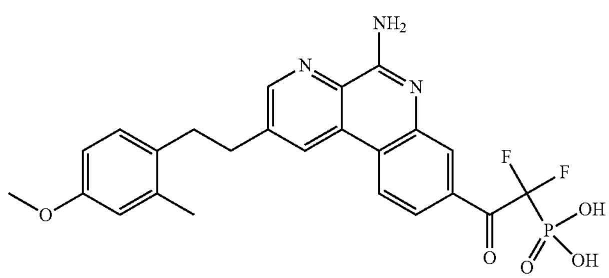 [SMILES: COc1ccc(CCc2cnc3c(N)nc4cc(C(=O)C(F)(F)P(=O)(O)O)ccc4c3c2)c(C)c1] | 502.6 | 390 |
| 10A | 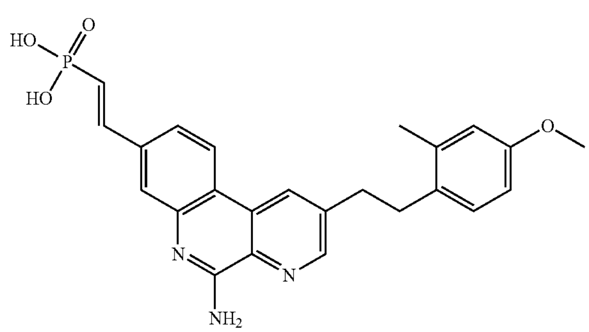 | 450.2 | 153 |

TABLE A-continued

| Compound Number | Structure | Physical Data NMR and/or MS (m/z) [M + H] | Human TLR7 EC50 (nM) HEK293 |
|---|---|---|---|
| 11A | 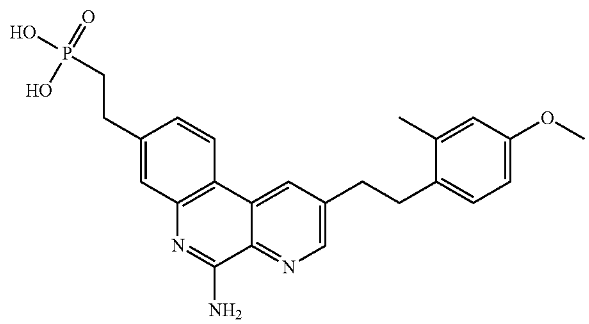 [SMILES: COc1ccc(CCc2cnc3c(N)nc4cc(CCP(=O)(O)O)ccc4c3c2)c(C)c1] | 452.2 | 90 |
| 12A | 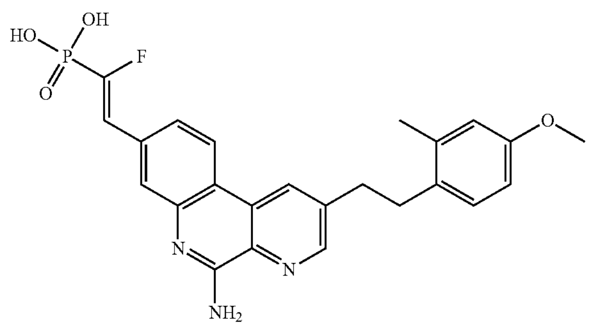 [SMILES: COc1ccc(CCc2cnc3c(N)nc4cc(/C=C(\F)P(=O)(O)O)ccc4c3c2)c(C)c1] | ¹H NMR TFA salt (dmso-d6): δ 9.81 (s, 1H), 9.41 (s, 1H), 9.05 (d, 1H), 8.87 (d, 1H), 8.65 (s, 1H), 8.08 (s, 1H), 7.76 (dd, 1H), 7.08 (d, 1H), 6.82-6.65 (m, 3H), 3.69 (s, 3H), 3.18-3.11 (m, 2H), 3.02-2.96 (m, 2H), 2.29 (s, 3H); ¹⁹F NMR (dmso-d6, TFA as external standard): δ - 176.833 (s); LRMS [M + H] = 468.1 | 201 |
| 13A | 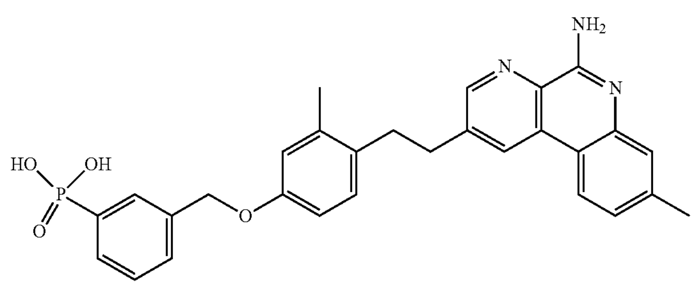 [SMILES: Cc1ccc2c(c1)nc(N)c1ncc(CCc3ccc(OCc4cccc(P(=O)(O)O)c4)cc3C)cc12] | 514.2 | 1051 |
| 14A | 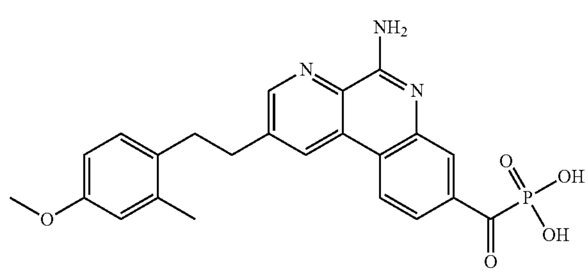 [SMILES: COc1ccc(CCc2cnc3c(N)nc4cc(C(=O)P(=O)(O)O)ccc4c3c2)c(C)c1] | ¹H NMR TFA salt (dmso-d6): δ 9.84 (s, 1H), 9.09 (d, 1H), 8.88 (d, 1H), 8.76 (d, 1H), 8.60 (d, 1H), 8.18 (dd, 1H), 7.04 (d, 1H), 6.69 (d, 1H), 6.62 (dd, 1H), 3.64 (s, 3H), 3.15-3.08 (m, 2H), 3.98-2.91 (m, 2H), 2.23 (s, 3H); LRMS [M + H] = 452.2 | 885 |

TABLE A-continued

| Compound Number | Structure | Physical Data NMR and/or MS (m/z) [M + H] | Human TLR7 EC50 (nM) HEK293 |
|---|---|---|---|
| 15A | 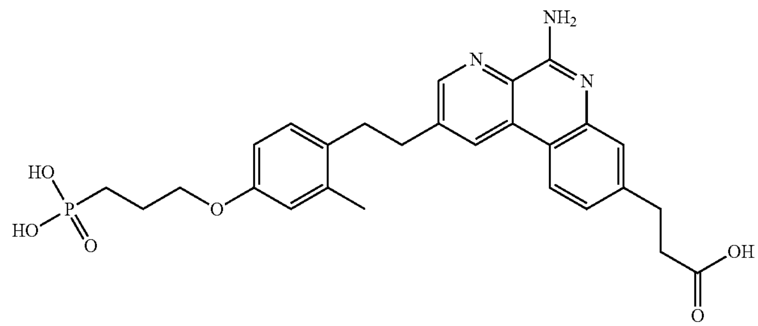 [SMILES: Cc1cc(OCCCP(=O)(O)O)ccc1CCc1cnc2c(N)nc3cc(CCC(=O)O)ccc3c2c1] | 524.2 | 65 |
| 16A | 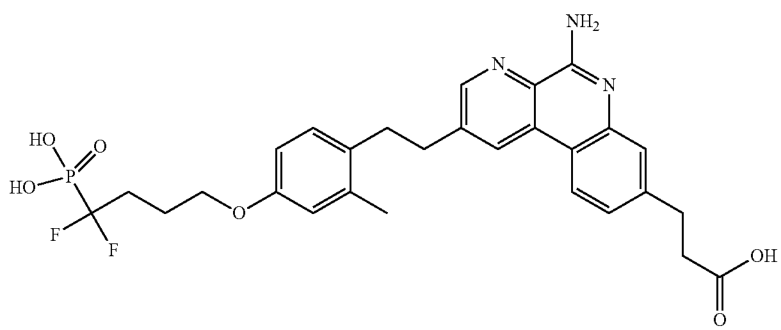 [SMILES: Cc1cc(OCCCC(F)(F)P(=O)(O)O)ccc1CCc1cnc2c(N)nc3cc(CCC(=O)O)ccc3c2c1] | 574.2 | 137 |
| 17A | 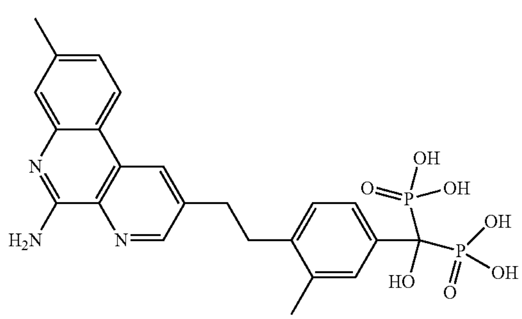 [SMILES: Cc1ccc2c(c1)nc(N)c1ncc(CCc3ccc(C(O)(P(=O)(O)O)P(=O)(O)O)cc3C)cc12] | 518.1 | — |
| 18A | 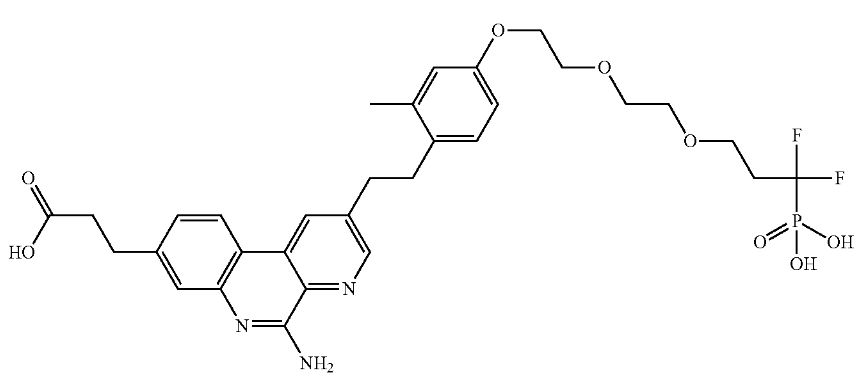 [SMILES: Cc1cc(OCCOCCOCCC(F)(F)P(=O)(O)O)ccc1CCc1cnc2c(N)nc3cc(CCC(=O)O)ccc3c2c1] | 648.2 | 5 |

TABLE A-continued

| Compound Number | Structure | Physical Data NMR and/or MS (m/z) [M + H] | Human TLR7 EC50 (nM) HEK293 |
|---|---|---|---|
| 19A | 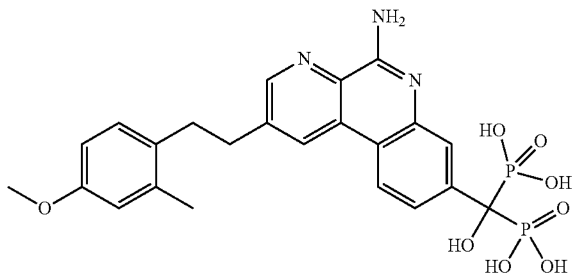 [SMILES: COc1ccc(CCc2cnc3c(N)nc4cc(C(O)(P(=O)(O)O)P(=O)(O)O)ccc4c3c2)c(C)c1] | 534.1 | 23750 |
| 20A | 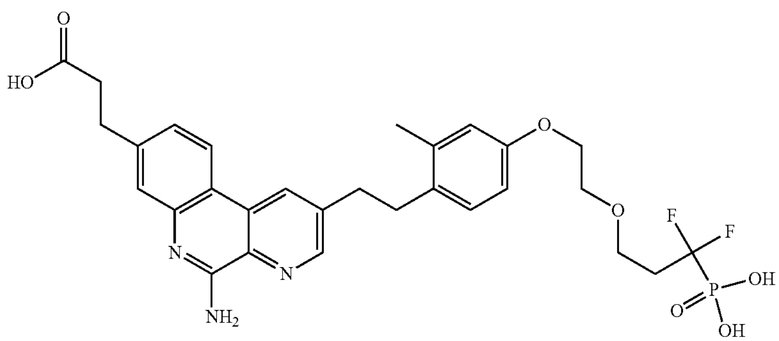 [SMILES: Cc1cc(OCCOCCC(F)(F)P(=O)(O)O)ccc1CCc1cnc2c(N)nc3cc(CCC(=O)O)ccc3c2c1] | 604.2 | 360 |
| 21A | 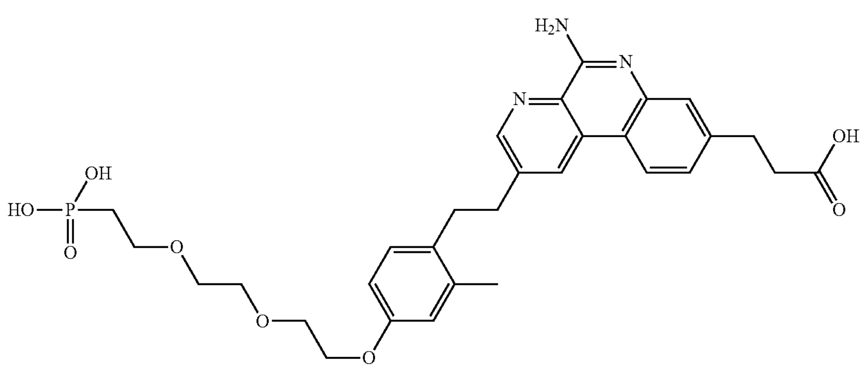 [SMILES: Cc1cc(OCCOCCOCCP(=O)(O)O)ccc1CCc1cnc2c(N)nc3cc(CCC(=O)O)ccc3c2c1] | 598.2 | 384 |
| 22A | 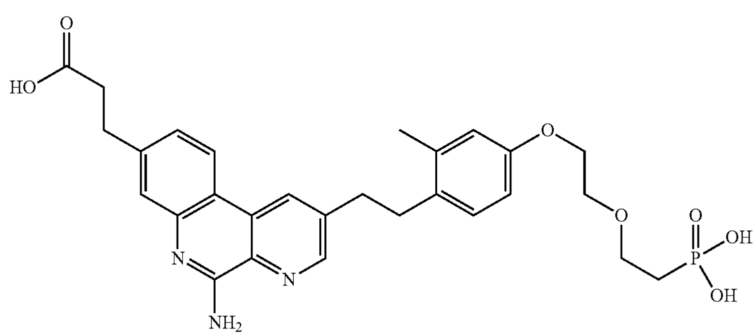 [SMILES: Cc1cc(OCCOCCP(=O)(O)O)ccc1CCc1cnc2c(N)nc3cc(CCC(=O)O)ccc3c2c1] | 554.2 | 204 |

TABLE A-continued

| Compound Number | Structure | Physical Data NMR and/or MS (m/z) [M + H] | Human TLR7 EC50 (nM) HEK293 |
|---|---|---|---|
| 23A | 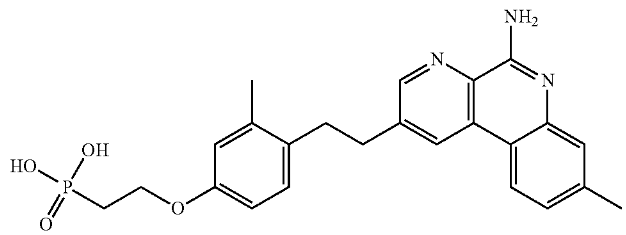 [SMILES: Cc1ccc2c(c1)nc(N)c1ncc(CCc3ccc(OCCP(=O)(O)O)cc3C)cc12] | 452.2 | 1160 |
| 24A | 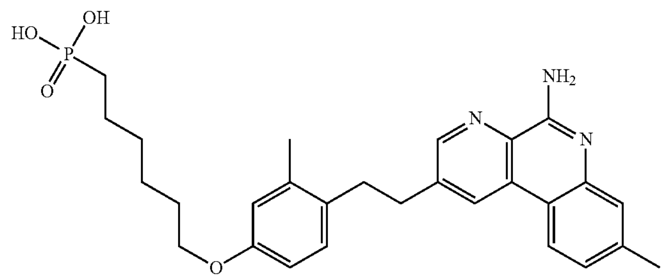 [SMILES: Cc1ccc2c(c1)nc(N)c1ncc(CCc3ccc(OCCCCCCP(=O)(O)O)cc3C)cc12] | 508.2 | 791 |
| 25A | 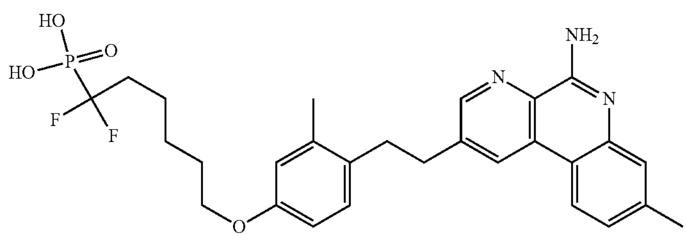 [SMILES: Cc1ccc2c(c1)nc(N)c1ncc(CCc3ccc(OCCCCCC(F)(F)P(=O)(O)O)cc3C)cc12] | 544.2 | 4260 |
| 26A | 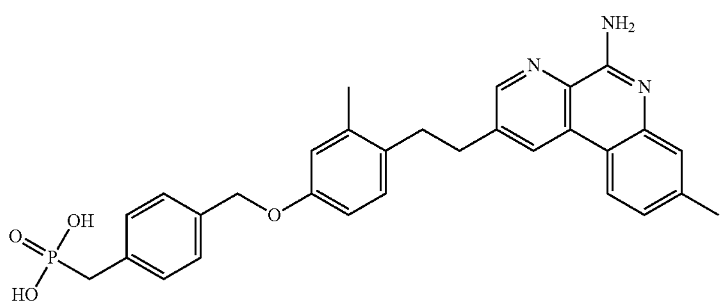 [SMILES: Cc1ccc2c(c1)nc(N)c1ncc(CCc3ccc(OCc4ccc(CP(=O)(O)O)cc4)cc3C)cc12] | 528.2 | 975 |
| 27A | 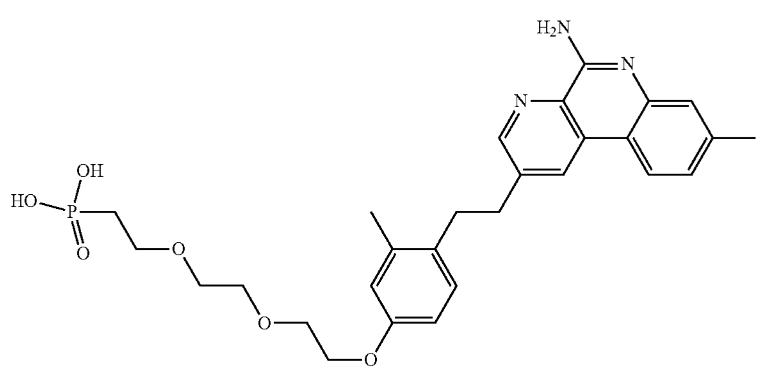 [SMILES: Cc1ccc2c(c1)nc(N)c1ncc(CCc3ccc(OCCOCCOCCP(=O)(O)O)cc3C)cc12] | 540.2 | 2592 |

Typical wt/wt ratios of antigen to benzonaphthyridine compound to polymers in the compositions of the present invention range from 0.05% to 25% by weight, for example, ranging from 0.05% to 0.1% to 0.25% to 0.5% to 1% to 2.5% to 5% to 10% to 25%, among other possibilities.

In certain embodiments of the immunogenic compositions provided herein, the benzonaphthyridine compound is a compound having a water solubility that is 0.1 mg/mL or greater, for example, ranging from 0.1 mg/mL to 0.25 mg/mL to 5 mg/mL to 1 mg/mL to 2.5 mg/mL to 5 mg/mL to 10 mg/mL or greater.

D. POLYMERIC PARTICLES

As indicated above, in addition to one or more antigens and one or more benzonaphthyridine compounds, compositions in accordance with certain embodiments comprise one or more types of polymeric particles.

The antigen(s) and benzonaphthyridine compound(s) may independently be, for example: (a) established within the polymeric particles, (b) attached to the polymeric particles, for example, adsorbed or conjugated to the surface of the polymeric particles, and/or (c) otherwise associated with the polymeric particles to varying degrees, for example, admixed with the polymeric particles in a liquid dispersion, admixed with the polymeric particles in a solid composition (e.g., co-lyophilized with the polymeric particles), and so forth.

In certain embodiments, the antigen(s) and benzonaphthyridine compound(s) may be independently adsorbed to, conjugated to, co-lyophilized with, or established within separate populations of polymeric particles.

Typical wt/wt ratios of antigen to polymer(s) in the compositions of the present invention range from 0.05% to 25% by weight, for example, ranging from 0.05% to 0.1% to 0.25% to 0.5% to 1% to 2.5% to 5% to 10% to 25%, among other possibilities.

As noted above, polymer particles for use in the invention include microparticles and nanoparticles. As also noted above, a "polymeric particle" is a particle that comprises one or more types of polymers, typically, 50 wt % or more polymers, for example, from 50 wt % to 75 wt % to 90 wt % to 95 wt % to 97.5 wt % to 99 wt % or more.

As used herein, "polymers" are molecules containing multiple copies (e.g., 5 to 10 to 25 to 50 to 100 to 250 to 500 to 1000 or more copies) of one or more constitutional units, commonly referred to as monomers. As used herein, "monomers" may refer to free monomers and to those are incorporated into polymers, with the distinction being clear from the context in which the term is used.

Polymers may take on a number of configurations, which may be selected, for example, from linear, cyclic, and branched configurations. Branched configurations include star-shaped configurations (e.g., configurations in which three or more chains emanate from a single branch region), comb configurations (e.g., configurations having a main chain and a plurality of side chains), dendritic configurations (e.g., arborescent and hyperbranched polymers), network configurations (e.g., crosslinked polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ, for instance, because a constitutional unit (i.e., monomer) is found in one polymer block that is not found in another polymer block.

As used herein, a "polymer block" is a grouping of constitutional units (e.g., 5 to 10 to 25 to 50 to 100 to 250 to 500 to 1000 or more units) that forms part or all of a polymer. Blocks can be branched or unbranched. Polymer blocks can contain a single type of constitutional unit (also referred to herein as "homopolymer blocks") or multiple types of constitutional units (also referred to herein as "copolymer blocks") which may be provided, for example, in a periodic (e.g., alternating), random, statistical or gradient distribution. As used herein, a polymer block is "biodegradable" if it undergoes bond cleavage along the polymer backbone in vivo, regardless of the mechanism of bond cleavage (e.g., enzymatic breakdown, hydrolysis, oxidation, etc.).

A few examples of block copolymer structures include the following, among others: (a) block copolymers having alternating blocks of the type $(AB)_m$, $B(AB)_m$ and $A(BA)_m$ where A is a first polymer block, B is a second polymer block that is different from the first polymer block, and m is a positive whole number of 1 or more, and (b) block copolymers having multi-arm architectures, such as $X(BA)_n$, and $X(AB)_n$, where n is a positive whole number of 2 or more and X is a hub species (e.g., an initiator molecule residue, a residue of a molecule to which preformed polymer chains are attached, etc.). In addition to the hub species mentioned above, polymers (including block copolymers) can contain a variety of other non-polymer-chain species, including initiator residues, linking molecule residues and capping molecules, among other species. Note that such non-polymeric species are generally ignored in describing polymers (including block copolymers). Thus, an $X(BA)_2$ block copolymer is generally designated as an ABA triblock copolymer, an $X(BA)_3$ block copolymer is generally referred to as a star polymer with a B midblock and three A endblocks. Other examples of block copolymers include comb copolymers having a B chain backbone and multiple A side chains, as well as comb copolymers having an A chain backbone and multiple B side chains.

As noted above a "polymer block" is defined herein as a grouping of constitutional units that forms part or all of a polymer. Thus, homopolymers may be said to contain a single homopolymer block. Copolymers, on the other hand, may contain a single copolymer block (e.g., a periodic copolymer block, a random copolymer block, a gradient copolymer block, etc.) or multiple homopolymer and/or copolymer blocks (e.g., a block copolymer comprising multiple homopolymer blocks, a block copolymer comprising multiple copolymer blocks, or a block copolymer comprising one or more homopolymer blocks and one or more copolymer blocks).

Polymers for use in the polymeric particles of the invention preferably are at least partially biodegradable.

Examples of polymers that are at least partially biodegradable include homopolymers formed from a single biodegradable homopolymer block, non-block copolymers formed from a single biodegradable copolymer block (e.g., selected from alternating, random, gradient, etc., blocks), and block copolymers containing at least one biodegradable polymer block, for example, a block copolymer containing two or more biodegradable polymer blocks or a block copolymer containing one or more bridgeable polymer blocks and one or more additional polymer blocks.

Examples of biodegradable polymers include, for example, homopolymers and copolymers of the following: polyesters (e.g., poly[hydroxy acids], poly[cyclic esters], etc.), polycarbonates, polyorthoesters, polyanhydrides, polycyanoacrylates (e.g., polyalkylcyanoacrylate or "PACA") and polyphosphazines.

Examples of biodegradable polymers include block copolymers containing combinations of two or more biodegradable polymer blocks corresponding to the foregoing (e.g., two or more blocks selected from polyester, polycarbonate, polyorthoester, polyanhydride, polycyanoacrylate and/or polyphosphazine blocks), and block copolymer comprising one or more of the foregoing biodegradable polymer blocks and one or more additional polymer blocks that differs from the foregoing biodegradable polymer blocks.

Examples of additional polymer blocks include hydrophilic polymer blocks such as polyether blocks, for example, polyethylene oxide (e.g. polyethylene glycol) blocks (see Park et al., Langmuir 20(6): 2456-2465 (2004)) and polypropylene oxide (e.g., polypropylene glycol) blocks, polyvinyl alcohol blocks, polyvinylpyrrolidone blocks, poly (acrylic acid) blocks, poly(methacrylic acid) blocks, poly (N-isopropylacrylamide-co-N,N-dimethylacrylamide) blocks (see Liu et al., Biomaterials 26(24): 5064-5074 (2005)), polyethylenimine blocks (see Nam et al., Biomaterials 24(12): 2053-2059 (2003)), poly(amino acid) blocks, and so forth. Examples of additional polymer blocks also include polymer blocks that are negatively charged at physiological pH, for instance, poly(carboxylic acids) such as poly(acrylic acid) blocks and poly(methacrylic acid) blocks, and certain polyaminoacid blocks (depending on the isoelectric point), as well as salts thereof, among others. Further examples of additional polymer blocks include polymer blocks that are positively charged at physiological pH, for instance, polyamine blocks such as polyethylenimine blocks and chitosan blocks, and certain polyaminoacid blocks (depending on the isoelectric point), as well as salts thereof, among others. Such polymers with charged polymer blocks may be employed, for example, as particle charge inducing agents (see below). In certain embodiments, AB diblock copolymers, ABA triblock copolymers, and BAB triblock copolymers are employed, where A designates an additional polymer block and B designates a biodegradable polymeric block.

In various preferred embodiments, biodegradable polymers are formed, for example, from the following: polyesters (e.g., polyhydroxy acids, polycaprolactone, polydioxanone, etc.), polycarbonates, polyorthoesters, polyanhydrides, polyphosphazines, and combinations thereof. More typical are polyesters, for example, homopolymers and copolymers of glycolic acid, L-lactic acid, D,L-lactic acid, hydroxybutyric acid, hydroxyvaleric acid, caprolactone and dioxanone, among others. Even more typical are homopolymers and copolymers of L-lactide, D,L-lactide, and glycolide, for example, polyglycolide, polylactide, for example, poly(L-lactide) or poly(D,L-lactide) (referred to as PLA herein) and poly(lactide-co-glycolide), for example, poly(L-lactide-co-glycolide) and poly (D,L-lactide-co-glycolide) (designated as "PLG" or "PLGA" herein).

The above polymers are available in a variety of molecular weights, and a suitable molecular weight for a given use is readily determined by one of skill in the art. Thus, for example, a suitable molecular weight for PLA may be on the order of about 2,000 to 5,000. A suitable molecular weight for PLG may range from about 5,000 to about 200,000.

Where copolymers are employed, copolymers with a variety of monomer ratios may be available. For example, where PLG is used to form the particles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Mixtures of particles with varying lactide:glycolide ratios may also find use herein in order to achieve the desired release kinetics. Degradation rate of the particles of the present invention can also be controlled by such factors as polymer molecular weight and polymer crystallinity.

Where used, PLG copolymers are typically those having a lactide/glycolide molar ratio ranging, for example, from 20:80 to 25:75 to 40:60 to 45:55 to 55:45 to 60:40 to 75:25 to 80:20, and having a molecular weight ranging, for example, from 5,000 to 10,000 to 20,000 to 40,000 to 50,000 to 70,000 to 100,000 to 200,00 Daltons, among others. PLG copolymers with varying lactide:glycolide ratios, molecular weights and end groups are readily available commercially from a number of sources including from Boehringer Ingelheim, Germany, Birmingham Polymers, Inc., Birmingham, Ala., USA and Lakeshore Biomaterials, Birmingham, Ala., USA. Some exemplary PLG copolymers, available from Boehringer Ingelheim, include: (a) RG 502, a PLG having predominantly alkyl ester end groups on one of the chain ends, a 50:50 lactide/glycolide molar ratio and a molecular weight of 12,000 Da, (b) RG 503, a PLG having predominantly alkyl ester end groups on one of the chain ends, a 50:50 lactide/glycolide molar ratio and a molecular weight of 34,000 Da, (c) RG 504, a PLG having predominantly alkyl ester end groups on one of the chain ends, a 50:50 lactide/glycolide molar ratio and a molecular weight of 48,000 Da, (d) RG 752, a PLG having predominantly alkyl ester end groups on one of the chain ends, a 75:25 lactide/ glycolide molar ratio and a molecular weight of 22,000 Da, (e) RG 755, a PLG having predominantly alkyl ester end groups on one of the chain ends, a 75:25 lactide/glycolide molar ratio and a molecular weight of 68,000 Da, (f) RG 502H, a PLG having a 50:50 lactide/glycolide molar ratio, and having predominantly free carboxyl end groups on one of the chain ends, and (g) RG 503H, a PLG having a 50:50 lactide/glycolide molar ratio, and having predominantly free carboxyl end groups on one of the chain ends.

In addition to free carboxyl and alkyl ester end groups, PLG may also be provided with amine, hydroxyl, thiol, succinimidyl ester or maleimide groups, among others, on at least one of the chain ends.

In certain embodiments the particles are formed using a charged biodegradable polymer. In certain other embodiments, particles are formed from a non-charged polymer (e.g., selected from those described above) in the presence of a charged species or subsequently treated with a charged species. Examples of such charged species include ionic small molecules, ionic peptides, ionic polymers and ionic surfactants, among others.

Such species may be provided, for example, in an amount effective to promote acceptable particle suspension (e.g., during particle formation and/or resuspension after lyophilization). Such species may also be provided, for example, in an amount effective to promote adsorption of species to the surfaces of the particles (e.g., antigens, immunological adjuvants, etc.). For example, in certain embodiments (e.g., where the antigen to be administered is a peptide-containing antigen), particles having a net negative charge may be employed to enhance adsorption. As another example, in certain other embodiments (e.g., where the antigen to be administered is a polynucleotide-containing antigen), particles having a net positive charge may be employed to enhance adsorption.

The net charge of a given particle population may be measured using known techniques including measurement of the particle zeta potential. In certain embodiments, upon the addition of water in an amount such that the particle composition is present in a concentration of 25 mg/ml, a suspension is formed in which the suspended particles have a zeta potential that is greater than +20 mV (for positively charged particles) or less than −20 mV (for negatively charged particles) at physiological pH.

In certain embodiments, charged surfactants are preferred to impart charge to the particles. Charged surfactants include cationic and anionic surfactants. Cationic surfactants include, for example, cetyltrimethylammonium bromide or "CTAB" (e.g., cetrimide), benzalkonium chloride, DDA (dimethyl dioctodecyl ammonium bromide), and DOTAP (dioleoyl-3-trimethylammonium-propane), among others. Anionic surfactants include, for example, SDS (sodium dodecyl sulfate), SLS (sodium lauryl sulfate), DSS (disulfosuccinate), and sulphated fatty alcohols, among others.

Various methods may be employed to produce polymeric particles in accordance with the invention.

For example, in some embodiments, polymeric particles can be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

In some embodiments, particles may be formed using an oil-in-water (o/w) or water-in-oil-in-water (w/o/w) solvent evaporation process or using a nanoprecipitation method.

The w/o/w solvent evaporation process is described, for example, in O'Hagan et al., *Vaccine* (1993) 11:965-969, Jeffery et al., *Pharm. Res.* (1993) 10:362, and WO 00/06123 to O'Hagan et al. In general, a polymer of interest, such as PLG, is dissolved in an organic solvent, such as dimethylchloride (also called methylene chloride and dichloromethane), ethyl acetate, acetonitrile, acetone, chloroform, and the like. The polymer solution is then combined with a first volume of aqueous solution and emulsified to form a water-in-oil emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution, among others. Typically, the volume ratio of polymer solution to aqueous solution ranges from about 5:1 to about 20:1, more typically about 10:1. Emulsification is conducted using any equipment appropriate for this task, and is typically a high-shear device such as, e.g., a homogenizer. A volume of the water-in-oil emulsion is then combined with a larger second volume of an aqueous solution, which typically contains a surfactant, for instance, an uncharged surfactant (e.g., PVA (polyvinyl alcohol), povidone (also known as polyvinylpyrrolidone or PVP), sorbitan esters, polysorbates, polyoxyethylated glycol monoethers, polyoxyethylated alkyl phenols, or poloxamers, among others), a cationic surfactant (discussed below) or an anionic surfactant (discussed below). The volume ratio of aqueous solution to the water-in-oil emulsion typically ranges from about 2:1 to 10:1, more typically about 4:1. This mixture is then homogenized to produce a stable w/o/w double emulsion. Organic solvents are then evaporated to yield particles. Particles manufactured in the presence of charged surfactants, such as anionic or cationic surfactants, can yield particles with a surface having a net negative or a net positive charge, which can adsorb a wide variety of molecules. For example, particles manufactured with anionic surfactants, such as sodium dodecyl sulfate (SDS), e.g., SDS-PLG particles, may adsorb positively charged species, for example, polypeptide-containing species such as proteins. Similarly, particles manufactured with cationic surfactants, such as CTAB, e.g., PLG/CTAB particles, may adsorb negatively charged species, for example, polynucleotide-containing species such as DNA, RNA or oligonucleotides.

The oil-in-water (o/w) solvent evaporation process is similar to the w/o/w solvent evaporation process described in the prior paragraph. In general, a polymer of interest, such as PLG, is dissolved in an organic solvent, such as dimethylchloride (also called methylene chloride and dichloromethane), ethyl acetate, acetonitrile, acetone, chloroform, and the like. The polymer solution is then combined with a volume of aqueous solution and emulsified to form an o/w emulsion. The aqueous solution can be, for example, water for injection, deionized water, normal saline, a buffered solution, for example, phosphate-buffered saline (PBS) or a sodium citrate/ethylenediaminetetraacetic acid (sodium citrate/ETDA) buffer solution, among others. The aqueous solution typically contains a surfactant, for instance, an uncharged surfactant, a cationic surfactant or an anionic surfactant. Typically, the volume ratio of the aqueous solution to the polymer solution ranges from about 1:1 to about 25:1, more typically about 8:1. Emulsification is conducted using any equipment appropriate for this task, and is typically a high-shear device such as, e.g., a homogenizer. Organic solvents are then evaporated to yield particles. As above, particles manufactured in the presence of charged surfactants, such as anionic or cationic surfactants, can yield particles with a surface having a net negative or a net positive charge, which can adsorb a wide variety of molecules.

The nanoprecipitation method, also referred to as the solvent displacement method, is another example of a suitable method for forming particles for use in the invention. See, e.g., European Patent No. 0274961B1 entitled "Process for the preparation of dispersible colloidal systems of a substance in the form of nanocapsules," Devissaguet et al., U.S. Pat. No. 5,049,322 by the same title, Fessi et al., U.S. Pat. No. 5,118,528, entitled "Process for the preparation of dispersible colloidal systems of a substance in the form of microparticles," and Wendorf et al., WO 2008/051245, entitled "Nanoparticles for use in Immunogenic compositions." In this technique, for instance, a polymer may be dissolved in an organic solvent (e.g., a hydrophilic organic solvent such as acetone, ethanol, etc.). The resulting organic solution may then be combined with a further solvent, which is miscible with the organic solvent while being a non-solvent for the polymer, typically an aqueous solution. The aqueous solution can be, for example, deionized water, normal saline, a buffered solution, such as for example, phosphate-buffered saline (PBS) or a sodium citrate/ethylenediaminetetraacetic acid (sodium citrate/EDTA) buffer solution. The organic solution and aqueous solution may then be combined in suitable relative volumes (e.g. typically from 1:2 to 2:1, more typically about 1:1). For example, the organic solution may be poured or injected into the non-solvent while stirring, or vice versa. By selecting a system in which the polymer is soluble in the organic solvent, while being significantly less soluble in the miscible blend of the organic solvent with the non-solvent, a suspension of particles may be formed virtually instantaneously. Subsequently, the organic solvent can be eliminated from the suspension, for example, by evaporation.

In some embodiments, it is desirable to provide one or more additional species (in addition to polymer), which may be associated with the interior (e.g., entrapped) and/or surface (e.g. by adsorption, covalent attachment, co-lyophilization, etc.) of the particles or may be non-associated with the particles. Such additional species can include, for instance, agents to adjust tonicity or pH, cryoprotective agents, particle charge inducing agents (e.g., charged surfactants, charged polymers, etc.), immunological adjuvants (e.g., a benzonaphthyridine compound or other adjuvant), antigens, and so forth.

Such additional species may be provided during the particle formation process. In the above described particle formation techniques (e.g., w/o/w solvent evaporation, o/w solvent evaporation, nanoprecipitation, etc.), the organic and/or aqueous solutions employed can thus further contain various additional species as desired. For example, these additional species may be added (a) to an organic solution, if in oil-soluble or oil-dispersible form or (b) to an aqueous solution, if in water-soluble or water-dispersible form. For instance, in Example 198 below, a benzonaphthyridine compound is added to the organic solution in order to encapsulate the benzonaphthyridine compound.

In other embodiments, one or more additional species may be added subsequent to particle formation (typically subsequent to organic solvent removal, as well as subsequent to washing steps, if any). These additional species are frequently added to the particles as an aqueous solution or dispersion. These species can, for instance, be in solution and/or accumulate at the particle-solution interface, for example, being adsorbed at the particle surface.

Once a suitable particle composition comprising particles is formed (e.g., using the above-described or other techniques), it may be lyophilized for future use. In various embodiments, one or more additional species is/are co-lyophilized with the particles. For instance, in Example 199 below, a benzonaphthyridine compound and three MenB antigens are co-lyophilized with the particles (see Vials 4 and 5).

E. ANTIGENS

Antigens for use with the immunogenic compositions provided herein include, but are not limited to, one or more of the following antigens set forth below, or antigens derived from one or more of the pathogens set forth below. Typical wt/wt ratios of antigen to polymer(s) in the compositions of the present invention range from 0.05% to 25% by weight, for example, ranging from 0.05% to 0.1% to 0.25% to 0.5% to 1% to 2.5% to 5% to 10% to 25%, among other possibilities.

Bacterial Antigens

Bacterial antigens suitable for use in immunogenic compositions provided herein include, but are not limited to, proteins, polysaccharides, lipopolysaccharides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis:* Meningitidis antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments meningitides protein antigens are be selected from adhesions, autotransporters, toxins, Fe acquisition proteins, and membrane associated proteins (preferably integral outer membrane protein).

*Streptococcus pneumoniae:* Streptococcus pneumoniae antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. 1 mm. (2006) 74:2453-2456, Hoskins et al., J. Bacteriol. (2001) 183: 5709-5717, Adamou et al., Infect. Immun (2001) 69(2): 949-958, Briles et al., J. Infect. Dis. (2000) 182:1694-1701, Talkington et al., Microb. Pathog. (1996) 21(1): 17-22, Bethe et al., FEMS Microbiol. Lett. (2001) 205(1):99-104, Brown et al., Infect. Immun (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis: Moraxella* antigens include, but are not limited to, antigens identified in WO 02/18595 and WO 99/58562, outer membrane protein antigens (HMW-OMP), C-antigen, and/or LPS.

*Bordetella pertussis:* Pertussis antigens include, but are not limited to, *pertussis* holotoxin (PT) and filamentous haemagglutinin (FHA) from *B. pertussis*, optionally also combination with pertactin and/or agglutinogens 2 and 3.

*Burkholderia: Burkholderia* antigens include, but are not limited to *Burkholderia mallei, Burkholderia pseudomallei* and *Burkholderia cepacia*.

*Staphylococcus aureus:* Staph aureus antigens include, but are not limited to, a polysaccharide and/or protein from *S. aureus. S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis: S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen.*

*Clostridium botulinums* (Botulism): Botulism antigens include, but are not limited to, those derived from *C. botulinum.*

*Cornynebacterium diphtheriae* (Diphtheria): Diphtheria antigens include, but are not limited to, diphtheria toxin, preferably detoxified, such as $CRM_{197}$. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen.

*Pseudomonas aeruginosa: Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Legionella pneumophila.* Bacterial antigens derived from *Legionella pneumophila.*

*Coxiella burnetii.* Bacterial antigens derived from *Coxiella burnetii.*

*Brucella.* Bacterial antigens derived from *Brucella*, including but not limited to, *B. abortus, B. canis, B. melitensis, B. neotomae, B. ovis, B. suis* and *B. pinnipediae.*

*Francisella.* Bacterial antigens derived from *Francisella*, including but not limited to, *F. novicida, F. philomiragia* and *F. tularensis.*

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisserria gonorrhoeae:* Gonorrhoeae antigens include, but are not limited to, Por (or porin) protein, such as PorB (see Zhu et al., *Vaccine* (2004) 22:660-669), a transferring binding protein, such as TbpA and TbpB (See Price et al., Infection and Immunity (2004) 71(1): 277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes $L_1, L_2$ & $L_3$ (associated with Lymphogranuloma venereum), and serotypes, D-K. In certain embodiments, chlamydia trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H. pylori* antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VlsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens or protein antigens of any of the above. Other bacterial antigens used in the immunogenic compositions provided herein include, but are not limited to, an outer membrane vesicle (OMV) preparation. Additionally, other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques,* 1996 and *CRC, Chemistry of Protein Conjugation and Cross-Linking,* 1993.

In certain embodiments useful for the treatment or prevention of *Neisseria* infection and related diseases and disorders, recombinant proteins from *N. meningitidis* for use in the immunogenic compositions provided herein may be found in WO99/24578, WO99/36544, WO99/57280, WO00/22430, WO96/29412, WO01/64920, WO03/020756, WO2004/048404, and WO2004/032958. Such antigens may be used alone or in combinations. Where multiple purified proteins are combined then it is helpful to use a mixture of 10 or fewer (e.g. 9, 8, 7, 6, 5, 4, 3, 2) purified antigens.

A particularly useful combination of antigens for use in the immunogenic compositions provided herein is disclosed in Giuliani et al. (2006) *Proc Natl Acad Sci USA* 103(29): 10834-9 and WO2004/032958, and so an immunogenic composition may include 1, 2, 3, 4 or 5 of: (1) a 'NadA' protein (aka GNA1994 and NMB1994); (2) a 'fHBP' protein (aka '741', LP2086, GNA1870, and NMB1870); (3) a '936' protein (aka GNA2091 and NMB2091); (4) a '953' protein (aka GNA1030 and NMB1030); and (5) a '287' protein (aka GNA2132 and NMB2132). Other possible antigen combinations may comprise a transferrin binding protein (e.g. TbpA and/or TbpB) and an Hsf antigen. Other possible purified antigens for use in the immunogenic compositions provided herein include proteins comprising one of the following amino acid sequences: SEQ ID NO:650 from WO99/24578; SEQ ID NO:878 from WO99/24578; SEQ ID NO:884 from WO99/24578; SEQ ID NO:4 from WO99/36544; SEQ ID NO:598 from WO99/57280; SEQ ID NO:818 from WO99/57280; SEQ ID NO:864 from WO99/57280; SEQ ID NO:866 from WO99/57280; SEQ ID NO:1196 from WO99/57280; SEQ ID NO:1272 from WO99/57280; SEQ ID NO:1274 from WO99/57280; SEQ ID NO:1640 from WO99/57280; SEQ ID NO:1788 from WO99/57280; SEQ ID NO:2288 from WO99/57280; SEQ ID NO:2466 from WO99/57280; SEQ ID NO:2554 from WO99/57280; SEQ ID NO:2576 from WO99/57280; SEQ ID NO:2606 from WO99/57280; SEQ ID NO:2608 from WO99/57280; SEQ ID NO:2616 from WO99/57280; SEQ ID NO:2668 from WO99/57280; SEQ ID NO:2780 from WO99/57280; SEQ ID NO:2932 from WO99/57280; SEQ ID NO:2958 from WO99/57280; SEQ ID NO:2970 from WO99/57280; SEQ ID NO:2988 from WO99/57280 (each of the forgoing amino acid sequences is hereby incorporated by reference from the cited document), or a polypeptide comprising an amino acid sequence which: (a) has 50% or more identity (e.g., 60%, 70%, 80%, 90%, 95%, 99% or more) to said sequences; and/or (b) comprises a fragment of at least n consecutive amino acids from said sequences, wherein n is 7 or more (e.g., 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g., 2, 3, 4, 5, 6) of these polypeptides may be included in the immunogenic compositions.

The fHBP antigen falls into three distinct variants (WO2004/048404). An *N. meningitidis* serogroup vaccine based upon the immunogenic compositions disclosed herein utilizing one of the compounds disclosed herein may include a single fHBP variant, but is will usefully include an fHBP from each of two or all three variants. Thus the immunogenic composition may include a combination of two or three different purified fHBPs, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3.

```
                                                    SEQ ID NO: 1
VAADIGAGLADALTAPLDKHDKGLQSLTLDQSVRKNEKLKLAAQGA
EKTYGNGDSLNTGKLKNDKVSRFDFIRQIEVDGQLITLESGEFQVY
KQSHSALTAFQTEQIQDSEHSGKMVAKRQFRIGDIAGEHTSFDKLP
EGGRATYRGTAFGSDDAGGKLTYTIDFAAKQGNGKIEHLKSPELNV
DLAAADIKPDGKRHAVISGSVLYNQAEKGSYSLGIFGGKAQEVAGS
AEVKTVNGIRHIGLAAKQ

SEQ ID NO: 2
VAADIGAGLADALTAPLDHKDKSLQLSTLDQSVRKNEKLKLAAQGA
EKTYGNGDSLNTGKLKNDKVSRFDFIRQIEVDGQLITLESGEFQIY
KQDHSAVVALQIEKINNPDKIDSLINQRSFLVSGLGGEHTAFNQLP
DGKAEYHGKAFSSDDAGGKLTYTIDFAAKQGHGKIEHLKTPEQNVE
LAAAELKADEKSHAVILGDTRYGSEEKGTYHLALFGDRAQEIAGSA
TVKIGEKVHEIGIAGKQ

SEQ ID NO: 3
VAADIGTGLADALTAPLDHKDKGLKSLTLEDSIPQNGFTLTLSAQGA
EKTFKAGDKDNSLNTGKLKNDKISRFDFVQKIEVDGQTITLASGEF
QIYKQNHSAVVALQIEKINNPDKTDSLINQRSFLVSGLGGEHTAFN
QLPGGKAEYHGHAFSSDDPNGRLHYSIDFTKKQGYGRIEHLKTLEQ
NVELAAAELKADEKSHAVILGDTRYGSEEKGTYHLALFGDRAQEIA
GSATVKIGEKVHEIGIAGKQ.
```

The value of a is at least 85, e.g., 86, 87, 88, 89, 90, 91, 92, 93, 94, 95, 96, 97, 98, 99, 99.5, or more. The value of b is at least 85, e.g., 86, 87, 88, 89, 90, 91, 92, 93, 94, 95, 96, 97, 98, 99, 99.5, or more. The value of c is at least 85, e.g., 86, 87, 88, 89, 90, 91, 92, 93, 94, 95, 96, 97, 98, 99, 99.5, or more. The values of a, b and c are not intrinsically related to each other.

The value of x is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

In some embodiments, the immunogenic compositions as disclosed herein will include fHBP protein(s) that are lipidated, e.g., at a N-terminal cysteine. In other embodiments they will not be lapidated.

A useful immunogenic composition as disclosed herein includes purified proteins comprises a mixture of: (i) a first polypeptide having amino acid sequence SEQ ID NO: 4; (ii) a second polypeptide having amino acid sequence SEQ ID NO: 5; and (iii) a third polypeptide having amino acid sequence SEQ ID NO: 6. See Giuliani et al. (2006) *Proc Natl Acad Sci USA* 103(29):10834-9 and WO2004/032958. A useful immunogenic composition as disclosed herein includes purified proteins comprises a mixture of: (i) a first polypeptide having at least a % sequence identity to amino acid sequence SEQ ID NO: 4; (ii) a second polypeptide having at least b % sequence identity to amino acid sequence SEQ ID NO: 5; and (iii) a third polypeptide having at least a % sequence identity to amino acid sequence SEQ ID NO: 6.

```
                                                    SEQ ID NO: 4
MASPDVKSADTLSKPAAPVVSEKETEAKEDAPQAGSQGQGAPSQGG
QDMAAVSEENTGNGGAAATDKPKNEDEGAQNDMPQNAADTDSLTPN
HTPASNMPAGNMENQAPDAGESEQPANQPDMANTADGMQGDDPSAG
GENAGNTAAQGTNQAENNQTAGSQNPASSTNPSATNSGGDFGRTNV
GNSVVIDGPSQNITLTHCKGDSCSGNNGLDEEVQLKSEFEKLSDAD
KISNYKKDGKNDGKNDKFVGLVADSVQMKGINQYIIFYKPKPTSFA
RFRRSARSRRSLPAEMPLIPVNQADTLIVDGEAVSLTGHSGNIFAP
EGNYRYLTYGAEKLPGGSYALRVQGEPSKGEMLAGTAVYNGEVLHF
HTENGRPSPSRGRFAAKVDFGSKSVDGIIDSGDGLHMGTQKFKAAI
DGNGFKGTWTENGGGDVSGKFYGPAGEEVAGKYSYRPTDAEKGGFG
VFAGKKEQDGSGGGGATYKVDEYHANARFAIDHFNTSTNVGGFYGL
TGSVEFDQAKRDGKIDITIPVANLQSGSQHFTDHLKSADIFDAAQY
PDIRFVSTKFNFNGKKLVSVDGNLTMHGKTAPVKLKAEKFNCYQSP
MAKTEVCGGDFSTTIDRTKWGVDYLVNVGMTKSVRIDIQIEAAKQ

SEQ ID NO: 5
MVSAVIGSAAVGAKSAVDRRTTGAQTDDNVMALRIETTARSYLRQN
NQTKGYTPQISVVGYNRHLLLLGQVATEGEKQFVGQIARSEQAAEG
VYNYITVASLPRTAGDIAGDTWNTSKVRATLLGISPATQARVKIVT
YGNVTYVMGILTPEEQAQITQKVSTTVGVQKVITLYQNYVQRGSGG
GGVAADIGAGLADALTAPLKHKDKGLQSLTLDQSVRKNEKLKLAAQ
GAEKTYGNGDSLNTGLKLKDKVSRFDFIRQIEVDGQLITLESGEFQ
VYKQSHSALTAFQTEQIQDSEHSGKMVAKRQFRIGDIAGEHTSFDK
LPEGGRATYRGTAFGSDDAGGKLTYTIDFAAKQGNGKIEHLKSPEL
NVDLAAADIKPDGKRHAVISGSVLYNQAEKGSYSLGIFGGKAQEVA
GSAEVKTVNGIRHIGLAAKQ

SEQ ID NO: 6
ATNDDDVKKAATVAIAAAYNNGQIENGFKAGETIYDIDEDGTITKK
DATAADVEADDFKGLGLKKVVTNLTKTVNENKQNVDAKVKAAESIE
KLTTKLADTDAALADTDAALDATTNALNKLGENITTFAEETKTNIV
KIDEKLEAVADTVDKHAEAFNDIADSLDETNTKADEAVKTANEAKQ
TAEEETKQNVDAKVKAAETAAGKAEAAAGTANTAADKAEAVAAKVTD
IKADIATNKDNIAKKANSADVYTREESDSKFVRIDGLNATTEKLDT
RLASAEKSIADHDTRLNGLDKTVSDLRKETRQGLAEQAALSGLFQP
YNVG.
```

Bacterial Vesicle Antigens

The immunogenic compositions as disclosed herein may include outer membrane vesicles. Such outer membrane vesicles may be obtained from a wide array of pathogenic bacteria and used as antigenic components of the immunogenic compositions as disclosed herein. Vesicles for use as antigenic components of such immunogenic compositions include any proteoliposomic vesicle obtained by disrupting a bacterial outer membrane to form vesicles therefrom that include protein components of the outer membrane. Thus the term includes OMVs (sometimes referred to as 'blebs'), microvesicles (MVs, see, e.g., WO02/09643) and 'native OMVs' ('NOMVs' see, e.g., Katial et al. (2002) *Infect. Immun.* 70:702-707) Immunogenic compositions as disclosed herein that include vesicles from one or more pathogenic bacteria can be used in the treatment or prevention of infection by such pathogenic bacteria and related diseases and disorders.

MVs and NOMVs are naturally-occurring membrane vesicles that form spontaneously during bacterial growth and are released into culture medium. MVs can be obtained by culturing bacteria such as *Neisseria* in broth culture medium, separating whole cells from the smaller MVs in the broth culture medium (e.g., by filtration or by low-speed centrifugation to pellet only the cells and not the smaller vesicles), and then collecting the MVs from the cell-depleted medium (e.g., by filtration, by differential precipitation or aggregation of MVs, by high-speed centrifugation to pellet the MVs). Strains for use in production of MVs can generally be selected on the basis of the amount of MVs produced in culture (see, e.g., U.S. Pat. No. 6,180,111 and WO01/34642 describing *Neisseria* with high MV production).

OMVs are prepared artificially from bacteria, and may be prepared using detergent treatment (e.g., with deoxycholate), or by non detergent means (see, e.g., WO04/019977). Methods for obtaining suitable OMV preparations are well known in the art. Techniques for forming OMVs include treating bacteria with a bile acid salt detergent (e.g., salts of lithocholic acid, chenodeoxycholic acid, ursodeoxycholic acid, deoxycholic acid, cholic acid, ursocholic acid, etc., with sodium deoxycholate (EP0011243 and Fredriksen et al. (1991) *NIPH Ann.* 14(2):67-80) being preferred for treating *Neisseria*) at a pH sufficiently high not to precipitate the detergent (see, e.g., WO01/91788). Other techniques may be performed substantially in the absence of detergent (see, e.g., WO04/019977) using techniques such as sonication, homogenisation, microfluidisation, cavitation, osmotic shock, grinding, French press, blending, etc. Methods using no or low detergent can retain useful antigens such as NspA in Neisserial OMVs. Thus a method may use an OMV extraction buffer with about 0.5% deoxycholate or lower, e.g., about 0.2%, about 0.1%, <0.05% or zero.

A useful process for OMV preparation is described in WO05/004908 and involves ultrafiltration on crude OMVs, rather than instead of high speed centrifugation. The process may involve a step of ultracentrifugation after the ultrafiltration takes place.

Vesicles can be prepared from any pathogenic strain such as *Neisseria minigtidis* for use with the invention. Vessicles from Neisserial meningitidis serogroup B may be of any serotype (e.g., 1, 2a, 2b, 4, 14, 15, 16, etc.), any serosubtype, and any immunotype (e.g., L1; L2; L3; L3,3,7; L10; etc.). The meningococci may be from any suitable lineage, including hyperinvasive and hypervirulent lineages, e.g., any of the following seven hypervirulent lineages: subgroup I; subgroup III; subgroup IV 1; ET 5 complex; ET 37 complex; A4 cluster; lineage 3. These lineages have been defined by multilocus enzyme electrophoresis (MLEE), but multilocus sequence typing (MLST) has also been used to classify meningococci, e.g., the ET 37 complex is the ST 11 complex by MLST, the ET 5 complex is ST-32 (ET-5), lineage 3 is ST 41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles included in the immunogenic compositions disclosed herein may be prepared from wild type pathogenic strains such as *N. meningitidis* strains or from mutant strains. By way of example, WO98/56901 discloses preparations of vesicles obtained from *N. meningitidis* with a modified fur gene. WO02/09746 teaches that nspA expression should be up regulated with concomitant porA and cps knockout. Further knockout mutants of *N. meningitidis* for OMV production are disclosed in WO02/0974, WO02/062378, and WO04/014417. WO06/081259 discloses vesicles in which fHBP is upregulated. Claassen et al. (1996) 14(10): 1001-8, disclose the construction of vesicles from strains modified to express six different PorA subtypes. Mutant *Neisseria* with low endotoxin levels, achieved by knockout of enzymes involved in LPS biosynthesis, may also be used (see, e.g., WO99/10497 and Steeghs et al. (2001) i20:6937-6945). These or others mutants can all be used with the invention.

Thus *N. meningitidis* serogroup B strains included in the immunogenic compositions disclosed herein may in some embodiments express more than one PorA subtype. Six valent and nine valent PorA strains have previously been constructed. The strain may express 2, 3, 4, 5, 6, 7, 8 or 9 of PorA subtypes: P1.7,16; P1.5-1, 2-2; P1,19,15-1; P1.5-2,10; P1.12 1,13; P1.7-2,4; P1.22,14; P1.7-1,1 and/or P1.18-1,3,6. In other embodiments a strain may have been down regulated for PorA expression, e.g., in which the amount of PorA has been reduced by at least 20% (e.g., >30%, >40%, >50%, >60%, >70%, >80%, >90%, >95%, etc.), or even knocked out, relative to wild type levels (e.g., relative to strain H44/76, as disclosed in WO03/105890).

In some embodiments *N. meningitidis* serogroup B strains may over express (relative to the corresponding wild-type strain) certain proteins. For instance, strains may over express NspA, protein 287 (WO01/52885—also referred to as NMB2132 and GNA2132), one or more fHBP (WO06/081259 and U.S. Pat. Pub. 2008/0248065—also referred to as protein 741, NMB1870 and GNA1870), TbpA and/or TbpB (WO00/25811), Cu,Zn-superoxide dismutase (WO00/25811), etc.

In some embodiments *N. meningitidis* serogroup B strains may include one or more of the knockout and/or over expression mutations. Preferred genes for down regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB (WO01/09350); (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB (WO02/09746); (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB (WO02/062378); and (d) CtrA, CtrB, CtrD, FrpB, OpA, OpC, PilC, PorB, SiaD, SynA, SynB, and/or SynC (WO04/014417).

Where a mutant strain is used, in some embodiments it may have one or more, or all, of the following characteristics: (i) down regulated or knocked-out LgtB and/or GalE to truncate the meningococcal LOS; (ii) up regulated TbpA; (iii) up regulated Hsf; (iv) up regulated Omp85; (v) up regulated LbpA; (vi) up regulated NspA; (vii) knocked-out PorA; (viii) down regulated or knocked-out FrpB; (ix) down regulated or knocked-out Opa; (x) down regulated or knocked-out Opc; (xii) deleted cps gene complex. A truncated LOS can be one that does not include a sialyl-lacto- N-neotetraose epitope, e.g., it might be a galactose-deficient LOS. The LOS may have no α chain.

If LOS is present in a vesicle then it is possible to treat the vesicle so as to link its LOS and protein components ("intra-bleb" conjugation (WO04/014417)).

The immunogenic compositions as disclosed herein may include mixtures of vesicles from different strains. By way of example, WO03/105890 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. WO06/024946 discloses useful combinations of different vesicles. A combination of vesicles from strains in each of the L2 and L3 immunotypes may be used in some embodiments.

Vesicle-based antigens can be prepared from *N. meningitidis* serogroups other than serogroup B (e.g., WO01/91788 discloses a process for serogroup A). The immunogenic compositions disclosed herein accordingly can include vesicles prepared serogroups other than B (e.g. A, C, W135 and/or Y) and from bacterial pathogens other than *Neisseria*.

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, and Virus Like Particles (VLPs). In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxyiridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Parechovirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limted to, those derived from rhinovirus. In certain embodiments, the rhinovirus antigens are selected from one or more of the following Capsid proteins: VP0, VP1, VP2, VP3 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J, K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$, $HIV-1_{SF162}$, $HIV-1_{TV1}$, $HIV-1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an *Orthoreovirus*, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Bocavirus and Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp 65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30 and US34A. CMV antigens may also be fusions of one or more CMV proteins, such as, by way of example only, pp 65/IE1 (Reap et al., *Vaccine* (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Arenavirus: Viral antigens include, but are not limited to, those derived from Arenaviruses.

Further provided are antigens, compositions, methods, and microbes included in *Vaccines*, 4th Edition (Plotkin and Orenstein ed. 2004); *Medical Microbiology* 4th Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the immunogenic compositions provided herein.

Fungal Antigens

Fungal antigens for use in the immunogenic compositions provided herein include, but are not limited to, those derived from one or more of the fungi set forth below.

Fungal antigens are derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum*, *Trichophyton violaceum*, and/or *Trichophyton faviforme*; and Fungal pathogens are derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida*

*kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microspiridium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Protazoan Antigens/Pathogens

Protazoan antigens/pathogens for use in the immunogenic compositions provided herein include, but are not limited to, those derived from one or more of the following protozoa: *Entamoeba histolytica, Giardia lambli, Cryptosporidium parvum, Cyclospora cayatanensis* and *Toxoplasma.*

Plant Antigens/Pathogens

Plant antigens/pathogens for use in the immunogenic compositions provided herein include, but are not limited to, those derived from *Ricinus communis.*

STD Antigens

In certain embodiments, the immunogenic compositions provided herein include one or more antigens derived from a sexually transmitted disease (STD). In certain embodiments, such antigens provide for prophylactis for STD's such as chlamydia, genital herpes, hepatitis (such as HCV), genital warts, gonorrhea, syphilis and/or chancroid. In other embodiments, such antigens provide for therapy for STD's such as chlamydia, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from *Neiserria gonorrhoeae, Chlamydia trachomatis, Treponema pallidum, Haemophilus ducreyi, E. coli,* and *Streptococcus agalactiae.* Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). In certain embodiments, the respiratory antigens are derived from a bacteria which causes respiratory disease, such as, by way of example only, *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

Pediatric Vaccine Antigen

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Corynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific antigens derived from these pathogens are described above.

Antigens Suitable for Use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens, are used in conjunction with the immunogenic compositions provided herein for the treatment of cancer. In certain embodiments, the, carrier proteins, such as $CRM_{197}$, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. influenzae* type B and serogroups B, C, W135 & Y of *N. meningitides*. In certain embodiments the immunogenic compositions containing at least one compound of Formula (I) include *H. influenzae* type B and serogroups A, B, C, W135 & Y of *N. meningitides*.

In certain embodiments the immunogenic compositions containing at least one compound of Formula (I) include *S. pneumoniae* and serogroups C, W135 & Y of *N. meningitides*. In certain embodiments the immunogenic compositions containing at least one compound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. influenzae* type B, *S. pneumoniae* and serogroups C, W135 & Y of *N. meningitides*. In certain embodiments the immunogenic compositions containing at least one compound of Formula (I) include *H. influenzae* type B, *S. pneumoniae* and serogroups A, C, W135 & Y of *N. meningitides*. In certain embodiments the immunogenic compositions containing at least one compound of Formula (I) include *H. influenzae* type B, *S. pneumoniae* and serogroups B, C, W135 & Y of *N. meningitides*. In certain embodiments the immunogenic compositions containing at least one compound of Formula (I) include *H. influenzae* type B, *S. pneumoniae* and serogroups A, B, C, W135 & Y of *N. meningitides*.

It is readily apparent that the present invention can be used to raise antibodies to a large number of antigens for diagnostic and immunopurification purposes, as well as to prevent or treat a wide variety of diseases.

E. SUPPLEMENTAL IMMUNOLOGICAL ADJUVANTS (IN ADDITION TO BENZONAPHTHYRIDINE COMPOUNDS)

Supplemental immunological adjuvants (in addition to benzonaphthyridine compounds) may be used to further enhance the effectiveness of the immunogenic compositions of the invention. For example, such supplemental immunological adjuvants may be administered concurrently with the immunogenic compositions of the present invention, e.g., in the same composition or in separate compositions. Such adjuvants may also be administered prior or subsequent to the immunogenic compositions of the present invention.

Examples of such supplemental immunological adjuvants include: saponin formulations; virosomes and virus-like particles; bacterial or microbial derivatives; immunostimulatory oligonucleotides; human immunomodulators; bioadhesives and mucoadhesives; liposomes; polyoxyethylene ether and polyoxyethylene ester formulations; polyphosphazene (PCPP); muramyl peptides; and imidazoquinolone compounds.

Saponins are a heterologous group of sterol glycosides and triterpenoid glycosides that are found in the bark, leaves, stems, roots and even flowers of a wide range of plant species. Saponin formulations suitable for use as supplemental immunological adjuvants include, but are not limited to, saponins from the bark of the *Quillaja saponaria* Molina tree, from *Smilax ornata* (sarsaprilla), *Gypsophilla paniculata* (brides veil), and *Saponaria officianalis* (soap root). In certain embodiments, saponin formulations suitable for use as supplemental immunological adjuvants include, but are not limited to, purified formulations including, but are not limited to, QS7, QS17, QS18, QS21, QH-A, QH-B and QH-C. QS21 is marketed as STIMULOM™. In other embodiments, saponin formulations include sterols, cholesterols and lipid formulations, such as unique particles formed by the combinations of saponins and cholesterols called immunostimulating complexes (ISCOMs). In certain embodiments, the ISCOMs also include a phospholipid such as phosphatidylethanolamine or phosphatidylcholine. Any known saponin can be used in ISCOMs. In certain embodiments, the ISCOM includes one or more of QuilA, QHA & QHC. In other embodiments, the ISCOMS are optionally devoid of an additional detergent.

Virosomes and virus-like particles (VLPs) suitable for use as supplemental immunological adjuvants include, but are not limited to, one or more proteins from a virus optionally combined or formulated with a phospholipid. Such virosomes and VLPs are generally non-pathogenic, non-replicating and generally do not contain any of the native viral genome. In certain embodiments, the viral proteins are recombinantly produced, while in other embodiments the viral proteins are isolated from whole viruses.

The viral proteins suitable for use in virosomes or VLPs include, but are not limited to, proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

Bacterial or microbial derivatives suitable for use as supplemental immunological adjuvants include, but are not limited to, bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Such non-toxic derivatives of LPS include, but are not limited to, monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives (e.g. RC-529). Lipid A derivatives include, but are not limited to, derivatives of lipid A from *Escherichia coli* (e.g. OM-174).

Immunostimulatory oligonucleotides suitable for use as supplemental immunological adjuvants include, but are not limited to, nucleotide sequences containing a CpG motif (a dinucleotide sequence containing an unmethylated cytosine linked by a phosphate bond to a guanosine). Such CpG sequences can be double-stranded or single-stranded. In certain embodiments, such nucleotide sequences are double-stranded RNAs or oligonucleotides containing palindromic or poly(dG) sequences. In other embodiments, the CpG's include nucleotide modifications/analogs such as phosphorothioate modifications.

In certain embodiments the CpG sequence are directed to TLR9, and in certain embodiments the motif is GTCGTT or TTCGTT. In certain embodiments the CpG sequence is specific for inducing a Th1 immune response, such as, by way of example only, a CpG-A ODN, or in other embodiments the CpG sequence is more specific for inducing a B cell response, such as, by way of example only, a CpG-B ODN. In certain embodiments the CpG is a CpG-A ODN.

In certain embodiments the CpG oligonucleotide is constructed so that the 5' end is accessible for receptor recognition. In other embodiments two CpG oligonucleotide sequences are optionally attached at their 3' ends to form "immunomers".

In certain embodiments, an adjuvant based around immunostimulatory oligonucleotides known as IC-31™ is suitable for use as a supplemental immunological adjuvant. In certain embodiments, a supplemental immunological adjuvant suitable for use in the immunogenic compositions described herein includes a mixture of (i) an oligonucleotide (such as, by way of example only, between 15-40 nucleotides) including at least one (and preferably multiple) CpI motifs (such as, by way of example only, a cytosine linked to an inosine to form a dinucleotide), and (ii) a polycationic polymer, such as, by way of example only, an oligopeptide (such as, by way of example only, between 5-20 amino acids) including at least one (and preferably multiple) Lys-Arg-Lys tripeptide sequence(s). In certain embodiments, the oligonucleotide is a deoxynucleotide comprising 26-mer sequence 5'-(IC)$_{13}$-3'. In other embodiments, the polycationic polymer is a peptide comprising 11-mer amino acid sequence KLKLLLLLKLK.

In certain embodiments, bacterial ADP-ribosylating toxins and detoxified derivatives thereof are suitable for use as supplemental immunological adjuvants in the immunogenic compositions described herein. In certain embodiments, such proteins are derived from *E. coli* (*E. coli* heat labile enterotoxin "LT"), cholera ("CT"), or pertussis ("PT"). In other embodiments, the toxin or toxoid is in the form of a holotoxin, comprising both A and B subunits. In other embodiments, the A subunit contains a detoxifying mutation; whereas the B subunit is not mutated. In other embodiments, the adjuvant is a detoxified LT mutant such as LT-K63, LT-R72, and LT-G192.

The human immunomodulators suitable for use as supplemental immunological adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

The bioadhesives and mucoadhesives suitable for use as supplemental immunological adjuvants in the immunogenic compositions described herein include, but are not limited to, esterified hyaluronic acid microspheres, and cross-linked derivatives of poly(acrylic acid), polyvinyl alcohol, polyvinyl pyrollidone, polysaccharides and carboxymethylcellulose. In certain embodiments, chitosan and derivatives thereof are used as supplemental immunological adjuvants in the immunogenic compositions described herein.

The polyoxyethylene ether and polyoxyethylene ester formulations suitable for use as supplemental immunological adjuvants include, but are not limited to, polyoxyethylene sorbitan ester surfactants in combination with an octoxynol, and polyoxyethylene alkyl ethers or ester surfactants in combination with at least one additional non-ionic surfactant such as an octoxynol. In certain embodiments, the polyoxyethylene ethers are selected from polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

The muramyl peptides suitable for use as supplemental immunological adjuvants include, but are not limited to, N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-s-n-glycero-3-hydroxyphosphoryloxy)-ethylamine MTP-PE).

F. FURTHER SUPPLEMENTAL COMPONENTS

As previously indicated, the compositions of the present invention may optionally include a variety of supplemental components. In addition to the supplemental immunological adjuvants described in the prior section, such optional supplemental components further include pharmaceutically acceptable excipients, for example, cryoprotective agents, biological buffering substances, tonicity adjusting agents and delivery vehicles, among other species.

Optional supplemental components can be, for example: (a) established within the polymeric particles, for example, entrapped in the polymeric particles, including separate populations of polymeric particles, (b) attached to the polymeric particles, for example, adsorbed or conjugated to the surface of the polymeric particles, including separate populations of polymeric particles, or (c) otherwise associated with the polymeric particles to varying degrees, for example, admixed with the polymeric particles in a liquid dispersion, admixed with the polymeric particles in a solid composition (e.g., co-lyophilized with the polymeric particles), and so forth.

Cryoprotective agents are particularly desirable, for instance, where sterile dry particle compositions are formed using a freeze-drying process (e.g., lyophilization). Examples of cryoprotective agents include polyols, carbohydrates and combinations thereof, among others.

As used herein, a "cryoprotective agent" is an agent that protects a composition from experiencing adverse effects upon freezing and thawing. For example, in the present invention, cryoprotective agents may be added to prevent substantial particle agglomeration from occurring when the lyophilized compositions of the invention are resuspended.

Cryoprotective agents include (a) amino acids such as glutamic acid and arginine, among others; (b) polyols, including diols such as ethylene glycol, propanediols such as 1,2-propylene glycol and 1,3-propylene glycol, and butane diols such as 2,3-butylene glycol, among others, triols such as glycerol, among others, as well as other higher polyols; and (c) carbohydrates including, for example, (i) monosaccharides (e.g., glucose, galactose, and fructose, among others), (ii) polysaccharides including disaccharides (e.g., sucrose, lactose, trehalose, maltose, gentiobiose and cellobiose, among others), trisaccharides (e.g., raffinose, among others), tetrasaccharides (e.g., stachyose among others), pentasaccharides (e.g., verbascose among others), as well as numerous other higher polysaccharides, and (iii) alditols such as xylitol, sorbitol, and mannitol, among others (in this regard, is noted that alditols are higher polyols, as well as being carbohydrates).

Compositions in accordance with the invention can contain varying amounts of cryoprotective agent, where provided, depending on the amount that is effective to prevent substantial particle agglomeration from occurring when the lyophilized compositions of the invention are resuspended.

G. FORMULATION AND ADMINISTRATION

As noted above, antigen(s), benzonaphthyridine compound(s) and/or various optional supplemental components may be established within (e.g., entrapped in) the polymeric particles of the invention, for example, by introducing these species during the polymeric particle manufacturing process. Antigen(s), benzonaphthyridine compound(s) and/or optional supplemental components may also be attached to the polymeric particles (e.g., conjugated or adsorbed) or otherwise associated with the polymeric particles, for example, by introducing these species to previously formed polymeric particles. Adsorption and other associations may be established by simply admixing these species and the polymeric particles. Conjugation of such species to polymeric particles may be based on various linking chemistries known in the art including carbodiimide coupling. In some embodiments, antigen(s), benzonaphthyridine compound(s) and/or optional supplemental components are otherwise associated with the polymeric particles to varying degrees, for example, by admixing them with the polymeric particles in a liquid dispersion, admixing them with the polymeric particles in a solid composition (e.g., by admixing them with the polymeric particles in a liquid dispersion, followed by lyophilization), and so forth.

As noted above, the compositions of the present invention will commonly include one or more pharmaceutically acceptable excipients as optional supplemental components. For example, pharmaceutically acceptable vehicles such as water, saline, glycerol, ethanol, etc. may be used. Other excipients, such as wetting or emulsifying agents, osmotic agents, biological buffering substances, cryoprotective agents and the like, may be present. A biological buffer can be virtually any solution which is pharmacologically acceptable and which provides the formulation with the desired pH, i.e., a pH in the physiological range. Examples include phosphate buffers, citrate buffers, borate buffers, succinate buffers, and histidine buffers, as well as saline buffer combinations, including phosphate buffered saline, Tris buffered saline, Hank's buffered saline, and the like. Examples of osmotic agents include salts, sugars, etc. Such agents also may act as cryoprotective agents.

Depending on the final dosage form, other excipients known in the art can also be introduced, including binders, disintegrants, fillers (diluents), lubricants, glidants (flow enhancers), compression aids, preservatives, suspending/dispersing agents, film formers/coatings, and so forth.

Once formulated, the compositions of the invention can be administered parenterally, e.g., by injection. The compositions can be injected, for example, subcutaneously, intraperitoneally, intravenously or intramuscularly. In this regard, the particle compositions are typically supplied lyophilized in a vial or other container which is supplied with a septum or other suitable means for supplying a resuspension medium (e.g., Water for Injection) and for withdrawing the resultant suspension.

In certain embodiments, kits are provided which comprise a sealed container which contains one or more antigens and a sealed container which contains the polymeric microparticles and the benzonaphthyridine compound. The antigens may be in lyophilized form or provided in the form of an aqueous fluid. The polymeric microparticles and the benzonaphthyridine compound may be in lyophilized form or provided in the form of an aqueous fluid. Typically the benzonaphthyridine compound is either entrapped within the polymeric microparticles or is co-lyophilized with the benzonaphthyridine compound.

Kits may further include one or more devices that can be used to administer the compositions of the invention to a vertebrate subject. Examples of such devices include, but are not limited to, syringes, drip bags, and inhalers.

Other modes of administration include oral and pulmonary administration, suppositories, mucosal and transdermal applications. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also be, at least in part, determined by the need of the subject and be dependent on the judgment of the practitioner. Furthermore, if prevention of disease is desired, the vaccines are generally administered prior to primary infection with the pathogen of interest or prior to the advent of tumor cells. If therapeutic treatment is desired, the vaccines are generally administered subsequent to primary infection or appearance of tumor cells.

In some embodiments, the compositions of the present invention can be used for site-specific targeted delivery. For example, intravenous administration of the compositions can be used for targeting the lung, liver, spleen, blood circulation, or bone marrow.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Preparation of Selected
Benzo[f][1,7]naphthyridin-5-amine analogs

The following examples illustrate methods for preparing certain compounds useful in the compositions and methods of the invention. The skilled person would be able to make a wide range of other compounds for use in the instant methods based on these examples.

Example 1

Benzo[f][1,7]naphthyridin-5-amine

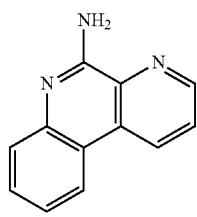 [SMILES: Nc1nc2ccccc2c2cccnc12]

A solution of 2-(tert-butoxycarbonylamino)phenylboronic acid (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude material was purified by flash chromatography on a COMBIFLASH® system (ISCO) using 0-80% ethyl acetate in hexane to give a white solid. $^1$H NMR (acetone d-6): δ 9.04 (d, 1H), 8.91 (d, 1H), 8.45 (d, 1H), 7.86 (dd, 1H), 7.53-7.62 (m, 2H), 7.35 (t, 1H), 6.65 (br, 2H). LRMS [M+H]=196.1

Example 2

9-chlorobenzo[f][1,7]naphthyridin-5-amine

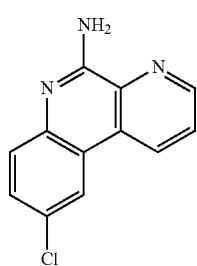 [SMILES: Nc1nc2ccc(Cl)cc2c2cccnc12]

Step 1: tert-butyl 2-bromo-4-chlorophenylcarbamate

To a solution of 2-bromo-4-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified y by flash chromatography on a COMBIFLASH® system (ISCO) using 0-5% ethyl acetate in hexane to give the product as light yellow oil.

Step 2: tert-butyl 4-chloro-2-(4,4,5,5-tetramethyl-1,3,2-dioxaborolan-2-yl)phenyl-carbamate Tert-butyl 2-bromo-4-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-10% ethyl acetate in hexane to give tert-butyl 4-chloro-2-(4,4,5,5-tetramethyl-1,3,2-dioxaborolan-2-yl)phenyl-carbamate.

Step 3: 9-chlorobenzo[f][1,7]naphthyridin-5-amine

A solution of tert-butyl 4-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-50% ethyl acetate in hexane and then re-purified using 0-5% methanol in dichloromethane to give a solid. $^1$H NMR (acetone d-6): δ 9.08 (d, 1H), 8.96 (d, 1H), 8.45 (s, 1H), 7.86-7.89 (dd, 1H), 7.60 (d, 1H), 7.54 (d, 1H), 6.78 (br, 2H). LRMS [M+H]=230.1

Example 3

8-chlorobenzo[f][1,7]naphthyridin-5-amine

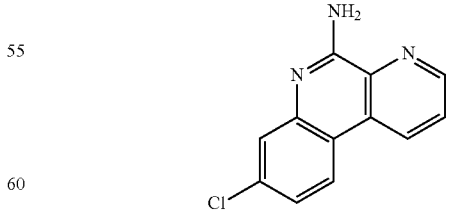

Step 1: tert-butyl 2-bromo-5-chlorophenylcarbamate

To a solution of 2-bromo-5-chloroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-chloro-2-(4,4,5,5-tetramethyl-1,3,2-dioxaborolan-2-yl)phenyl-carbamate Tert-butyl 2-bromo-5-chlorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude mixture was purified by flash chromatography on a COMBIFLASH® system (ISCO) using 0-5% ethyl acetate in hexane to give tert-butyl 5-chloro-2-(4,4,5,5-tetramethyl-1,3,2-dioxaborolan-2-yl)phenyl-carbamate.

Step 3: 8-chlorobenzo[f][1,7]naphthyridin-5-amine

A solution of tert-butyl 5-chloro-2-(4,4,5,5-tetramethyl-1,3,2-dioxaborolan-2-yl)phenyl-carbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then stirred in hot 10% ethyl acetate in hexane, filtered, and dried to give a pure solid. $^1H$ NMR (acetone d-6): δ 9.03 (d, 1H), 8.93 (d, 1H), 8.46 (d, 1H), 7.85-7.88 (dd, 1H), 7.57 (s, 1H), 7.32 (d, 1H), 6.94 (br, 2H). LRMS [M+H]=230.1

Example 4

8-methylbenzo[f][1,7]naphthyridin-5-amine

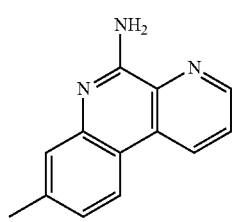 [SMILES: Cc1ccc2c(c1)nc(N)c1ncccc12]

Step 1: tert-butyl 2-bromo-5-methylphenylcarbamate

To a solution of 2-bromo-5-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Step 3: 8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a pure solid. $^1H$ NMR (acetone d-6): δ 8.98 (d, 1H), 8.87 (d, 1H), 8.32 (d, 1H), 7.79-7.82 (dd, 1H), 7.42 (s, 1H), 7.18 (d, 1H), 6.6 (br, 2H), 2.45 (s, 3H). LRMS [M+H]=210.1

Example 5

9-methylbenzo[f][1,7]naphthyridin-5-amine

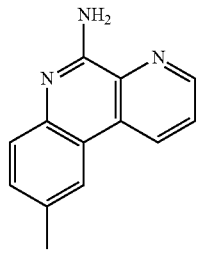 [SMILES: Cc1ccc2nc(N)c3ncccc3c2c1]

Step 1: tert-butyl 2-bromo-4-methylphenylcarbamate

To a solution of 2-bromo-4-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1NHCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 4-methyl-2-(4,4,5,5-tetramethyl-1,3,2-dioxaborolan-2-yl)phenylcarbamate Tert-butyl 2-bromo-4-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 4-methyl-2-(4,4,5,5-tetramethyl-1,3,2-dioxaborolan-2-yl)phenylcarbamate.

Step 3: 9-methylbenzo[f][1,7]naphthyridin-5-amine

A solution of tert-butyl 4-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then swirled in hot ethyl acetate, filtered, and dried to give a pure solid. $^1H$ NMR (acetone d-6): δ 9.02 (d, 1H), 8.89 (d, 1H), 8.25 (s, 1H), 7.80-7.84 (dd, 1H), 7.52 (d, 1H), 7.40 (d, 1H), 6.5 (br, 2H), 2.48 (s, 3H). LRMS [M+H]=210.2

Example 6

10-methylbenzo[f][1,7]naphthyridin-5-amine

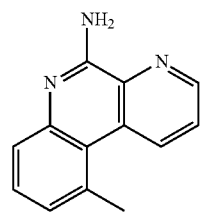 [SMILES: Cc1cccc2nc(N)c3ncccc3c12]

Step 1: tert-butyl 2-bromo-3-methylphenylcarbamate

To a solution of 2-bromo-3-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 3-methyl-2-(4,4,5,5-tetramethyl-1,3,2-dioxaborolan-2-yl)phenylcarbamate Tert-butyl 2-bromo-3-methylphenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to tert-butyl 3-methyl-2-(4,4,5,5-tetramethyl-1,3,2-dioxaborolan-2-yl)phenylcarbamate.

Step 3: 10-methylbenzo[f][1,7]naphthyridin-5-amine

A solution of tert-butyl 3-methyl-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.22 (d, 1H), 8.90 (d, 1H), 7.82-7.85 (dd, 1H), 7.54 (d, 1H), 7.45 (t, 1H), 7.19 (d, 1H), 6.6 (br, 2H), 2.98 (s, 3H). LRMS [M+H]=210.2.

Example 7

Ethyl 5-aminobenzo[f][1,7]naphthyridine-9-carboxylate

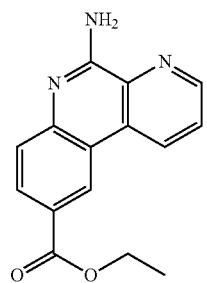 [SMILES: CCOC(=O)c1ccc2nc(N)c3ncccc3c2c1]

Step 1: ethyl 3-bromo-4-(tert-butoxycarbonylamino)benzoate

To a solution of 4-amino-3-bromobenzoate (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give product as light yellow oil.

Step 2: Ethyl 4-(tert-butoxycarbonylamino)-3-(4,4,5,5-tetramethyl-1,3,2-dioxaborolan-2-yl)benzoate Ethyl 3-bromo-4-(tert-butoxycarbonylamino)benzoate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give ethyl 4-(tert-butoxycarbonylamino)-3-(4,4,5,5-tetramethyl-1,3,2-dioxaborolan-2-yl)benzoate.

Step 3: ethyl 5-aminobenzo[f][1,7]naphthyridine-9-carboxylate

A solution of ethyl 4-(tert-butoxycarbonylamino)-3-(4,4,5,5-tetramethyl-1,3,2-dioxaborolan-2-yl)benzoate (from step 2) (1.0 eq.) and 3-bromopicolino-nitrile (1.0 eq.) in toluene/ethanol (10:1, 0.23 M) was mixed with tetrakis(triphenyl-phosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude material was purified by flash chromatography on a COMBIFLASH® system (ISCO) using 0-40% ethyl acetate in toluene to give a semipure solid, which was then swirled in hot 10% ethyl acetate in hexane, filtered, and dried to give a pure solid. $^1$H NMR (acetone d-6): δ 9.11 (d, 1H), 9.05 (s, 1H), 8.95 (d, 1H), 8.14 (d, 1H), 7.89-7.92 (dd, 1H), 7.63 (d, 1H), 4.38 (q, 2H), 1.40 (t, 3H). LRMS [M+H]=268.2.

Example 8

5-aminobenzo[f][1,7]naphthyridine-9-carboxylic acid

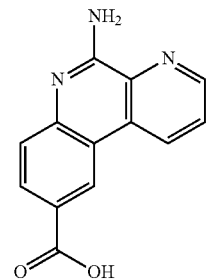 [SMILES: Nc1nc2ccc(C(=O)O)cc2c2cccnc12]

Ethyl 5-aminobenzo[f][1,7]naphthyridine-9-carboxylate (Example 7) (1.0 eq.) was mixed with 1N NaOH (2.0 eq.) in ethanol (0.12 M). The reaction was heated to 80° C. and stirred for 36 hours. The solvent was removed en vacuo. The residue was suspended in water, and the pH was adjusted to neutral using 5% citric acid aqueous solution. The suspension was centrifuged (2500 rpm, 5 min), and the supernatant was removed. The resulting solids was re-suspended in water by vortexing, centrifuged (2500 rpm, 5 min), and the supernatant was removed. The re-suspension, centrifugation, and removal of supernatant steps were repeated with hot methanol, hot ethyl acetate, and ether to give a pure solid. $^1$H NMR (DMSO): δ 12.86 (s, 1H), 9.15 (d, 1H), 9.00 (s, 1H), 8.97 (d, 1H), 8.07 (d, 1H), 7.88-7.91 (dd, 1H), 7.56-7.59 (m, 3H). LRMS [M+H]=240.1

Example 9

8-methoxybenzo[f][1,7]naphthyridin-5-amine

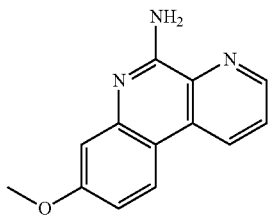 [SMILES: COc1ccc2c(c1)nc(N)c1ncccc12]

Step 1: 2-bromo-5-methoxyaniline

A solution of 1-bromo-4-methoxy-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous $MgSO_4$, and concentrated en vacuo. The crude material was purified by flash chromatography on a COMBIFLASH® system (ISCO) using 0-15% ethyl acetate in hexane to give the product as oil.

Step 2: tert-butyl 2-bromo-5-methoxyphenylcarbamate

To a solution of 2-bromo-5-methoxyaniline (1.0 eq.) (from step 1) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 3: tert-butyl 5-methoxy-2-(4,4,5,5-tetramethyl-1,3,2-dioxaborolan-2-yl)phenylcarbamate Tert-butyl 2-bromo-5-methoxyphenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-15% ether in hexane to give tert-butyl 5-methoxy-2-(4,4,5,5-tetramethyl-1,3,2-dioxaborolan-2-yl)phenylcarbamate.

Step 4: 8-methoxybenzo[f][1,7]naphthyridin-5-amine

A solution of tert-butyl 5-methoxy-2-(4,4,5,5-tetramethyl-1,3,2-dioxaborolan-2-yl)phenylcarbamate (from step 3) (1.0 eq.) and 3-bromopicolino-nitrile (1.0 eq.) in toluene/ethanol (10:1, 0.23 M) was mixed with tetrakis(triphenylphosphine)palladium (5 mol %) and anhydrous potassium carbonate (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-5% methanol in dichloromethane to give a semipure solid, which was then recrystallized in ethyl acetate, filtered, and dried to give a pure solid. $^1$H NMR (acetone d-6): δ 8.91 (d, 1H), 8.82 (d, 1H), 8.33 (d, 1H), 7.76-7.79 (dd, 1H), 7.07 (s, 1H), 6.96 (d, 1H), 6.6 (br, 2H), 3.90 (s, 3H). LRMS [M+H]=226.1

Example 10

7-fluorobenzo[f][1,7]naphthyridin-5-amine

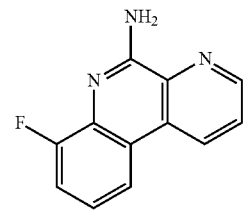 [SMILES: Nc1nc2c(F)cccc2c2cccnc12]

Step 1: tert-butyl 2-fluorophenylcarbamate

To a solution of 2-fluoroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: 2-(tert-butoxycarbonylamino)-3-fluorophenylboronic acid

To a solution of tert-butyl 2-fluorophenylcarbamate (from step 1) (1.0 eq.) in tetrahydrofuran (0.25 M) at −78° C. under $N_2$ atmosphere was added dropwise 1.7 M tert-butyllithium (2.4 eq.). The reaction was warmed to −40° C. slowly over 2 hours, and neat trimethyl borate (3.8 eq.) was added. The reaction was warmed to room temperature over 30 minutes.

An aqueous solution of 1N NaOH was slowly added to the reaction and stirred for 15 minutes. The mixture was poured into ethyl acetate and acidified with 3N HCl to dissolve the solids. The aqueous layer was extracted twice with ethyl acetate, and the combined organic layers were washed with brine, dried over anhydrous MgSO$_4$, and concentrated en vacuo. The resulting solids were stirred in 1:1 ether/hexane, filtered, and dried. The solids were carried onto the next step without further purification.

Step 3: 7-fluorobenzo[f][1,7]naphthyridin-5-amine

A solution of 2-(tert-butoxycarbonylamino)-3-fluorophenylboronic acid (from step 2) (1.0 eq.) and 3-bromopicolinonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. After workup, the crude product was suspended in hot toluene, centrifuged (2500 rpm, 5 min), and the supernatant was removed. The suspension, centrifugation, and removal of supernatant steps were repeated with hot ethyl acetate, ether, and hexane to give a pure solid. $^1$H NMR (acetone d-6): δ 9.04 (d, 1H), 8.96 (d, 1H), 8.27 (d, 1H), 7.86-7.90 (dd, 1H), 7.28-7.34 (m, 2H), 6.9 (br, 2H). LRMS [M+H]=214.1

Example 11

8-(methylsulfonyl)benzo[f][1,7]naphthyridin-5-amine

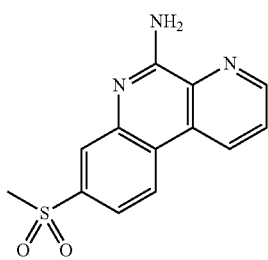 [SMILES: CS(=O)(=O)c1ccc2c(c1)nc(N)c1ncccc12]

Step 1: 2-bromo-5-(methylsulfonyl)aniline

A solution of 1-bromo-4-(methylsulfonyl)-2-nitrobenzene (1.0 eq.), iron powder (3.0 eq.), and concentrated HCl (1.04 eq.) were mixed together in ethanol (0.64 M) and heated to reflux. The reaction was stirred for 24 hours, and the solvent was evaporated. The resulting residue was diluted with ethyl acetate and saturated aqueous ammonium chloride solution. The aqueous layer was extracted three times with ethyl acetate, and the combined organic layers were washed with water, brine, dried over anhydrous MgSO$_4$, and concentrated en vacuo. The crude material was purified by triturating in 1:1 hexane/ether to give a light yellow solid.

Step 2: tert-butyl 2-bromo-5-(methylsulfonyl)phenylcarbamate

To a solution of 2-bromo-5-(methylsulfonyl)aniline (from step 1) (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give tert-butyl 2-bromo-5-(methylsulfonyl)phenylcarbamate.

Step 3: tert-butyl 5-(methylsulfonyl)-2-(4,4,5,5-tetramethyl-1,3,2-dioxaborolan-2-yl)phenylcarbamate Tert-butyl 2-bromo-5-(methylsulfonyl)phenylcarbamate (from step 2) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-50% ethyl acetate in hexane to give a solid which was then triturated in 10% ether/hexane to give tert-butyl 5-(methylsulfonyl)-2-(4,4,5,5-tetramethyl-1,3,2-dioxaborolan-2-yl)phenylcarbamate as a white solid.

Step 4: 8-(methylsulfonyl)benzo[f][1,7]naphthyridin-5-amine

A solution of tert-butyl 5-(methylsulfonyl)-2-(4,4,5,5-tetramethyl-1,3,2-dioxaborolan-2-yl)phenylcarbamate (from step 3) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude material was purified by flash chromatography on a COMBIFLASH® system (ISCO) using 0-5% methanol in dichloromethane to give a solid which was then triturated in 1:1 hexane/ethyl acetate to give 8-(methylsulfonyl)benzo[f][1,7]naphthyridin-5-amine $^1$H NMR (acetone d-6): δ 9.16 (d, 1H), 9.03 (d, 1H), 8.71 (d, 1H), 8.11 (s, 1H), 7.93-7.96 (dd, 1H), 7.81 (d, 1H), 7.0 (br, 2H), 3.19 (s, 3H). LRMS [M+H]=274.1

Example 12

8-(trifluoromethyl)benzo[f][1,7]naphthyridin-5-amine

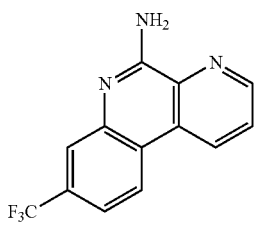 [SMILES: Nc1nc2cc(C(F)(F)F)ccc2c2cccnc12]

Step 1: tert-butyl 2-bromo-5-(trifluoromethyl)phenylcarbamate

To a solution of 2-bromo-5-(trifluoromethyl)aniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give product as light yellow oil.

Step 2: tert-butyl 2-(4,4,5,5-tetramethyl-1,3,2-dioxaborolan-2-yl)-5-(trifluoromethyl)phenylcarbamate Tert-butyl 2-bromo-5-(trifluoromethyl)phenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-10% ether in hexane to give an impure product which was carried onto the next step without further purification.

Step 3: 8-(trifluoromethyl)benzo[f][1,7]naphthyridin-5-amine

A solution of tert-butyl 2-(4,4,5,5-tetramethyl-1,3,2-dioxaborolan-2-yl)-5-(trifluoromethyl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous $MgSO_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-(trifluoromethyl)benzo[f][1,7]naphthyridin-5-amine $^1$H NMR (acetone d-6): δ 9.13 (d, 1H), 9.00 (d, 1H), 8.67 (d, 1H), 7.91-7.94 (dd, 1H), 7.86 (s, 1H), 7.58 (d, 1H), 6.9 (br, 2H). LRMS [M+H]=264.1

Example 13

8-fluorobenzo[f][1,7]naphthyridin-5-amine

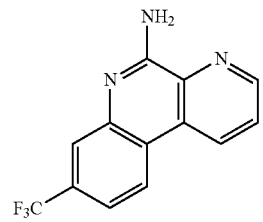 [SMILES: Nc1nc2cc(C(F)(F)F)ccc2c2cccnc12]

Step 1: tert-butyl 2-bromo-5-fluorophenylcarbamate

To a solution of 2-bromo-5-fluoroaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give the product as light yellow oil.

Step 2: tert-butyl 5-fluoro-2-(4,4,5,5-tetramethyl-1,3,2-dioxaborolan-2-yl)phenylcarbamate Tert-butyl 2-bromo-5-fluorophenylcarbamate (from step 1) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-5% ether in hexane to give the product as a yellow solid.

Step 3: 8-fluorobenzo[f][1,7]naphthyridin-5-amine

A solution of tert-butyl 5-fluoro-2-(4,4,5,5-tetramethyl-1,3,2-dioxaborolan-2-yl)phenylcarbamate (from step 2) (1.0 eq.) and 3-bromopicolino-nitrile (1.0 eq.) in toluene (0.24 M) was mixed with tetrakis(triphenyl-phosphine)palladium (5 mol %) and 2N aqueous potassium carbonate solution (4.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-40% ethyl acetate in toluene to give a solid which was then triturated in 10% ethyl acetate in hexane to give 8-fluorobenzo[f][1,7]naphthyridin-5-amine $^1$H NMR (acetone d-6): δ 9.00 (d, 1H), 8.90 (d, 1H), 8.46-8.50 (dd, 1H), 7.83-7.87 (dd, 1H), 7.26 (d, 1H), 7.15 (t, 1H), 6.9 (br, 2H). LRMS [M+H]=214.1

Example 14

3-methoxybenzo[f][1,7]naphthyridin-5-amine

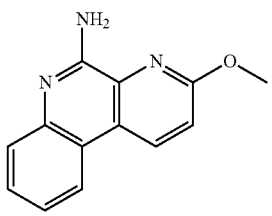 [SMILES: COc1ccc2c(n1)c(N)nc1ccccc12]

Step 1: 3-bromo-6-methoxypicolinonitrile

A solution of 3-bromo-6-oxo-1,6-dihydropyridine-2-carbonitrile (1.0 eq.), silver carbonate (1.3 eq.), and iodomethane (1.2 eq.) in toluene (0.2 M) was stirred in the dark at room temperature overnight. The solvent was concentrated en vacuo, and the resulting residue was purified by a COMBIFLASH® system (ISCO) using 0-80% ethyl acetate in hexane to give 3-bromo-6-methoxypicolinonitrile.

Step 2:
3-methoxybenzo[f][1,7]naphthyridin-5-amine

A solution of 2-(tert-butoxycarbonylamino)phenylboronic acid (1.0 eq.) and 3-bromo-6-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give 3-methoxybenzo[f][1,7]naphthyridin-5-amine as a yellow solid. $^1$H NMR (acetone d-6): δ 8.91 (d, 1H), 8.34 (d, 1H), 7.63 (d, 1H), 7.51-7.53 (dd, 1H), 7.27-7.33 (m, 2H), 6.65 (br, 2H), 4.11 (s, 3H). LRMS [M+H]=226.1

Example 15

3-butoxybenzo[f][1,7]naphthyridin-5-amine

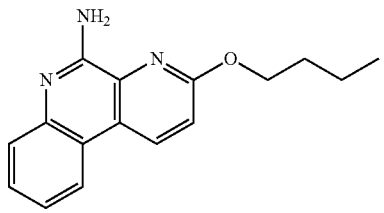 [SMILES: CCCCOc1ccc2c(n1)c(N)nc1ccccc12]

Step 1: 3-bromo-6-butoxypicolinonitrile

A solution of 3-bromo-6-oxo-1,6-dihydropyridine-2-carbonitrile (1.0 eq.), potassium carbonate (1.3 eq.), and 1-iodobutane (1.2 eq.) in acetone (0.3 M) was stirred at 70° C. overnight. The solvent was concentrated en vacuo, and the resulting residue was taken up in water and ethyl acetate. The aqueous layer was extracted with ethyl acetate three times. The combined organic layers were washed with brine, dried over anhydrous MgSO$_4$, and concentrated en vacuo. The crude product was purified by a COMBIFLASH® system (ISCO) using 0-30% ethyl acetate in hexane to give a colorless solid.

Step 2: 3-butoxybenzo[f][1,7]naphthyridin-5-amine

A solution of 2-(tert-butoxycarbonylamino)phenylboronic acid (1.0 eq.) and 3-bromo-6-butoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-5% ethyl acetate in methanol to give 3-butoxybenzo[f][1,7]naphthyridin-5-amine as a white solid. $^1$H NMR (acetone d-6): δ 8.91 (d, 1H), 8.34 (d, 1H), 7.61 (d, 1H), 7.48-7.52 (dd, 1H), 7.27-7.33 (m, 2H), 6.51 (br, 2H), 6.55 (t, 2H), 1.81-1.88 (m, 2H), 1.50-1.59 (m, 2H), 1.00 (t, 3H). LRMS [M+H]=268.1

Example 16

3-(benzyloxy)benzo[f][1,7]naphthyridin-5-amine

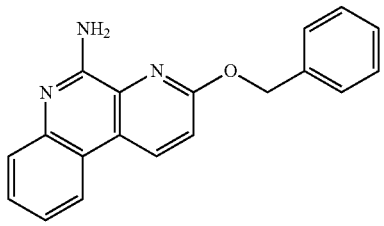 [SMILES: Nc1nc2ccccc2c2ccc(OCc3ccccc3)nc12]

Step 1: 6-(benzyloxy)-3-bromopicolinonitrile

A solution of 3-bromo-6-oxo-1,6-dihydropyridine-2-carbonitrile (1.0 eq.), silver carbonate (1.3 eq.), and benzyl bromide (1.2 eq.) in toluene (0.16 M) was stirred in the dark at 50° C. overnight. The solvent was concentrated en vacuo, and the resulting residue was purified by a COMBIFLASH® system (ISCO) using 0-20% ethyl acetate in hexane to give 6-(benzyloxy)-3-bromopicolinonitrile.

Step 2: 3-(benzyloxy)benzo[f][1,7]naphthyridin-5-amine

A solution of 2-(tert-butoxycarbonylamino)phenylboronic acid (1.0 eq.) and 6-(benzyloxy)-3-bromopicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give 3-(benzyloxy)benzo[f][1,7]naphthyridin-5-amine as a yellow solid. $^1$H NMR (acetone d-6): δ 8.95 (d, 1H), 8.35 (d, 1H), 7.58-7.63 (m, 2H), 7.49-7.53 (dd, 1H), 7.30-7.44 (m, 5H), 6.61 (br, 2H), 5.64 (s, 2H). LRMS [M+H]=302.1

Example 17

3-methylbenzo[f][1,7]naphthyridin-5-amine

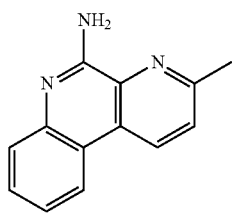 [SMILES: Cc1ccc2c(n1)c(N)nc1ccccc12]

Step 1: 5-bromo-2-methylpyridine 1-oxide

To a solution of 5-bromo-2-methylpyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-methylpicolinonitrile

To a solution of 5-bromo-2-methylpyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-methylpicolinonitrile.

Step 3: 3-methylbenzo[f][1,7]naphthyridin-5-amine

A solution of 2-(tert-butoxycarbonylamino)phenylboronic acid (1.0 eq.) and 3-bromo-6-methylpicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-70% ethyl acetate in hexane to give 3-methylbenzo[f][1,7]naphthyridin-5-amine as a yellow solid. $^1$H NMR (methanol d-4): δ 8.85 (d, 1H), 8.38 (d, 1H), 7.72 (d, 1H), 7.53-7.61 (m, 2H), 7.34-7.38 (dd, 1H), 2.76 (s, 3H). LRMS [M+H]=210.1

Example 18

3-chlorobenzo[f][1,7]naphthyridin-5-amine

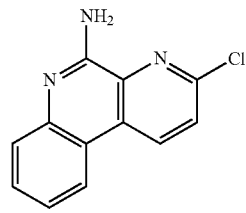 [SMILES: Nc1nc2ccccc2c2ccc(Cl)nc12]

Step 1: 5-bromo-2-chloropyridine 1-oxide

To a solution of 5-bromo-2-chloropyridine (1.0 eq.) in chloroform (0.38 M) was added 77% meta-chloroperbenzoic acid (mCPBA) (4.0 eq.) and heated at 60° C. for 20 hours. After cooling to room temperature, Ca(OH)$_2$ (5.3 eq.) was added, and the resulting precipitate was stirred for 30 minutes. The precipitate was filtered and washed with 3:1 CHCl$_3$/methanol. The filtrate was concentrated en vacuo to give a solid, which was stirred in 30% ethyl acetate in hexane and filtered to give the desired N-oxide. The filtrate was concentrated en vacuo, and the residue was purified by a COMBIFLASH® system (ISCO) using 0-100% ethyl acetate in hexane to give more of the desired N-oxide. The two batches were combined and carried onto the next step.

Step 2: 3-bromo-6-chloropicolinonitrile

To a solution of 5-bromo-2-chloropyridine 1-oxide (from step 1) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBI-FLASH® system (ISCO) using 0-40% ethyl acetate in hexane to give 3-bromo-6-chloropicolinonitrile.

Step 3: 3-chlorobenzo[f][1,7]naphthyridin-5-amine

A solution of 2-(tert-butoxycarbonylamino)phenylboronic acid (1.0 eq.) and 3-bromo-6-chloropicolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give a solid, which was then triturated in 10% ethyl acetate in hexane to give 3-chlorobenzo[f][1,7]naphthyridin-5-amine $^1$H NMR (acetone d-6): δ 9.10 (d, 1H), 8.45 (d, 1H), 7.89 (d, 1H), 7.58-7.65 (m, 2H), 7.35-7.39 (dd, 1H), 6.67 (br, 2H). LRMS [M+H]=230.1

Example 19

N$^3$,N$^3$-dimethylbenzo[f][1,7]naphthyridine-3,5-diamine

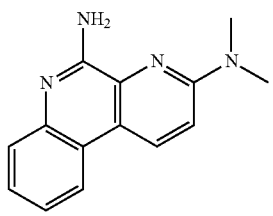 [SMILES: CN(C)c1ccc2c(n1)c(N)nc1ccccc12]

A solution of 3-chlorobenzo[f][1,7]naphthyridin-5-amine (Example 18) (1.0 eq.) was dissolved in 40% aqueous dimethylamine (0.26 M) and heated in a microwave reactor at 100° C. for 30 minutes. The reaction mixture was concentrated en vacuo, and the residue was purified by a COMBIFLASH® system (ISCO) using 0-90% ethyl acetate in hexane to give N$^3$,N$^3$-dimethylbenzo[f][1,7]naphthyridine-3,5-diamine. $^1$H NMR (methanol d-4): δ 8.63 (d, 1H), 8.20 (d, 1H), 7.55 (d, 1H), 7.41-7.45 (dd, 1H), 7.29-7.33 (dd, 1H), 7.27 (d, 1H), 3.26 (s, 6H). LRMS [M+H]=239.1

Example 20

N$^3$-butylbenzo[f][1,7]naphthyridine-3,5-diamine

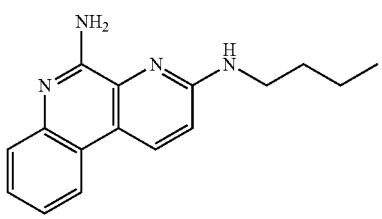 [SMILES: CCCCNc1ccc2c(n1)c(N)nc1ccccc12]

A solution of 3-chlorobenzo[f][1,7]naphthyridin-5-amine (Example 18) (1.0 eq.) was dissolved in n-butylamine (0.1 M) and heated at 110° C. overnight. The reaction mixture was concentrated en vacuo, and the residue was purified by a COMBIFLASH® system (ISCO) using 0-90% ethyl acetate in hexane to give N$^3$-butylbenzo[f][1,7]naphthyridine-3,5-diamine. $^1$H NMR (methanol d-4): δ 8.42 (d, 1H), 8.13 (d, 1H), 7.53 (d, 1H), 7.38-7.42 (dd, 1H), 7.25-7.29 (dd, 1H), 6.96 (d, 1H), 3.48 (t, 2H), 1.63-1.71 (m, 2H), 1.43-1.52 (m, 2H), 0.99 (t, 3H). LRMS [M+H]=267.2

Example 21

3-vinylbenzo[f][1,7]naphthyridin-5-amine

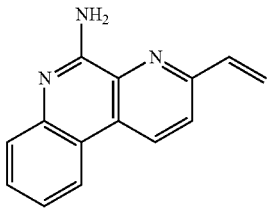 [SMILES: C=Cc1ccc2c(n1)c(N)nc1ccccc12]

A solution of 3-chlorobenzo[f][1,7]naphthyridin-5-amine (Example 18) (1.0 eq.), 4,4,5,5-tetramethyl-2-vinyl-1,3,2-dioxaborolane (1.2 eq.), tetrakis(triphenyl-phosphine)palladium (5 mol %), and 2N aqueous potassium carbonate solution (2.0 eq.) in toluene/ethanol (4:1, 0.1 M) was heated to 100° C. and stirred overnight. After cooling to ambient temperature, the reaction content was diluted with ethyl acetate and water. The two phases were separated, and the aqueous layer was extracted with ethyl acetate three times. The combined organic layers were washed with brine, dried over anhydrous MgSO$_4$, and concentrated en vacuo. The crude material was purified by flash chromatography on a COMBIFLASH® system (ISCO) using 0-50% ethyl acetate in hexane to give a solid, which was then triturated in 10% ethyl acetate in hexane to give 3-vinylbenzo[f][1,7]naphthyridin-5-amine $^1$H NMR (acetone d-6): δ 8.99 (d, 1H), 8.42 (d, 1H), 8.01 (d, 1H), 7.53-7.62 (m, 2H), 7.30-7.35 (dd, 1H), 7.03-7.10 (dd, 1H), 6.77 (br, 2H), 6.56 (d, 1H), 5.66 (d, 1H). LRMS [M+H]=222.1

Example 22

3-ethylbenzo[f][1,7]naphthyridin-5-amine

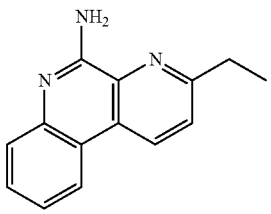 [SMILES: CCc1ccc2c(n1)c(N)nc1ccccc12]

To a solution of 3-vinylbenzo[f][1,7]naphthyridin-5-amine (Example 21) in ethyl acetate/ethanol (1:1, 0.07 M) was added 10% wt palladium on carbon (0.2 eq.). Hydrogen gas was introduced via a balloon, and the reaction was stirred overnight. The mixture was filtered through a pad of celite, washing with dichloromethane. The filtrate was concentrated en vacuo giving 3-ethylbenzo[f][1,7]naphthyridin-5-amine as a white solid. $^1$H NMR (acetone d-6): δ 8.93 (d, 1H), 8.41 (d, 1H), 7.76 (d, 1H), 7.61 (d, 1H), 7.51-7.55 (dd, 1H), 7.30-7.34 (dd, 1H), 6.55 (br, 2H), 6.03 (q, 2H), 1.41 (t, 3H). LRMS [M+H]=224.1

Example 23

3-fluorobenzo[f][1,7]naphthyridin-5-amine

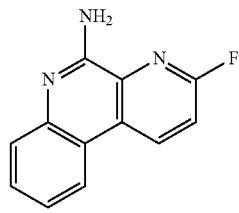 [SMILES: Nc1nc2ccccc2c2ccc(F)nc12]

A solution of 3-chlorobenzo[f][1,7]naphthyridin-5-amine (Example 18) (1.0 eq.), potassium fluoride (3.0 eq.), and 18-crown-6 (0.2 eq.) in N-methylpyrrolidone (NMP) (0.4 M) was heated in a microwave reactor at 210° C. for 80 minutes. After cooling to room temperature, the crude reaction mixture was purified by HPLC using 10-50% acetonitrile in water to give 3-fluorobenzo[f][1,7]naphthyridin-5-amine $^1$H NMR (acetone d-6): δ 11.40 (br, 2H), 9.38-9.42 (dd, 1H), 8.60 (d, 1H), 7.89-7.92 (dd, 1H), 7.81-7.83 (m, 2H), 7.59-7.66 (m, 1H). LRMS [M+H]=214.1

Example 24

2-(trifluoromethyl)benzo[f][1,7]naphthyridin-5-amine

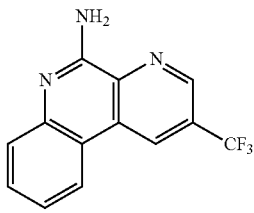 [SMILES: Nc1nc2ccccc2c2cc(C(F)(F)F)cnc12]

Step 1: 3-chloro-5-(trifluoromethyl)picolinaldehyde oxime

A solution of 3-chloro-5-(trifluoromethyl)picolinaldehyde (1.0 eq.), hydroxylamine hydrochloride (5.0 eq.), and pyridine (4.0 eq.) in ethanol was heated to 95° C. and stirred for 1 hour. The reaction was cooled to room temperature and diluted with ethyl acetate and water. The organic layer was washed with brine, water, dried over anhydrous MgSO$_4$, and concentrated en vacuo to give a solid that was carried onto the next step without further purification.

Step 2: 3-chloro-5-(trifluoromethyl)picolinonitrile

A solution of 3-chloro-5-(trifluoromethyl)picolinaldehyde oxime (1.0 eq.) and Burgess reagent (1.5 eq.) in tetrahydrofuran (0.5 M) was heated to 65° C. and stirred for 1 hour. The reaction was cooled to room temperature and diluted with ethyl acetate and water. The organic layer was washed with water, brine, dried over anhydrous MgSO$_4$, and concentrated en vacuo to give a solid that was carried onto the next step without further purification.

Step 3: 2-(trifluoromethyl)benzo[f][1,7]naphthyridin-5-amine

A solution of 2-(tert-butoxycarbonylamino)phenylboronic acid (1.0 eq.) and 3-chloro-5-(trifluoromethyl)picolinonitrile (from step 2) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 0-50% ethyl acetate in hexane to give 2-(trifluoromethyl)benzo[f][1,7]naphthyridin-5-amine. $^1$H NMR (acetone d-6): δ 9.44 (s, 1H), 9.20 (s, 1H), 8.65-8.63 (d, 1H), 7.70-7.61 (m, 2H), 7.44-7.36 (m, 1H), 6.84 (br, 2H). LRMS [M+H]=264.2

Example 25

2-methoxybenzo[f][1,7]naphthyridin-5-amine

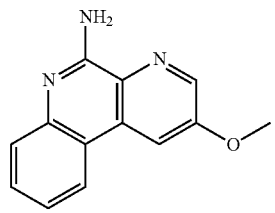 [SMILES: COc1cnc2c(N)nc3ccccc3c2c1]

Step 1: 3-chloro-5-methoxypicolinonitrile

To a solution of 3,5-dichloropicolinonitrile (1.0 eq.) in dimethyl formamide (DMF) (0.5 M) was added sodium methoxide (1.5 eq.) and heated to 75° C. After stirring for 14 hours, the reaction was diluted with ethyl acetate and water. The organic layer was washed with saturated aqueous NaHCO$_3$ three times, water twice, dried over anhydrous MgSO$_4$, and concentrated en vacuo. The crude residue was purified by a COMBIFLASH® system (ISCO) using 15% ethyl acetate in hexane to give a mixture of two methoxy regioisomers, one of which was the desired product. The mixture was carried onto the next step without further purification.

Step 2: 2-methoxybenzo[f][1,7]naphthyridin-5-amine

A solution of 2-(tert-butoxycarbonylamino)phenylboronic acid (1.0 eq.) and 3-chloro-5-methoxypicolinonitrile (from step 1) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 50-100% ethyl acetate in hexane to give 2-methoxybenzo[f][1,7]naphthyridin-5-amine Example 26

2-(benzyloxy)benzo[f][1,7]naphthyridin-5-amine

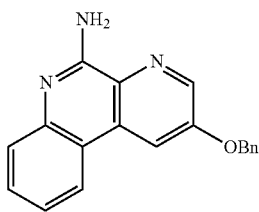 [SMILES: Nc1nc2ccccc2c2cc(OCc3ccccc3)cnc12]

Step 1: 3-(benzyloxy)-5-bromopyridine

A solution of 5-bromopyridin-3-ol (1.0 eq.), benzyl bromide (1.2 eq.), and silver carbonate (1.3 eq.) in toluene (0.1 M) was heated to 50° C. and stirred for 18 hours. After cooling to room temperature, the reaction mixture was filtered, eluting with ethyl acetate. The filtrate was concentrated en vacuo into a residue that was purified by a COMBIFLASH® system (ISCO) using 20% ethyl acetate in hexane to give 3-(benzyloxy)-5-bromopyridine.

Step 2: 3-(benzyloxy)-5-bromopyridine 1-oxide

A solution of 3-(benzyloxy)-5-bromopyridine (from step 1) (1.0 eq.) and meta-chloroperbenzoic acid (mCPBA) (4.0 eq.) in dichloromethane (0.1 M) was stirred at room temperature for 18 hours. The reaction was quenched with saturated aqueous NaHCO$_3$ solution and extracted with dichloromethane three times. The combined organic layers were dried over anhydrous MgSO$_4$ and concentrated en vacuo. The crude residue was purified by a COMBIFLASH® system (ISCO) using 0-100% ethyl acetate in hexane to give 3-(benzyloxy)-5-bromopyridine 1-oxide.

Step 3: 5-(benzyloxy)-3-bromopicolinonitrile

To a solution of 53-(benzyloxy)-5-bromopyridine 1-oxide (from step 2) (1.0 eq.) in acetonitrile (0.2 M) was added trimethylsilyl cyanide (TMSCN) (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-40% ethyl acetate in hexane to give a mixture of two benzoxy regioisomers, one of which was the desired product. The mixture was carried onto the next step without further purification.

Step 4:
2-(benzyloxy)benzo[f][1,7]naphthyridin-5-amine

A solution of 2-(tert-butoxycarbonylamino)phenylboronic acid (1.0 eq.) and 5-(benzyloxy)-3-bromopicolinonitrile (from step 3) (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction content was diluted with 2% methanol in dichloromethane and water. The two phases were separated, and the aqueous layer was extracted twice with 2% methanol in dichloromethane. The combined organic layers were washed with brine, dried over anhydrous MgSO$_4$, and concentrated en vacuo. The crude product was purified by flash chromatography on a COMBIFLASH® system (ISCO) using 50-100% ethyl acetate in hexane to give 2-(benzyloxy)benzo[f][1,7]naphthyridin-5-amine $^1$H NMR (acetone d-6): δ 8.36 (s, 1H), 7.86 (s, 1H), 7.59-7.56 (d, 2H), 7.46-7.42 (dd, 2H), 7.40-7.37 (d, 1H), 7.20-7.15 (dd, 1H), 7.12-7.09 (d, 1H), 6.88-6.86 (d, 1H), 6.77-6.73 (dd, 1H), 5.51 (s, 2H), 4.74 (br, 2H). LRMS [M+H]=302.3.

Example 27

2-vinylbenzo[f][1,7]naphthyridin-5-amine

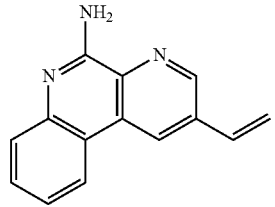 [SMILES: C=Cc1cnc2c(N)nc3ccccc3c2c1]

Step 1: 3-chloro-5-vinylpicolinonitrile

A solution of 3,5-dichloropicolinonitrile (1.0 eq.), 4,4,5,5-tetramethyl-2-vinyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-vinylbenzo[f][1,7]naphthyridin-5-amine

A solution of 2-(tert-butoxycarbonylamino)phenylboronic acid (1.0 eq.) and 3-chloro-5-vinylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude material was purified by flash chromatography on a COMBIFLASH® system (ISCO) using 0-80% ethyl acetate in hexane to give 2-vinylbenzo[f][1,7]naphthyridin-5-amine as a yellow solid. 1H NMR (methanol-d$_4$-CDCl$_3$): δ 8.87 (d, 1H), 8.69 (d,

Example 28

2-ethylbenzo[f][1,7]naphthyridin-5-amine

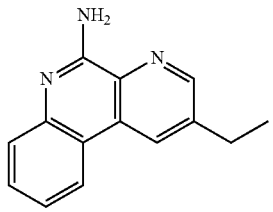 [SMILES: CCc1cnc2c(N)nc3ccccc3c2c1]

To a solution of 2-vinylbenzo[f][1,7]naphthyridin-5-amine (Example 27) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and purified by a COMBIFLASH® system (ISCO) using 0-80% ethyl acetate in hexane to give 2-ethylbenzo[f][1,7]naphthyridin-5-amine as a solid. $^1$H NMR (methanol-d4): δ 8.78-8.81 (m, 2H), 8.45 (d, 1H), 7.55-7.63 (m, 2H), 7.35-7.40 (m, 1H), 2.97 (q, 2H), 1.43 (t, 2H). LRMS [M+H]=224.1.

Example 29

2-phenylbenzo[f][1,7]naphthyridin-5-amine

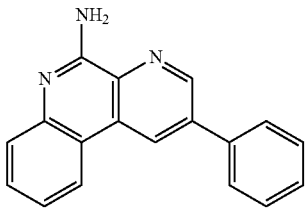 [SMILES: Nc1nc2ccccc2c2cc(-c3ccccc3)cnc12]

Step 1: 3-chloro-5-phenylpicolinonitrile

A solution of 3,5-dichloropicolinonitrile (1.0 eq.), 4,4,5,5-tetramethyl-2-phenyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-80% ethyl acetate in hexane to give a white solid.

Step 2: 2-phenylbenzo[f][1,7]naphthyridin-5-amine

A solution of 2-(tert-butoxycarbonylamino)phenylboronic acid (1.0 eq.) and 3-chloro-5-phenylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-phenylbenzo[f][1,7]naphthyridin-5-amine as a white solid. $^1$H NMR (dmso-d6): δ 9.13 (d, 1H), 9.03 (d, 1H), 8.56 (d, 1H), 7.98 (d, 2H), 7.43-7.56 (m, 5H), 7.27 (m, 1H), 7.13 (bs, 2H). LRMS [M+H]=272.2.

Example 30

(E)-2-styrylbenzo[f][1,7]naphthyridin-5-amine

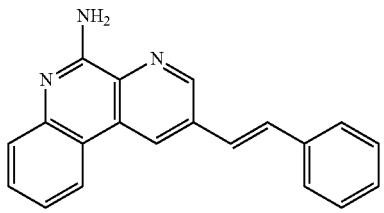 [SMILES: Nc1nc2ccccc2c2cc(/C=C/c3ccccc3)cnc12]

Step 1: (E)-3-chloro-5-styrylpicolinonitrile

A solution of 3,5-dichloropicolinonitrile (1.0 eq.), (E)-4,4,5,5-tetramethyl-2-styryl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give a white solid.

Step 2: (E)-2-styrylbenzo[f][1,7]naphthyridin-5-amine

A solution of 2-(tert-butoxycarbonylamino)phenylboronic acid (1.0 eq.) and (E)-3-chloro-5-styrylpicolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-styrylbenzo[f][1,7]naphthyridin-5-amine as a brown solid. $^1$H NMR (dmso-d6): δ 9.22 (d, 1H), 9.06 (d, 1H), 8.51 (d, 1H), 7.78 (d, 1H), 7.66 (d, 2H), 7.46-7.56 (m, 3H), 7.70 (t, 2H), 7.26-7.32 (m, 2H), 7.08 (bs, 2H). LRMS [M+H]=298.2.

Example 31

2-phenethylbenzo[f][1,7]naphthyridin-5-amine

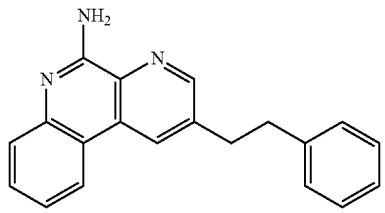 [SMILES: Nc1nc2ccccc2c2cc(CCc3ccccc3)cnc12]

To a solution of (E)-2-styrylbenzo[f][1,7]naphthyridin-5-amine (Example 30) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-phenethylbenzo[f][1,7]naphthyridin-5-amine as a yellow solid. $^1$H NMR (CDCl$_3$): δ 8.54 (d, 1H), 8.32 (d, 1H), 8.10 (dd, 1H), 7.63 (dd, 1H), 7.51 (m, 1H), 7.03-7.32 (m, 6H), 6.16 (bs, 2H), 3.11 (t, 2H), 2.97 (t, 2H). LRMS [M+H]=300.1.

Example 32

(E)-2-(3-methoxyprop-1-enyl)benzo[f][1,7]naphthyridin-5-amine

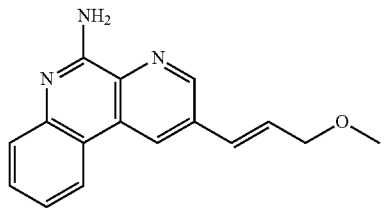 [SMILES: COC/C=C/c1cnc2c(N)nc3ccccc3c2c1]

Step 1: (E)-3-chloro-5-(3-methoxyprop-1-enyl)picolinonitrile

A solution of 3,5-dichloropicolinonitrile (1.0 eq.), (E)-2-(3-methoxyprop-1-enyl)-4,4,5,5-tetramethyl-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give (E)-3-chloro-5-(3-methoxyprop-1-enyl)picolinonitrile as a white solid.

Step 2: (E)-2-(3-methoxyprop-1-enyl)benzo[f][1,7]naphthyridin-5-amine

A solution of 2-(tert-butoxycarbonylamino)phenylboronic acid (1.0 eq.) and (E)-3-chloro-5-(3-methoxyprop-1-enyl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give (E)-2-(3-methoxyprop-1-enyl)benzo[f][1,7]naphthyridin-5-amine as a yellow solid. $^1$H NMR (dmso-d6): δ 9.24 (d, 1H), 9.18 (d, 1H), 8.54 (d, 1H), 7.52-7.58 (m, 2H), 7.31 (m, 1H), 7.11 (bs, 2H), 6.86-7.00 (m, 2H), 4.18 (d, 2H), 3.36 (s, 3H). LRMS [M+H]=266.2.

Example 33

2-(3-methoxypropyl)benzo[f][1,7]naphthyridin-5-amine

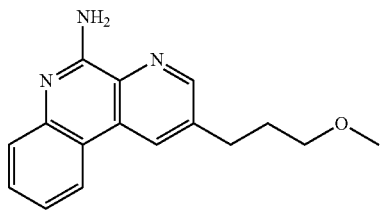 [SMILES: COCCCc1cnc2c(N)nc3ccccc3c2c1]

To a solution of (E)-2-(3-methoxyprop-1-enyl)benzo[f][1,7]naphthyridin-5-amine (Example 32) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-(3-methoxypropyl)benzo[f][1,7]naphthyridin-5-amine as a white solid. $^1$H NMR (CDCl$_3$): δ 8.64 (d, 1H), 8.46 (d, 1H), 8.19 (d, 1H), 7.66 (d, 1H), 7.53 (m, 1H), 7.31 (m, 1H), 6.56 (bs, 2H), 3.37 (t, 2H), 3.31 (s, 3H), 2.91 (t, 2H), 1.93-2.00 (m, 2H). LRMS [M+H]=268.1.

Example 34

2-(prop-1-en-2-yl)benzo[f][1,7]naphthyridin-5-amine

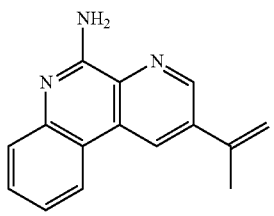 [SMILES: C=C(C)c1cnc2c(N)nc3ccccc3c2c1]

Step 1: 3-chloro-5-(prop-1-en-2-yl)picolinonitrile

A solution of 3,5-dichloropicolinonitrile (1.0 eq.), 4,4,5,5-tetramethyl-2-(prop-1-en-2-yl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 100° C. for 2 hours, then 80° C. for 4 hours. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vacuo. The crude product was purified by flash chromatography on a COMBIFLASH® system (ISCO) using 0-80% ethyl acetate in hexane to give 3-chloro-5-(prop-1-en-2-yl)picolinonitrile as a white solid.

Step 2: 2-(prop-1-en-2-yl)benzo[f][1,7]naphthyridin-5-amine

A solution of 2-(tert-butoxycarbonylamino)phenylboronic acid (1.0 eq.) and 3-chloro-5-(prop-1-en-2-yl)picolinonitrile (from step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 2-(prop-1-en-2-yl)benzo[f][1,7]naphthyridin-5-amine as a white solid. $^1$H NMR (dmso-d6): δ 9.03 (d, 1H), 8.96 (d, 1H), 8.55 (d, 1H), 7.47-7.53 (m, 2H), 7.25 (m, 1H), 7.07 (bs, 2H) 5.80 (s, 1H), 5.36 (s, 1H), 2.27 (s, 3H). LRMS [M+H]=236.2.

Example 35

2-isopropylbenzo[f][1,7]naphthyridin-5-amine

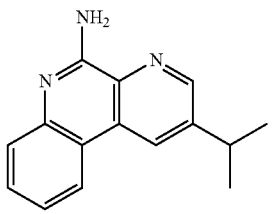 [SMILES: CC(C)c1cnc2c(N)nc3ccccc3c2c1]

To a solution of 2-(prop-1-en-2-yl)benzo[f][1,7]naphthyridin-5-amine (Example 34) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vacuo and the crude product was purified by flash chromatography on a COMBIFLASH® system (ISCO) using 0-80% ethyl acetate in hexane to give 2-isopropylbenzo[f][1,7]naphthyridin-5-amine as a yellow solid. $^1$H NMR (CDCl$_3$): δ 8.69 (d, 1H), 8.49 (d, 1H), 8.25 (dd, 1H), 7.65 (dd, 1H), 7.53 (m, 1H), 7.31 (m, 1H), 6.02 (bs, 2H), 3.15 (septet, 1H), 1.37 (d, 6H). LRMS [M+H]=238.2.

Example 36

1-methylbenzo[f][1,7]naphthyridin-5-amine

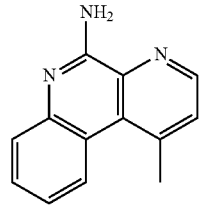 [SMILES: Cc1ccnc2c(N)nc3ccccc3c12]

Step 1: 5-bromo-2-chloro-4-methylpyridine 1-oxide

A solution of 5-bromo-2-chloro-4-methylpyridine (1.0 eq.) and meta-chloroperbenzoic acid (mCPBA) (2.5 eq.) in chloroform (0.1 M) was stirred at 50° C. overnight. After cooling to room temperature, Ca(OH)$_2$ (2.5 eq.) was added to the reaction mixture. The precipitate was filtered and washed with 5% methanol in dichloromethane and ethyl acetate. The filtrate was washed with saturated aqueous Na$_2$S$_2$O$_3$ solution and saturated aqueous NaHCO$_3$ solution. The combined organic layers were washed with brine, dried over anhydrous MgSO$_4$, and concentrated en vacuo into a pale solid that was carried onto the next step without further purification.

Step 2: 3-bromo-6-chloro-4-methylpicolinonitrile

To a solution of 5-bromo-2-chloro-4-methylpyridine 1-oxide (from step 1) (1.0 eq.) in acetonitrile (0.2 M) was added TMSCN (4.0 eq.) and triethylamine (3.0 eq.). The reaction was heated at 100° C. overnight. After cooling to room temperature, the solvent was concentrated en vacuo, and the residue was purified by a COMBIFLASH® system (ISCO) using 0-50% ethyl acetate in hexane to give 3-bromo-6-chloro-4-methylpicolinonitrile.

Step 3: 3-chloro-1-methylbenzo[f][1,7]naphthyridin-5-amine

A solution of 2-(tert-butoxycarbonylamino)phenylboronic acid (1.0 eq.) and 3-bromo-6-chloro-4-methylpicolinonitrile (from step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give 3-chloro-1-methylbenzo[f][1,7]naphthyridin-5-amine as a white solid. $^1$H NMR (dmso-d6): δ 8.44 (d, 1H), 7.83 (s, 1H), 7.50-7.58 (m, 2H), 7.02 (bs, 2H), 2.98 (s, 3H). LRMS [M+H]=244.1.

Step 4: 1-methylbenzo[f][1,7]naphthyridin-5-amine

To a solution of 3-chloro-1-methylbenzo[f][1,7]naphthyridin-5-amine (from step 3) in ethyl acetate/methanol (1:2, 0.03 M) was added 10% wt palladium on carbon (0.2 eq.). The reaction vessel was shaken on a hydrogen Parr apparatus under 50 psi of hydrogen overnight. The mixture was filtered through a pad of celite, washing with dichloromethane. The filtrate was concentrated en vacuo and purified by a COMBIFLASH® system (ISCO) using 0-80% ethyl acetate in hexane to give 1-methylbenzo[f][1,7]naphthyridin-5-amine as a white solid. $^1$H NMR (CDCl$_3$): δ 8.63 (d, 1H), 8.44 (d, 1H), 7.71 (dd, 1H), 7.54 (m, 1H), 7.45 (d, 1H), 7.30 (m, 1H), 6.20 (bs, 2H), 3.01 (s, 3H). LRMS [M+H]=210.1.

Example 37 pyrido[3,2-f][1,7]naphthyridin-6-amine

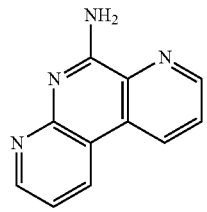 [SMILES: Nc1nc2ncccc2c2cccnc12]

A solution of tert-butyl 3-(4,4,5,5-tetramethyl-1,3,2-dioxaborolan-2-yl)pyridin-2-ylcarbamate (1.0 eq.) and 3-bromopicolinonitrile (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vacuo to obtain a crude residue. The crude product was purified by flash chromatography on a COMBIFLASH® system (ISCO) using 0-80% ethyl acetate in hexane to give pyrido[3,2-f][1,7]naphthyridin-6-amine as a white solid. $^1$H NMR (dmso-d6): δ 9.14 (dd, 1H), 8.98 (dd, 1H), 8.90 (dd, 1H), 7.93 (dd, 1H), 7.60 (bs, 2H), 7.30 (dd, 1H). LRMS [M+H]=197.

Example 38

2-ethyl-8-methylbenzo[f][1,7]naphthyridin-5-amine

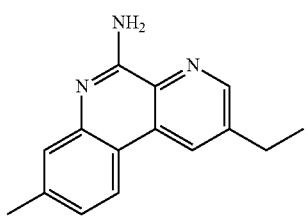 [SMILES: CCc1cnc2c(N)nc3cc(C)ccc3c2c1]

Step 1:
8-methyl-2-vinylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 4/step 2) (1.0 eq.) and 3-chloro-5-vinylpicolinonitrile (from Example 27/Step 1) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 8-methyl-2-vinylbenzo[f][1,7]naphthyridin-5-amine as a yellow solid.

Step 2:
2-ethyl-8-methylbenzo[f][1,7]naphthyridin-5-amine

To a solution of 8-methyl-2-vinylbenzo[f][1,7]naphthyridin-5-amine (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite and washed with dichloromethane. The filtrate was concentrated en vaccuo and purified by a COMBIFLASH® system (ISCO) using 0-80% ethyl acetate in hexane to give 2-ethyl-8-methylbenzo[f][1,7]naphthyridin-5-amine as an offwhite solid. $^1$H NMR (CDCl$_3$): δ 8.61 (d, 1H), 8.42 (d, 1H), 8.10 (d, 1H), 7.44 (s, 1H), 7.12 (dd, 1H), 6.00 (bs, 2H), 2.84 (q, 2H), 2.45 (s, 3H), 1.33 (t, 3H). LRMS [M+H]=238.1.

Example 39

(5-amino-8-methylbenzo[f][1,7]naphthyridin-2-yl)methanol

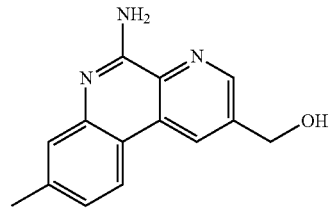 [SMILES: Cc1ccc2c(c1)nc(N)c1ncc(CO)cc12]

Step 1: ethyl 5-chloro-6-cyanonicotinate

A solution of ethyl 5,6-dichloronicotinate (1 eq), zinc cyanide (0.75 eq) and tetrakis(triphenyl-phosphine)palladium (0.10 eq.) in DMF (0.3 M) was degassed and then heated at 100° C. for 3 hours. Solvent was removed en vaccuo to obtain a crude residue. The crude material was purified by flash chromatography on a COMBIFLASH® system (ISCO) using 0-80% ethyl acetate in hexane to give ethyl 5-chloro-6-cyanonicotinate as a white solid.

Step 2: ethyl 5-amino-8-methylbenzo[f][1,7]naphthyridine-2-carboxylate

A solution of tert-butyl 5-methyl-2-(4,4,5,5-tetramethyl-1,3,2-dioxaborolan-2-yl)phenylcarbamate (from Example 4/step 2) (1.0 eq.) and ethyl 5-chloro-6-cyanonicotinate (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give ethyl 5-amino-8-methylbenzo[f][1,7]naphthyridine-2-carboxylate.

Step 3:
2-ethyl-8-methylbenzo[f][1,7]naphthyridin-5-amine

To a stirred solution of ethyl 5-amino-8-methylbenzo[f][1,7]naphthyridine-2-carboxylate (from the previous step) in THF (0.2 M) cooled in an ice-water bath was added 1 N solution of super hydride in THF (10 eq.). Upon completion of the reaction the reaction was quenched with 1 N HCl, and extracted with EtOAc. Combined organic extracts were concentrated en vaccuo to obtain a crude residue. The crude material was purified by flash chromatography on a COMBIFLASH® system (ISCO) using 0-80% ethyl acetate in hexane to give (5-amino-8-methylbenzo[f][1,7]naphthyridin-2-yl)methanol as a white solid. $^1$H NMR (CDCl$_3$): δ 8.68 (d, 1H), 8.52 (d, 1H), 8.04 (d, 1H), 7.44 (s, 1H), 7.12 (dd, 1H), 6.00 (bs, 2H), 4.90 (s, 2H), 2.45 (s, 3H). LRMS [M+H]=240.1

Example 40

8-methyl-2-propylbenzo[f][1,7]naphthyridin-5-amine

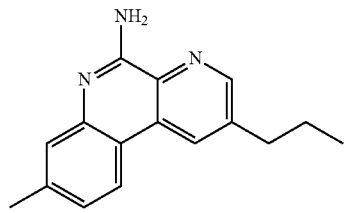 [SMILES: CCCc1cnc2c(N)nc3cc(C)ccc3c2c1]

Step 1: (E)-3-chloro-5-(prop-1-enyl)picolinonitrile

A solution of 3,5-dichloropicolinonitrile (1.0 eq.), (E)-4,4,5,5-tetramethyl-2-(prop-1-enyl)-1,3,2-dioxaborolane (1.0 eq.), tetrakis(triphenyl-phosphine)palladium (5 mol %), and 2N aqueous sodium carbonate solution (3.4 eq.) in toluene/ethanol (2:1, 0.04 M) was stirred at 95° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO$_4$, and concentrated en vaccuo to obtain a crude residue. The crude material was purified by flash chromatography on a COMBIFLASH® system (ISCO) using 0-80% ethyl acetate in hexane to give a white solid (E)-3-chloro-5-(prop-1-enyl)picolinonitrile.

Step 2: (E)-8-methyl-2-(prop-1-enyl)benzo[f][1,7]naphthyridin-5-amine

A solution of tert-butyl 5-methyl-2-(4,4,5,5-tetramethyl-1,3,2-dioxaborolan-2-yl)phenylcarbamate (from Example 4/Step 2) (1.0 eq.) and (E)-3-chloro-5-(prop-1-enyl)picolinonitrile (from the previous step) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction content was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give (E)-8-methyl-2-(prop-1-enyl)benzo[f][1,7]naphthyridin-5-amine as a yellow solid.

Step 3:
8-methyl-2-propylbenzo[f][1,7]naphthyridin-5-amine

To a solution of (E)-8-methyl-2-(prop-1-enyl)benzo[f][1,7]naphthyridin-5-amine (from the previous step) in ethyl acetate/methanol (1:4, 0.05 M) was added 10% palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give 8-methyl-2-propylbenzo[f][1,7]naphthyridin-5-amine as offwhite solid. $^1$H NMR (CDCl$_3$): δ 8.59 (d, 1H), 8.41 (d, 1H), 8.10 (d, 1H), 7.43 (s, 1H), 7.13 (dd, 1H), 5.94 (bs, 2H), 2.78 (t, 2H), 2.44 (s, 3H), 1.75 (m, 2H), 0.95 (t, 3H). LRMS [M+H]=252.1

Example 41

2-(2-(1H-indol-5-yl)ethyl)-8-methylbenzo[f][1,7]naphthyridin-5-amine

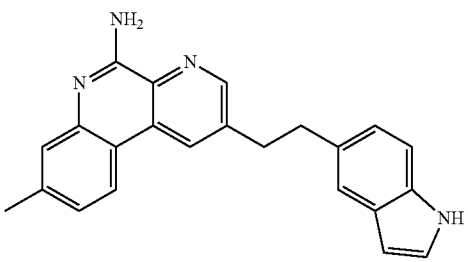 [SMILES: Cc1ccc2c(c1)nc(N)c1ncc(CCc3ccc4[nH]ccc4c3)cc12]

Step 1: 5-((triethylsilyl)ethynyl)-1H-indole

To a scintillation vial was added -iodo-1H-indole (1.1 eq.), triethyl(ethynyl)silane (1 eq.), triethylamine (5 eq.), and anhydrous DMF (0.2 M). Vacuumed and nitrogen flushed for three times. CuI (0.1 eq.) and bis(triphenylphosphine)dichloro-palladium(II) (0.1 eq) were added. The vial was sealed and heated at 60° C. overnight. Upon completion of the reaction as monitored by TLC, the content of the vial was loaded onto a silica gel column pretreated with hexanes. Column was washed with hexanes and diethylether until all eluents containing product were collected. Carefully distill off hexanes and ether using rotary evaporator with minim heating afforded product 5-((triethylsilyl)ethynyl)-1H-indole as colorless oil, which was carried directly on to the next step.

Step 2: 5-ethynyl-1H-indole

To a stirred solution of 5-((triethylsilyl)ethynyl)-1H-indole (from the previous step) in THF (0.2 M) cooled at 0° C. was treated with a solution (0.5 eq.) of tetrabutylammonium fluoride in a dropwise fashion. The reaction mixture turned black and was continued to stir for 30 minutes before warming up to rt. TLC showed full conversion. The reaction was quenched with water and was extracted with diethylether. Combined organic layers were dried over anhydrous Na₂SO₄ and concentrated using rotary evaporator with minim heating. Chromatography (silica gel, diethylether) afforded the product 5-ethynyl-1H-indole as colorless oil.

Step 3:
5-((1H-indol-5-yl)ethynyl)-3-chloropicolinonitrile

To a round bottom flask capped with septa was added 5-ethynyl-1H-indole (from the previous step) (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine) dichloro-palladium(II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 5-((1H-indol-5-yl)ethynyl)-3-chloropicolinonitrile.

Step 4: 2-((1H-indol-5-yl)ethynyl)-8-methylbenzo[f][1,7]naphthyridin-5-amine

To a round bottom flask with refluxing condenser were added 5-((1H-indol-5-yl)ethynyl)-3-chloropicolinonitrile (from the previous step) (1 eq.), tert-butyl 2-(4,4,5,5-tetramethyl-1,3,2-dioxaborolan-2-yl)phenylcarbamate (from Example 4/Step 2) (1.25 eq.), K₃PO₄ (2 eq.), tris(dibenzylideneacetone)dipalladium(0) (0.05 eq.), and 2-Dicyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na₂SO₄) and concentrated. Flash chromatography (silica gel, 0-50% EtOAc in CH₂Cl₂) afforded the product 2-((1H-indol-5-yl)ethynyl)-8-methylbenzo[f][1,7]naphthyridin-5-amine as a yellow solid.

Step 5: 2-(2-(2,3-dihydrobenzofuran-5-yl)ethyl)-8-methylbenzo[f][1,7]naphthyridin-5-amine To a round bottom flask was added 2-((1H-indol-5-yl) ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The content were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH₂Cl₂) afforded the product 2-(2-(2,3-Dihydrobenzofuran-5-yl)ethyl)-8-methylbenzo[f][1,7]naphthyridin-5-amine as a yellow solid. ¹H NMR (CDCl₃): δ 8.54 (d, 1H), 8.34 (d, 1H), 8.28 (s, 1H), 7.99 (d, 1H), 7.64-7.56 (m, 1H), 7.50-7.35 (m, 1H), 7.24 (d, 1H), 7.12 (t, 1H), 7.08 (dd, 1H), 6.92 (dd, 1H), 6.41 (s, 1H), 6.01 (bs, 2H), 3.16-3.12 (m, 2H), 3.10-3.05 (m, 2H), 2.43 (s, 3H). LRMS [M+H]=353.2

Example 42

2-(4-ethoxyphenethyl)-8-methylbenzo[f][1,7]naphthyridin-5-amine

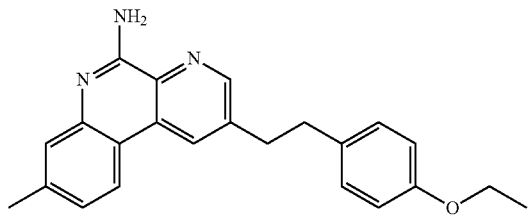 [SMILES: CCOc1ccc(CCc2cnc3c(N)nc4cc(C)ccc4c3c2)cc1]

Step 1: 3-chloro-5-((4-ethoxyphenyl)ethynyl)picolinonitrile

To a round bottom flask capped with septa was added 1-ethoxy-4-ethynylbenzene (1.1 eq), 3,5-dichloropicolinonitrile (1 eq.), triethylamine (5 eq.), and anhydrous DMF (0.2 M). Vacuumed and nitrogen flushed for three times. CuI (0.05 eq.) and bis(triphenylphosphine)dichloro-palladium (II) (0.05 eq) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-ethoxyphenyl) ethynyl)picolinonitrile.

Step 2: 2((4-ethoxyphenyl)ethynyl)-8-methylbenzo [f][1,7]naphthyridin-5-amine

To a round bottom flask with refluxing condenser were added 3-chloro-5-((4-ethoxyphenyl)ethynyl)picolinonitrile (from the previous step) (1 eq.), tert-butyl 5-methyl-2-(4,4,5,5-tetramethyl-1,3,2-dioxaborolan-2-yl)phenylcarbamate (from Example 4/Step 2) (1.25 eq.), K₃PO₄ (2 eq.), tris (dibenzylideneacetone)dipalladium(0) (0.05 eq.), and 2-di-cyclohexylphosphino-2',6'-dimethoxybiphenyl (0.1 eq.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The content were cooled down and were taken up in 200 mL of water followed by extraction with methylene chloride. Combined organic layers were dried (Na₂SO₄) and concentrated. Flash chromatography (silica gel, 0-50% EtOAc in CH₂Cl₂) afforded the product 2-((4-ethoxyphenyl)ethynyl)-8-methyl-benzo[f][1,7]naphthyridin-5-amine.

Step 3: 2-(4-ethoxyphenethyl)-8-methylbenzo[f][1,7]naphthyridin-5-amine

To a round bottom flask was added 2-((4-ethoxyphenyl) ethynyl)-8-methylbenzo[f][1,7]naphthyridin-5-amine (from the previous step) (1 eq.) with a stirring bar. Ethanol and methylene chloride (1:2, 0.2 M) were added, followed by palladium in carbon (activated powder, wet, 10% on carbon, 0.1 eq.). The contents were degassed under vacuum followed by hydrogen flush (three times). The reaction mixture was stirred vigorously under hydrogen balloon at room temperature overnight. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH$_2$Cl$_2$) afforded the product as a yellow solid. Further recrystallization using toluene afforded product 2-(4-ethoxyphenethyl)-8-methylbenzo[f][1,7]naphthyridin-5-amine as a white fine crystal. $^1$H NMR (CDCl$_3$): δ 8.52 (d, 1H), 8.30 (d, 1H), 8.10 (d, 1H), 7.46 (s, 1H), 7.12 (dd, 1H), 7.06 (d, 2H), 6.75 (d, 2H), 5.95 (bs, 2H), 3.93 (q, 2H), 3.11-3.05 (dd, 2H), 2.95-2.90 (dd, 2H), 2.44 (s, 3H), 1.33 (t, 3H). LRMS [M+H]=358.2

Example 43

8-methyl-2-(4-phenoxyphenethyl)benzo[f][1,7]naphthyridin-5-amine

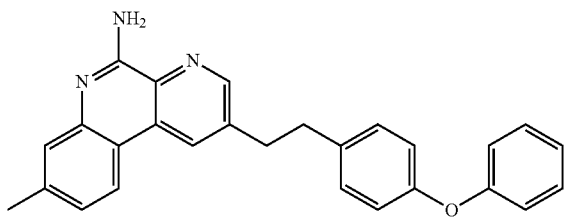 [SMILES: Cc1ccc2c(c1)nc(N)c1ncc(CCc3ccc(Oc4ccccc4)cc3)cc12]

Step 1: 3-chloro-5-((4-phenoxyphenyl)ethynyl)picolinonitrile

3-Chloro-5-((4-phenoxyphenyl)ethynyl)picolinonitrile was prepared from 1-ethynyl-4-phenoxybenzene (commercially available) following the procedures described for Example 42, step 1.

Step 2: 8-methyl-2-((4-phenoxyphenyl)ethynyl)benzo[f][1,7]naphthyridin-5-amine

8-Methyl-2-((4-phenoxyphenyl)ethynyl)benzo[f][1,7]naphthyridin-5-amine was prepared from 3-chloro-5-((4-phenoxyphenyl)ethynyl)picolinonitrile (from the previous step) following the procedures described for Example 42, step 2.

Step 3: 8-methyl-2-(4-phenoxyphenethyl)benzo[f][1,7]naphthyridin-5-amine

8-Methyl-2-(4-phenoxyphenethyl)benzo[f][1,7]naphthyridin-5-amine was prepared from 8-methyl-2-((4-phenoxyphenyl)ethynyl)benzo[f][1,7]naphthyridin-5-amine (from the previous step) following the procedures described for Example 42, step 3. $^1$H NMR (CDCl$_3$): δ 8.54 (d, 1H), 8.30 (d, 1H), 8.01 (d, 1H), 7.45 (s, 1H), 7.25-7.20 (m, 2H), 7.12 (dd, 1H), 7.07-6.84 (m, 8H), 6.00 (bs, 2H), 3.13-3.08 (dd, 2H), 2.99-2.94 (dd, 2H), 2.44 (s, 3H). LRMS [M+H]=406.2

Example 44

2-(2,4-dimethylphenethyl)benzo[f][1,7]naphthyridin-5-amine

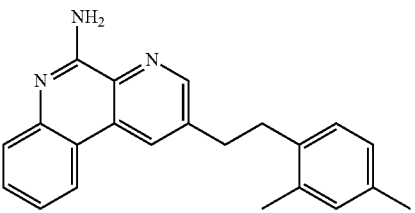 [SMILES: Cc1ccc(CCc2cnc3c(N)nc4ccccc4c3c2)c(C)c1]

Step 1: ((2,4-dimethylphenyl)ethynyl)triethylsilane ((2,4-Dimethylphenyl)ethynyl)triethylsilane was prepared from 1-iodo-2,4-dimethylbenzene (commercially available) following the procedures described for Example 41, step 1.

Step 2: 1-ethynyl-2,4-dimethylbenzene

1-Ethynyl-2,4-dimethylbenzene was prepared from ((2,4-dimethylphenyl)ethynyl)triethylsilane (from the previous step) following the procedures described for Example 41, step 2.

Step 3: 3-chloro-5-((2,4-dimethylphenyl)ethynyl)picolinonitrile

3-Chloro-5-((2,4-dimethylphenyl)ethynyl)picolinonitrile was prepared from 1-ethynyl-2,4-dimethylbenzene (from the previous step) following the procedures described for Example 41, step 3.

Step 4: 2-((2,4-dimethylphenyl)ethynyl)benzo[f][1,7]naphthyridin-5-amine 2-((2,4-Dimethylphenyl)ethynyl)benzo[f][1,7]naphthyridin-5-amine was prepared from 3-chloro-5-((2,4-dimethylphenyl)ethynyl)-picolinonitrile (from the previous step) following the procedures described for Example 41, step 4.

Step 5: 2-(2,4-dimethylphenethyl)benzo[f][1,7]naphthyridin-5-amine 2-(2,4-Dimethylphenethyl)benzo[f][1,7]naphthyridin-5-amine was prepared from 2-((2,4-dimethylphenyl)ethynyl)benzo[f][1,7]naphthyridin-5-amine (from the previous step) following the procedures described for Example 41, step 5. $^1$H NMR (CDCl$_3$): δ 8.60 (d, 1H), 8.33 (d, 1H), 8.14 (d, 1H), 7.67 (d, 1H), 7.54 (t, 1H), 7.31 (t, 1H), 6.96-6.86 (m, 3H), 6.29 (bs, 2H), 3.04-3.10 (dd, 2H), 2.97-2.91 (dd, 2H), 2.24 (s, 3H), 2.20 (s, 3H). LRMS [M+H]=328.2.

Example 45

2-(2,4-dimethylphenethyl)-8-methylbenzo[f][1,7]naphthyridin-5-amine

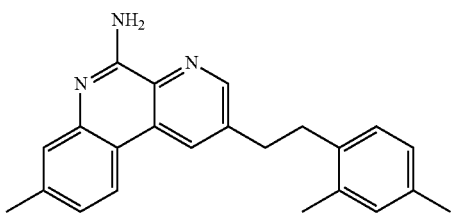

Step 1: 2-((2,4-dimethylphenyl)ethynyl)-8-methyl-benzo[f][1,7]naphthyridin-5-amine 2-((2,4-Dimethylphenyl)ethynyl)-8-methylbenzo[f][1,7]naphthyridin-5-amine was prepared from 3-chloro-5-((2,4-dimethylphenyl)ethynyl)picolinonitrile (from Example 44/Step 3) and tert-butyl 5-methyl-2-(4,4,5,5-tetramethyl-1,3,2-dioxaborolan-2-yl)phenylcarbamate (from Example 4/Step 2) following the procedures described for Example 41, step 4.

Step 2: 2-(2,4-dimethylphenethyl)-8-methylbenzo[f][1,7]naphthyridin-5-amine 2-(2,4-Dimethylphenethyl)-8-methylbenzo[f][1,7]naphthyridin-5-amine was prepared from 1-ethynyl-4-phenoxybenzene (from the previous step) following the procedures described for Example 41, step 5. $^1$H NMR (CDCl$_3$): δ 8.56 (d, 1H), 8.28 (d, 1H), 8.00 (d, 1H), 7.46 (s, 1H), 7.14 (dd, 1H), 6.95-6.85 (m, 3H), 6.26 (bs, 2H), 3.08-3.02 (dd, 2H), 2.96-2.90 (dd, 2H), 2.45 (s, 3H), 2.23 (s, 3H), 2.19 (s, 3H). LRMS [M+H]=342.2

Example 46

2-(4-methoxy-2-methylphenethyl)-8-methylbenzo[f][1,7]naphthyridin-5-amine

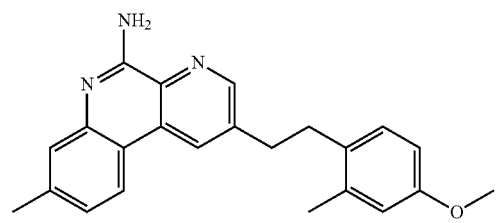

Step 1: 3-chloro-5-((4-methoxy-2-methylphenyl)ethynyl)picolinonitrile

3-Chloro-5-((4-methoxy-2-methylphenyl)ethynyl)picolinonitrile was prepared from 1-ethynyl-4-methoxy-2-methylbenzene (commercially available) following the procedure described for Example 41/Step 3.

Step 2: 2-((4-methoxy-2-methylphenyl)ethynyl)-8-methylbenzo[f][1,7]naphthyridin-5-amine 2-((4-Methoxy-2-methylphenyl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 41, step 4.

Step 3: 2-(4-methoxy-2-methylphenethyl)-8-methyl-benzo[f][1,7]naphthyridin-5-amine 2-(4-Methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step) following the procedures described for Example 41, step 5. $^1$H NMR (CDCl$_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Example 47

4-(2-(5-amino-8-methylbenzo[f][1,7]naphthyridin-2-yl)ethyl)-3-methylphenol

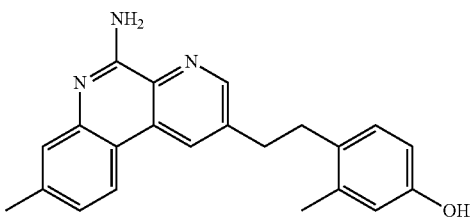 [SMILES: Cc1ccc2c(c1)nc(N)c1ncc(CCc3ccc(O)cc3C)cc12]

To a stirred solution of 2-(4-methoxy-2-methylphenethyl)-8-methylbenzo[f][1,7]naphthyridin-5-amine (Example 46) in methylene chloride (0.2 M) in an ice-water bath was added 1 N solution of BBr$_3$ (2 eq) in CH$_2$Cl$_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-d$_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2

Example 48

2-(2-(2,3-dihydrobenzofuran-5-yl)ethyl)-8-methyl-benzo[f][1,7]naphthyridin-5-amine

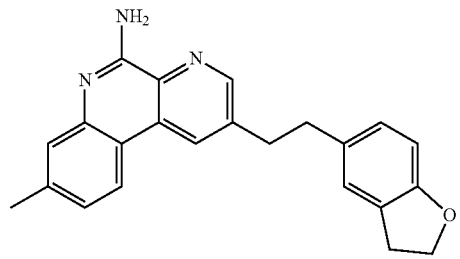 [SMILES: Cc1ccc2c(c1)nc(N)c1ncc(CCc3ccc4c(c3)CCO4)cc12]

Step 1: ((2,3-dihydrobenzofuran-5-yl)ethynyl)triethylsilane ((2,3-Dihydrobenzofuran-5-yl)ethynyl)triethylsilane was prepared from 5-iodo-2,3-dihydrobenzofuran (commercially available) following the procedures described for Example 41, step 1.

Step 2: 5-ethynyl-2,3-dihydrobenzofuran

5-Ethynyl-2,3-dihydrobenzofuran was prepared from ((2,3-dihydrobenzofuran-5-yl)ethynyl)triethylsilane (from the previous step) following the procedures described for Example 41/Step 2.

Step 3: 3-chloro-5-((2,3-dihydrobenzofuran-5-yl)ethynyl)picolinonitrile

3-Chloro-5-((2,3-dihydrobenzofuran-5-yl)ethynyl)picolinonitrile was prepared from 5-ethynyl-2,3-dihydrobenzofuran (from the previous step) following the procedures described for Example 41/Step 3.

Step 4: 2-((2,3-dihydrobenzofuran-5-yl)ethynyl)-8-methylbenzo[f][1,7]naphthyridin-5-amine 2-((2,3-Dihydrobenzofuran-5-yl)ethynyl)-8-methylbenzo[f][1,7]naphthyridin-5-amine was prepared from 3-chloro-5-(4-methoxy-2-methylphenethyl)picolinonitrile (from the previous step) following the procedures described for Example 41/Step 4.

Step 5: 2-(2-(2,3-dihydrobenzofuran-5-yl)ethyl)-8-methylbenzo[f][1,7]naphthyridin-5-amine 2-(2-(2,3-Dihydrobenzofuran-5-yl)ethyl)-8-methylbenzo[f][1,7]naphthyridin-5-amine was prepared from 2-((2,3-dihydrobenzofuran-5-yl)ethynyl)-8-methylbenzo[f][1,7]naphthyridin-5-amine (from the previous step) following the procedures described for Example 41/Step 5. $^1$H NMR (CDCl$_3$): δ 8.62 (d, 1H), 8.40 (d, 1H), 8.11 (d, 1H), 7.53 (s, 1H), 7.21 (dd, 1H), 6.99 (s, 1H), 6.95 (dd, 1H), 6.74 (d, 1H), 6.05 (bs, 2H), 4.57 (t, 2H), 3.19-3.13 (m, 4H), 3.03-2.98 (dd, 2H), 2.54 (s, 3H). LRMS [M+H]=356.2

Example 49

2-(5-amino-8-methylbenzo[f][1,7]naphthyridin-2-yl)ethanol

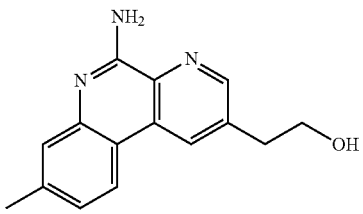 [SMILES: Cc1ccc2c(c1)nc(N)c1ncc(CCO)cc12]

Step 1: (Z)-3-chloro-5-(2-ethoxyvinyl)picolinonitrile (Z)-3-Chloro-5-(2-ethoxyvinyl)picolinonitrile was prepared from (Z)-2-(2-ethoxyvinyl)-4,4,5,5-tetramethyl-1,3,2-dioxaborolane (commercially available) following the procedures described for Example 40/Step 1.

Step 2: (Z)-2-(2-ethoxyvinyl)-8-methylbenzo[f][1,7]naphthyridin-5-amine (Z)-2-(2-Ethoxyvinyl)-8-methylbenzo[f][1,7]naphthyridin-5-amine was prepared from (Z)-3-chloro-5-(2-ethoxyvinyl)picolinonitrile (from the previous step) following the procedures described for Example 40/Step 2.

Step 3: 2-(5-amino-8-methylbenzo[f][1,7]naphthyridin-2-yl)ethanol

A solution of (Z)-2-(2-ethoxyvinyl)-8-methylbenzo[f][1,7]naphthyridin-5-amine (from the previous step) in a mixture of 2:5 conc. HCl and dioxane (0.1 M) was heated at 60° C. overnight. Upon cooling down to rt, the reaction mixture was treated with excess NaHCO$_3$ saturated solution, followed by extraction with EtOAc. Combined organic extracts were concentrated and was taken up in THF (0.2 M), and was treated with 1 N super hydride solution in THF (10 eq.) at 0° C. The reaction mixture was allowed to warm to room temperature and stirred overnight. The reaction was worked up following the procedures described for Example 39/Step 3, to afford 2-(5-amino-8-methylbenzo[f][1,7]naphthyridin-2-yl)ethanol as white solid. $^1$H NMR (CDCl$_3$): δ 8.61 (d, 1H), 8.47 (d, 1H), 8.01 (d, 1H), 7.41 (s, 1H), 7.10 (d, 1H), 6.40 (s, 1H), 6.01 (bs, 2H), 4.01 (t, 2H), 3.06 (t, 2H), 2.43 (s, 3H). LRMS [M+H]=254.1

Example 50

3-methyl-9-phenyl-9,10-dihydrobenzo[f]furo[2,3-b][1,7]naphthyridin-6-amine

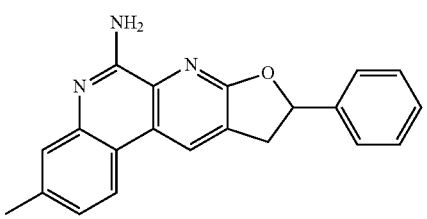 [SMILES: Cc1ccc2c(c1)nc(N)c1nc3c(cc12)CC(c1ccccc1)O3]

141

Step 1: 5-bromo-2-chloro-3-methylpyridine 1-oxide

5-Bromo-2-chloro-3-methylpyridine 1-oxide was prepared from 5-bromo-2-chloro-3-methylpyridine (commercially available) following the procedures described for Example 17/Step 1.

Step 2: 3-bromo-6-chloro-5-methylpicolinonitrile

3-Bromo-6-chloro-5-methylpicolinonitrile was prepared from (Z)-3-chloro-5-(2-ethoxyvinyl)picolinonitrile (from the previous step) following the procedures described for Example 17/Step 2.

Step 3: 3-bromo-6-chloro-5-(2-hydroxy-2-phenylethyl)picolinonitrile

A solution of 3-bromo-6-chloro-5-methylpicolinonitrile (from the previous step) in THF (0.2 M) was cooled to −78° C. LDA (2N solution, 2 eq) was added dropwise. The reaction was kept stirring at −78° C. for 1 hour, followed by addition of benzaldehyde (1 eq). The reaction was kept stirring at −78° C. for another 30 minutes before allowing it to slowly warm to room temperature. The reaction was quenched with sat. NH$_4$Cl and extracted with EtOAc. Combined organic washes were concentrated. Flash chromatography (silica gel, 20-50% EtOAc in hexanes) afforded the product 3-bromo-6-chloro-5-(2-hydroxy-2-phenylethyl)picolinonitrile as a yellow solid.

Step 4: 3-methyl-9-phenyl-9,10-dihydrobenzo[f]furo[2,3-b][1,7]naphthyridin-6-amine 3-Methyl-9-phenyl-9,10-dihydrobenzo[f]furo[2,3-b][1,7]naphthyridin-6-amine was prepared from 3-bromo-6-chloro-5-methylpicolinonitrile (from the previous step) following the procedures described for Example 41/Step 4. $^1$H NMR (CDCl$_3$): δ 8.45 (s, 1H), 7.98 (d, 1H), 7.45 (s, 1H), 7.40-7.28 (m, 5H), 7.12 (d, 1H), 5.93 (t, 1H), 5.93 (brs, 2H), 3.86 (dd, 1H), 3.40 (dd, 1H), 2.44 (s, 3H). LRMS [M+H]=328.1

Example 51

8-methylbenzo[f][1,7]naphthyridine-2,5-diamine

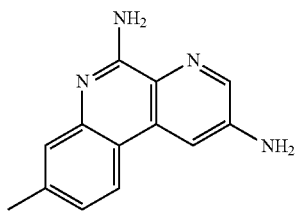 [SMILES: Cc1ccc2c(c1)nc(N)c1ncc(N)cc12]

Step 1: tert-butyl 5,6-dichloropyridin-3-ylcarbamate

To a solution of 5,6-dichloropyridin-3-amine (commercially available) in THF (0.2 M) stirred at 0° C. was added (BOC)$_2$O (1.2 eq). The reaction mixture was heated at 40° C. until full conversion as monitored by TLC. The reaction mixture was then concentrated. Flash chromatography (silica gel, 20-50% EtOAc in hexanes) of the crude afforded tert-butyl 5,6-dichloropyridin-3-ylcarbamate.

Step 2: tert-butyl 5-chloro-6-cyanopyridin-3-ylcarbamate

Tert-butyl 5-chloro-6-cyanopyridin-3-ylcarbamate was prepared from tert-butyl 5,6-dichloropyridin-3-ylcarbamate (from the previous step) following the procedures described for Example 39/Step 1.

Step 3: 8-methylbenzo[f][1,7]naphthyridine-2,5-diamine 8-methylbenzo[f][1,7]naphthyridine-2,5-diamine was prepared (as minor product) together with tert-butyl 5-amino-8-methylbenzo[f][1,7]naphthyridin-2-ylcarbamate (as major product) from tert-butyl 5-chloro-6-cyanopyridin-3-ylcarbamate (from the previous step) following the procedures described for Example 4/Step 2. $^1$H NMR (DMSO-d$_6$): δ 10.11 (s, 1H), 9.02 (s, 1H), 8.82 (d, 1H), 8.06 (d, 1H), 7.34 (s, 1H), 7.15 (dd, 1H), 6.99 (s, 2H), 2.44 (s, 3H). LRMS [M+H]=225.1

Example 52

1-(5-amino-8-methylbenzo[f][1,7]naphthyridin-2-yl)propan-2-ol

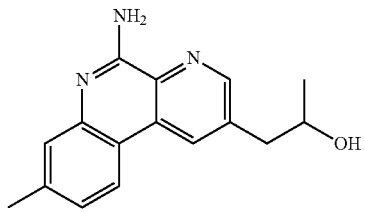 [SMILES: Cc1ccc2c(c1)nc(N)c1ncc(CC(C)O)cc12]

Step 1: 3-bromo-5-methylpicolinonitrile

3-Bromo-5-methylpicolinonitrile was prepared from 2,3-dibromo-5-methylpyridine (commercially available) following the procedures described for Example 39/Step 1.

Step 2: 3-bromo-5-(2-hydroxypropyl)picolinonitrile

3-Bromo-5-(2-hydroxypropyl)picolinonitrile was prepared from 3-bromo-5-methylpicolinonitrile (from the previous step) and acetaldehyde following the procedures described for Example 50/Step 3.

Step 3: 1-(5-amino-8-methylbenzo[f][1,7]naphthyridin-2-yl)propan-2-ol 1-(5-Amino-8-methylbenzo[f][1,7]naphthyridin-2-yl)propan-2-ol was prepared from 3-bromo-5-(2-hydroxypropyl)picolinonitrile (from the previous step) following the procedures described for Example 50, step 4. $^1$H NMR (methanol-d$_4$): δ 8.72 (d, 1H), 8.68 (d, 1H), 8.24 (d, 1H), 7.38 (s, 1H), 7.18 (dd, 1H), 4.16-4.07 (m, 1H), 3.05-2.99 (m, 2H), 2.97-2.90 (m, 2H), 2.47 (s, 3H), 1.28 (d, 3H). LRMS [M+H]=268.1

Example 53

2-(5-amino-8-methylbenzo[f][1,7]naphthyridin-2-yl)acetonitrile

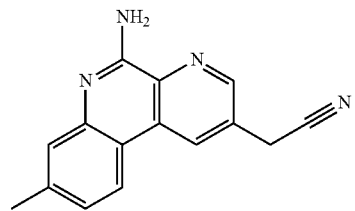 [SMILES: Cc1ccc2c(c1)nc(N)c1ncc(CC#N)cc12]

Step 1: 2,3-dichloro-5-((methoxymethoxy)methyl)pyridine

To a stirred solution of (5,6-dichloropyridin-3-yl)methanol (commercially available) in $CH_2Cl_2$ (0.2 M) at 0° C. was added triethylamine (3 eq.) and chloro(methoxy)methane (2 eq.). After stirring at 0° C. for 3 hours the reaction mixture was concentrated and the crude was purified by chromatography (silica gel, 20-50% EtOAc in hexanes) to afford 2,3-dichloro-5-((methoxymethoxy)methyl)pyridine as a colorless oil.

Step 2: 3-chloro-5-((methoxymethoxy)methyl)picolinonitrile

3-Chloro-5-((methoxymethoxy)methyl)picolinonitrile was prepared from 2,3-dichloro-5-((methoxymethoxy)methyl)pyridine (from the previous step) following the procedures described for Example 39/Step 1.

Step 3: 3-chloro-5-(hydroxymethyl)picolinonitrile

To a stirred solution of 2,3-dichloro-5-((methoxymethoxy)methyl)pyridine (from the previous step) in methanol (0.2 M) was added conc. HCl (10 eq). After stirring at room temperature overnight the reaction mixture was concentrated under vacuum and the resulting crude was purified by chromatography (silica gel, 20-50% EtOAc in hexanes) to afford 3-chloro-5-(hydroxymethyl) picolinonitrile.

Step 4: 3-chloro-5-(chloromethyl)picolinonitrile

To a stirred solution of 3-chloro-5-(hydroxymethyl)picolinonitrile (from the previous step) in $CH_2Cl_2$ (0.2 M) at 0° C. was added thionyl chloride (10 eq). After stirring at room temperature overnight the reaction mixture was concentrated under vacuum and the resulting crude was purified by chromatography (silica gel, 20-50% EtOAc in hexanes) to afford 3-chloro-5-(chloromethyl)picolinonitrile as a colorless oil.

Step 5: 3-chloro-5-(cyanomethyl)picolinonitrile

To a solution of 3-chloro-5-(chloromethyl)picolinonitrile (from the previous step) in DMSO (0.2 M) was added sodium cyanide (1.25 eq). The reaction mixture was heated at 130° C. under microwave irradiation. The reaction mixture taken up in water and EtOAc, and extracted with EtOAc. Organic phases were dried over anhydrous $Na_2SO_4$, and concentrated. Flash chromatography (silica gel, 20-50% EtOAc in hexanes) of the crude afforded 3-chloro-5-(cyanomethyl)picolinonitrile.

Step 6: 2-(5-amino-8-methylbenzo[f][1,7]naphthyridin-2-yl)acetonitrile 2-(5-amino-8-methylbenzo[f][1,7]naphthyridin-2-yl)acetonitrile was prepared from 3-chloro-5-(cyanomethyl)picolinonitrile (from the previous step) following the procedures described for Example 41/Step 4. $^1$H NMR (methanol-$d_4$): δ 8.79 (d, 1H), 8.78 (d, 1H), 8.20 (d, 1H), 7.66 (s, 2H), 7.36 (s, 1H), 7.18 (dd, 1H), 4.15 (d, 2H), 2.43 (s, 3H). LRMS [M+H]=249.1

Example 54

N-(5-amino-8-methylbenzo[f][1,7]naphthyridin-2-yl)acetamide

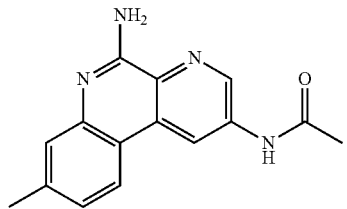 [SMILES: CC(=O)Nc1cnc2c(N)nc3cc(C)ccc3c2c1]

Step 1: N-(5,6-dichloropyridin-3-yl)acetamide

To a stirred solution of 5,6-dichloropyridin-3-amine (commercially available) and triethyl amine (3 eq) in $CH_2Cl_2$ (0.2 M) at 0° C. was added acetyl chloride (2 eq). After stirring at room temperature overnight the reaction mixture was concentrated under vacuum and the resulting crude residue was purified by chromatography (silica gel, 20-50% EtOAc in hexanes) to afford N-(5,6-dichloropyridin-3-yl)acetamide.

Step 2: N-(5-chloro-6-cyanopyridin-3-vpacetamide

N-(5-chloro-6-cyanopyridin-3-yl)acetamide was prepared from N-(5,6-dichloropyridin-3-yl)acetamide (from the previous step) following the procedures described for Example 39/Step 1.

Step 3: N-(5-amino-8-methylbenzo[f][1,7]naphthyridin-2-yl)acetamide

N-(5-amino-8-methylbenzo[f][1,7]naphthyridin-2-yl)acetamide was prepared from N-(5-chloro-6-cyanopyridin-3-yl)acetamide (from the previous step) following the procedures described for Example 41/Step 4. $^1$H NMR (DMSO-$d_6$): δ 10.99 (s, 1H), 8.18 (d, 1H), 8.95 (d, 1H), 8.12 (d, 1H), 7.44 (s, 1H), 7.35 (dd, 1H), 2.43 (s, 3H), 2.16 (s, 3H). LRMS [M+H]=267.1

Example 55

2-(5-amino-8-methylbenzo[f][1,7]naphthyridin-2-yl)-1-(2,4-dimethylphenyl)ethanol

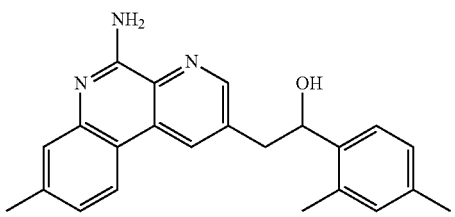

Step 1: 3-bromo-5-(2-(2,4-dimethylphenyl)-2-hydroxyethyl)picolinonitrile 3-bromo-5-(2-(2,4-dimethylphenyl)-2-hydroxyethyl)picolinonitrile was prepared from 3-bromo-5-methylpicolinonitrile (Example 52/Step 1) and 2,4-dimethylbenzaldehyde following the procedures described for Example 50/Step 3.

Step 2: 2-(5-amino-8-methylbenzo[f][1,7]naphthyridin-2-yl)-1-(2,4-dimethylphenyl)ethanol 2-(5-Amino-8-methylbenzo[f][1,7]naphthyridin-2-yl)-1-(2,4-dimethylphenyl)ethanol was prepared from 3-bromo-5-(2-(2,4-dimethylphenyl)-2-hydroxyethyl)picolinonitrile (from the previous step) following the procedures described for Example 50/Step 4. $^1$H NMR (CDCl$_3$): δ 8.67 (d, 1H), 8.45 (d, 1H), 8.06 (d, 1H), 7.57 (s, 1H), 7.42 (d, 1H), 7.23 (d, 1H), 7.11 (d, 1H), 7.01 (s, 1H), 5.31 (dd, 1H), 3.28-3.25 (m, 2H), 2.53 (s, 3H), 2.35 (s, 3H), 2.33 (s, 3H). LRMS [M+H]=358.2

Example 56

2-(2-(6-methoxy-4-methylpyridin-3-yl)ethyl)-8-methylbenzo[f][1,7]naphthyridin-5-amine

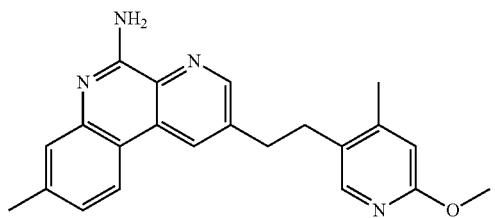

Step 1: 2-methoxy-4-methyl-5-((triethylsilyl)ethynyl)pyridine

2-Methoxy-4-methyl-5-((triethylsilyl)ethynyl)pyridine was prepared from 5-bromo-2-methoxy-4-methylpyridine (commercially available) following the procedures described for Example 41/Step 1.

Step 2: 5-ethynyl-2-methoxy-4-methylpyridine

5-Ethynyl-2-methoxy-4-methylpyridine was prepared from 2-methoxy-4-methyl-5-((triethylsilyl)ethynyl)pyridine (from the previous step) following the procedures described for Example 41/Step 2.

Step 3: 3-chloro-54(6-methoxy-4-methylpyridin-3-yl)ethynyl)picolinonitrile

3-Chloro-5-((6-methoxy-4-methylpyridin-3-yl)ethynyl)picolinonitrile was prepared from 5-ethynyl-2-methoxy-4-methylpyridine (from the previous step) following the procedures described for Example 41/Step 3.

Step 4: 24(6-methoxy-4-methylpyridin-3-yl)ethynyl)-8-methylbenzo[f][1,7]naphthyridin-5-amine 2-((6-Methoxy-4-methylpyridin-3-yl)ethynyl)-8-methylbenzo[f][1,7]naphthyridin-5-amine was prepared from 3-chloro-5-((6-methoxy-4-methylpyridin-3-yl)ethynyl)picolinonitrile (from the previous step) following the procedures described for Example 41/Step 4.

Step 5: 2-(2-(6-methoxy-4-methylpyridin-3-yl)ethyl)-8-methylbenzo[f][1,7]naphthyridin-5-amine 2-(2-(6-Methoxy-4-methylpyridin-3-yl)ethyl)-8-methylbenzo[f][1,7]naphthyridin-5-amine was prepared from 2-((6-methoxy-4-methylpyridin-3-yl)ethynyl)-8-methylbenzo[f][1,7]naphthyridin-5-amine (from the previous step) following the procedures described for Example 41/Step 5. $^1$H NMR (CDCl$_3$): δ 8.65 (d, 1H), 8.43 (d, 1H), 8.13 (d, 1H), 7.87 (s, 1H), 7.57 (s, 1H), 7.24 (dd, 1H), 6.60 (s, 1H), 6.39 (bs, 2H), 3.91 (s, 3H), 3.17-3.11 (dd, 2H), 3.03-2.98 (dd, 2H), 2.54 (s, 3H), 2.28 (s, 3H). LRMS [M+H]=359.2

Example 57

4-(4-(2-(5-amino-8-methylbenzo[f][1,7]naphthyridin-2-yl)ethyl)phenyl)butan-1-ol

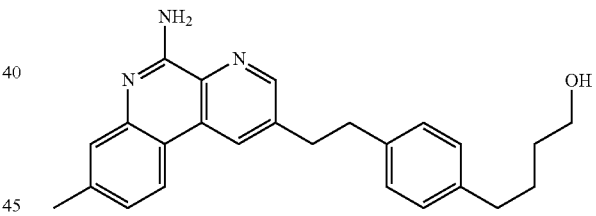

Step 1: 4-(4-((trimethylsilyl)ethynyl)phenyl)but-3-yn-1-ol 4-(4-((trimethylsilyl)ethynyl)phenyl)but-3-yn-1-ol was prepared from ((4-bromophenyl)ethynyl)trimethylsilane (commercially available) and but-3-yn-1-ol (commercially available) following the procedures described for Example 41/Step 1.

Step 2: 4-(4-ethynylphenyl)but-3-yn-1-ol 4-(4-ethynylphenyl)but-3-yn-1-ol was prepared from 4-(4-((trimethylsilyl)ethynyl)phenyl)but-3-yn-1-ol following the procedures described for Example 41/Step 2.

Step 3: 54(4-(4-hydroxybut-1-ynyl)phenyl)ethynyl)-3-methylpicolinonitrile 5-((4-(4-hydroxybut-1-ynyl)phenyl)ethynyl)-3-methylpicolinonitrile was prepared from 4-(4-ethynylphenyl)but-3- yn-1-ol (from the previous step) following the procedures described for Example 41/Step 3.

Step 4: 4-(44(5-amino-8-methylbenzo[f][1,7]naphthyridin-2-yl)ethynyl)phenyl)but-2-yn-1-ol 4-(4-((5-amino-8-methylbenzo[f][1,7]naphthyridin-2-yl)ethynyl)phenyl)but-2-yn-1-ol was prepared from 5-((4-(4-hydroxybut-1-ynyl)phenyl)ethynyl)-3-methylpicolinonitrile (from the previous step) following the procedures described for Example 41/Step 4.

Step 5: 4-(4-(2-(5-amino-8-methylbenzo[f][1,7]naphthyridin-2-yl)ethyl)phenyl)butan-1-ol 4-(4-(2-(5-amino-8-methylbenzo[f][1,7]naphthyridin-2-yl)ethyl)phenyl)butan-1-ol was prepared from 4-(4-((5-amino-8-methylbenzo[f][1,7]naphthyridin-2-yl)ethynyl)phenyl)but-2-yn-1-ol (from the previous step) following the procedures described for Example 41/Step 5. $^1$H NMR (CDCl$_3$): δ 8.58 (d, 1H), 8.36 (d, 1H), 8.07 (d, 1H), 7.53 (s, 1H), 7.20 (dd, 1H), 7.10 (dd, 4H), 6.20 (bs, 2H), 3.68 (t, 2H), 3.20-3.15 (dd, 2H), 3.06-3.01 (dd, 2H), 2.64 (t, 2H), 2.52 (s, 3H), 1.75-1.57 (m, 4H). LRMS [M+H]=386.2

Example 58 methyl 3-(4-(2-(5-amino-8-methylbenzo[f][1,7]naphthyridin-2-yl)ethyl)phenyl)propanoate

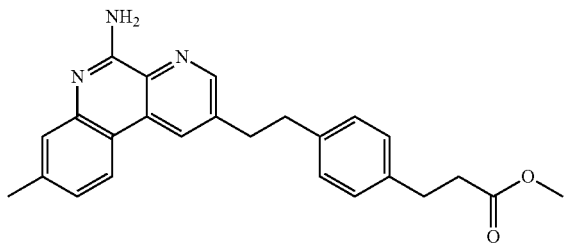

Step 1: methyl 3-(4-iodophenyl)propanoate

To a stirred solution of 3-(4-iodophenyl)propanoic acid (commercially available) in toluene and methanol (9:1, 0.2 M) 0° C. was added (diazomethyl)trimethylsilane (1 N solution in Et$_2$O, 2 eq). After stirring at room temperature overnight the reaction mixture was concentrated under vacuum and the resulting crude residue was purified by chromatography (silica gel, 20-50% EtOAc in hexanes) to afford methyl 3-(4-iodophenyl)propanoate.

Step 2: methyl 3-(4-ethynylphenyl)propanoate

Methyl 3-(4-ethynylphenyl)propanoate was prepared from methyl 3-(4-iodophenyl)propanoate (from the previous step) following the procedures described for Example 41/Steps 1 and 2.

Step 3: methyl 3-(4-((5-chloro-6-cyanopyridin-3-yl)ethynyl)phenyl)propanoate

Methyl 3-(4-((5-chloro-6-cyanopyridin-3-yl)ethynyl)phenyl)propanoate was prepared from methyl 3-(4-ethynylphenyl)propanoate (from the previous step) following the procedures described for Example 41/Step 3.

Step 4: methyl 3-(44(5-amino-8-methylbenzo[f][1,7]naphthyridin-2-yl)ethynyl)phenyl)propanoate Methyl 3-(4-((5-amino-8-methylbenzo[f][1,7]naphthyridin-2-yl)ethynyl)phenyl)propanoate was prepared from methyl 3-(4-((5-chloro-6-cyanopyridin-3-yl)ethynyl)phenyl)propanoate (from the previous step) following the procedures described for Example 41/Step 4.

Step 5: methyl 3-(4-(2-(5-amino-8-methylbenzo[f][1,7]naphthyridin-2-yl)ethyl)phenyl)propanoate Methyl 3-(4-(2-(5-amino-8-methylbenzo[f][1,7]naphthyridin-2-yl)ethyl)phenyl)propanoate was prepared from methyl 3-(4-((5-amino-8-methylbenzo[f][1,7]naphthyridin-2-yl)ethynyl)phenyl)propanoate (from the previous step) following the procedures described for Example 41/Step 5. $^1$H NMR (DMSO-d$_6$): δ 8.83 (d, 1H), 8.72 (d, 1H), 8.32 (d, 1H), 7.35 (s, 1H), 7.21-7.12 (m, 5H), 7.05 (br s, 2H), 7.05 (dd, 2H), 3.57 (s, 3H), 3.19-3.13 (dd, 2H), 3.06-3.00 (dd, 2H), 2.81 (t, 2H), 2.60 (t, 2H), 2.45 (s, 3H). LRMS [M+H]=400.2

Example 59

3-(4-(2-(5-amino-8-methylbenzo[f][1,7]naphthyridin-2-yl)ethyl)phenyl)propan-1-ol

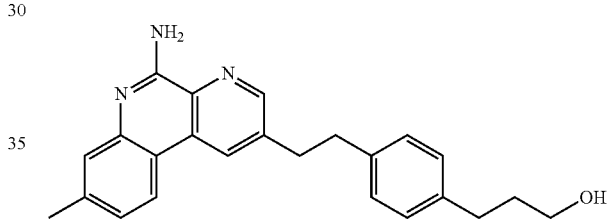

3-(4-(2-(5-amino-8-methylbenzo[f][1,7]naphthyridin-2-yl)ethyl)phenyl)propan-1-ol was prepared from methyl 3-(4-(2-(5-amino-8-methylbenzo[f][1,7]naphthyridin-2-yl)ethyl)phenyl)propanoate (from Example 58) following the procedures described for Example 39/Step 3. $^1$H NMR of the TFA salt: (DMSO-d$_6$): δ 9.56 (s, 1H), 9.24 (s, 1H), 8.92 (d, 1H), 8.81 (d, 1H), 8.43 (d, 1H), 7.44 (d, 1H), 7.35 (d, 1H), 7.13 (dd, 2H), 7.05 (dd, 2H), 3.32 (t, 2H), 3.18-3.12 (dd, 2H), 3.02-2.95 (dd, 2H), 2.50 (t, 2H), 2.44 (s, 3H), 1.65-1.57 (m, 2H). LRMS [M+H]=372.2

Example 60

4-(4-(2-(5-amino-8-methylbenzo[f][1,7]naphthyridin-2-yl)ethyl)phenyl)-2-methylbutan-2-ol

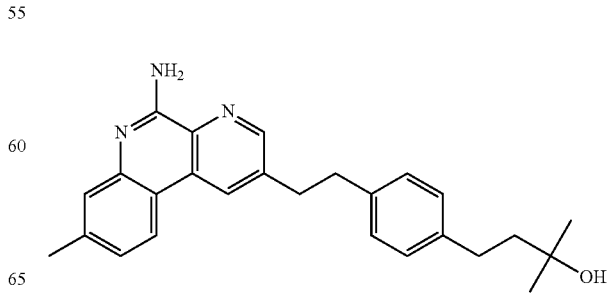

To a solution of methyl 3-(4-(2-(5-amino-8-methylbenzo[f][1,7]naphthyridin-2-yl)ethyl)phenyl)propanoate (from Example 58) in THF (0.2 M) at 0° C. was added in a dropwise fashion a solution of methylmagnesium bromide in THF (1.0 M, 2 eq). After stirring at room temperature overnight the reaction mixture was concentrated under vacuum and the resulting crude residue was purified by chromatography (silica gel, 50-100% EtOAc in hexanes) to afford 4-(4-(2-(5-amino-8-methylbenzo[f][1,7]naphthyridin-2-yl)ethyl)phenyl)-2-methylbutan-2-ol. $^1$H NMR (CDCl$_3$): δ 8.64 (d, 1H), 8.34 (d, 1H), 8.06 (t, 1H), 7.57 (d, 1H), 7.30-7.20 (m, 2H), 7.18-7.07 (m, 4H), 6.67 (bs, 2H), 3.24-3.16 (dd, 2H), 3.08-3.01 (dd, 2H), 2.73-2.66 (m, 2H), 2.53 (s, 3H), 1.82-1.75 (m, 2H), 1.31 (s, 3H), 1.29 (s, 3H). LRMS [M+H]=400.2

Example 61

2-(4-(aminomethyl)phenethyl)-8-methylbenzo[f][1,7]naphthyridin-5-amine

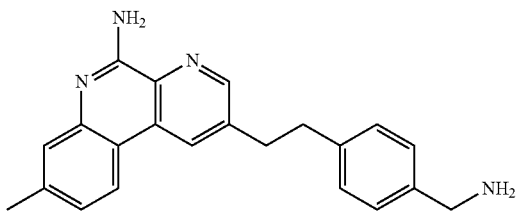 [SMILES: Cc1ccc2c(c1)nc(N)c1ncc(CCc3ccc(CN)cc3)cc12]

Step 1: 4-(2-(5-amino-8-methylbenzo[f][1,7]naphthyridin-2-yl)ethyl)benzonitrile 4-(2-(5-amino-8-methylbenzo[f][1,7]naphthyridin-2-yl)ethyl)benzonitrile was prepared from 4-ethynylbenzonitrile (commercially available) following the procedures described for Example 41/Steps 3 to 5.

Step 2: 2-(4-(aminomethyl)phenethyl)-8-methylbenzo[f][1,7]naphthyridin-5-amine To a solution of 4-(2-(5-amino-8-methylbenzo[f][1,7]naphthyridin-2-yl)ethyl)benzonitrile (from the previous step) in ethanol and ammonium hydroxide (4:1, 0.2 M) stirred at room temperature was added raney nickel (10 eq). The reaction mixture was stirred under hydrogen atmosphere until the conversion was complete as shown by TLC. The reaction mixture was filtered through a short celite pad. The celite pad was washed with EtOAc. Combined organic extracts were concentrated under vacuum and the resulting crude residue was purified by chromatography (silica gel, 50-100% EtOAc in hexanes) to afford product 2-(4-(aminomethyl)phenethyl)-8-methylbenzo[f][1,7]naphthyridin-5-amine. $^1$H NMR of the TFA salt: (methanol-d$_4$): δ 8.81 (d, 1H), 8.79 (d, 1H), 8.38 (d, 1H), 7.51 (s, 1H), 7.44 (dd, 1H), 7.36 (dd, 4H), 4.07 (s, 2H), 3.29 (s, 2H), 3.20-3.14 (dd, 2H), 2.55 (s, 3H). LRMS [M+H]=343.2

Example 62

(E)-ethyl 3-(4-(2-(5-amino-8-methylbenzo[f][1,7]naphthyridin-2-yl)ethyl)-3-methylphenyl)acrylate

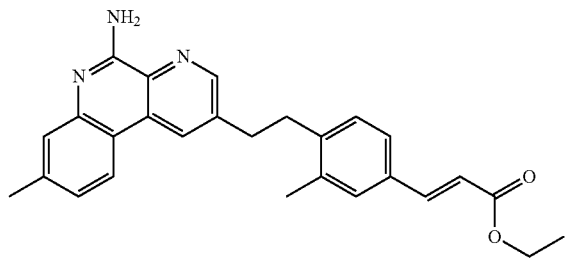 [SMILES: CCOC(=O)/C=C/c1ccc(CCc2cnc3c(N)nc4cc(C)ccc4c3c2)c(C)c1]

Step 1: (4-(2-(5-amino-8-methylbenzo[f][1,7]naphthyridin-2-yl)ethyl)-3-methylphenyl)methanol (4-(2-(5-amino-8-methylbenzo[f][1,7]naphthyridin-2-yl)ethyl)-3-methylphenyl)methanol was prepared from methyl 4-(2-(5-amino-8-methylbenzo[f][1,7]naphthyridin-2-yl)ethyl)-3-methylbenzoate (Example 112) following the procedures described for Example 39/Step 3.

Step 2: 4-(2-(5-amino-8-methylbenzo[f][1,7]naphthyridin-2-yl)ethyl)-3-methylbenzaldehyde To a solution of (4-(2-(5-amino-8-methylbenzo[f][1,7]naphthyridin-2-yl)ethyl)-3-methylphenyl)methanol (from the previous step) in DMSO was added 2-iodoxybenzoic acid (IBX, 2.5 eq). The reaction was stirred at room temperature for 3 hours before being diluted with water. Extraction with EtOAc followed by concentration gave a crude residue which was purified by chromatography (silica gel, 50-100% EtOAc in hexanes) to afford 4-(2-(5-amino-8-methylbenzo[f][1,7]naphthyridin-2-yl)ethyl)-3-methylbenzaldehyde.

Step 3: (E)-ethyl 3-(4-(2-(5-amino-8-methylbenzo[f][1,7]naphthyridin-2-yl)ethyl)-3-methylphenyl)acrylate To a suspension of NaH (3 eq) in THF (0.2 M) stirred at 0° C. was added ethyl 2-(diethoxyphosphoryl)acetate (commercially available) (3 eq). After stirring for 30 minutes, a solution of 4-(2-(5-amino-8-methylbenzo[f][1,7]naphthyridin-2-yl)ethyl)-3-methylbenzaldehyde (from the previous step) in THF (0.2 M) was added dropwise. The reaction was allowed to warm to room temperature and stirred overnight. The reaction was quenched with sat. NH4Cl solution, and was extracted with EtOAc. Combined organic extracts were dried and concentrated to give a crude residue which was purified by chromatography (silica gel, 50-100% EtOAc in hexanes) to afford (E)-ethyl 3-(4-(2-(5-amino-8-methylbenzo[f][1,7]naphthyridin-2-yl)ethyl)-3-methylphenyl)acrylate as a white solid. $^1$H NMR: (CDCl$_3$): δ 8.54 (d, 1H), 8.29 (d, 1H), 7.99 (d, 1H), 7.57 (d, 1H), 7.44 (s, 1H), 7.23 (dd, 1H), 7.11 (dd, 1H), 7.05 (d, 1H), 6.33 (d, 1H), 5.93 (s, 2H), 4.19 (q, 2H), 3.10-2.95 (m, 4H), 2.44 (s, 3H), 2.23 (s, 3H), 1.26 (t, 3H). LRMS [M+H]=426.2

Example 63 ethyl 3-(4-(2-(5-amino-8-methylbenzo[f][1,7]naphthyridin-2-yl)ethyl)-3-methylphenyl)propanoate

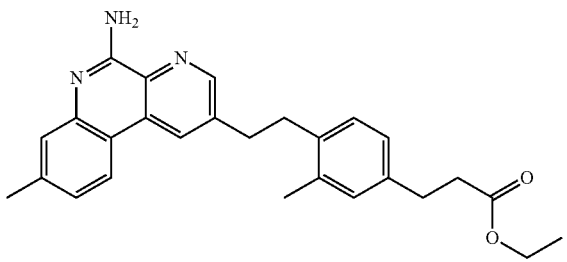 [SMILES: CCOC(=O)CCc1ccc(CCc2cnc3c(N)nc4cc(C)ccc4c3c2)c(C)c1]

Ethyl 3-(4-(2-(5-amino-8-methylbenzo[f][1,7]naphthyridin-2-yl)ethyl)-3-methylphenyl)propanoate was prepared from (E)-ethyl 3-(4-(2-(5-amino-8-methylbenzo[f][1,7]naphthyridin-2-yl)ethyl)-3-methylphenyl)acrylate (from Example 62) following the procedures described for Example 41/Step 5. $^1$H NMR: (CDCl$_3$): δ 8.55 (d, 1H), 8.26 (d, 1H), 7.99 (d, 1H), 7.45 (s, 1H), 7.12 (dd, 1H), 6.98-6.88 (m, 3H), 6.02 (s, 2H), 4.06 (q, 2H), 3.04 (dd, 2H), 2.93 (dd, 2H), 2.83 (t, 2H), 2.53 (t, 2H), 2.44 (s, 3H), 2.19 (s, 3H), 1.17 (t, 3H). LRMS [M+H]=428.2

Example 64

2-(4-(2-(5-amino-8-methylbenzo[f][1,7]naphthyridin-2-yl)ethyl)-3-methylbenzyl)propane-1,3-diol

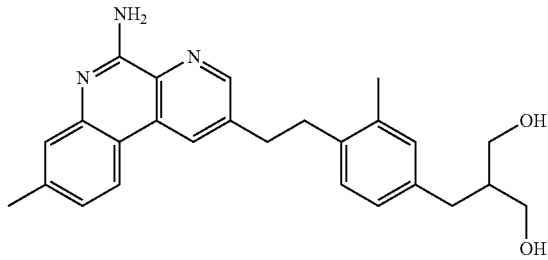 [SMILES: Cc1ccc2c(c1)nc(N)c1ncc(CCc3ccc(CC(CO)CO)cc3C)cc12]

Step 1: diethyl 2-(4-(2-(5-amino-8-methylbenzo[f][1,7]naphthyridin-2-yl)ethyl)-3-methylbenzyl)malonate To a stirred solution of (4-(2-(5-amino-8-methylbenzo[f][1,7]naphthyridin-2-yl)ethyl)-3-methylphenyl)methanol (from Example 62/Step 1) (0.2 M) and diethyl malonate (2 eq) in dry toluene was added tributylphosphine (2 eq) and N$^1$,N$^1$,N$^2$,N$^2$-tetramethyldiazene-1,2-dicarboxamide (2 eq). The reaction mixture was stirred at 120° C. overnight. Upon completion of the reaction, the reaction mixture was concentrated under vacuum and the resulting crude residue was purified by chromatography (silica gel, 50-100% EtOAc in hexanes) to afford diethyl 2-(4-(2-(5-amino-8-methylbenzo[f][1,7]naphthyridin-2-yl)ethyl)-3-methylbenzyl)malonate as a white solid.

Step 2: 2-(4-(2-(5-amino-8-methylbenzo[f][1,7]naphthyridin-2-yl)ethyl)-3-methylbenzyl)propane-1,3-diol 2-(4-(2-(5-Amino-8-methylbenzo[f][1,7]naphthyridin-2-yl)ethyl)-3-methylbenzyl)propane-1,3-diol was prepared from diethyl 2-(4-(2-(5-amino-8-methylbenzo[f][1,7]naphthyridin-2-yl)ethyl)-3-methylbenzyl)malonate (from the previous step) following the procedures described for Example 39/Step 3. $^1$H NMR: (methanol-d$_4$): δ 8.51 (d, 1H), 8.39 (d, 1H), 8.05 (d, 1H), 7.45 (s, 1H), 7.10 (dd, 1H), 6.91-6.87 (m, 2H), 6.83 (dd, 1H), 3.42 (d, 4H), 3.08-3.02 (m, 2H), 2.96-2.91 (m, 2H), 2.47 (d, 2H), 2.38 (s, 3H), 2.13 (s, 3H). LRMS [M+H]=416.2

Example 65

3-(4-(2-(5-amino-8-methylbenzo[f][1,7]naphthyridin-2-yl)ethyl)-3-methylphenyl)propanoic acid

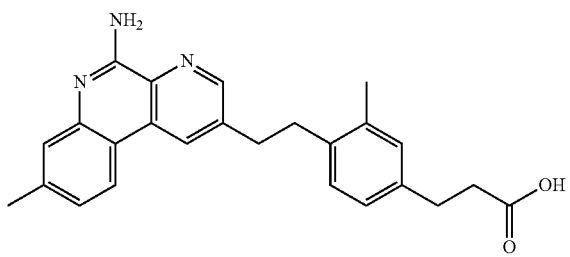 [SMILES: Cc1ccc2c(c1)nc(N)c1ncc(CCc3ccc(CCC(=O)O)cc3C)cc12]

A solution of ethyl 3-(4-(2-(5-amino-8-methylbenzo[f][1,7]naphthyridin-2-yl)ethyl)-3-methylphenyl)propanoate (from Example 63) in 1 N NaOH, THF and methanol (1:5:2, 0.1 N) was heated at 60° C. for 3 hours. After cooling to room temperature the reaction mixture was neutralized with 1 N HCl to pH 7, and was concentrated to give a crude residue which was purified by chromatography (silica gel, 0-20% methanol in dichloromethane) to afford (E)-ethyl 3-(4-(2-(5-amino-8-methylbenzo[f][1,7]naphthyridin-2-yl)ethyl)-3-methylphenyl)acrylate as a white solid. $^1$H NMR: (methanol-d$_4$): δ 8.73 (d, 1H), 8.54 (d, 1H), 8.20 (d, 1H), 7.45 (s, 1H), 7.37 (d, 1H), 7.00-6.97 (m, 2H), 6.92 (d, 1H), 3.19 (t, 2H), 3.04 (t, 2H), 2.81 (t, 2H), 2.53 (t, 2H), 2.50 (s, 3H), 2.25 (s, 3H). LRMS [M+H]=400.2

Example 66

5-amino-2-(4-methoxy-2-methylphenethyl)benzo[f][1,7]naphthyridine-8-carbaldehyde

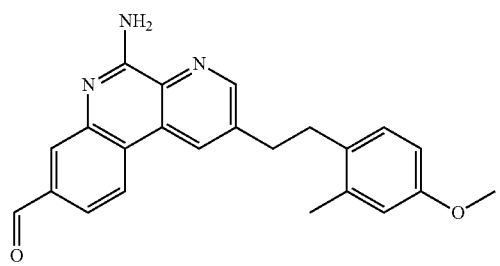 [SMILES: COc1ccc(CCc2cnc3c(N)nc4cc(C=O)ccc4c3c2)c(C)c1]

5-amino-2-(4-methoxy-2-methylphenethyl)benzo[f][1,7]naphthyridine-8-carbaldehyde was prepared from (5-amino-2-(4-methoxy-2-methylphenethyl)benzo[f][1,7]naphthyridin-8-yl)methanol (from Example 105) following the procedures described for Example 62/Step 2. $^1$H NMR: (CDCl$_3$): δ 10.19 (s, 1H), 8.74 (d, 1H), 8.43 (d, 1H), 8.32 (d, 1H), 8.18 (d, 1H), 7.88 (dd, 1H), 7.00 (d, 1H), 6.76 (d, 1H), 6.70 (dd, 1H), 6.30 (s, 2H), 3.80 (s, 3H), 3.16 (dd, 2H), 3.02 (dd, 2H), 2.29 (s, 3H). LRMS [M+H]=372.2

Example 67 ethyl 4-(2-(5-amino-8-methylbenzo[f][1,7]naphthyridin-2-yl)ethyl)benzoate

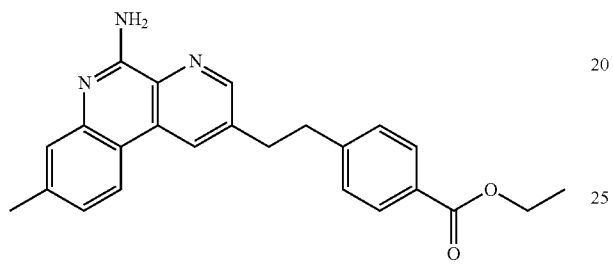

Step 1: ethyl 4-((5-chloro-6-cyanopyridin-3-yl)ethynyl)benzoate

A solution of 3,5-dichloropicolinonitrile (commercially available) (1.0 eq.), ethyl 4-ethynylbenzoate (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH®system (ISCO) using 0-20% ethyl acetate in hexane to give ethyl 4-((5-chloro-6-cyanopyridin-3-yl)ethynyl)benzoate as a white solid.

Step 2: ethyl 4-((5-amino-8-methylbenzo[f][1,7]naphthyridin-2-yl)ethynyl)benzoate A solution of ethyl 4-((5-chloro-6-cyanopyridin-3-yl)ethynyl)benzoate (from the previous step) (1.0 eq.), tert-butyl 5-methyl-2-(4,4,5,5-tetramethyl-1,3,2-dioxaborolan-2-yl)phenylcarbamate (from Example 4/Step 2) (2.6 eq.), tetrakis(triphenylphosphine)palladium (10 mol %), and potassium carbonate (5.3 eq.) in toluene/ethanol (2:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)benzoate.

Step 3: ethyl 4-(2-(5-amino-8-methylbenzo[f][1,7]naphthyridin-2-yl)ethyl)benzoate A solution of ethyl 4-((5-amino-8-methylbenzo[f][1,7]naphthyridin-2-yl)ethynyl)benzoate (from the previous step) (1.0 eq.) in THF/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give ethyl 4-(2-(5-amino-8-methylbenzo[f][1,7]naphthyridin-2-yl)ethyl)benzoate. $^1$H NMR (Acetone-d$_6$): δ 8.80 (s, 1H), 8.69 (s, 1H), 8.25 (d, 1H), 7.90 (d, 2H), 7.40-7.42 (m, 3H), 7.12 (d, 1H), 6.55 (br, 2H), 4.28 (q, 2H), 3.2-3.3 (m, 4H), 2.44 (s, 3H), 1.31 (t, 3H). LRMS [M+H]=386.2

Example 68

8-methyl-2-(4-methylphenethyl)benzo[f][1,7]naphthyridin-5-amine

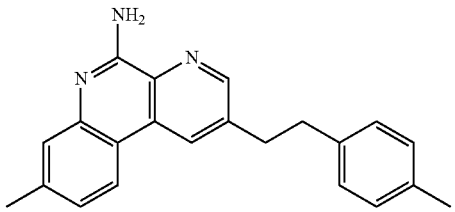

Step 1: 3-chloro-5-(p-tolylethynyl)picolinonitrile

A solution of 3,5-dichloropicolinonitrile (commercially available) (1.0 eq.), 1-ethynyl-4-methylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by stirring in hot ether/hexane mixtures and filtered to give 3-chloro-5-(p-tolylethynyl)picolinonitrile.

Step 2: 8-methyl-2-(p-tolylethynyl)benzo[f][1,7]naphthyridin-5-amine

A solution of 3-chloro-5-(p-tolylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 4/Step 2) (1.2 eq.), tetrakis(triphenylphosphine)palladium (10 mol %), and 2N sodium carbonate aqueous solution (4.0 eq.) in toluene/ethanol (2:1, 0.2 M) was stirred at 100° C. overnight. After cooling to ambient temperature, the reaction mixture was diluted with 2% MeOH in DCM. The two phases were separated, and the aqueous layer was extracted with 2% MeOH in DCM twice. The combined organic layers were washed with brine, dried over anhydrous MgSO₄, and concentrated en vaccuo. The crude material was purified by flash chromatography on a COMBIFLASH® system (ISCO) using 0-40% ethyl acetate in toluene to give 8-methyl-2-(p-tolylethynyl)benzo[f][1,7]naphthyridin-5-amine Step 3: 8-methyl-2-(4-methylphenethyl)benzo[f][1,7]naphthyridin-5-amine A solution of 8-methyl-2-(p-tolylethynyl)benzo[f][1,7]naphthyridin-5-amine (from the previous step) (1.0 eq.) in EtOH/ethyl acetate (1:1, 0.05M) was flushed with nitrogen and palladium on carbon (10 wt %) was added. The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 0-5% MeOH in DCM to give 8-methyl-2-(4-methylphenethyl)benzo[f][1,7]naphthyridin-5-amine. ¹H NMR (Acetone-d₆): δ 8.74 (s, 1H), 8.68 (s, 1H), 8.24 (d, 1H), 7.41 (s, 1H), 7.13-7.15 (m, 3H), 7.06 (d, 2H), 6.6 (br, 2H), 3.19 (t, 2H), 3.06 (t, 2H), 2.44 (s, 3H), 2.25 (s, 3H). LRMS [M+H]=328.1

Example 69

2-(4-(2-(5-amino-8-methylbenzo[f][1,7]naphthyridin-2-yl)ethyl)phenyl)propan-2-ol

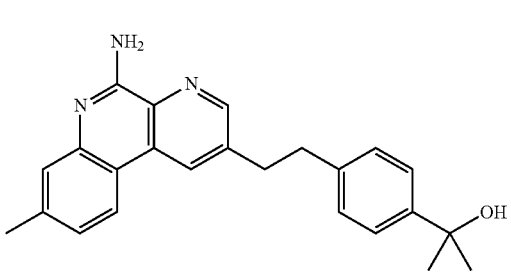 [SMILES: Cc1ccc2c(c1)nc(N)c1ncc(CCc3ccc(C(C)(C)O)cc3)cc12]

To a solution of ethyl 4-(2-(5-amino-8-methylbenzo[f][1,7]naphthyridin-2-yl)ethyl)benzoate (from Example 67) (1.0 eq.) in DCM at 0° C. was added 3.0 M methyl magnesium iodide (10 eq.) in ether and warmed to room temperature overnight. The reaction was cooled to 0° C. and quenched with 1N HCl aqueous solution and ether. After stirring for 15 minutes, the reaction mixture was neutralized with saturated aqueous sodium bicarbonate solution. The two phases were separated, and the aqueous layer was extracted with ether. The combined organic layers were washed with brine, dried over anhydrous MgSO₄, and concentrated en vaccuo. The crude material was purified by RP-HPLC using a 10-50% MeCN in water gradient followed by extraction in DCM to give 2-(4-(2-(5-amino-8 methylbenzo[f][1,7]naphthyridin-2-yl)ethyl)phenyl)propan-2-ol. ¹H NMR (Acetone-d₆): δ 8.73 (m, 2H), 8.22 (d, 1H), 7.40-7.44 (m, 3H), 7.20 (d, 2H), 7.12 (d, 1H), 6.5 (br, 2H), 3.94 (s, 1H), 3.21 (t, 2H), 3.08 (t, 2H), 2.44 (s, 3H), 1.47 (s, 6H). LRMS [M+H]=372.2

Example 70

(4-(2-(5-amino-8-methylbenzo[f][1,7]naphthyridin-2-yl)ethyl)phenyl)methanol

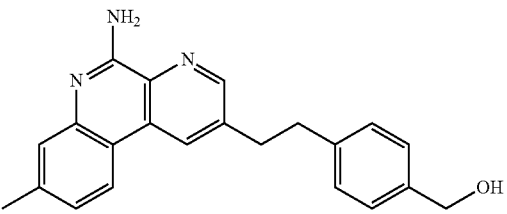 [SMILES: Cc1ccc2c(c1)nc(N)c1ncc(CCc3ccc(CO)cc3)cc12]

To a solution of ethyl 4-(2-(5-amino-8-methylbenzo[f][1,7]naphthyridin-2-yl)ethyl)benzoate (Example 67) (1.0 eq.) in THF (0.1 M) at 0° C. was added 1.0 M lithium triethylborohydride in THF (10 eq.) and warmed to room temperature over 2 hours. 1N HCl aqueous solution was added slowly to quench the reaction, and the mixture was heated to reflux for 30 minutes. The reaction mixture was neutralized with saturated aqueous sodium bicarbonate solution. The two phases were separated, and the aqueous layer was extracted with ethyl acetate (EA). The combined organic layers were washed with brine, dried over anhydrous MgSO₄, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)phenyl)methanol. ¹H NMR (Acetone-d₆): δ 8.77 (s, 1H), 8.69 (s, 1H), 8.26 (d, 1H), 7.40 (s, 1H), 7.21-7.28 (m, 4H), 7.13 (d, 1H), 6.5 (br, 2H), 4.56 (s, 2H), 4.1 (br t, 1H), 3.10-3.23 (m, 4H), 2.44 (s, 3H). LRMS [M+H]=344.2

Example 71 ethyl 4-(2-(5-amino-8-methylbenzo[f][1,7]naphthyridin-2-yl)ethyl)-3-methylbenzoate

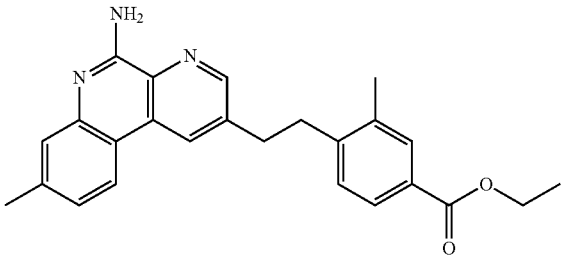

Step 1: ethyl 4-bromo-3-methylbenzoate

To a solution of 4-bromo-3-methylbenzoic acid (commercially available) (1.0 eq.) in EtOH (0.3 M) was added thionyl chloride (1.5 eq.) and heated to reflux for 2 hours. The solvent was concentrated en vaccuo, and the residue was diluted in ether and neutralized with saturated aqueous sodium bicarbonate solution. The two phases were separated, and the aqueous layer was extracted with ether. The combined organic layers were washed with brine, dried over anhydrous MgSO₄, and concentrated en vaccuo to give ethyl 4-bromo-3-methylbenzoate.

Step 2: ethyl 3-methyl-4-((triethylsilyl)ethynyl)benzoate

A solution of ethyl 4-bromo-3-methylbenzoate (from the previous step) (1.0 eq.), triethyl(ethynyl)silane (1.1 eq.), trans-dichlororbis(triphenylphosphine)palladium (II) (10 mol %), copper (I) iodide (20 mol %), and triethylamine (5.0 eq.) in DMF (0.3 M) was stirred at 60° C. overnight. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-5% ethyl acetate in hexane to give ethyl 3-methyl-4-((triethylsilyl)ethynyl)benzoate as a yellow oil.

Step 3: ethyl 4-ethynyl-3-methylbenzoate

To a solution of ethyl 3-methyl-4-((triethylsilyl)ethynyl)benzoate (from the previous step) (1.0 eq.) in THF (0.3 M) at 0° C. was added dropwise 1.0 M TBAF in THF (1.2 eq.). After stirring for 10 minutes at 0° C., the reaction was quenched with saturated aqueous sodium bicarbonate solution. The two phases were separated, and the aqueous layer was extracted with ether. The combined organic layers were washed with brine, dried over anhydrous MgSO$_4$, and concentrated en vaccuo. The crude material was purified by flash chromatography on a COMBIFLASH® system (ISCO) using 0-5% ethyl acetate in hexane to give ethyl 4-ethynyl-3-methylbenzoate as a white solid.

Step 4: ethyl 4-((5-chloro-6-cyanopyridin-3-yl)ethynyl)-3-methylbenzoate

A solution of 3,5-dichloropicolinonitrile (1.0 eq.), ethyl 4-ethynyl-3-methylbenzoate (from the previous step) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-10% ethyl acetate in hexane to give ethyl 4-((5-chloro-6-cyanopyridin-3-yl)ethynyl)-3-methylbenzoate as a white solid.

Step 5: ethyl 4-((5-amino-8-methylbenzo[f][1,7]naphthyridin-2-yl)ethynyl)-3-methylbenzoate A solution of ethyl 4-((5-chloro-6-cyanopyridin-3-yl)ethynyl)-3-methylbenzoate (from the previous step) (1.0 eq.), tert-butyl 5-methyl-2-(4,4,5,5-tetramethyl-1,3,2-dioxaborolan-2-yl)phenylcarbamate (from Example 4/Step 2) (1.1 eq.), tetrakis(triphenylphosphine)palladium (8 mol %), and potassium carbonate (3.0 eq.) in toluene/ethanol (9:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO$_4$, and concentrated en vaccuo. The crude material was purified by flash chromatography on a COMBIFLASH® system (ISCO) using 0-40% ethyl acetate in toluene to give ethyl 4-((5-amino-8-methylbenzo[f][1,7]naphthyridin-2-yl)ethynyl)-3-methylbenzoate.

Step 6: ethyl 4-(2-(5-amino-8-methylbenzo[f][1,7]naphthyridin-2-yl)ethyl)-3-methylbenzoate A solution of ethyl 4-((5-amino-8-methylbenzo[f][1,7]naphthyridin-2-yl)ethynyl)-3-methylbenzoate (from the previous step) (1.0 eq.) in THF/ethyl acetate (1:1, 0.05M) was flushed with nitrogen and added 10% palladium on carbon (10 wt %). The reaction vessel was evacuated, flushed with hydrogen, and stirred overnight at room temperature. The reaction mixture was filtered through celite, washed with 2% MeOH in DCM, and concentrated en vaccuo. The crude material was purified by flash chromatography on a COMBIFLASH® system (ISCO) using 30-100% EA in hexane to give ethyl 4-(2-(5-amino-8-methylbenzo[f][1,7]naphthyridin-2-yl)ethyl)-3-methylbenzoate. $^1$H NMR (Acetone-d$_6$): δ 8.79 (s, 1H), 8.71 (s, 1H), 8.24 (d, 1H), 7.80 (s, 1H), 7.73 (d, 1H), 7.40 (s, 1H), 7.31 (d, 1H), 7.12 (d, 1H), 6.5 (br, 2H), 4.29 (q, 2H), 3.19-3.22 (m, 4H), 2.44 (s, 3H), 2.39 (s, 3H), 1.31 (t, 3H). LRMS [M+H]=400.2

Example 72

4-(2-(5-amino-8-methylbenzo[f][1,7]naphthyridin-2-yl)ethyl)-3-methylbenzoic acid

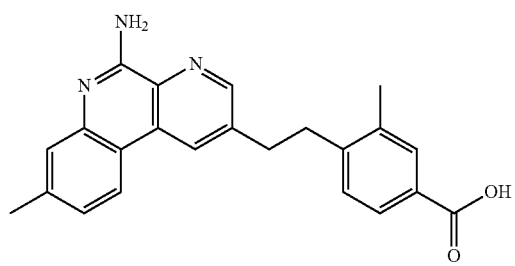 [SMILES: Cc1ccc2c(c1)nc(N)c1ncc(CCc3ccc(C(=O)O)cc3C)cc12]

To a solution of ethyl 4-(2-(5-amino-8-methylbenzo[f][1,7]naphthyridin-2-yl)ethyl)-3-methylbenzoate (from Example 71) (1.0 eq.) in EtOH was added 1N aqueous sodium hydroxide (1.5 eq.) and heated to 80° C. for 5 hours. The reaction mixture was neutralized by adding 1N aqueous HCl (1.5 eq.) and concentrated en vaccuo. The crude material was purified by RP-HPLC using a 10-50% MeCN in water gradient followed by concentration en vaccuo to give the TFA salt. $^1$H NMR (DMSO-d$_6$) of the TFA salt: δ 7.94-7.96 (m, 2H), 7.55 (d, 1H), 7.00 (s, 1H), 6.91 (d, 1H), 6.62-6.66 (m, 2H), 6.39 (d, 1H), 2.36-2.5 (m, 4H), 1.73 (s, 3H), 1.54 (s, 3H). LRMS [M+H]=372.2

Example 73

(4-(2-(5-amino-8-methylbenzo[f][1,7]naphthyridin-2-yl)ethyl)-3-methylphenyl)methanol

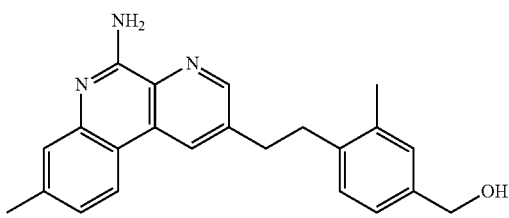 [SMILES: Cc1ccc2c(c1)nc(N)c1ncc(CCc3ccc(CO)cc3C)cc12]

To a solution of ethyl 4-(2-(5-amino-8-methylbenzo[f][1,7]naphthyridin-2-yl)ethyl)-3-methylbenzoate (from Example 71) (1.0 eq.) in THF (0.1M) at −78° C. was added 1.0 M DIBAL-H in toluene (10 eq.) and warmed to room temperature over 2 hours. 1.5 M Rochelle salt aqueous solution was added slowly to quench the reaction followed by addition of EA, and the mixture was stirred for 45 minutes. The two phases were separated, and the aqueous layer was extracted twice with EA. The combined organic layers were washed with brine, dried over anhydrous $MgSO_4$, and concentrated en vaccuo. The crude material was purified by RP-HPLC using a 10-50% MeCN in water gradient followed by extraction in DCM to give (4-(2-(5-amino-8-methylbenzo[f][1,7]naphthyridin-2-yl)ethyl)-3-methylphenyl)methanol. $^1$H NMR (Acetone-$d_6$): δ 8.77 (s, 1H), 8.71 (s, 1H), 8.25 (d, 1H), 7.41 (s, 1H), 7.10-7.15 (m, 4H), 6.5 (br, 2H), 4.54 (s, 2H), 4.05 (br, 1H), 3.08-3.18 (m, 4H), 2.44 (s, 3H), 2.31 (s, 3H). LRMS [M+H]=358.2

Example 74

8-methyl-2-(2,4,6-trimethylphenethyl)benzo[f][1,7]naphthyridin-5-amine

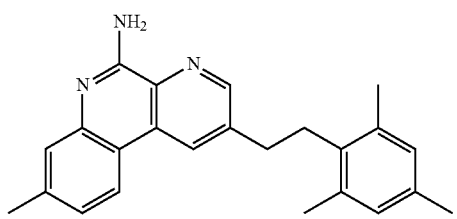

Step 1: 3-chloro-5-(mesitylethynyl)picolinonitrile

A solution of 3,5-dichloropicolinonitrile (1.0 eq.), 2-ethynyl-1,3,5-trimethylbenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBI-FLASH® system (ISCO) using 0-10% ethyl acetate in hexane to give 3-chloro-5-(mesitylethynyl)picolinonitrile a as white solid.

Step 2: 2-(mesitylethynyl)-8-methylbenzo[f][1,7]naphthyridin-5-amine

A solution of 3-chloro-5-(mesitylethynyl)picolinonitrile (from the previous step) (1.0 eq.), tert-butyl 5-methyl-2-(4,4,5,5-tetramethyl-1,3,2-dioxaborolan-2-yl)phenylcarbamate (from Example 4/Step 2) (1.1 eq.), tetrakis(triphenylphosphine)palladium (8 mol %), and 2N aqueous sodium carbonate solution (3.0 eq.) in toluene/ethanol (4:1, 0.2 M) was stirred at 100° C. overnight. After cooling to ambient temperature, the reaction mixture was diluted with 2% MeOH in DCM. The two phases were separated. The combined organic layers were washed with brine, dried over anhydrous $MgSO_4$, and concentrated en vaccuo. The crude material was purified by flash chromatography on a COMBIFLASH® system (ISCO) using 0-40% ethyl acetate in toluene to give 2-(mesitylethynyl)-8-methylbenzo[f][1,7]naphthyridin-5-amine.

Step 3: 8-methyl-2-(2,4,6-trimethylphenethyl)benzo[f][1,7]naphthyridin-5-amine A solution of 2-(mesitylethynyl)-8-methylbenzo[f][1,7]naphthyridin-5-amine (from the previous step) (1.0 eq.) in EtOH (0.05M) was flushed with nitrogen and added palladium on carbon (10 wt %). The reaction vessel was evacuated, flushed with hydrogen, and stirred overnight at rt. The reaction mixture was filtered through celite, washed with 2% MeOH in DCM, and concentrated en vaccuo. The crude material was purified by flash chromatography on a COMBIFLASH® system (ISCO) using 0-50% ethyl acetate in hexane to give 8-methyl-2-(2,4,6-trimethylphenethyl)benzo[f][1,7]naphthyridin-5-amine $^1$H NMR (Acetone-$d_6$): δ 8.73-8.74 (m, 2H), 8.25 (d, 1H), 7.42 (s, 1H), 7.14 (d, 1H), 6.83 (s, 2H), 6.55 (br, 2H), 3.07 (m, 4H), 2.47 (s, 3H), 2.29 (s, 6H), 2.22 (s, 3H). LRMS [M+H]=356.2

Example 75

2-(4-(2-(5-amino-8-methylbenzo[f][1,7]naphthyridin-2-yl)ethyl)-3-methylphenyl)propan-2-ol

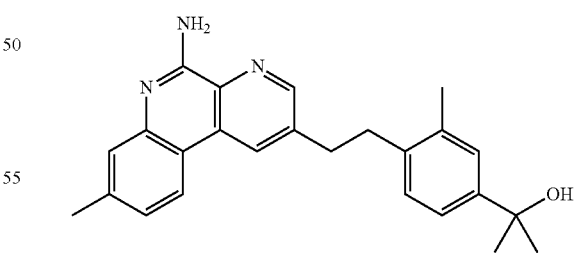

To a solution of ethyl 4-(2-(5-amino-8-methylbenzo[f][1,7]naphthyridin-2-yl)ethyl)-3-methylbenzoate (from Example 71) (1.0 eq.) in DCM at 0° C. was added 3.0 M methyl magnesium iodide (10 eq.) in ether and warmed to room temperature overnight. The reaction was cooled to 0° C. and quenched with water. After stirring for 15 min, the reaction mixture was neutralized with saturated aqueous sodium bicarbonate solution and added EA. The two phases were separated, and the aqueous layer was extracted three times with EA. The combined organic layers were washed with brine, dried over anhydrous MgSO₄, and concentrated en vaccuo. The crude material was purified by flash chromatography on a COMBIFLASH® system (ISCO) using 0-5% MeOH in DCM to give a 2-(4-(2-(5-amino-8-methyl-benzo[f][1,7]naphthyridin-2-yl)ethyl)-3-methylphenyl)propan-2-ol. ¹H NMR (Acetone-d₆): δ 8.72-8.75 (m, 2H), 8.23 (d, 1H), 7.41 (s, 1H), 7.32 (s, 1H), 7.25 (d, 1H), 7.12-7.14 (m, 2H), 6.6 (br, 2H), 3.91 (s, 1H), 3.07-3.18 (m, 4H), 2.44 (s, 3H), 2.31 (s, 3H), 1.48 (s, 6H). LRMS [M+H]=386.2

Example 76

8-methyl-2-(4-propoxyphenethyl)benzo[f][1,7]naphthyridin-5-amine

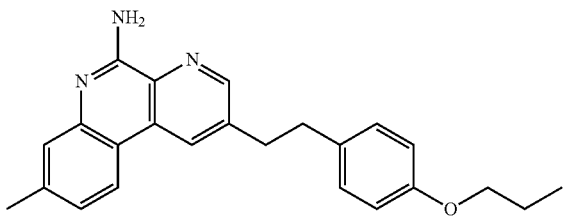 [SMILES: CCCOc1ccc(CCc2cnc3c(N)nc4cc(C)ccc4c3c2)cc1]

Step 1: 3-chloro-5-((4-propoxyphenyl)ethynyl)picolinonitrile

A solution of 3,5-dichloropicolinonitrile (1.0 eq.), 1-ethynyl-4-propoxybenzene (commercially available) (1.0 eq.), trans-dichlororbis(triphenylphosphine)palladium (II) (10 mol %), copper (I) iodide (20 mol %), and triethylamine (5.0 eq.) in DMF (0.3 M) was stirred at 50° C. for 3 hours. After cooling to ambient temperature, the reaction mixture was diluted with ethyl acetate and 10% aqueous ammonium hydroxide. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-10% ethyl acetate in hexane to give 3-chloro-5-((4-propoxyphenyl)ethynyl)picolinonitrile as a white solid.

Step 2: 3-chloro-5-(4-propoxyphenethyl)picolinonitrile

A solution of 3-chloro-5-((4-propoxyphenyl)ethynyl)picolinonitrile (from the previous step) (1.0 eq.) in EtOH (0.05M) was flushed with nitrogen and added platinum (VI) oxide (0.5 eq.). The reaction vessel was evacuated, flushed with hydrogen, and stirred for 5 hours at room temperature. The reaction mixture was filtered through celite, washed with 2% MeOH in DCM, and concentrated en vaccuo. The crude material was purified by flash chromatography on a COMBIFLASH® system (ISCO) using 0-15% ethyl acetate in hexane to give 3-chloro-5-(4-propoxyphenethyl)picolinonitrile.

Step 3: 8-methyl-2-(4-propoxyphenethyl)benzo[f][1,7]naphthyridin-5-amine

A solution of 3-chloro-5-(4-propoxyphenethyl)picolinonitrile (from the previous step) (1.0 eq.), tert-butyl 5-methyl-2-(4,4,5,5-tetramethyl-1,3,2-dioxaborolan-2-yl)phenylcarbamate (from Example 4/Step 2) (1.1 eq.), tetrakis(triphenylphosphine)palladium (8 mol %), and 2N aqueous sodium carbonate solution (3.0 eq.) in toluene (0.2 M) was stirred at 100° C. overnight. After cooling to ambient temperature, the reaction mixture was diluted with 2% MeOH in DCM. The two phases were separated. The combined organic layers were washed with brine, dried over anhydrous MgSO₄, and concentrated en vaccuo. The crude material was purified by flash chromatography on a COMBIFLASH® system (ISCO) using 0-40% ethyl acetate in toluene to give 8-methyl-2-(4-propoxyphenethyl)benzo[f][1,7]naphthyridin-5-amine ¹H NMR (Acetone-d₆): δ 8.74 (s, 1H), 8.67 (s, 1H), 8.24 (d, 1H), 7.41 (s, 1H), 7.15-7.17 (m, 3H), 6.81 (d, 2H), 6.5 (br, 2H), 3.87 (t, 2H), 3.18 (t, 2H), 3.04 (t, 2H), 2.44 (s, 3H), 1.73 (m, 2H), 0.99 (t, 3H). LRMS [M+H]=372.2

Example 77

(E)-ethyl 3-(5-amino-2-(4-methoxy-2-methylphenethyl)benzo[f][1,7]naphthyridin-8-yl)acrylate

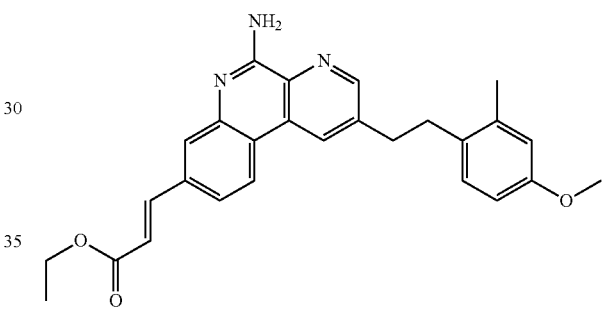

(E)-ethyl 3-(5-amino-2-(4-methoxy-2-methylphenethyl)benzo[f][1,7]naphthyridin-8-yl)acrylate was prepared from 5-amino-2-(4-methoxy-2-methylphenethyl)benzo[f][1,7]naphthyridine-8-carbaldehyde (from Example 66) and ethyl 2-(diethoxyphosphoryl)acetate (commercially available) following the procedures described for Example 62/Step 3. LRMS [M+H]=442.2

Example 78

(E)-3-(5-amino-2-(4-methoxy-2-methylphenethyl)benzo[f][1,7]naphthyridin-8-yl)acrylic acid

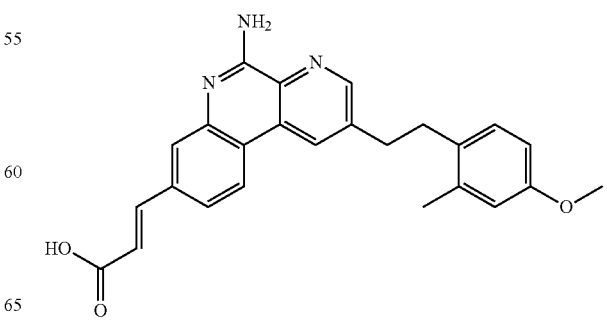

(E)-3-(5-amino-2-(4-methoxy-2-methylphenethyl)benzo[f][1,7]naphthyridin-8-yl)acrylic acid was prepared from (E)-ethyl 3-(5-amino-2-(4-methoxy-2-methylphenethyl)benzo[f][1,7]naphthyridin-8-yl)acrylate (from Example 77) following the procedures described for Example 65. $^1$H NMR of TFA salt (DMSO-d$_6$): δ 12.66 (s, 1H), 9.09 (s, 1H), 8.88 (s, 1H), 8.66 (d, 1H), 7.95 (d, 1H), 7.91 (s, 1H), 7.75 (d, 1H), 7.10 (d, 1H), 6.77-6.71 (m, 2H), 6.68 (dd, 1H), 3.70 (s, 3H), 3.16 (t, 2H), 3.00 (t, 2H), 2.30 (s, 3H). LRMS [M+H]=414.2

Example 79 ethyl 3-(5-amino-2-(4-methoxy-2-methylphenethyl)benzo[f][1,7]naphthyridin-8-yl)propanoate

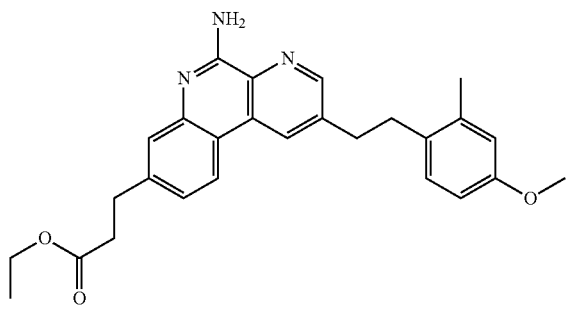 [SMILES: CCOC(=O)CCc1ccc2c(c1)nc(N)c1ncc(CCc3ccc(OC)cc3C)cc12]

Ethyl 3-(5-amino-2-(4-methoxy-2-methylphenethyl)benzo[f][1,7]naphthyridin-8-yl)propanoate was prepared from (E)-ethyl 3-(5-amino-2-(4-methoxy-2-methylphenethyl)benzo[f][1,7]naphthyridin-8-yl)acrylate (from Example 77) following the procedures described for Example 41/Step 5. $^1$H NMR (CDCl$_3$): δ 8.63 (d, 1H), 8.37 (d, 1H), 8.13 (d, 1H), 7.56 (d, 1H), 7.24 (dd, 1H), 7.02 (d, 1H), 6.75 (d, 1H), 6.69 (dd, 1H), 6.15 (br s, 2H), 4.17 (q, 2H), 3.79 (s, 3H), 3.12 (dd, 4H), 2.99 (dd, 2H), 2.75 (t, 2H), 2.29 (s, 3H), 1.27 (t, 2H), 0.99 (t, 3H). LRMS [M+H]=444.2

Example 80

3-(5-amino-2-(4-methoxy-2-methylphenethyl)benzo[f][1,7]naphthyridin-8-yl)propanoic acid

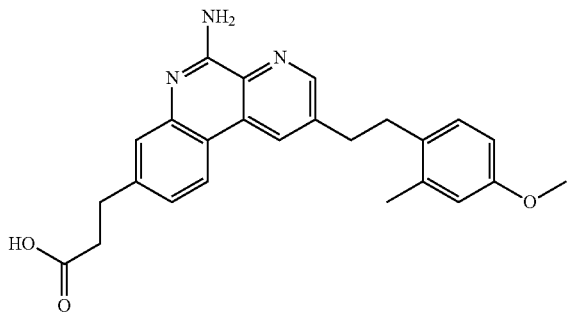 [SMILES: COc1ccc(CCc2cnc3c(N)nc4cc(CCC(=O)O)ccc4c3c2)c(C)c1]

3-(5-Amino-2-(4-methoxy-2-methylphenethyl)benzo[f][1,7]naphthyridin-8-yl)propanoic acid was prepared from ethyl 3-(5-amino-2-(4-methoxy-2-methylphenethyl)benzo[f][1,7]naphthyridin-8-yl)propanoate (from Example 79) following the procedures described for Example 65. $^1$H NMR (DMSO-d$_6$): δ 12.18 (s, 1H), 8.84 (d, 1H), 8.70 (d, 1H), 8.36 (d, 1H), 7.39 (d, 1H), 7.20 (dd, 1H), 7.09 (m, 2H), 6.74 (d, 1H), 6.68 (dd, 1H), 3.70 (s, 3H), 3.09 (dd, 2H), 2.96 (dd, 4H), 2.63 (t, 2H), 2.27 (s, 3H). LRMS [M+H]=416.2

Example 81

3-(5-amino-2-(4-methoxy-2-methylphenethyl)benzo[f][1,7]naphthyridin-8-yl)propan-1-ol

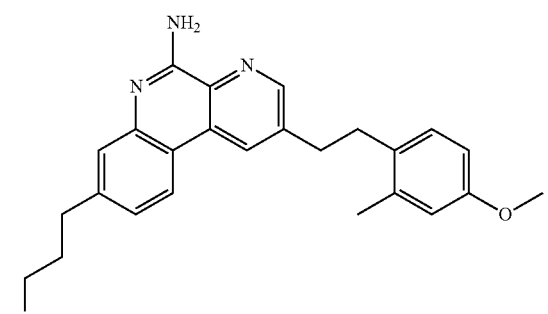

3-(5-Amino-2-(4-methoxy-2-methylphenethyl)benzo[f][1,7]naphthyridin-8-yl)propan-1-ol was prepared from ethyl 3-(5-amino-2-(4-methoxy-2-methylphenethyl)benzo[f][1,7]naphthyridin-8-yl)propanoate (from Example 79) following the procedures described for Example 39/Step 3. $^1$H NMR (CDCl$_3$): δ 8.54 (d, 1H), 8.30 (d, 1H), 8.05 (d, 1H), 7.48 (d, 1H), 7.15 (dd, 1H), 6.93 (d, 1H), 6.66 (d, 1H), 6.61 (dd, 1H), 5.98 (br s, 2H), 3.71 (s, 3H), 3.66 (t, 2H), 3.03 (dd, 2H), 2.91 (dd, 2H), 2.81 (t, 2H), 2.20 (s, 3H), 1.98-1.90 (m, 2H). LRMS [M+H]=402.2

Example 82

(5-aminobenzo[f][1,7]naphthyridin-8-yl)methanol

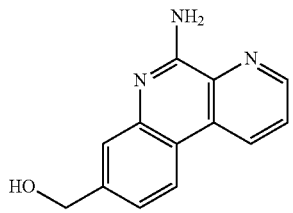 [SMILES: Nc1nc2cc(CO)ccc2c2cccnc12]

Step 1: 2-(tert-butoxycarbonylamino)-4-(methoxycarbonyl)phenylboronic acid

A solution of 2-amino-4-(methoxycarbonyl)phenylboronic acid hydrochloride (commercially available) (1.0 eq.), triethylamine (3.0 eq.), di-tert-butyl dicarbonate (1.1 eq.), and DMAP (0.1 eq.) in CH$_3$CN (0.3 M) was stirred at 40° C. overnight. After cooling to ambient temperature, the reaction mixture was concentrated en vaccuo to obtain a crude residue. The crude material was purified by flash chromatography on a COMBIFLASH® system (ISCO) using 0-30% MeOH/DCM to give 2-(tert-butoxycarbonylamino)-4-(methoxycarbonyl)phenylboronic acid as a brown solid.

Step 2: methyl 5-aminobenzo[f][1,7]naphthyridine-8-carboxylate

A solution of 2-(tert-butoxycarbonylamino)-4-(methoxycarbonyl)phenylboronic acid (from the previous step) (1.0 eq.) and 3-bromopicolinonitrile (1.0 eq.), tetrakis(triphenylphosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was filtered to collect the precipitate. The precipitate was rinsed with EtOAc to give methyl 5-aminobenzo[f][1,7]naphthyridine-8-carboxylate as a pale brown solid.

Step 3: (5-aminobenzo[f][1,7]naphthyridin-8-yl)methanol

To a solution of methyl 5-aminobenzo[f][1,7]naphthyridine-8-carboxylate (from the previous step) (1.0 eq.) in EtOH (0.03M) was added $NaBH_4$ (10 eq.) at 25° C. The solution was heated to 80° C. for 5 hours. After cooling to ambient temperature, the reaction mixture was concentrated en vaccuo. The residue was portionized between saturated $NaHCO_3$ and EtOAc. The layers were separated and aqueous layer was extracted with EtOAc twice. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give (5-aminobenzo[f][1,7]naphthyridin-8-yl)methanol as an off white solid: $^1$H NMR (methanol-$d_4$): δ 8.82 (dd, 1H), 8.77 (dd, 1H), 7.26 (d, 1H), 7.70 (dd, 1H), 7.50 (d, 1H), 7.27 (dd, 1H), 4.66 (s, 2H). LRMS [M+H]=226.1.

Example 83

5-aminobenzo[f][1,7]naphthyridin-8-ol

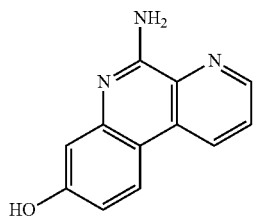 [SMILES: Nc1nc2cc(O)ccc2c2cccnc12]

To a solution of 8-methoxybenzo[f][1,7]naphthyridin-5-amine (from Example 9) (1.0 eq.) in DCM (0.04 M) was added $BBr_3$ (2.5 eq.) dropwise under $N_2$ at −20° C. The reaction was allowed to warm to ambient temperature over 30 minutes. The reaction was then stirred overnight. The reaction was quenched with saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-20% MeOH/DCM to give 5-aminobenzo[f][1,7]naphthyridin-8-ol as a yellow solid: $^1$H NMR (acetone-$d_6$): δ 8.90 (dd, 1H), 8.83 (dd, 1H), 8.32 (d, 1H), 7.83 (dd, 1H), 7.11 (br s, 2H), 7.10 (d, 1H), 6.96 (dd, 1H), 5.86 (br s, 1H). LRMS [M+H]=212.1.

Example 84

5-aminobenzo[f][1,7]naphthyridine-8-carbaldehyde

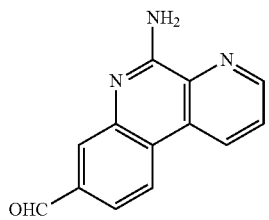 [SMILES: Nc1nc2cc(C=O)ccc2c2cccnc12]

A solution of (5-aminobenzo[f][1,7]naphthyridin-8-yl)methanol (from Example 82) (1.0 eq.) and activated $MnO_2$ (20 eq.) in DCM (0.1 M) was stirred at ambient temperature over night. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-10% MeOH/DCM to give 5-aminobenzo[f][1,7]naphthyridine-8-carbaldehyde as a yellow solid: $^1$H NMR (acetone-$d_6$): δ 10.19 (s, 1H), 9.14 (dd, 1H), 9.01 (dd, 1H), 8.63 (d, 1H), 8.14 (d, 1H), 7.93 (dd, 1H), 7.81 (dd, 1H), 6.96 (br s, 2H). LRMS [M+H]=224.1

Example 85

1-(5-aminobenzo[f][1,7]naphthyridin-8-yl)ethanol

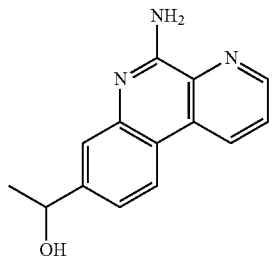 [SMILES: CC(O)c1ccc2c(c1)nc(N)c1ncccc12]

To a solution of 5-aminobenzo[f][1,7]naphthyridine-8-carbaldehyde (from Example 85) (1.0 eq.) in THF (0.02M) was added MeLi (2.5 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanol as a yellow solid: $^1$H NMR (methanol-$d_4$): δ 8.94 (dd, 1H), 8.88 (dd, 1H), 8.38 (d, 1H), 7.81 (dd, 1H), 7.62 (d, 1H), 7.41 (dd, 1H), 4.97 (q, 1H), 1.53 (d, 3H). LRMS [M+H]=240.1.

Example 86

1-(5-aminobenzo[f][1,7]naphthyridin-8-yl)ethanone

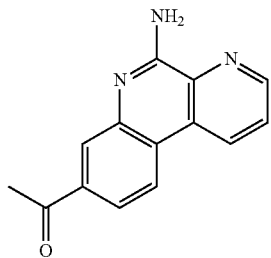 [SMILES: CC(=O)c1ccc2c(c1)nc(N)c1ncccc12]

A solution 1-(5-aminobenzo[f][1,7]naphthyridin-8-yl)ethanol (from Example 85) (1.0 eq.) and activated $MnO_2$ (20 eq.) in DCM (0.1 M) was stirred at ambient temperature overnight. The reaction mixture was diluted with DCM. The $MnO_2$ was filtered off, and the filtrate was concentrated en vaccuo to obtain a crude residue. The crude material was purified by flash chromatography on a COMBIFLASH® system (ISCO) using 0-5% MeOH/DCM to give 1-(5-aminobenzo[f][1,7]naphthyridin-8-yl)ethanone as a yellow solid: $^1$H NMR (acetone-$d_6$): δ 9.11 (dd, 1H), 8.99 (dd, 1H), 8.56 (d, 1H), 8.20 (d, 1H), 7.94-7.88 (m, 2H), 6.90 (br s, 2H), 2.70 (s, 3H). LRMS [M+H]=238.1.

Example 87

8-isopropylbenzo[f][1,7]naphthyridin-5-amine

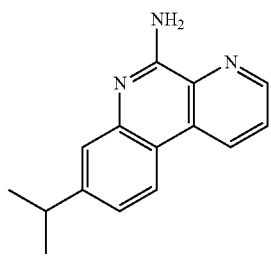 [SMILES: CC(C)c1ccc2c(c1)nc(N)c1ncccc12]

Step 1: 2-(5-aminobenzo[f][1,7]naphthyridin-8-yl)propan-2-ol

To a solution of methyl 5-aminobenzo[f][1,7]naphthyridine-8-carboxylate (from Example 82/Step 2) (1.0 eq.) in THF (0.02M) was added MeLi (10 eq.) at −78° C. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-10% MeOH/DCM to give 2-(5-aminobenzo[f][1,7]naphthyridin-8-yl)propan-2-ol as a yellow oil.

Step 2: 8-(prop-1-en-2-yl)benzo[f][1,7]naphthyridin-5-amine

A solution of 2-(5-aminobenzo[f][1,7]naphthyridin-8-yl)propan-2-ol (from the previous step) (1.0 eq.) and p-TsOH (2 eq.) in toluene (0.01 M) was stirred at 90° C. for 6 hours. The reaction was quenched by saturated $NaHCO_3$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-5% MeOH/DCM to give 8-(prop-1-en-2-yl)benzo[f][1,7]naphthyridin-5-amine as a yellow solid.

Step 3: 8-isopropylbenzo[f][1,7]naphthyridin-5-amine

A mixture of 8-(prop-1-en-2-yl)benzo[f][1,7]naphthyridin-5-amine (from the previous step) (1.0 eq) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-isopropylbenzo[f][1,7]naphthyridin-5-amine as a yellow solid: $^1$H NMR (acetone-$d_6$): δ 8.98 (dd, 1H), 8.88 (dd, 1H), 8.37 (d, 1H), 7.83 (dd, 1H), 7.49 (d, 1H), 7.27 (dd, 1H), 6.66 (br s, 2H), 3.10-3.00 (m, 1H), 1.33 (d, 6H). LRMS [M+H]=238.1.

Example 88

8-vinylbenzo[f][1,7]naphthyridin-5-amine

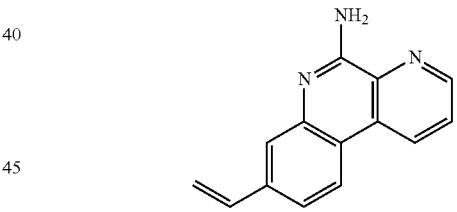

To a solution of methyl triphenyl phosphonium iodide (6.0 eq.) was added nBuLi (7.0 eq.) at −78° C. The reaction mixture was allowed to warm to 0° C. and stirred for 30 minutes (deep orange color). The reaction was again cooled down to −78° C. and 5-aminobenzo[f][1,7]naphthyridine-8-carbaldehyde (from Example 84) (1.0 eq.) in THF was introduced dropwise to the reaction. The reaction was allowed to warm to ambient temperature overnight. The reaction was quenched by saturated $NH_4Cl$ and extracted with EtOAc. The combined organic layer was washed with brine, dried over $MgSO_4$ and concentrated en vaccuo to obtain a crude residue. The crude material was purified by flash chromatography on a COMBIFLASH® system (ISCO) using 0-50% EtOAc/Hexanes to give 8-vinylbenzo[f][1,7]naphthyridin-5-amine as a white solid: $^1$H NMR (acetone-$d_6$): δ 9.00 (dd, 1H), 8.90 (dd, 1H), 8.41 (d, 1H), 7.84 (dd, 1H), 7.65 (d, 1H), 7.52 (dd, 1H), 6.91 (dd, 1H), 6.77 (br s, 2H), 5.97 (dd, 1H), 5.34 (dd, 1H). LRMS [M+H]=222.1.

Example 89

8-ethylbenzo[f][1,7]naphthyridin-5-amine

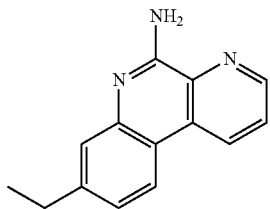 [SMILES: CCc1ccc2c(c1)nc(N)c1ncccc12]

A mixture of 8-vinylbenzo[f][1,7]naphthyridin-5-amine (1.0 eq) (from Example 88) and Pd/C (wet, 10% wt) in EtOH was stirred under $H_2$ balloon overnight. The reaction mixture was diluted with DCM. The Pd/C was filtered off through celite, and the filtrate was concentrated en vaccuo to obtain a crude residue. The crude material was purified by flash chromatography on a COMBIFLASH® system (ISCO) using 0-60% EtOAc/Hexanes to give 8-ethylbenzo[f][1,7]naphthyridin-5-amine as a white foam: $^1$H NMR (acetone-$d_6$): δ 8.98 (dd, 1H), 8.88 (dd, 1H), 8.35 (d, 1H), 7.82 (dd, 1H), 7.46 (d, 1H), 7.22 (dd, 1H), 6.63 (br s, 2H), 2.78 (q, 2H), 1.30 (t, 3H). LRMS [M+H]=224.1.

Example 90

8-(methoxymethyl)benzo[f][1,7]naphthyridin-5-amine

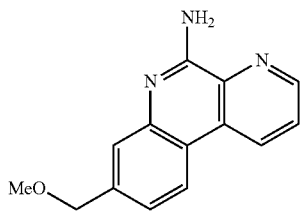

Step 1: tert-butyl 2-chloro-5-(methoxymethyl)phenylcarbamate

To a solution of 2-chloro-5-(methoxymethyl)aniline (commercially available) (1.0 eq.) in THF (0.2M) at 0° C. under $N_2$ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous $MgSO_4$, and concentrated en vaccuo. The crude material was purified by flash chromatography on a COMBIFLASH® system (ISCO) using 0-30% EtOAc/Hexanes to give tert-butyl 2-chloro-5-(methoxymethyl)phenylcarbamate as a colorless oil.

Step 2: tert-butyl 5-(methoxymethyl)-2-(4,4,5,5-tetramethyl-1,3,2-dioxaborolan-2-yl)phenylcarbamate Tert-butyl 2-chloro-5-(methoxymethyl)phenylcarbamate (from the previous step) (1.0 eq.), 4,4,4',4',5,5,5',5'-octamethyl-2,2'-bi(1,3,2-dioxaborolane) (3.0 eq.), $Pd_2$ $dba_3$ (2.5%), XPhos (10%), and KOAc (3 eq.) were mixed in dioxane (0.2 M) under $N_2$ atmosphere. The reaction was heated to 110° C. and stirred overnight. The resulting suspension was cooled to ambient temperature, diluted with ether, filtered through celite, and the filtrate was concentrated en vaccuo. The combined organic layers were washed with brine, dried over anhydrous $MgSO_4$, and concentrated en vaccuo. The crude material was purified by flash chromatography on a COMBIFLASH® system (ISCO) using 0-20% EtOAc/Hexanes to give tert-butyl 5-(methoxymethyl)-2-(4,4,5,5-tetramethyl-1,3,2-dioxaborolan-2-yl)phenylcarbamate as a white foam.

Step 3: 8-(methoxymethyl)benzo[f][1,7]naphthyridin-5-amine

A solution of tert-butyl 5-(methoxymethyl)-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with 2% MeOH in DCM and water. The two phases were separated, and the aqueous layer was extracted twice with 2% MeOH in DCM. The combined organic layers were washed with brine, dried over anhydrous $MgSO_4$, and concentrated en vaccuo. The crude material was purified by flash chromatography on a COMBIFLASH® system (ISCO) using 0-100% EtOAc/Hexanes to give 8-(methoxymethyl)benzo[f][1,7]naphthyridin-5-amine as a white solid: $^1$H NMR (methanol-$d_4$): δ 8.97 (dd, 1H), 8.91 (dd, 1H), 8.41 (dd, 1H), 7.83 (dd, 1H), 7.59 (d, 1H), 7.37 (dd, 1H), 4.62 (s, 2H), 3.45 (s, 3H). LRMS [M+H]=240.1.

Example 91

(5-amino-2-phenethylbenzo[f][1,7]naphthyridin-8-yl)methanol

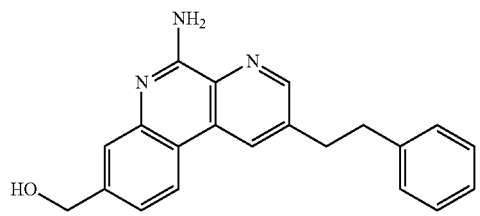 [SMILES: Nc1nc2cc(CO)ccc2c2cc(CCc3ccccc3)cnc12]

Step 1: methyl 5-amino-2-phenethylbenzo[f][1,7]naphthyridine-8-carboxylate

A solution of 2-(tert-butoxycarbonylamino)-4-(methoxycarbonyl)phenylboronic acid (from Example 82/Step 1) (1.0 eq.) and 2-chloro-6-phenethylnicotinonitrile (prepared from (E)-3-chloro-5-styrylpicolinonitrile (from Example 30/Step 1) following the procedure described in Example 111/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO₄, and concentrated en vaccuo. The crude material was purified by flash chromatography on a COMBIFLASH® system (ISCO) using 0-60% EtOAc/Hexanes to give methyl 5-amino-2-phenethylbenzo[f][1,7]naphthyridine-8-carboxylate as a white solid.

Step 2: (5-amino-2-phenethylbenzo[f][1,7]naphthyridin-8-yl)methanol

To a solution of methyl 5-amino-2-phenethylbenzo[f][1,7]naphthyridine-8-carboxylate (from the previous step) (1.0 eq.) in THF (0.03M) was added Super-H (10 eq.) at 0° C. The solution was allowed to warm to ambient temperature over 30 min. The reaction was quenched by water until no bubbling. The layers were separated and aqueous layer was extracted with EtOAc. The combined organic layer was washed with brine, dried over MgSO₄ and concentrated en vaccuo to obtain a crude residue. The crude material was purified by flash chromatography on a COMBIFLASH® system (ISCO) using 0-10% MeOH/DCM to give (5-amino-2-phenethylbenzo[f][1,7]naphthyridin-8-yl)methanol as an off white solid: $^1$H NMR (methanol-d₄): δ 8.63 (dd, 1H), 8.56 (dd, 1H), 8.24 (d, 1H), 7.57 (d, 1H), 7.35 (dd, 1H), 7.27-7.15 (m, 5H), 4.75 (s, 2H), 3.20 (t, 2H), 3.06 (t, 2H). LRMS [M+H]=330.1.

Example 92

(5-amino-2-(4-methoxyphenethyl)benzo[f][1,7]naphthyridin-8-yl)methanol

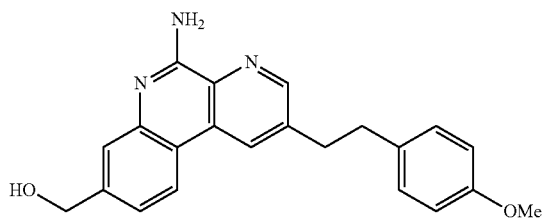 [SMILES: COc1ccc(CCc2cnc3c(N)nc4cc(CO)ccc4c3c2)cc1]

Step 1: methyl 5-amino-2-(4-methoxyphenethyl)benzo[f][1,7]naphthyridine-8-carboxylate A solution of 2-(tert-butoxycarbonylamino)-4-(methoxycarbonyl)phenylboronic acid (from Example 82/Step1) (1.0 eq.) and 2-chloro-6-(4-methoxyphenethyl)nicotinonitrile (prepared from reaction of 3,5-dichloropicolinonitrile with 1-ethynyl-4-methoxybenzene following the procedure described in Example 41/Step 3 and reduction of the product following the procedure described in Example 111/Step 3) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO₄, and concentrated en vaccuo. The crude material was purified by flash chromatography on a COMBIFLASH® system (ISCO) using 0-80% EtOAc/Hexanes to give methyl 5-amino-2-(4-methoxyphenethyl)benzo[f][1,7]naphthyridine-8-carboxylate as a white solid.

Step 2: (5-amino-2-(4-methoxyphenethyl)benzo[f][1,7]naphthyridin-8-yl)methanol

To a solution of methyl 5-amino-2-(4-methoxyphenethyl)benzo[f][1,7]naphthyridine-8-carboxylate (from the previous step) (1.0 eq.) in THF (0.03M) was added Super-H (10 eq.) at 0° C. The solution was allowed to warm to ambient temperature over 30 minutes. The reaction was quenched by water until no bubbling. The layers were separated and aqueous layer was extracted with EtOAc. The combined organic layer was washed with brine, dried over MgSO₄ and concentrated en vaccuo to obtain a crude residue. The crude material was purified by flash chromatography on a COMBIFLASH® system (ISCO) using 0-100% EtOAc/Hexanes to give (5-amino-2-(4-methoxyphenethyl)benzo[f][1,7]naphthyridin-8-yl)methanol as an off white solid (31%): $^1$H NMR (acetone-d₆): δ 8.79 (d, 1H), 8.70 (d, 1H), 8.35 (d, 1H), 7.61 (d, 1H), 7.33 (dd, 1H), 7.13 (d, 2H), 6.83 (d, 2H), 6.62 (br s, 2H), 4.47 (s, 2H), 4.40 (br s, 1H), 3.75 (s, 3H), 3.22 (t, 2H), 3.06 (t, 2H). LRMS [M+H]=360.2.

Example 93 benzo[f][1,7]naphthyridine-5,8-diamine

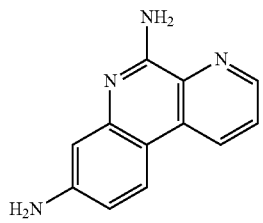

Step 1: tert-butyl 2-bromo-5-nitrophenylcarbamate

To a solution of 2-bromo-5-nitroaniline (commercially available) (1.0 eq.) in THF (0.2M) at 0° C. under N₂ atmosphere was added dropwise 1M NaHMDS (2.5 eq.). The reaction was stirred for 15 minutes at 0° C., and a solution of di-tert-butyl dicarbonate in THF was added. The reaction was warmed to ambient temperature overnight. The solvent was evaporated, and the resulting residue was quenched with 0.1N HCl aqueous solution. The aqueous suspension was extracted twice with EtOAc. The combined organic layers were washed with brine, dried over anhydrous MgSO₄, and concentrated en vaccuo. The crude material was purified by flash chromatography on a COMBIFLASH® system (ISCO) using 0-30% EtOAc/Hexanes to give tert-butyl 2-bromo-5-nitrophenylcarbamate as a colorless oil.

Step 2: tert-butyl 5-nitro-2-(4,4,5,5-tetramethyl-1,3,2-dioxaborolan-2-yl)phenyl carbamate Tert-butyl 2-bromo-5-nitrophenylcarbamate (from the previous step) (1.0 eq.), 4,4,4',4',5,5,5',5'-octamethyl-2,2'-bi (1,3,2-dioxaborolane) (1.8 eq.), dichloro[1,1'-bis(diphenyl phosphino)ferrocene]palladium (II) (5%), and sodium acetate (4.5 eq.) were mixed in dioxane (0.2 M) under N₂ atmosphere. The reaction was heated to 100° C. and stirred overnight. The resulting suspension was cooled to ambient temperature, diluted with ether, filtered through celite, and the filtrate was concentrated en vaccuo. The residue was purified by flash chromatography on a COMBIFLASH® system (ISCO) using 0-30% EtOAc/Hexanes to give tert-butyl 5-nitro-2-(4,4,5,5-tetramethyl-1,3,2-dioxaborolan-2-yl)phenyl carbamate as a white foam.

Step 3: 8-nitrobenzo[f][1,7]naphthyridin-5-amine

A solution of tert-butyl 5-nitro-2-(4,4,5,5-tetramethyl-1,3,2-dioxaborolan-2-yl)phenylcarbamate (from the previous step) (1.0 eq.) and 3-bromopicolinonitrile (1.0 eq.) in toluene (0.44 M) was mixed with tetrakis(triphenyl-phosphine) palladium (5 mol %) and 2N aqueous potassium carbonate solution (2.0 eq.). The reaction was heated to 100° C. and stirred overnight. After cooling to ambient temperature, the reaction mixture was filtered to collect the precipitate. The precipitate was rinsed with EtOAc to give 8-nitrobenzo[f][1,7]naphthyridin-5-amine as a yellow solid.

Step 4: benzo[f][1,7]naphthyridine-5,8-diamine

A mixture of 8-nitrobenzo[f][1,7]naphthyridin-5-amine (from the previous step) (1.0 eq) and Pd/C (wet, 10% wt) in EtOH was stirred under H₂ balloon overnight. The reaction mixture was diluted with DCM. The insoluble solid was filtered off through celite, and the filtrate was concentrated en vaccuo to obtain a crude residue. The crude material was washed with acetone to give benzo[f][1,7]naphthyridine-5,8-diamine as an off white solid: ¹H NMR (methanol-d₄): δ 8.73 (dd, 1H), 8.71 (dd, 1H), 8.11 (d, 1H), 7.69 (dd, 1H), 6.86 (d, 1H), 6.82 (dd, 1H). LRMS [M+H]=211.1.

Example 94

8-(aminomethyl)benzo[f][1,7]naphthyridin-5-amine

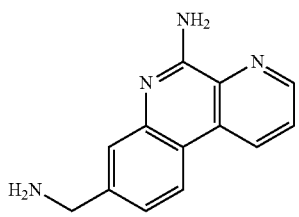 [SMILES: NCc1ccc2c(c1)nc(N)c1ncccc12]

Step 1:
2-(tert-butoxycarbonylamino)-4-cyanophenylboronic acid

The titled compound was prepared according to the procedure described in Example 82/Step 1, but using 2-amino-4-cyanophenylboronic acid hydrochloride (commercially available) as the starting material. The crude material was purified by flash chromatography on a COMBIFLASH® system (ISCO) using 0-30% MeOH/DCM to give 2-(tert-butoxycarbonylamino)-4-cyanophenylboronic acid as an off white solid.

Step 2:
5-aminobenzo[f][1,7]naphthyridine-8-carbonitrile

The titled compound was prepared according to the procedure described in Example 93/Step 3, but using 2-(tert-butoxycarbonylamino)-4-cyanophenylboronic acid (from the previous step) as the starting material. The crude material was rinsed with 1:1 EtOAc/Hexanes to give 5-aminobenzo[f][1,7]naphthyridine-8-carbonitrile as a pale yellow solid.

Step 4: benzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH/ammonia (2:1) was stirred under H₂ balloon overnight. The reaction mixture was diluted with DCM. The insoluble solid was filtered off through celite, and the filtrate was concentrated en vaccuo to obtain a crude residue. The crude material was washed with 10% MeOH/DCM and 70% EtOAc/Hexanes to give benzo[f][1,7]naphthyridine-5,8-diamine as an off white solid: ¹H NMR (methanol-d₄): δ 8.97 (dd, 1H), 8.90 (dd, 1H), 8.41 (d, 1H), 7.83 (dd, 1H), 7.57 (d, 1H), 7.39 (dd, 1H), 3.96 (s, 2). LRMS [M+H]=229.1.

Example 95

3-fluoro-8-methylbenzo[f][1,7]naphthyridin-5-amine

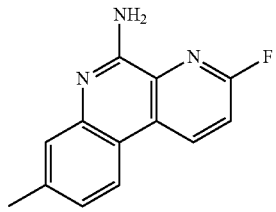 [SMILES: Cc1ccc2c(c1)nc(N)c1nc(F)ccc12]

Step 1:
3-chloro-8-methylbenzo[f][1,7]naphthyridin-5-amine

A solution of tert-butyl 5-methyl-2-(4,4,5,5-tetramethyl-1,3,2-dioxaborolan-2-yl)phenylcarbamate (from Example 4/Step 2) (1.0 eq.) and 3-bromo-6-chloropicolinonitrile (from Example 18/Step 2) (1.0 eq.), tetrakis(triphenyl-phosphine)palladium (5 mol %), and 2N aqueous sodium carbonate solution (2.0 eq.) in toluene/ethanol (2:1, 0.03 M) was stirred at 100° C. overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO₄, and concentrated en vaccuo. The crude material was purified by flash chromatography on a COMBIFLASH® system (ISCO) using 0-40% EtOAc/Hexanes to give 3-chloro-8-methylbenzo[f][1,7]naphthyridin-5-amine as a pale yellow solid.

Step 2:
3-fluoro-8-methylbenzo[f][1,7]naphthyridin-5-amine

A mixture of 3-chloro-8-methylbenzo[f][1,7]naphthyridin-5-amine (from the previous step) (1.0 eq.) potassium fluoride (4.0 eq.), and 18-crown-6 (0.4 eq.) in NMP (0.1M) was heated in microwave reactor at 210° C. for 2 hours. After cooling to ambient temperature, the reaction redisue was purified by flash chromatography on a COMBIFLASH® system (ISCO) using 0-30% EtOAc/Hexanes to give 3-fluoro-8-methylbenzo[f][1,7]naphthyridin-5-amine as a white solid. $^1$H NMR (acetone-d$_6$): δ 9.20 (dd, 1H), 8.32 (d, 1H), 7.58 (dd, 1H), 7.46 (d, 1H), 7.21 (dd, 1H), 6.51 (br s, 2H), 2.47 (s, 3H). LRMS [M+H]=228.1.

Example 96

(5-amino-3-fluorobenzo[f][1,7]naphthyridin-8-yl)methanol

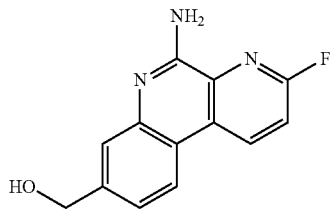 [SMILES: Nc1nc2cc(CO)ccc2c2ccc(F)nc12]

Step 1: tert-butyl 5-((tert-butyldimethylsilyloxy)methyl)-2-(4,4,5,5-tetramethyl-1,3,2-dioxaborolan-2-yl)phenylcarbamate The titled compound was prepared according to the procedure described in Example 90/Step 1 and 2, but using 5-((tert-butyldimethylsilyloxy)methyl)-2-chloroaniline (commercially available) as the starting material. The crude material was purified by flash chromatography on a COMBIFLASH® system (ISCO) using 0-20% EtOAc/Hexanes to give tert-butyl 5-((tert-butyldimethylsilyloxy)methyl)-2-(4,4,5,5-tetramethyl-1,3,2-dioxaborolan-2-yl)phenylcarbamate as a white foam.

Step 2: 8-((tert-butyldimethylsilyloxy)methyl)-3-chlorobenzo[f][1,7]naphthyridin-5-amine The titled compound was prepared according to the procedure described in Example 95/Step 1, but using tert-butyl 5-((tert-butyldimethylsilyloxy)methyl)-2-(4,4,5,5-tetramethyl-1,3,2-dioxaborolan-2-yl)phenylcarbamate (from the previous step) as the starting material. The crude material was purified by flash chromatography on a COMBIFLASH® system (ISCO) using 0-15% EtOAc/Hexanes to give 8-((tert-butyldimethylsilyloxy)methyl)-3-chlorobenzo[f][1,7]naphthyridin-5-amine as a pale yellow solid.

Step 3: (5-amino-3-chlorobenzo[f][1,7]naphthyridin-8-yl)methanol

A solution of 8-((tert-butyldimethylsilyloxy)methyl)-3-chlorobenzo[f][1,7]naphthyridin-5-amine (from the previous step) (1.0 eq.) and TBAF (1.1 eq.) in THF was stirred at ambient temperature overnight. The reaction was quenched with saturated NaHCO$_3$. The two phases were separated, and the aqueous layer was extracted twice with Et$_2$O. The combined organic layers were washed with brine, dried over anhydrous MgSO$_4$, and concentrated en vaccuo. The crude material was purified by flash chromatography on a COMBIFLASH® system (ISCO) using 0-5% MeOH/DCM to give (5-amino-3-chlorobenzo[f][1,7]naphthyridin-8-yl)methanol as a white solid.

Step 4: (5-amino-3-fluorobenzo[f][1,7]naphthyridin-8-yl)methanol

The titled compound was prepared according to the procedure described in Example 95/Step 2, but using (5-amino-3-chlorobenzo[f][1,7]naphthyridin-8-yl)methanol (from the previous step) as the starting material. The crude material was purified by flash chromatography on a COMBIFLASH® system (ISCO) using 0-40% EtOAc/Hexanes to give (5-amino-3-fluorobenzo[f][1,7]naphthyridin-8-yl)methanol as a white solid. $^1$H NMR (methanol-d$_4$): δ 9.15 (dd, 1H), 8.38 (d, 1H), 7.64 (d, 1H), 7.55 (dd, 1H), 7.41 (dd, 1H), 4.77 (s, 2H). LRMS [M+H]=244.1.

Example 97

3-chlorobenzo[f][1,7]naphthyridine-5,8-diamine

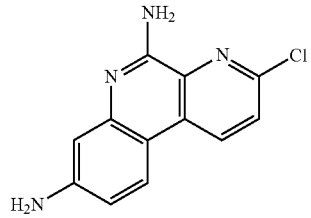 [SMILES: Nc1ccc2c(c1)nc(N)c1nc(Cl)ccc12]

Step 1: 3-chloro-8-nitrobenzo[f][1,7]naphthyridin-5-amine

The titled compound was prepared according to the procedure described in Example 95/Step 1, but using tert-butyl 5-nitro-2-(4,4,5,5-tetramethyl-1,3,2-dioxaborolan-2-yl)phenylcarbamate (commercially available) as the starting material. The crude material was purified by flash chromatography on a COMBIFLASH® system (ISCO) using 0-40% EtOAc/Hexanes to give 3-chloro-8-nitrobenzo[f][1,7]naphthyridin-5-amine as a pale yellow solid.

Step 2: 3-chlorobenzo[f][1,7]naphthyridine-5,8-diamine

A mixture of 8-nitrobenzo[f][1,7]naphthyridin-5-amine (from the previous step) (1.0 eq) and Raney Nickel (wet, 10% wt) in EtOH was stirred under H$_2$ balloon overnight. The reaction mixture was diluted with DCM. The insoluble solid was filtered off through celite, and the filtrate was concentrated en vaccuo to obtain a crude residue. The crude material was purified by flash chromatography on a COMBIFLASH® system (ISCO) using 0-100% EtOAc/Hexanes to give 3-chlorobenzo[f][1,7]naphthyridine-5,8-diamine as a white solid. $^1$H NMR (methanol-d$_4$): δ 8.75 (d, 1H), 8.08 (dd, 1H), 7.70 (d, 1H), 6.84-6.81 (m, 2H). LRMS [M+H]=245.1.

Example 98

3-fluorobenzo[f][1,7]naphthyridine-5,8-diamine

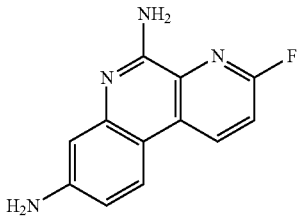 [SMILES: Nc1ccc2c(c1)nc(N)c1nc(F)ccc12]

The titled compound was prepared according to the procedure described in Example 95/Step 2, but using 3-chlorobenzo[f][1,7]naphthyridine-5,8-diamine (from Example 97) as the starting material. The crude material was purified by flash chromatography on a COMBIFLASH® system (ISCO) using 0-7% MeOH/DCM to give 3-fluorobenzo[f][1,7]naphthyridine-5,8-diamine as a white solid. $^1$H NMR (methanol-d$_4$): δ 8.93 (dd, 1H), 8.09 (d, 1H), 7.44 (dd, 1H), 6.86-6.83 (m, 2H). LRMS [M+H]=229.1.

Example 99

8-isobutylbenzo[f][1,7]naphthyridin-5-amine

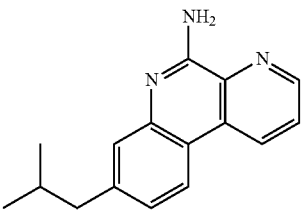 [SMILES: CC(C)Cc1ccc2c(c1)nc(N)c1ncccc12]

8-Isobutylbenzo[f][1,7]naphthyridin-5-amine was prepared from 5-aminobenzo[f][1,7]naphthyridine-8-carbaldehyde (from Example 84) with isopropyl(triphenyl)phosphonium bromide following the procedures described for Example 88 (wittig reaction) and Example 89 (reduction). $^1$H NMR (acetone-d$_6$): δ 8.98 (dd, 1H), 8.88 (dd, 1H), 8.35 (d, 1H), 7.82 (dd, 1H), 7.44 (d, 1H), 7.18 (dd, 1H), 6.73 (br s, 2H), 2.63 (d, 2H), 2.04-1.94 (m, 1H), 0.94 (d, 6H). LRMS [M+H]=252.1.

Example 100

(E)-8-(prop-1-enyl)benzo[f][1,7]naphthyridin-5-amine

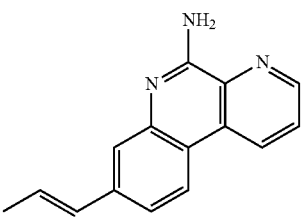 [SMILES: C/C=C/c1ccc2c(c1)nc(N)c1ncccc12]

(E)-8-(prop-1-enyl)benzo[f][1,7]naphthyridin-5-amine was prepared from 5-aminobenzo[f][1,7]naphthyridine-8-carbaldehyde (from Example 84) with ethyl(triphenyl)phosphonium bromide following the procedures described for Example 88. $^1$H NMR (acetone-d$_6$): δ 8.98 (dd, 1H), 8.88 (dd, 1H), 8.36 (d, 1H), 7.83 (dd, 1H), 7.54 (d, 1H), 7.43 (dd, 1H), 6.67 (br s, 2H), 6.60-6.42 (m, 2H), 1.92 (dd, 3H). LRMS [M+H]=236.1.

Example 101

8-propylbenzo[f][1,7]naphthyridin-5-amine

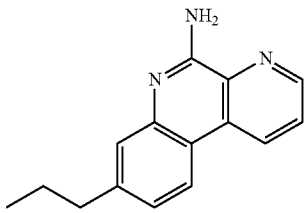 [SMILES: CCCc1ccc2c(c1)nc(N)c1ncccc12]

8-Propylbenzo[f][1,7]naphthyridin-5-amine was prepared from (E)-8-(prop-1-enyl)benzo[f][1,7]naphthyridin-5-amine (from Example 100) following the procedures described for Example 89. $^1$H NMR (acetone-d$_6$): δ 8.99 (dd, 1H), 8.88 (dd, 1H), 8.35 (d, 1H), 7.83 (dd, 1H), 7.45 (d, 1H), 7.21 (dd, 1H), 6.64 (br s, 2H), 2.74 (t, 2H), 1.74 (qt, 2H), 0.98 (t, 3H). LRMS [M+H]=238.1.

Example 102

8-(2-cyclopropylethyl)benzo[f][1,7]naphthyridin-5-amine

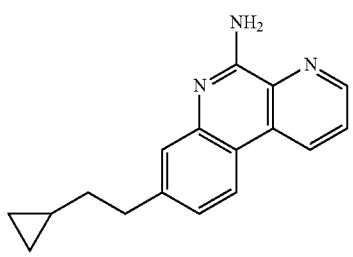 [SMILES: Nc1nc2cc(CCC3CC3)ccc2c2cccnc12]

8-(2-Cyclopropylethyl)benzo[f][1,7]naphthyridin-5-amine was prepared from 5-aminobenzo[f][1,7]naphthyridine-8-carbaldehyde (from Example 84) with (cyclopropylmethyl)triphenylphosphonium bromide following the procedures described for Example 88 (wittig reaction) and Example 89 (reduction). $^1$H NMR (acetone-d$_6$): δ 8.99 (dd, 1H), 8.88 (dd, 1H), 8.35 (d, 1H), 7.83 (dd, 1H), 7.47 (d, 1H), 7.23 (dd, 1H), 6.64 (br s, 2H), 1.60 (q, 2H), 1.34-1.25 (m, 1H), 0.91-0.72 (m, 2H), 0.45-0.41 (m, 2H), 0.11-0.07 (m, 2H). LRMS [M+H]=264.1.

Example 103

8-phenethylbenzo[f][1,7]naphthyridin-5-amine

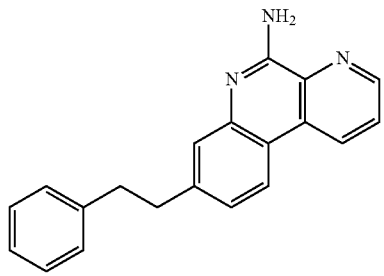 [SMILES: Nc1nc2cc(CCc3ccccc3)ccc2c2cccnc12]

8-Phenethylbenzo[f][1,7]naphthyridin-5-amine was prepared from 5-aminobenzo[f][1,7]naphthyridine-8-carbaldehyde (from Example 84) with benzyltriphenylphosphonium bromide following the procedures described for Example 88 (wittig reaction) and Example 89 (reduction). $^1$H NMR (acetone-$d_6$): δ 8.99 (dd, 1H), 8.88 (dd, 1H), 8.35 (d, 1H), 7.83 (dd, 1H), 7.49 (d, 1H), 7.29-7.15 (dd, 6H), 6.70 (br s, 2H), 3.10-3.00 (m, 4H). LRMS [M+H]=300.1.

Example 104

(5-amino-2-(4-bromophenethyl)benzo[f][1,7]naphthyridin-8-yl)methanol

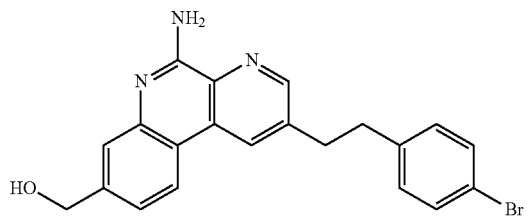 [SMILES: Nc1nc2cc(CO)ccc2c2cc(CCc3ccc(Br)cc3)cnc12]

(5-Amino-2-(4-bromophenethyl)benzo[f][1,7]naphthyridin-8-yl)methanol was prepared from (5-amino-2-(4-methoxyphenethyl)benzo[f][1,7]naphthyridin-8-yl)methanol (from Example 92) following the procedures described for Example 83. $^1$H NMR (acetone-$d_6$): δ 8.81 (d, 1H), 8.72 (d, 1H), 8.40 (d, 1H), 7.68 (d, 1H), 7.39 (dd, 1H), 7.08 (d, 2H), 6.74 (d, 2H), 6.66 (br s, 2H), 4.49 (s, 2H), 3.21 (t, 2H), 3.03 (t, 2H). LRMS [M+H]=408.1.

Example 105

(5-amino-2-(4-methoxy-2-methylphenethyl)benzo[f][1,7]naphthyridin-8-yl)methanol

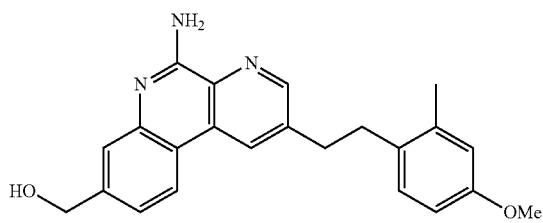

(5-Amino-2-(4-methoxy-2-methylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (Example 96/Step 1) and 3-chloro-5-((4-methoxy-2-methylphenyl)ethynyl)picolinonitrile (from Example 46/Step 1) following the procedures described for Example 41/Step 4 and deprotection of TBS group following the procedure describes from Example 96/Step 3. $^1$H NMR (acetone-$d_6$): δ 8.79 (s, 1H), 8.73 (s, 1H), 8.35 (d, 1H), 7.61 (s, 1H), 7.33 (d, 1H), 7.09 (d, 1H), 6.75 (d, 1H), 6.68 (dd, 1H), 6.57 (br s, 2H), 4.47 (d, 2H), 4.32 (t, 1H), 3.58 (s, 3H), 3.17 (t, 2H), 3.04 (t, 2H), 2.30 (s, 3H). LRMS [M+H]=374.2.

Example 106

2-(4-methoxy-2-methylphenethyl)-8-pentylbenzo[f][1,7]naphthyridin-5-amine

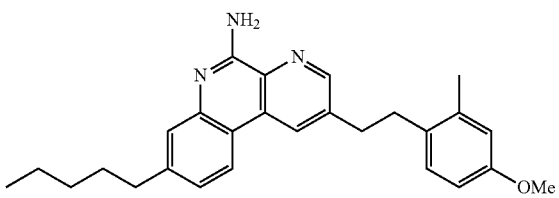 [SMILES: CCCCCc1ccc2c(c1)nc(N)c1ncc(CCc3ccc(OC)cc3C)cc12]

and

Example 107

8-(2-cyclopropylethyl)-2-(4-methoxy-2-methylphenethyl)benzo[f][1,7]naphthyridin-5-amine

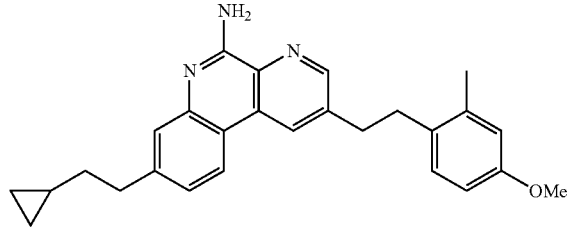 [SMILES: COc1ccc(CCc2cnc3c(N)nc4cc(CCC5CC5)ccc4c3c2)c(C)c1]

Step 1: tert-butyl 5-bromo-2-chlorophenylcarbamate

The titled compound was prepared according to the procedure described in Example 4/Step 1, but using 5-bromo-2-chloroaniline (commercially available) as the starting material. The crude material was purified by flash chromatography on a COMBIFLASH® system (ISCO) using 0-40% EtOAc/Hexanes to give tert-butyl 5-bromo-2-chlorophenylcarbamate as a pale yellow solid.

Step 2: (E)-tert-butyl 2-chloro-5-(2-cyclopropylvinyl)phenylcarbamate

A solution of tert-butyl 5-bromo-2-chlorophenylcarbamate (from the previous step) (1.0 eq.) and (E)-2-(2-cyclopropylvinyl)-4,4,5,5-tetramethyl-1,3,2-dioxaborolane (commercially available) (1.0 eq.) in toluene (0.2 M) was mixed with tetrakis(triphenyl-phosphine)palladium (5 mol %) and 2N aqueous potassium carbonate solution (2.0 eq.). The reaction was heated to 100° C. and stirred overnight. After cooling to ambient temperature, the reaction mixture was diluted with EtOAc and water. The two phases were separated, and the aqueous layer was extracted twice with EtOAc. The combined organic layers were washed with brine, dried over anhydrous MgSO$_4$, and concentrated en vaccuo. The crude product was purified by flash chromatography on a COMBIFLASH® system (ISCO) using 0-5% EtOAc/Hexanes to give (E)-tert-butyl 2-chloro-5-(2-cyclopropylvinyl)phenylcarbamate as a pale yellow solid.

Step 3: (E)-tert-butyl 5-(2-cyclopropylvinyl)-2-(4,4,5,5-tetramethyl-1,3,2-dioxaborolan-2-yl)phenylcarbamate The titled compound was prepared according to the procedure described in Example 90/Step 2, but using (E)-tert-butyl 2-chloro-5-(2-cyclopropylvinyl)phenylcarbamate (from prevous step) as the starting material. The crude product was purified by flash chromatography on a COMBIFLASH® system (ISCO) using 0-10% EtOAc/Hexanes to give (E)-tert-butyl 5-(2-cyclopropylvinyl)-2-(4,4,5,5-tetramethyl-1,3,2-dioxaborolan-2-yl)phenylcarbamate as a pale yellow solid.

Step 4: 2-(4-methoxy-2-methylphenethyl)-8-pentyl-benzo[f][1,7]naphthyridin-5-amine and 8-(2-cyclopropylethyl)-2-(4-methoxy-2-methylphenethyl)benzoN [1,7]naphthyridin-5-amine The titled compounds were prepared according to the procedure described in Example 41/Step 4 (Suzuki coupling) and 5 (reduction), but using (E)-tert-butyl 5-(2-cyclopropylvinyl)-2-(4,4,5,5-tetramethyl-1,3,2-dioxaborolan-2-yl)phenylcarbamate (from previous step) and 3-chloro-5-((4-methoxy-2-methylphenyl)ethynyl) picolinonitrile (from Example 46/Step 1) as the starting material. The crude product was purified by flash chromatography on a COMBIFLASH® system (ISCO) using 0-40% EtOAc/Hexanes to give Example 106 as a white solid: $^1$H NMR (acetone-d$_6$): δ 8.76 (d, 1H), 8.70 (d, 1H), 8.29 (d, 1H), 7.44 (d, 1H), 7.18 (dd, 1H), 7.08 (d, 1H), 6.74 (d, 1H), 6.68 (dd, 1H), 6.59 (br s, 2H), 3.74 (s, 3H), 3.18 (t, 2H), 3.04 (t, 2H), 2.75 (t, 2H), 2.29 (s, 3H), 1.75-1.68 (m, 2H), 1.40-1.35 (m, 4H), 0.90 (s, 3H); LRMS [M+H]=414.3; and Example 107 as an off white solid: $^1$H NMR (acetone-d$_6$): δ 8.76 (d, 1H), 8.70 (d, 1H), 8.28 (d, 1H), 7.45 (d, 1H), 7.19 (dd, 1H), 7.08 (d, 1H), 6.74 (d, 1H), 6.67 (dd, 1H), 6.55 (br s, 2H), 3.73 (s, 3H), 3.16 (t, 2H), 3.03 (t, 2H), 2.29 (s, 3H), 1.60 (q, 2H), 1.29-1.28 (m, 1H), 0.89-0.74 (m, 2H), 0.44-0.41 (m, 2H), 0.10-0.07 (m, 2H). LRMS [M+H]=412.3.

Example 108

(5-amino-2-(2,4,6-trimethylphenethyl)benzo[f][1,7]naphthyridin-8-yl)methanol

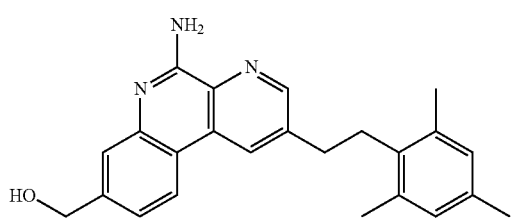 [SMILES: Cc1cc(C)c(CCc2cnc3c(N)nc4cc(CO)ccc4c3c2)c(C)c1]

(5-Amino-2-(2,4,6-trimethylphenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 96/step 1), 2-ethynyl-1,3,5-trimethylbenzene (commercially available) and 3-chloro-5-(mesitylethynyl) picolinonitrile (from Example 74/Step 1) following the procedures described for Example 41/Step 4, Example 96/step 3 (deprotection of TBS) and Example 74/step 3 (reduction). $^1$H NMR (acetone-d$_6$): δ 8.77 (s, 2H), 8.34 (d, 1H), 7.61 (s, 1H), 7.33 (d, 1H), 6.84 (s, 2H), 6.60 (br s, 2H), 4.77 (d, 2H), 4.35 (t, 1H), 3.08 (s, 3H), 2.84 (s, 6H), 2.30-2.29 (m, 4H). LRMS [M+H]=372.2.

Example 109

(5-amino-2-(4-propoxyphenethyl)benzo[f][1,7]naphthyridin-8-yl)methanol

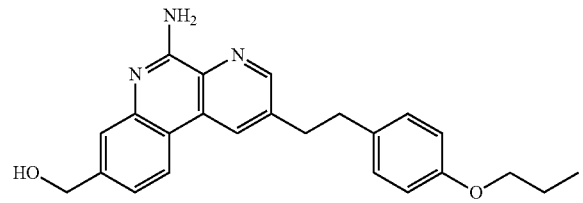 [SMILES: CCCOc1ccc(CCc2cnc3c(N)nc4cc(CO)ccc4c3c2)cc1]

(5-Amino-2-(4-propoxyphenethyl)benzo[f][1,7]naphthyridin-8-yl)methanol was prepared from 8-((tert-butyldimethylsilyloxy)methyl)-3-chlorobenzo[f][1,7]naphthyridin-5-amine (from Example 96/step 1) and 3-chloro-5-(4-propoxyphenethyl) picolinonitrile (from Example 76/step 2) following the procedures described for Example 41/Step 4 and Example 96/step 3 (deprotection of TBS). $^1$H NMR (acetone-d$_6$): δ 8.79 (d, 1H), 8.70 (d, 1H), 8.35 (d, 1H), 7.61 (d, 1H), 7.33 (dd, 1H), 7.17 (d, 2H), 6.83 (d, 2H), 6.57 (br s, 2H), 4.77 (d, 2H), 4.34 (t, 1H), 3.89 (t, 2H), 3.22 (t, 2H), 3.06 (t, 2H), 1.83-1.70 (m, 2H), 1.00 (t, 3H). LRMS [M+H]=388.2.

Example 110

(2-(2-(1H-indol-5-yl)ethyl)-5-aminobenzo[f][1,7]naphthyridin-8-yl)methanol

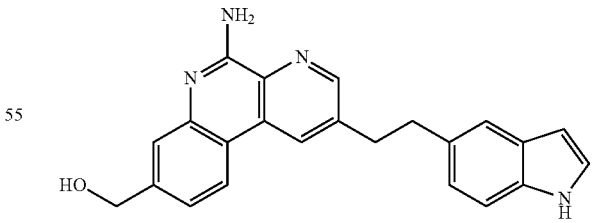

(2-(2-(1H-indol-5-yl)ethyl)-5-aminobenzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 96/step 1) and 5-((1H-indol-5-yl)ethynyl)-3-chloropicolinonitrile (from Example 41/step 3) following the procedures described for Example 41/Step 4 and Example 96/step 3 (deprotection of TBS). $^1$H NMR (acetone-$d_6$): δ 10.19 (t, 1H), 8.83 (d, 1H), 8.71 (d, 1H), 8.35 (d, 1H), 7.60 (d, 1H), 7.46 (d, 1H), 7.36-7.27 (m, 3H), 7.04 (dd, 1H), 6.57 (br s, 2H), 6.38 (dt, 1H), 4.77 (d, 2H), 4.36 (t, 1H), 3.29 (t, 2H), 3.19 (t, 2H). LRMS [M+H]=369.2.

Example 111

N-(4-(2-(5-amino-8-methylbenzo[f][1,7]naphthyridin-2-yl)ethyl)phenyl)acetamide

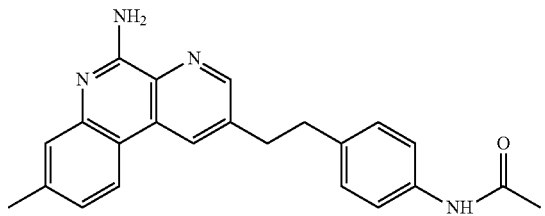 [SMILES: CC(=O)Nc1ccc(CCc2cnc3c(N)nc4cc(C)ccc4c3c2)cc1]

Step 1: N-(4-ethynylphenyl)acetamide

To a solution of 4-ethynylaniline (commercially available) (1.0 eq.), and triethylamine (1.0 eq.) in methylene chloride (0.04 M), acetyl chloride (1.5 eq.) was added slowly. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-ethynylphenyl)acetamide as a white solid.

Step 2: N-(4-((5-chloro-6-cyanopyridin-3-yl)ethynyl)phenyl)acetamide

A solution of 3,5-dichloropicolinonitrile (1.0 eq.), N-(4-ethynylphenyl)acetamide (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-80% ethyl acetate in hexane to give N-(4-((5-chloro-6-cyanopyridin-3-yl)ethynyl)phenyl)acetamide as a white solid.

Step 3: N-(4-(2-(5-chloro-6-cyanopyridin-3-yl)ethyl)phenyl)acetamide

To a solution of N-(4-((5-chloro-6-cyanopyridin-3-yl)ethynyl)phenyl)acetamide (from the previous step) in ethyl acetate/methanol (1:4, 0.05 M) was added 10% wt palladium on carbon (0.2 eq.). Hydrogen gas was introduced via a balloon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give N-(4-(2-(5-chloro-6-cyanopyridin-3-yl)ethyl)phenyl)acetamide.

Step 4: N-(4-(2-(5-amino-8-methylbenzo[f][1,7]naphthyridin-2-yl)ethyl)phenyl)acetamide A solution of N-(4-(2-(5-chloro-6-cyanopyridin-3-yl)ethyl)phenyl)acetamide (from the previous step) (1.0 eq.), tert-butyl 4-methyl-2-(4,4,5,5-tetramethyl-1,3,2-dioxaborolan-2-yl)phenylcarbamate (from Example 4/Step 2) (1.5 eq.), Tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H$_2$O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(4-(2-(5-amino-8-methylbenzo[f][1,7]naphthyridin-2-yl)ethyl)phenyl)acetamide as a white solid. $^1$H NMR (CDCl$_3$): δ 8.51 (s, 1H), 8.32 (s, 1H), 8.01 (d, 1H), 7.44 (s, 1H), 7.33-7.36 (m, 2H), 7.03-7.19 (m, 3H), 5.98 (br, 2H), 3.07-3.11 (m, 2H), 2.94-2.98 (m, 2H), 2.44 (s, 3H), 2.10 (s, 3H). LRMS [M+H]=371.2.

Example 112 methyl 4-(2-(5-amino-8-methylbenzo[f][1,7]naphthyridin-2-yl)ethyl)-3-methylbenzoate

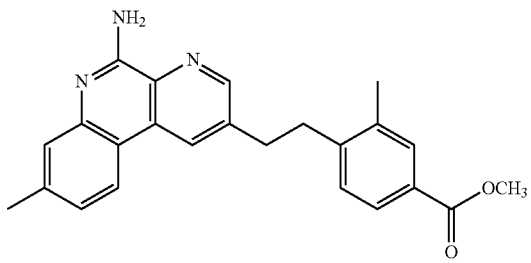 [SMILES: COC(=O)c1ccc(CCc2cnc3c(N)nc4cc(C)ccc4c3c2)c(C)c1]

Step 1: methyl 3-methyl-4-((triethylsilyl)ethynyl)benzoate

A solution of methyl 4-bromo-3-methylbenzoate (1.0 eq.), triethyl(ethynyl)silane (1.0 eq.), bis(triphenyl-phosphine) palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO$_4$, and concentrated en vaccuo. The crude material was purified by flash chromatography on a COMBIFLASH® system (ISCO) using 0-50% ethyl acetate in hexane to give methyl 3-methyl-4-((triethylsilyl)ethynyl)benzoate as a white solid.

Step 2: methyl 4-ethynyl-3-methylbenzoate

To a solution of methyl 3-methyl-4-((triethylsilyl)ethynyl)benzoate (from the previous step) (1.0 eq.) in THF (0.2

M), was added TBAF (0.2 eq.) slowly at 0° C. Then the reaction mixture was stirred at 0° C. for 1 hour. After warmed to ambient temperature, the reaction mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-80% ethyl acetate in hexane to give methyl 4-ethynyl-3-methylbenzoate as a white solid.

Step 3: methyl 4-((5-chloro-6-cyanopyridin-3-yl)ethynyl)-3-methylbenzoate

A solution of 3,5-dichloropicolinonitrile (1.0 eq.), methyl 4-ethynyl-3-methylbenzoate (from the previous step) (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO₄, and concentrated en vaccuo. The crude material was purified by flash chromatography on a COMBIFLASH® system (ISCO) using 0-80% ethyl acetate in hexane to give methyl 4-((5-chloro-6-cyanopyridin-3-yl)ethynyl)-3-methylbenzoate as a white solid.

Step 4: methyl methyl 4-((5-amino-8-methylbenzo[f][1,7]naphthyridin-2-yl)ethynyl)-3-methylbenzoate A solution of methyl 4-((5-chloro-6-cyanopyridin-3-yl)ethynyl)-3-methylbenzoate (from the previous step) (1.0 eq.), tert-butyl 4-methyl-2-(4,4,5,5-tetramethyl-1,3,2-dioxaborolan-2-yl)phenylcarbamate (From Example 4/Step 2) (1.5 eq.), tris(dibenzylideneacetone)dipalladium(0) (10 mol %), dicyclohexyl(2',6'-dimethoxybiphenyl-2-yl)phosphine (20 mol %), and potassium phosphate (2.0 eq.) in n-butanol/H₂O (2.5:1, 0.04 M) was stirred at 100° C. overnight. After cooling to ambient temperature, the reaction mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-80% ethyl acetate in hexane to give methyl methyl-4-((5-amino-8-methylbenzo[f][1,7]naphthyridin-2-yl)ethynyl)-3-methylbenzoate as a white solid.

Step 5: methyl 4-(2-(5-amino-8-methylbenzo[f][1,7]naphthyridin-2-yl)ethyl)-3-methylbenzoate To a solution of methyl methyl 4-((5-amino-8-methylbenzo[f][1,7]naphthyridin-2-yl)ethynyl)-3-methylbenzoate (from the previous step) in ethyl acetate/methanol (1:4, 0.05 M) was added 10% wt palladium on carbon (0.2 eq.). Hydrogen gas was introduced via a ballon, and the reaction was stirred for 3 hours. The mixture was filtered through a pad of celite, washing with dichloromethane. The filtrate was concentrated en vaccuo and purified by a COMBIFLASH® system (ISCO) using 0-80% ethyl acetate in hexane to give methyl 4-(2-(5-amino-8-methylbenzo[f][1,7]naphthyridin-2-yl)ethyl)-3-methylbenzoate. ¹H NMR (CDCl₃): δ 8.61 (s, 1H), 8.40 (s, 1H), 8.09 (d, 1H), 7.83 (s, 1H), 7.81 (d, 1H), 7.54 (s, 1H), 7.18-7.20 (m, 2H), 6.17 (br, 2H), 3.92 (s, 3H), 3.10-3.16 (m, 4H), 2.53 (s, 3H), 2.36 (s, 3H). LRMS [M+H]=386.2.

Example 113

4-(2-(5-amino-8-methylbenzo[f][1,7]naphthyridin-2-yl)ethyl)-N,3-dimethylbenzamide

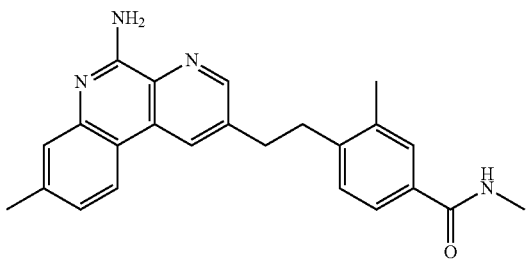

Step 1: 4-(2-(5-amino-8-methylbenzo[f][1,7]naphthyridin-2-yl)ethyl)-3-methylbenzoic acid A solution of methyl 4-(2-(5-amino-8-methylbenzo[f][1,7]naphthyridin-2-yl)ethyl)-3-methylbenzoate (from Example 112) (1.0 eq.), and 1N sodium hydroxide (1.5 eq.) in methanol (0.04 M) was stirred at 60° C. for 4 hours. After cooling to ambient temperature, the reaction mixture was diluted with ethyl acetate and water. The two phases were separated. The organic layer was washed twice with water, dried over anhydrous MgSO₄, and concentrated en vaccuo. The crude material was purified by flash chromatography on a COMBIFLASH® system (ISCO) using 0-50% ethyl acetate in hexane to give 4-(2-(5-amino-8-methylbenzo[f][1,7]naphthyridin-2-yl)ethyl)-3-methylbenzoic acid as a white solid.

Step 2: 4-(2-(5-amino-8-methylbenzo[f][1,7]naphthyridin-2-yl)ethyl)-3-methylbenzoyl chloride A solution of 4-(2-(5-amino-8-methylbenzo[f][1,7]naphthyridin-2-yl)ethyl)-3-methylbenzoic acid (from the previous step) in thionyl chloride was stirred at 60° C. for 3 hour. After cooling to ambient temperature, the reaction mixture was concentrated en vaccuo. The crude material was used for next step without purification.

Step 3: 4-(2-(5-amino-8-methylbenzo[f][1,7]naphthyridin-2-yl)ethyl)-N,3-dimethylbenzamide To a solution of 4-(2-(5-amino-8-methylbenzo[f][1,7]naphthyridin-2-yl)ethyl)-3-methylbenzoyl chloride (from the previous step) (Example 4) and triethylamine (2.5 eq.) in ether (0.05 M) was added methanamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-80% ethyl acetate in hexane to give 4-(2-(5-amino-8-methylbenzo[f][1,7]naphthyridin-2-yl)ethyl)-N,3-dimethylbenzamide as a white solid. ¹H NMR (CDCl₃): δ

8.62 (s, 1H), 8.32 (s, 1H), 8.04 (d, 1H), 7.60 (s, 1H), 7.46-7.52 (m, 2H), 7.09-7.11 (m, 2H), 6.05 (br, 2H), 3.09-3.17 (m, 4H), 3.00 (d, 3H), 2.52 (s, 3H), 2.33 (s, 3H). LRMS [M+H]=385.2.

Example 114

4-(2-(5-amino-8-methylbenzo[f][1,7]naphthyridin-2-yl)ethyl)-N-(2-(dimethylamino)ethyl)-N,3-dimethylbenzamide

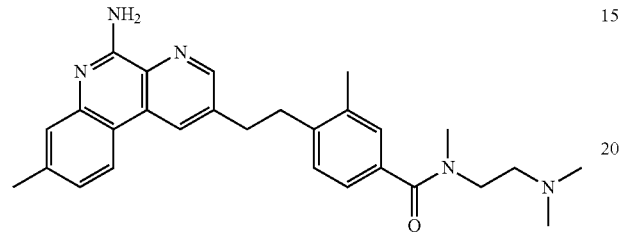

To a solution of 4-(2-(5-amino-8-methylbenzo[f][1,7]naphthyridin-2-yl)ethyl)-3-methylbenzoyl chloride (Example 113/Step 2) and triethylamine (2.5 eq.) in ether (0.05 M) was added $N^1,N^1,N^2$-trimethylethane-1,2-diamine (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBI-FLASH® system (ISCO) using 0-80% ethyl acetate in hexane to give 4-(2-(5-amino-8-methylbenzo[f][1,7]naphthyridin-2-yl)ethyl)-N-(2-(dimethylamino)ethyl)-N,3-dimethylbenzamide as a white solid. ¹H NMR (CDCl₃): δ 8.66 (s, 1H), 8.37 (s, 1H), 8.07 (d, 1H), 7.63 (s, 1H), 7.09-7.30 (m, 4H), 3.90 (br, 2H), 3.01-3.19 (m, 4H), 3.08 (s, 6H), 2.72 (br, 5H), 2.52 (s, 3H), 2.33 (s, 3H). LRMS [M+H]=456.3.

Example 115

2-(4-methoxyphenethyl)benzo[f][1,7]naphthyridin-5-amine

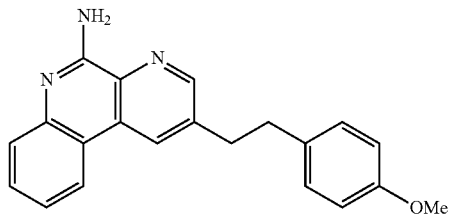

2-(4-Methoxyphenethyl)benzo[f][1,7]naphthyridin-5-amine was prepared from 1-ethynyl-4-methoxybenzene (Example 113/Step 2) following the procedures described for Example 41/Steps 1 to 3. ¹H NMR (CDCl₃): δ 8.69 (s, 1H), 8.47 (s, 1H), 8.27 (d, 1H), 7.80 (d, 2H), 7.58-7.66 (m, 1H), 7.33-7.42 (m, 1H), 7.15 (d, 2H), 6.90 (d, 2H), 6.25 (br, 2H), 3.86 (s, 3H), 3.13-3.23 (m, 2H), 2.97-3.10 (m, 2H). LRMS [M+H]=330.2.

Example 116

2-(4-methoxy-2-methylphenethyl)benzo[f][1,7]naphthyridin-5-amine

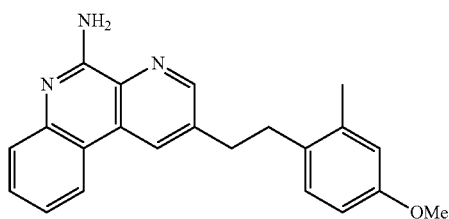 [SMILES: COc1ccc(CCc2cnc3c(N)nc4ccccc4c3c2)c(C)c1]

2-(4-Methoxy-2-methylphenethyl)benzo[f][1,7]naphthyridin-5-amine was prepared from 1-ethynyl-4-methoxy-2-methylbenzene (commercially available) following the procedures described for Example 42/Step 1 to 3. ¹H NMR (CDCl₃): δ 8.60 (s, 1H), 8.37 (s, 1H), 8.18 (d, 1H), 7.69 (d, 1H), 7.49-7.57 (m, 1H), 7.24-7.34 (m, 1H), 6.98 (d, 1H), 6.56-6.70 (m, 2H), 6.00 (br, 2H), 3.70 (s, 3H), 3.00-3.09 (m, 2H), 2.83-2.96 (m, 2H), 2.20 (s, 3H). LRMS [M+H]=344.2.

Example 117

4-(2-(5-amino-8-methylbenzo[f][1,7]naphthyridin-2-yl)ethyl)-3-methylbenzamide

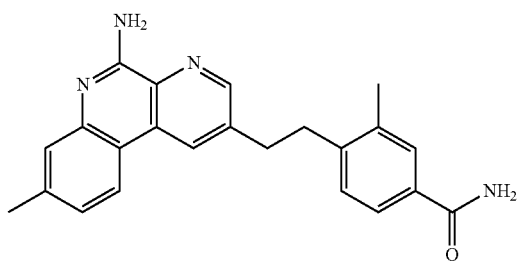 [SMILES: Cc1ccc2c(c1)nc(N)c1ncc(CCc3ccc(C(N)=O)cc3C)cc12]

4-(2-(5-Amino-8-methylbenzo[f][1,7]naphthyridin-2-yl)ethyl)-3-methylbenzamide was prepared from 4-(2-(5-amino-8-methylbenzo[f][1,7]naphthyridin-2-yl)ethyl)-3-methylbenzoyl chloride (Example 113/Step 2) and ammonia following the procedures described for Example 114. ¹H NMR (CDCl₃): δ 8.60 (s, 1H), 8.35 (s, 1H), 8.05 (d, 1H), 7.65 (s, 1H), 7.51-7.53 (m, 2H), 7.13-7.21 (m, 2H), 3.09-3.16 (m, 4H), 2.51 (s, 3H), 2.34 (s, 3H). LRMS [M+H]=371.2

Example 118

4-(2-(5-amino-8-methylbenzo[f][1,7]naphthyridin-2-yl)ethyl)-N,N,3-trimethylbenzamide

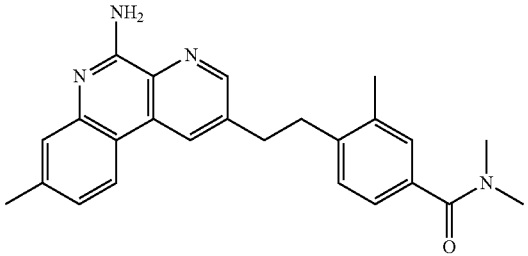

4-(2-(5-Amino-8-methylbenzo[f][1,7]naphthyridin-2-yl)ethyl)-N,N,3-trimethylbenzamide was prepared from 4-(2-(5-amino-8-methylbenzo[f][1,7]naphthyridin-2-yl)ethyl)-3-methylbenzoyl chloride (Example 113/Step 2) and dimethylamine following the procedures described for Example 114. $^1$H NMR (CDCl$_3$): δ 8.68 (s, 1H), 8.32 (s, 1H), 8.04 (d, 1H), 7.66 (s, 1H), 7.31 (d, 1H), 7.06-7.18 (m, 3H), 3.08-3.19 (m, 4H), 2.96 (d, 3H), 2.54 (s, 3H), 2.33 (s, 3H), 2.05 (s, 3H). LRMS [M+H]=399.2

Example 119

4-(2-(5-amino-8-methylbenzo[f][1,7]naphthyridin-2-yl)ethyl)-N-(2-hydroxyethyl)-3-methylbenzamide

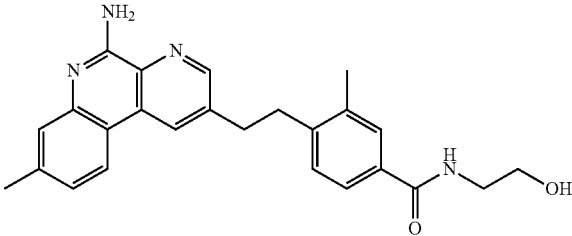 [SMILES: Cc1ccc2c(c1)nc(N)c1ncc(CCc3ccc(C(=O)NCCO)cc3C)cc12]

4-(2-(5-Amino-8-methylbenzo[f][1,7]naphthyridin-2-yl)ethyl)-N-(2-hydroxyethyl)-3-methylbenzamide was prepared from 4-(2-(5-amino-8-methylbenzo[f][1,7]naphthyridin-2-yl)ethyl)-3-methylbenzoyl chloride (Example 113/Step 2) and 2-aminoethanol following the procedures described for Example 114. $^1$H NMR (CDCl$_3$): δ 8.59 (s, 1H), 8.34 (s, 1H), 8.04 (d, 1H), 7.50-7.62 (m, 3H), 7.08-7.25 (m, 2H), 3.80 (t, 2H), 3.63 (t, 2H), 3.07-3.16 (m, 4H), 2.51 (s, 3H), 2.32 (s, 3H). LRMS [M+H]=415.2

Example 120

4-(2-(5-amino-8-methylbenzo[f][1,7]naphthyridin-2-yl)ethyl)-N-(2-(dimethylamino)ethyl)-3-methylbenzamide

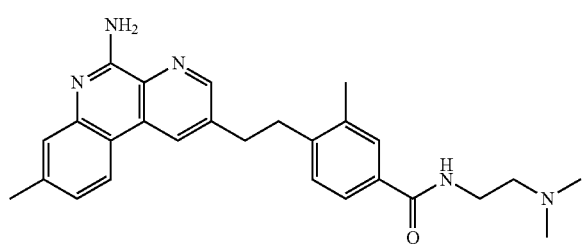

4-(2-(5-Amino-8-methylbenzo[f][1,7]naphthyridin-2-yl)ethyl)-N-(2-(dimethylamino)ethyl)-3-methylbenzamide was prepared from 4-(2-(5-amino-8-methylbenzo[f][1,7]naphthyridin-2-yl)ethyl)-3-methylbenzoyl chloride (Example 113/Step 2) and N$^1$,N$^1$-dimethylethane-1,2-diamine following the procedures described for Example 114. $^1$H NMR (methanol-d$_4$): δ 8.60 (s, 1H), 8.39 (s, 1H), 8.08 (d, 1H), 7.68 (s, 1H), 7.57-7.59 (m, 2H), 7.19-7.22 (m, 2H), 3.57-3.61 (m, 2H), 3.07-3.16 (m, 4H), 2.64-2.67 (m, 2H), 2.52 (s, 3H), 2.38 (s, 6H), 2.35 (s, 3H). LRMS [M+H]=442.3

Example 121

(4-(2-(5-amino-8-methylbenzo[f][1,7]naphthyridin-2-yl)ethyl)-3-methylphenyl)(pyrrolidin-1-yl)methanone

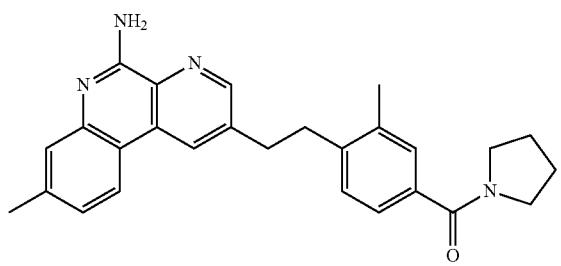 [SMILES: Cc1ccc2c(c1)nc(N)c1ncc(CCc3ccc(C(=O)N4CCCC4)cc3C)cc12]

(4-(2-(5-Amino-8-methylbenzo[f][1,7]naphthyridin-2-yl)ethyl)-3-methylphenyl)(pyrrolidin-1-yl)methanone was prepared from 4-(2-(5-amino-8-methylbenzo[f][1,7]naphthyridin-2-yl)ethyl)-3-methylbenzoyl chloride (Example 113/Step 2) and pyrrolidine following the procedures described for Example 114. $^1$H NMR (methanol-d$_4$): δ 8.60 (s, 1H), 8.42 (s, 1H), 8.09 (d, 1H), 7.34 (s, 1H), 7.23 (s, 1H), 7.05-7.15 (m, 3H), 3.49 (t, 2H), 3.27 (t, 2H), 3.05-3.17 (m, 4H), 2.42 (s, 3H), 2.26 (s, 3H), 1.88-1.91 (m, 2H), 1.73-1.77 (m, 2H). LRMS [M+H]=425.2

Example 122

4-(2-(5-amino-8-methylbenzo[f][1,7]naphthyridin-2-yl)ethyl)-N-(2-(diethylamino)ethyl)-3-methylbenzamide

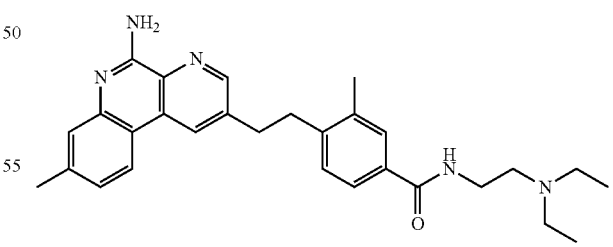

4-(2-(5-Amino-8-methylbenzo[f][1,7]naphthyridin-2-yl)ethyl)-N-(2-(diethylamino)ethyl)-3-methylbenzamide was prepared from 4-(2-(5-amino-8-methylbenzo[f][1,7]naphthyridin-2-yl)ethyl)-3-methylbenzoyl chloride (Example 113/Step 2) and N$^1$,N$^1$-diethylethane-1,2-diamine following the procedures described for Example 114. $^1$H NMR (methanol-d$_4$): δ 8.55 (s, 1H), 8.48 (s, 1H), 8.10 (d, 1H), 7.56 (s, 1H), 7.47-7.50 (m, 1H), 7.33 (s, 1H), 7.10-7.14 (m, 2H), 3.44 (t, 2H), 3.25 (t, 2H), 3.08-3.14 (m, 4H), 2.62-2.72 (m, 4H), 2.42 (s, 3H), 2.27 (s, 3H), 1.05 (t, 6H). LRMS [M+H]=470.3

Example 123

(4-(2-(5-amino-8-methylbenzo[f][1,7]naphthyridin-2-yl)ethyl)-3-methylphenyl)(4-ethylpiperazin-1-yl)methanone

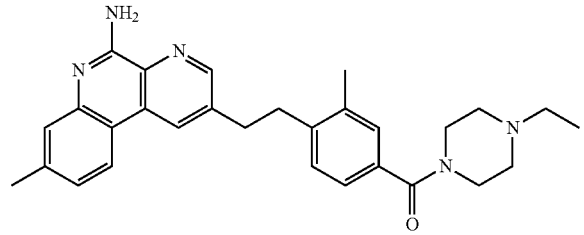 [SMILES: CCN1CCN(C(=O)c2ccc(CCc3cnc4c(N)nc5cc(C)ccc5c4c3)c(C)c2)CC1]

(4-(2-(5-Amino-8-methylbenzo[f][1,7]naphthyridin-2-yl)ethyl)-3-methylphenyl)(4-ethylpiperazin-1-yl)methanone was prepared from 4-(2-(5-amino-8-methylbenzo[f][1,7]naphthyridin-2-yl)ethyl)-3-methylbenzoyl chloride (Example 113/Step 2) and 1-ethylpiperazine following the procedures described for Example 114. $^1$H NMR (Methanol-$d_4$): δ 8.59 (s, 1H), 8.37 (s, 1H), 8.06 (d, 1H), 7.32 (s, 1H), 7.00-7.12 (m, 4H), 3.67 (br, 2H), 3.06-3.13 (m, 4H), 2.45 (br, 4H), 2.37 (q, 2H), 2.41 (s, 3H), 2.26 (s, 3H), 2.19 (br, 2H), 1.04 (t, 3H). LRMS [M+H]=468.3

Example 124

(4-(2-(5-amino-8-methylbenzo[f][1,7]naphthyridin-2-yl)ethyl)-3-methylphenyl)(piperazin-1-yl)methanone

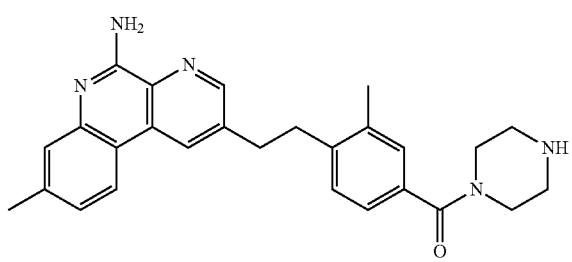 [SMILES: Cc1ccc2c(c1)nc(N)c1ncc(CCc3ccc(C(=O)N4CCNCC4)cc3C)cc12]

(4-(2-(5-Amino-8-methylbenzo[f][1,7]naphthyridin-2-yl)ethyl)-3-methylphenyl)(piperazin-1-yl)methanone was prepared from 4-(2-(5-amino-8-methylbenzo[f][1,7]naphthyridin-2-yl)ethyl)-3-methylbenzoyl chloride (Example 113/Step 2) and piperazine following the procedures described for Example 114. $^1$H NMR (methanol-$d_4$): δ 8.66 (s, 1H), 8.55 (s, 1H), 8.19 (d, 1H), 7.38 (s, 1H), 7.21-7.23 (m, 2H), 7.10-7.15 (m, 2H), 3.66 (br, 6H), 3.08-3.18 (m, 6H), 2.45 (s, 3H), 2.30 (s, 3H). LRMS [M+H]=440.2

Example 125

4-(2-(5-amino-8-methylbenzo[f][1,7]naphthyridin-2-yl)ethyl)-3-methyl-N-(2-(pyrrolidin-1-yl)ethyl)benzamide

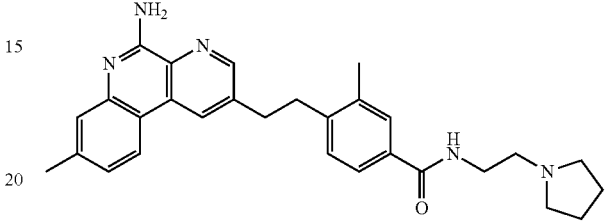

4-(2-(5-Amino-8-methylbenzo[f][1,7]naphthyridin-2-yl)ethyl)-3-methyl-N-(2-(pyrrolidin-1-yl)ethyl)benzamide was prepared from 4-(2-(5-amino-8-methylbenzo[f][1,7]naphthyridin-2-yl)ethyl)-3-methylbenzoyl chloride (Example 113/Step 2) and 2-(pyrrolidin-1-yl)ethanamine following the procedures described for Example 114. $^1$H NMR (CDCl$_3$): δ 8.58 (s, 1H), 8.38 (s, 1H), 8.07 (d, 1H), 7.64 (s, 1H), 7.51-7.55 (m, 2H), 7.12-7.20 (m, 2H), 6.26 (br, 2H), 3.61 (dd, 2H), 3.05-3.12 (m, 4H), 2.81 (t, 2H), 2.69 (br, 4H), 2.50 (s, 3H), 2.33 (s, 3H), 1.83-1.85 (m, 4H). LRMS [M+H]=468.3

Example 126

4-(2-(5-amino-8-methylbenzo[f][1,7]naphthyridin-2-yl)ethyl)-N-(2-aminoethyl)-3-methylbenzamide

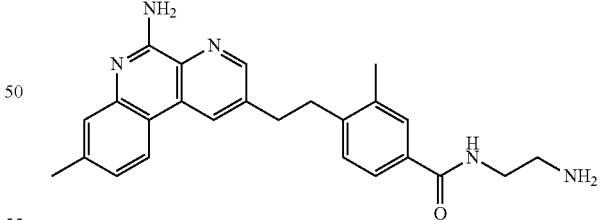

4-(2-(5-Amino-8-methylbenzo[f][1,7]naphthyridin-2-yl)ethyl)-N-(2-aminoethyl)-3-methylbenzamide was prepared from 4-(2-(5-amino-8-methylbenzo[f][1,7]naphthyridin-2-yl)ethyl)-3-methylbenzoyl chloride (Example 113/Step 2) and ethane-1,2-diamine following the procedures described for Example 114. $^1$H NMR (CDCl$_3$): δ 8.59 (s, 1H), 8.37 (s, 1H), 8.07 (d, 1H), 7.63 (s, 1H), 7.51 (br, 2H), 7.12-7.21 (m, 2H), 6.25 (br, 2H), 3.48-3.52 (m, 2H), 3.08-3.15 (m, 4H), 2.94 (t, 2H), 2.51 (s, 3H), 2.34 (s, 3H). LRMS [M+H]=414.2

Example 127

4-(2-(5-aminobenzo[f][1,7]naphthyridin-2-yl)ethyl)-N-(2-(dimethylamino)ethyl)-N,3-dimethylbenzamide

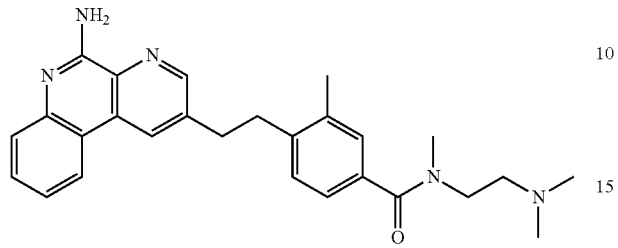

4-(2-(5-Aminobenzo[f][1,7]naphthyridin-2-yl)ethyl)-N-(2-(dimethylamino)ethyl)-N,3-dimethylbenzamide was prepared from 4-(2-(5-aminobenzo[f][1,7]naphthyridin-2-yl)ethyl)-3-methylbenzoyl chloride (Example 113/Step 2) and $N^1,N^1,N^2$-trimethylethane-1,2-diamine following the procedures described for Example 114. $^1$H NMR (methanol-$d_4$): δ 8.84 (s, 1H), 8.63 (s, 1H), 8.39 (d, 1H), 7.76-7.83 (m, 2H), 7.60-7.64 (m, 1H), 7.37 (s, 1H), 7.19-7.29 (m, 2H), 3.96 (t, 2H), 3.48 (t, 2H), 3.32 (t, 2H), 3.20 (t, 2H), 3.09 (s, 3H), 3.06 (s, 6H), 2.42 (s, 3H). LRMS [M+H]=442.3

Example 128

4-(2-(5-amino-8-methylbenzo[f][1,7]naphthyridin-2-yl)ethyl)-N-(2-(dimethylamino)ethyl)-N-methylbenzamide

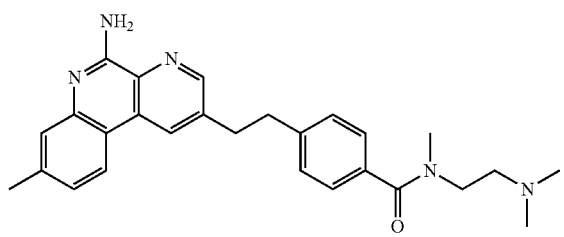

4-(2-(5-Amino-8-methylbenzo[f][1,7]naphthyridin-2-yl)ethyl)-N-(2-(dimethylamino)ethyl)-N-methylbenzamide was prepared from 4-(2-(5-amino-8-methylbenzo[f][1,7]naphthyridin-2-yl)ethyl)-3-methylbenzoyl chloride (Example 113/Step 2) and $N^1,N^1,N^2$-trimethylethane-1,2-diamine following the procedures described for Example 114. $^1$H NMR (CDCl$_3$): δ 8.64 (s, 1H), 8.36 (s, 1H), 8.05 (d, 1H), 7.60 (s, 1H), 7.41 (d, 2H), 7.31 (d, 1H), 7.21 (d, 2H), 3.91 (t, 2H), 3.44 (t, 2H), 3.25 (t, 2H), 3.12 (t, 2H), 3.03 (s, 3H), 3.01 (s, 6H), 2.53 (s, 3H). LRMS [M+H]=442.3

Example 129

2-(4-(2-(5-aminobenzo[f][1,7]naphthyridin-2-yl)ethyl)-3-methylphenyl)propan-2-ol

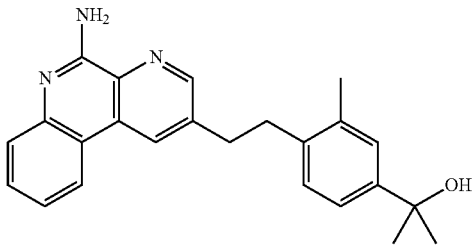 [SMILES: Cc1cc(C(C)(C)O)ccc1CCc1cnc2c(N)nc3ccccc3c2c1]

2-(4-(2-(5-Aminobenzo[f][1,7]naphthyridin-2-yl)ethyl)-3-methylphenyl)propan-2-ol was prepared following the procedures described for Example 75, but using methyl 4-(2-(5-aminobenzo[f][1,7]naphthyridin-2-yl)ethyl)-3-methylbenzoate which was prepared analogous to Example 112 but using tert-butyl 2-(4,4,5,5-tetramethyl-1,3,2-dioxaborolan-2-yl)phenylcarbamate in Step 4. LRMS [M+H]=372.2

Example 130

2-(4-butoxyphenethyl)-8-methylbenzo[f][1,7]naphthyridin-5-amine

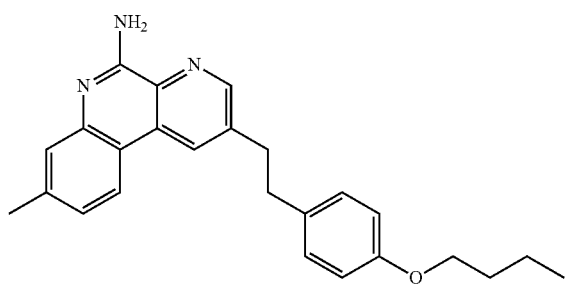 [SMILES: CCCCOc1ccc(CCc2cnc3c(N)nc4cc(C)ccc4c3c2)cc1]

2-(4-Butoxyphenethyl)-8-methylbenzo[f][1,7]naphthyridin-5-amine was prepared following the procedures described for Example 42/Steps 1 to 3, but using 1-butoxy-4-ethynylbenzene (commercially available) with 3,5-dichloropicolinonitrile (commercially available) in step 1. $^1$H NMR (Acetone-$d_6$): δ 8.75 (s, 1H), 8.68 (s, 1H), 8.28 (d, 1H), 7.42 (s, 1H), 7.10-7.18 (m, 3H), 6.84 (d, 2H), 6.58 (br, 2H), 3.94 (t, 2H), 3.21 (t, 2H), 3.05 (t, 2H), 2.46 (s, 3H), 1.65-1.75 (m, 2H), 1.41-1.58 (m, 2H), 0.94 (s, 3H). LRMS [M+H]=386.2.

Example 131

2-(2-(biphenyl-4-yl)ethyl)-8-methylbenzo[f][1,7]naphthyridin-5-amine

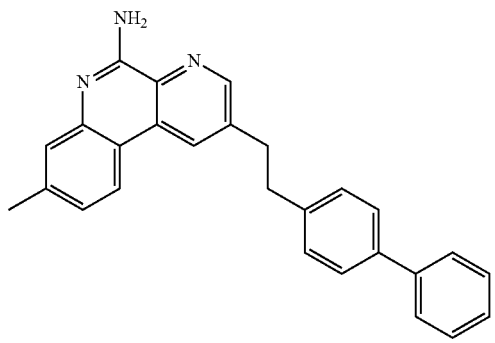 [SMILES: Cc1ccc2c(c1)nc(N)c1ncc(CCc3ccc(-c4ccccc4)cc3)cc12]

2-(2-(Biphenyl-4-yl)ethyl)-8-methylbenzo[f][1,7]naphthyridin-5-amine was prepared following the procedures described for Example 42/Steps 1 to 3, but using 4-ethynylbiphenyl (commercially available) with 3,5-dichloropicolinonitrile (commercially available) in Step 1. $^1$H NMR (Acetone-$d_6$): δ 8.80 (s, 1H), 8.75 (s, 1H), 8.26 (d, 2H), 7.55-7.69 (m, 4H), 7.30-7.46 (m, 4H), 7.13 (d, 2H), 6.58 (br, 2H), 3.30 (t, 2H), 3.18 (t, 2H), 2.45 (s, 3H). LRMS [M+H]=390.2

Example 132

2-((1,3-dihydroisobenzofuran-1-yl)methyl)-8-methylbenzo[f][1,7]naphthyridin-5-amine

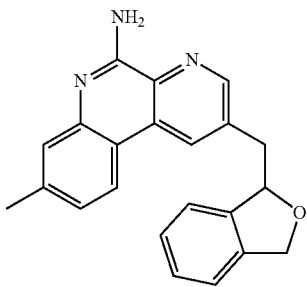 [SMILES: Cc1ccc2c(c1)nc(N)c1ncc(CC3OCc4ccccc43)cc12]

Step 1: 2-((5-amino-8-methylbenzo[f][1,7]naphthyridin-2-yl)ethynyl)phenyl)methanol 2-((5-Amino-8-methylbenzo[f][1,7]naphthyridin-2-yl)ethynyl)phenyl)methanol was prepared following the procedures described for Example 42/Steps 1 to 2, but using (2-ethynylphenyl)methanol (commercially available) with 3,5-dichloropicolinonitrile (commercially available) in Step 1.

Step 2: 2-((1,3-dihydroisobenzofuran-1-yl)methyl)-8-methylbenzo[f][1,7]naphthyridin-5-amine To a solution of 2-((5-amino-8-methylbenzo[f][1,7]naphthyridin-2-yl)ethynyl)phenyl)methanol (1.0 equiv.) (from the previous step) in ethanol (0.05 M) was added 10% wt palladium on carbon (0.2 equiv. by weight). Hydrogen gas was then introduced via a balloon, and the reaction was allowed to stir for 18 hours. At this point, the mixture was filtered through a pad of celite, washing with methanol. The volatiles were removed in vacuo and the resulting residue was purified by a COMBIFLASH® system (ISCO) using 0-60% ethyl acetate in hexanes to give 2-((1,3-dihydroisobenzofuran-1-yl)methyl)-8-methylbenzo[f][1,7]naphthyridin-5-amine as a solid. $^1$H NMR (Acetone-$d_6$): δ 8.78 (s, 1H), 8.74 (s, 1H), 8.24 (d, 2H), 7.40-7.44 (m, 2H), 7.20-7.34 (m, 3H), 6.61 (br, 2H), 5.63-5.69 (m, 1H), 4.89-5.00 (dd, 2H), 3.51-3.56 (dd, 1H), 3.28-3.34 (dd, 1H), 2.46 (s, 3H). LRMS [M+H]=342.1

Example 133

8-methyl-2-(4-(2-methylallyloxy)phenethyl)benzo[f][1,7]naphthyridin-5-amine

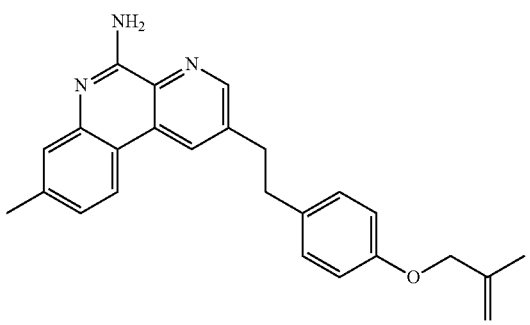 [SMILES: C=C(C)COc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 167) (1.0 equiv.) in dimethylformamide (0.10 M) was added anhydrous potassium carbonate (1.5 equiv.) followed by methallyl bromide (1.2 equiv.). The resulting mixture was allowed to stir for 18 hours at 100° C. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-60% ethyl acetate in hexanes to provide 8-methyl-2-(4-(2-methylallyloxy)phenethyl)benzo[f][1,7]naphthyridin-5-amine as a solid. $^1$H NMR (Acetone-$d_6$): δ 8.75 (s, 1H), 8.68 (s, 1H), 8.27 (d, 1H), 7.41 (s, 1H), 7.12-7.19 (m, 3H), 6.87 (d, 2H), 6.60 (br, 2H), 5.06 (s, 1H), 4.93 (s, 1H), 4.43 (s, 2H), 3.20 (t, 2H), 3.05 (t, 2H), 2.45 (s, 3H), 1.79 (s, 3H). LRMS [M+H]=384.2

Example 134

2-(4-(isopentyloxy)phenethyl)-8-methylbenzo[f][1,7]naphthyridin-5-amine

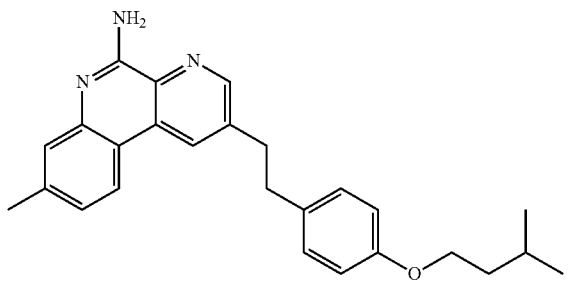 [SMILES: Cc1ccc2c(c1)nc(N)c1ncc(CCc3ccc(OCCC(C)C)cc3)cc12]

2-(4-(Isopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 167) following the procedure described for Example 133, but using 1-bromo-3-methylbutane. $^1$H NMR (Acetone-d$_6$): δ 8.72 (s, 1H), 8.69 (s, 1H), 8.26 (d, 1H), 7.43 (s, 1H), 7.12-7.18 (m, 3H), 6.84 (d, 2H), 6.50 (br, 2H), 3.98 (t, 2H), 3.21 (t, 2H), 3.06 (t, 2H), 2.46 (s, 3H), 1.78-1.87 (m, 1H), 1.61-1.67 (dd, 2H), 0.96 (s, 3H), 0.95 (3H). LRMS [M+H]=400.2

Example 135

4-(2-(5-amino-8-methylbenzo[f][1,7]naphthyridin-2-yl)ethyl)phenyl propyl carbonate

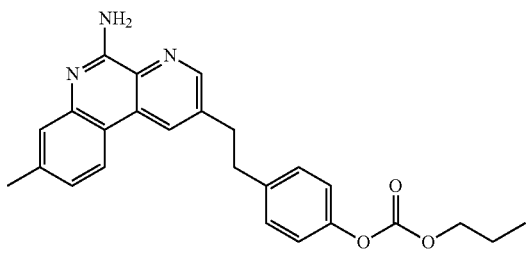 [SMILES: CCCOC(=O)Oc1ccc(CCc2cnc3c(N)nc4cc(C)ccc4c3c2)cc1]

To a solution of 4-(2-(5-amino-8-methylbenzo[f][1,7]naphthyridin-2-yl)ethyl)phenol (from Example 167) (1.0 equiv.) and triethyl amine (2 equiv.) in dichloromethane (0.10 M) at 0° C. was added ethyl chloroformate (1.2 equiv.). The resulting mixture was allowed to stir for 30 minutes at 0° C., after which it was diluted with water and dichloromethane. The biphasic layers were separated and the aqueous layer was washed twice with dichloromethane. The combined organic layers were dried over anhydrous Na$_2$SO$_4$ and the volatiles were removed in vacuo. The resulting residue was purified by a COMBIFLASH® system (ISCO) using 0-50% ethyl acetate in hexanes to provide 4-(2-(5-amino-8-methylbenzo[f][1,7]naphthyridin-2-yl)ethyl)phenyl ethyl carbonate as a solid. $^1$H NMR (Acetone-d$_6$): δ 8.78 (s, 1H), 8.73 (s, 1H), 8.28 (d, 1H), 7.43 (s, 1H), 7.33 (d, 2H), 7.10-7.17 (m, 3H), 6.64 (br, 2H), 4.18 (t, 2H), 3.25 (t, 2H), 3.14 (t, 2H), 2.45 (s, 3H), 1.68-1.77 (m, 2H), 0.97 (t, 3H). LRMS [M+H]=416.2

Example 136 ethyl 5-(4-(2-(5-amino-8-methylbenzo[f][1,7]naphthyridin-2-yl)ethyl)phenoxy)pentanoate

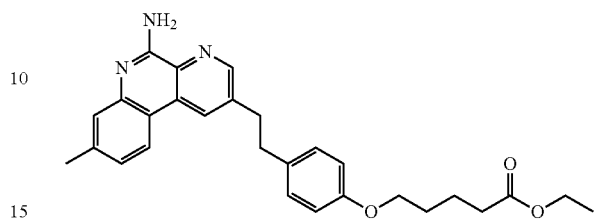

To a solution of 4-(2-(5-amino-8-methylbenzo[f][1,7]naphthyridin-2-yl)ethyl)phenol (from Example 167) (1.0 equiv.) in dimethylformamide (0.10 M) 22° C. was added 60% dispersion of sodium hydride in mineral oil (1.5 equiv.) and the resulting mixture was allowed to stir for 30 min. At this point, ethyl 5-bromopentanoate (1.2 equiv.) was added to this mixture. The reaction mixture was then allowed to stir for 18 hours. after which it was diluted with ethyl acetate and water. The biphasic layers were separated and the organic layer was washed twice with water. The organic layer was dried over anhydrous Na$_2$SO$_4$ and the volatiles were removed in vacuo. The resulting residue was purified by RP-HPLC using a 10-50% MeCN in water gradient. The resulting trifluoroacetate salt was then converted to the free base form by utilizing a StratoSpheres™ PL-SO3H SPE ion exchange resin, delivering ethyl 5-(4-(2-(5-amino-8-methylbenzo[f][1,7]naphthyridin-2-yl)ethyl)phenoxy)pentanoate as a solid. $^1$H NMR (Acetone-d$_6$): δ 8.80 (s, 1H), 8.74 (s, 1H), 8.33 (d, 1H), 7.47 (s, 1H), 7.24 (d, 1H), 7.17 (d, 2H), 6.85 (d, 2H), 4.10 (q, 2H), 3.97 (t, 2H), 3.25 (t, 2H), 3.07 (t, 2), 2.50 (s, 3H), 2.37 (t, 3H), 1.74-1.84 (m, 4H), 1.21 (t, 3H). LRMS [M+H]=458.2

Example 137

2-(4-(cyclopentyloxy)phenethyl)-8-methylbenzo[f][1,7]naphthyridin-5-amine

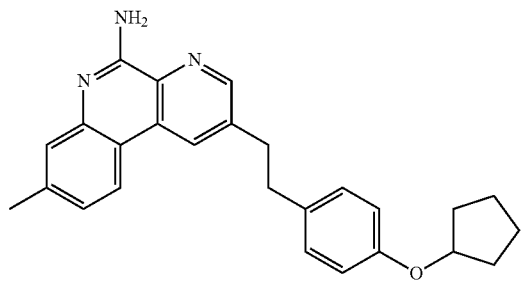 [SMILES: Cc1ccc2c(c1)nc(N)c1ncc(CCc3ccc(OC4CCCC4)cc3)cc12]

2-(4-(Cyclopentyloxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 167) following the procedure described for Example 133, but using bromocyclopentane. $^1$H NMR (Acetone-d$_6$): δ 8.75 (d, 2H), 8.30 (d, 1H), 7.45 (s, 1H), 7.20 (d, 1H), 7.14 (d, 2H), 6.79 (d, 2H), 4.73-4.81 (m, 1H), 3.22 (t, 2H), 3.05 (t, 2H), 2.47 (s, 3H), 1.85-1.96 (m, 2H), 1.70-1.79 (m, 4H), 1.56-1.64 (m, 2H). LRMS [M+H]=398.2

Example 138

2-(4-(cyclobutylmethoxy)phenethyl)-8-methylbenzo[f][1,7]naphthyridin-5-amine

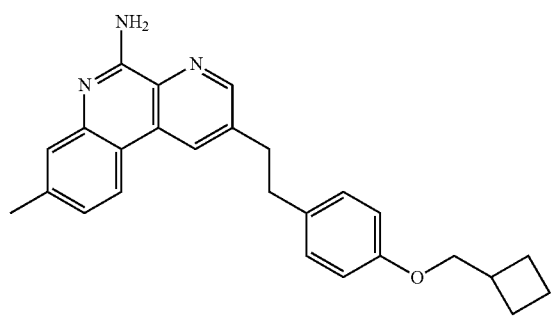 [SMILES: Cc1ccc2c(c1)nc(N)c1ncc(CCc3ccc(OCC4CCC4)cc3)cc12]

2-(4-(Cyclobutylmethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 167) following the procedure described for Example 133, but using (bromomethyl)cyclobutane. $^1$H NMR (Acetone-$d_6$): δ 8.79 (s, 1H), 8.73 (s, 1H), 8.33 (d, 1H), 7.47 (s, 1H), 7.26 (d, 1H), 7.16 (d, 2H), 6.82 (d, 2H), 3.90 (d, 2H), 3.23 (t, 2H), 3.06 (t, 2H), 2.68-2.79 (m, 1H), 2.49 (s, 3H), 2.05-2.14 (m, 2H), 1.80-1.98 (m, 4H). LRMS [M+H]=398.2

Example 139

8-methyl-2-(4-(2-morpholinoethoxy)phenethyl)benzo[f][1,7]naphthyridin-5-amine

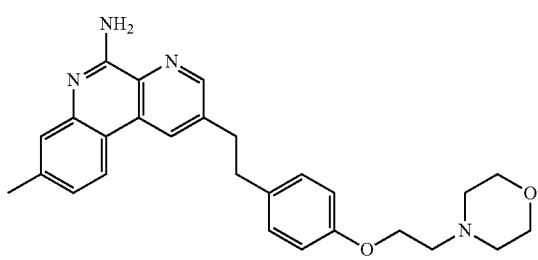 [SMILES: Cc1ccc2c(c1)nc(N)c1ncc(CCc3ccc(OCCN4CCOCC4)cc3)cc12]

8-Methyl-2-(4-(2-morpholinoethoxy)phenethyl)benzo[f][1,7]naphthyridin-5-amine was prepared from 4-(2-(5-amino-8-methylbenzo[f][1,7]naphthyridin-2-yl)ethyl)phenol (from Example 167) following the procedure described for Example 136, but using 4-(2-bromoethyl)morpholine. $^1$H NMR (Acetone-$d_6$): δ 8.78 (s, 1H), 8.72 (s, 1H), 8.30 (d, 1H), 7.46 (s, 1H), 7.17-7.24 (m, 3H), 6.85 (d, 2H), 4.08 (t, 2H), 3.56-3.62 (m, 4H), 3.45-3.53 (m, 2H), 3.24 (t, 2H), 3.07 (t, 2H), 2.73 (t, 2H), 2.52-2.56 (m, 2H), 2.49 (s, 3H). LRMS [M+H]=443.2

Example 140

2-(4-(2-(5-amino-8-methylbenzo[f][1,7]naphthyridin-2-yl)ethyl)phenoxy)-1-phenylethanone

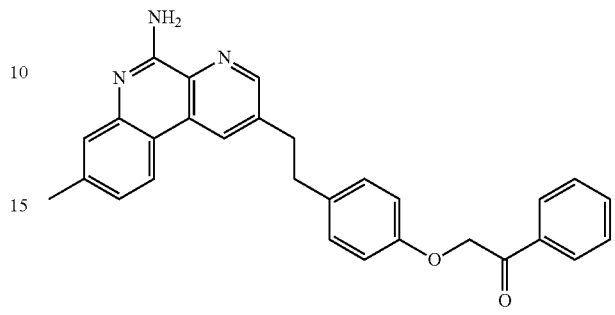

2-(4-(2-(5-Amino-8-methylbenzo[f][1,7]naphthyridin-2-yl)ethyl)phenoxy)-1-phenylethanone was prepared from 4-(2-(5-amino-8-methylbenzo[f][1,7]naphthyridin-2-yl)ethyl)phenol (from Example 167) following the procedure described for Example 136, but using 2-bromo-1-phenylethanone. $^1$H NMR (Acetone-$d_6$): δ 8.76 (s, 1H), 8.71 (s, 1H), 8.27 (d, 1H), 8.06 (d, 2H), 7.67 (t, 1H), 7.57 (t, 2H), 7.43 (s, 1H), 7.17 (d, 3H), 6.90 (d, 2H), 5.45 (s, 2H), 3.21 (t, 2H), 3.06 (t, 2H), 2.45 (s, 3H). LRMS [M+H]=448.2

Example 141

5-(4-(2-(5-amino-8-methylbenzo[f][1,7]naphthyridin-2-yl)ethyl)phenoxy)pentanoic acid

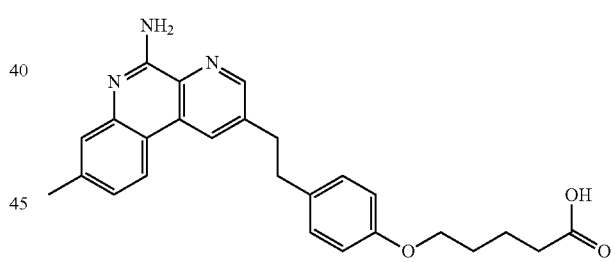

To a solution of ethyl 5-(4-(2-(5-amino-8-methylbenzo[f][1,7]naphthyridin-2-yl)ethyl)phenoxy)pentanoate (1.0 equiv.) (from Example 136) in ethanol (0.10 M) was added anhydrous sodium hydroxide (2.0 equiv.) and the resulting mixture was allowed to stir at 80° C. for 2 hours. After cooling to ambient temperature, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 5-(4-(2-(5-amino-8-methylbenzo[f][1,7]naphthyridin-2-yl)ethyl)phenoxy)pentanoic acid as a solid. $^1$H NMR (Methanol-$d_4$): δ 8.61 (s, 1H), 8.57 (s, 1H), 8.20 (d, 1H), 7.40 (s, 1H), 7.20 (d, 1H), 7.07 (d, 2H), 6.81 (d, 2H), 3.93 (t, 2H), 3.18 (t, 2H), 3.00 (t, 2H), 2.48 (s, 3H), 2.25 (t, 2H), 1.74-1.81 (m, 2H), 0.86-0.96 (m, 2H). LRMS [M+H]=430.2

Example 142

2-(4-(2-(5-amino-8-methylbenzo[f][1,7]naphthyridin-2-yl)ethyl)phenoxy)ethanol

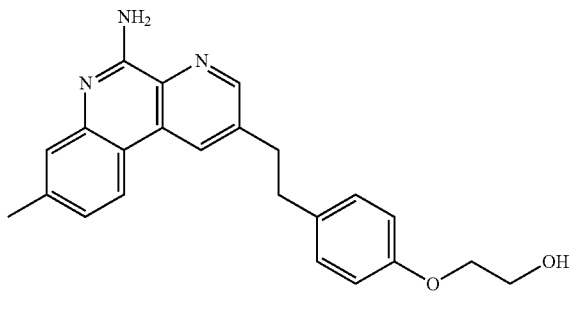 [SMILES: Cc1ccc2c(c1)nc(N)c1ncc(CCc3ccc(OCCO)cc3)cc12]

Step 1: 2-(4-(2-(tert-butyldimethylsilyloxy)ethoxy)phenethyl)-8-methylbenzo[f][1,7]naphthyridin-5-amine 2-(4-(2-(Tert-butyldimethylsilyloxy)ethoxy)phenethyl)-8-methylbenzo[f][1,7]naphthyridin-5-amine was prepared from 4-(2-(5-amino-8-methylbenzo[f][1,7]naphthyridin-2-yl)ethyl)phenol (from Example 167) following the procedure described for Example 136, but using (2-bromoethoxy)(tert-butyl)dimethylsilane.

Step 2: 2-(4-(2-(5-amino-8-methylbenzo[f][1,7]naphthyridin-2-yl)ethyl)phenoxy)ethanol To a solution of 2-(4-(2-(tert-butyldimethylsilyloxy)ethoxy)phenethyl)-8-methylbenzo[f][1,7]naphthyridin-5-amine (from the previous step) (1.0 equiv.) in tetrahydrofuran (0.10 M) was added a 1.0 M solution of tetrabutylammonium fluoride (5 equiv.) in THF and the resulting mixture was allowed to stir at 22° C. for 2 hours. At this point, the mixture was diluted with ethyl acetate and water. The biphasic layers were separated and the aqueous layer was washed twice with ethyl acetate. The combined organic layers were dried over anhydrous $Na_2SO_4$ and the volatiles were removed in vacuo. The resulting residue was purified by a COMBIFLASH® system (ISCO) using 0-10% methanol in dichloromethane to furnish 2-(4-(2-(5-amino-8-methylbenzo[f][1,7]naphthyridin-2-yl)ethyl)phenoxy)ethanol as a solid. $^1$H NMR (Acetone-$d_6$): δ 8.76 (s, 1H), 8.67 (s, 1H), 8.28 (d, 1H), 7.40 (s, 1H), 7.15 (t, 3H), 6.84 (d, 2H), 6.54 (br, 2H), 4.00 (t, 2H), 3.83 (t, 2H), 3.21 (t, 2H), 3.05 (t, 2H), 2.45 (s, 3H). LRMS [M+H]=374.2

Example 143

2-(4-(2-(5-amino-8-methylbenzo[f][1,7]naphthyridin-2-yl)ethyl)phenoxy)-N,N-dimethylacetamide

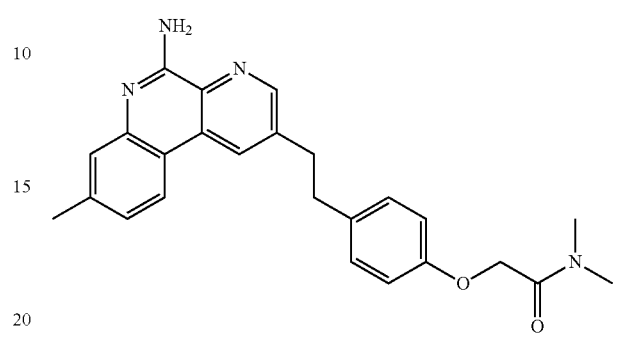

2-(4-(2-(5-Amino-8-methylbenzo[f][1,7]naphthyridin-2-yl)ethyl)phenoxy)-N,N-dimethylacetamide was prepared from 4-(2-(5-amino-8-methylbenzo[f][1,7]naphthyridin-2-yl)ethyl)phenol (from Example 167) and following the procedure described for Example 136, but using 2-bromo-N,N-dimethylacetamide. $^1$H NMR (Acetone-$d_6$): δ 8.75 (s, 1H), 8.70 (s, 1H), 8.28 (d, 1H), 7.40 (s, 1H), 7.18 (t, 3H), 6.87 (d, 2H), 6.56 (br, 2H), 4.72 (s, 2H), 3.20 (t, 2H), 3.07 (s, 3H), 3.05 (t, 2H), 2.87 (s, 3H), 2.45 (s, 3H). LRMS [M+H]=415.2

Example 144

8-methyl-2-(2-methyl-4-(2-morpholinoethoxy)phenethyl)benzo[f][1,7]naphthyridin-5-amine

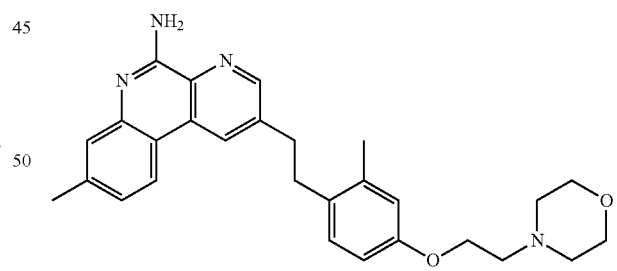

8-Methyl-2-(2-methyl-4-(2-morpholinoethoxy)phenethyl)benzo[f][1,7]naphthyridin-5-amine was prepared following an analogous procedure to the preparation described for Example 136, but using 4-(2-(5-amino-8-methylbenzo[f][1,7]naphthyridin-2-yl)ethyl)-3-methylphenol (from Example 47) and 4-(2-bromoethyl)morpholine. $^1$H NMR (Acetone-$d_6$): δ 8.73 (d, 2H), 8.26 (d, 1H), 7.44 (s, 1H), 7.17 (d, 1H), 7.05 (d, 1H), 6.76 (s, 1H), 6.67 (d, 1), 4.04-4.08 (m, 3H), 3.60-3.62 (m, 4H), 3.30 (s, 1H), 3.16 (t, 2H), 3.04 (t, 2H), 2.71 (t, 2H), 2.50-2.52 (m, 2H), 2.47 (s, 3H), 2.28 (s, 3H). LRMS [M+H]=457.3

Example 145

2-(2-(4-(2-(5-amino-8-methylbenzo[f][1,7]naphthyridin-2-yl)ethyl)-3-methylphenoxy)ethoxy)ethanol

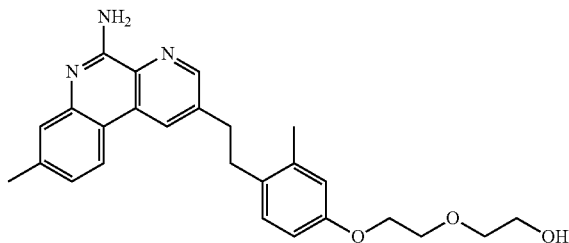 [SMILES: Cc1ccc2c(c1)nc(N)c1ncc(CCc3ccc(OCCOCCO)cc3C)cc12]

Step 1: 2-(4-(2-(2-(tert-butyldimethylsilyloxy)ethoxy)ethoxy)-2-methylphenethyl)-8-methylbenzo[f][1,7]naphthyridin-5-amine 2-(4-(2-(2-(Tert-butyldimethylsilyloxy)ethoxy)ethoxy)-2-methylphenethyl)-8-methylbenzo[f][1,7]naphthyridin-5-amine was prepared following an analogous procedure to the preparation described for Example 142/Step 1, but using 4-(2-(5-amino-8-methylbenzo[f][1,7]naphthyridin-2-yl)ethyl)-3-methylphenol (from Example 47) with tert-butyl(2-(2-chloroethoxy)ethoxy)dimethylsilane.

Step 2: 2 (2 (4 (2 (5 Amino-8-methylbenzo[f][1,7]naphthyridin-2-yl)ethyl)-3-methylphenoxy)ethoxy)ethanol 2-(2-(4-(2-(5-Amino-8-methylbenzo[f][1,7]naphthyridin-2-yl)ethyl)-3-methylphenoxy)ethoxy)ethanol was prepared from 2-(4-(2-(2-(tert-butyldimethylsilyloxy)ethoxy)ethoxy)-2-methylphenethyl)-8-methylbenzo[f][1,7]naphthyridin-5-amine (from the previous step) following the procedures described for Example 142/Step 2. $^1$H NMR (Acetone-$d_6$): δ 8.74 (s, 1H), 8.69 (s, 1H), 8.27 (d, 1H), 7.41 (s, 1H), 7.14 (d, 1H), 7.06 (d, 1H), 6.75 (s, 1H), 6.69 (d, 1), 6.54 (br, 2H), 4.07 (t, 2H), 3.79 (t, 2H), 3.64 (t, 2H), 3.59 (t, 2H), 3.16 (t, 2H), 3.03 (t, 2H), 2.45 (s, 3H), 2.29 (s, 3H). LRMS [M+H]=432.2

Example 146 diethyl 3-(4-(2-(5-amino-8-methylbenzo[f][1,7]naphthyridin-2-yl)ethyl)-3-methylphenoxy)propylphosphonate

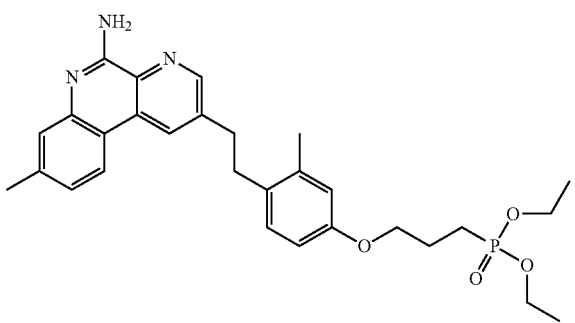 [SMILES: CCOP(=O)(CCCOc1ccc(CCc2cnc3c(N)nc4cc(C)ccc4c3c2)c(C)c1)OCC]

Diethyl 3-(4-(2-(5-amino-8-methylbenzo[f][1,7]naphthyridin-2-yl)ethyl)-3-methylphenoxy)propylphosphonate was prepared following an analogous procedure to the preparation described for Example 136, but using 4-(2-(5-amino-8-methylbenzo[f][1,7]naphthyridin-2-yl)ethyl)-3-methylphenol (from Example 47) with diethyl 3-bromopropylphosphonate. $^1$H NMR (Acetone-$d_6$): δ 9.52 (s, 1H), 9.47 (s, 1H), 9.03 (d, 1H), 8.21 (s, 1H), 7.93 (d, 1H), 7.84 (d, 1H), 7.60 (br, 2H), 7.53 (s, 1), 7.45 (d, 1H), 4.76-4.91 (m, 6H), 3.93 (t, 2H), 3.81 (t, 2H), 3.24 (s, 3H), 3.06 (s, 3H), 2.76-2.86 (m, 2H), 2.61-2.72 (m, 2H), 2.07 (t, 6H). LRMS [M+H]=522.2

Example 147

3-(4-(2-(5-amino-8-methylbenzo[f][1,7]naphthyridin-2-yl)ethyl)-3-methylphenoxy)propylphosphonic acid

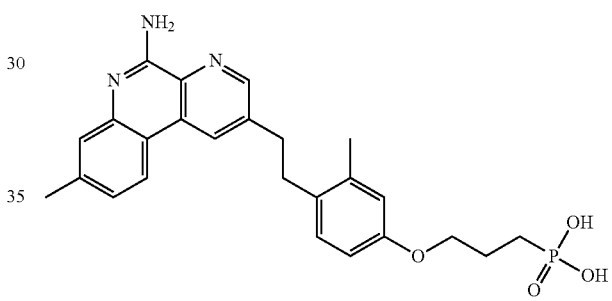

A 12 N solution of hycrochloric acid (0.10 M) was added to diethyl 3-(4-(2-(5-amino-8-methylbenzo[f][1,7]naphthyridin-2-yl)ethyl)-3-methylphenoxy)propylphosphonate (from Example 146) and the resulting mixture was allowed to stir at 100° C. for 18 hours. At this point, hydrochloric acid was removed under reduced pressure and the resulting residue was purified by RP-HPLC using a 10-50% MeCN in water gradient. The resulting trifluoroacetate salt was then converted to the free base form by the addition of a saturated aqueous solution of sodium bicarbonate, followed by washing three times with ethyl acetate. The combined organic layers were dried with anhydrous $Na_2SO_4$, and the volatiles were removed in vacuo to deliver 3-(4-(2-(5-amino-8-methylbenzo[f][1,7]naphthyridin-2-yl)ethyl)-3-methylphenoxy)propylphosphonic acid as a solid. $^1$H NMR (Dimethylsulfoxide-$d_6$): δ 9.72 (br, 1H), 9.01 (s, 1H), 8.96 (br, 1H), 8.85 (s, 1H), 8.54 (d, 1H), 7.54 (s, 1H), 7.42 (d, 1H), 7.08 (d, 1), 6.74 (s, 1H), 6.66 (d, 1H), 3.95 (t, 2H), 3.14 (t, 2H), 2.97 (t, 2H), 2.50 (s, 3H), 2.27 (s, 3H), 1.81-1.91 (m, 2H), 1.56-1.67 (m, 2H). LRMS [M+H]=466.2

Example 148

2-(4-butoxy-2-methylphenethyl)-8-methylbenzo[f][1,7]naphthyridin-5-amine

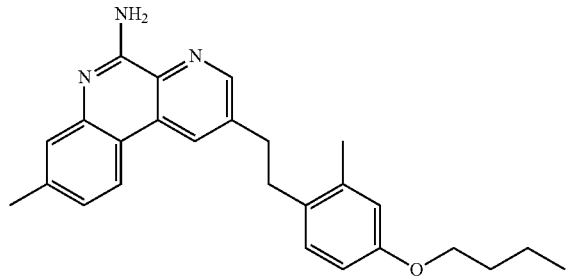 [SMILES: CCCCOc1ccc(CCc2cnc3c(N)nc4cc(C)ccc4c3c2)c(C)c1]

2-(4-Butoxy-2-methylphenethyl)-8-methylbenzo[f][1,7]naphthyridin-5-amine was prepared following an analogous procedure to the preparation described for Example 136, but using 4-(2-(5-amino-8-methylbenzo[f][1,7]naphthyridin-2-yl)ethyl)-3-methylphenol (from Example 47) with 1-bromobutane. $^1$H NMR (Acetone-$d_6$): δ 8.75 (s, 1H), 8.71 (s, 1H), 8.28 (d, 1H), 7.43 (s, 1H), 7.15 (d, 1H), 7.07 (d, 1H), 6.75 (s, 1H), 6.69 (d, 1H), 6.54 (br, 2H) 3.95 (t, 2H), 3.16 (t, 2H), 3.04 (t, 2H), 2.47 (s, 3H), 2.30 (s, 3H), 1.69-1.77 (m, 2H), 1.43-1.54 (m, 2H), 0.97 (t, 3H). LRMS [M+H]=400.2

Example 149

2-(4-(2-(5-aminobenzo[f][1,7]naphthyridin-2-yl)ethyl)-3-methylphenoxy)ethanol

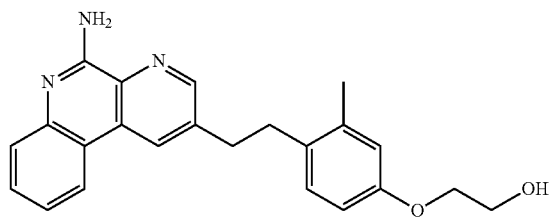 [SMILES: Cc1cc(OCCO)ccc1CCc1cnc2c(N)nc3ccccc3c2c1]

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 142, but using 2-(4-Methoxy-2-methylphenethyl)benzo[f][1,7]naphthyridin-5-amine (from Example 116).

Step 2: 2-(4-(2-(5-Aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared from 4-(2-(5-aminobenzo[f][1,7]naphthyridin-2-yl)ethyl)-3-methylphenol (from the previous step) following the procedures described for Example 142/Steps 1 to 2. LRMS [M+H]=374.2

Example 150

2-(4-(2-(5-aminobenzo[f][1,7]naphthyridin-2-yl)ethyl)-3-methylphenoxy)ethanol

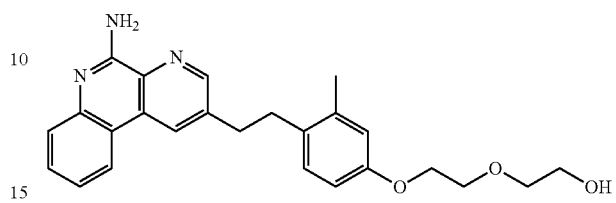

Step 1: 4-(2-(5-aminobenzo[f][1,7]naphthyridin-2-yl)ethyl)-3-methylphenol 4-(2-(5-Aminobenzo[f][1,7]naphthyridin-2-yl)ethyl)-3-methylphenol was prepared following an analogous procedure to the preparation described for Example 47, but using 2-(4-Methoxy-2-methylphenethyl)benzo[f][1,7]naphthyridin-5-amine (from Example 116).

Step 2: 2-(4-(2-(5-aminobenzo[f][1,7]naphthyridin-2-yl)ethyl)-3-methylphenoxy)ethanol 2-(4-(2-(5-Aminobenzo[f][1,7]naphthyridin-2-yl)ethyl)-3-methylphenoxy)ethanol was prepared following the procedures described for Example 145/Steps 1 to 2. LRMS [M+H]=418.2

Example 151 ethyl 5-(4-(2-(5-amino-8-methylbenzo[f][1,7]naphthyridin-2-yl)ethyl)-3-methylphenoxy)pentanoate

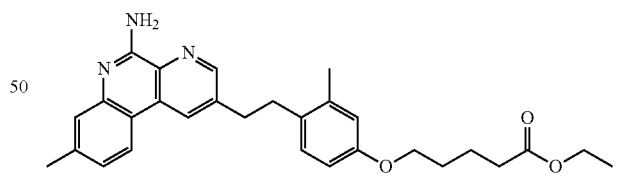

Ethyl 5-(4-(2-(5-amino-8-methylbenzo[f][1,7]naphthyridin-2-yl)ethyl)-3-methylphenoxy)pentanoate was prepared from 4-(2-(5-amino-8-methylbenzo[f][1,7]naphthyridin-2-yl)ethyl)-3-methylphenol (from Example 47) following the procedure described for Example 136, but using ethyl 5-bromopentanoate. $^1$H NMR (CDCl$_3$): δ 8.64 (s, 1H), 8.27 (s, 1H), 8.02 (d, 1H), 7.66 (s, 1H), 7.32 (d, 1H), 6.91 (d, 1H), 6.66 (s, 1H), 6.63 (d, 1H), 4.13 (q, 2H), 3.93 (t, 2H), 3.14 (t, 2H), 2.99 (t, 2H), 2.54 (s, 3H), 2.38 (t, 2H), 2.25 (s, 3H), 1.79-1.83 (m, 4H), 1.26 (t, 3H). LRMS [M+H]=472.3

Example 152

5-(4-(2-(5-amino-8-methylbenzo[f][1,7]naphthyridin-2-yl)ethyl)-3-methylphenoxy)pentanoic acid

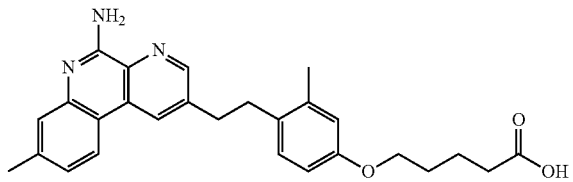 [SMILES: Cc1ccc2c(c1)nc(N)c1ncc(CCc3ccc(OCCCCC(=O)O)cc3C)cc12]

5-(4-(2-(5-Amino-8-methylbenzo[f][1,7]naphthyridin-2-yl)ethyl)-3-methylphenoxy)pentanoic acid was prepared from ethyl 5-(4-(2-(5-amino-8-methylbenzo[f][1,7]naphthyridin-2-yl)ethyl)-3-methylphenoxy)pentanoate (from the previous step) following the procedure described for Example 141. $^1$H NMR (CDCl$_3$): δ 8.52 (s, 1H), 8.27 (s, 1H), 8.02 (d, 1H), 7.65 (s, 1H), 7.32 (d, 1H), 6.86 (d, 1H), 6.72 (s, 1H), 6.63 (d, 1H), 3.95 (t, 2H), 3.15 (t, 2H), 2.99 (t, 2H), 2.54 (s, 3H), 2.45 (t, 2H), 2.23 (s, 3H), 1.79-1.83 (m, 4H). LRMS [M+H]=444.2

Example 153

2-(4-(2-(5-amino-8-methylbenzo[f][1,7]naphthyridin-2-yl)ethyl)-3-methylphenoxy)ethanol

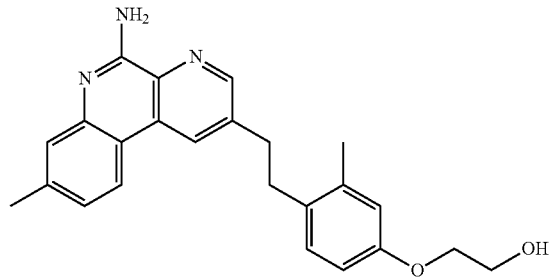 [SMILES: Cc1ccc2c(c1)nc(N)c1ncc(CCc3ccc(OCCO)cc3C)cc12]

2-(4-(2-(5-Amino-8-methylbenzo[f][1,7]naphthyridin-2-yl)ethyl)-3-methylphenoxy)ethanol was prepared following the procedures described for Example 142/Steps 1 to 2, but using 4-(2-(5-amino-8-methylbenzo[f][1,7]naphthyridin-2-yl)ethyl)-3-methylphenol (from Example 47). $^1$H NMR (Acetone-d$_6$): δ 8.76 (s, 1H), 8.69 (s, 1H), 8.28 (d, 1H), 7.40 (s, 1H), 7.15 (d, 1H), 7.09 (d, 1H), 6.75 (s, 1H), 6.68 (d, 1H), 6.57 (br, 2H), 4.00 (t, 2H), 3.79-3.88 (m, 2H), 3.17 (t, 2H), 3.04 (t, 2H), 2.46 (s, 2H), 2.29 (s, 2H). LRMS [M+H]=388.5.

Example 154

4-(2-(5-amino-8-methylbenzo[f][1,7]naphthyridin-2-yl)ethyl)phenyl ethyl carbonate

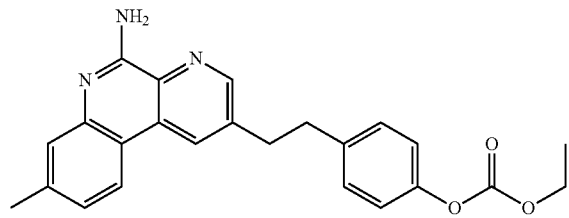 [SMILES: CCOC(=O)Oc1ccc(CCc2cnc3c(N)nc4cc(C)ccc4c3c2)cc1]

4-(2-(5-Amino-8-methylbenzo[f][1,7]naphthyridin-2-yl)ethyl)phenyl ethyl carbonate was prepared from 4-(2-(5-amino-8-methylbenzo[f][1,7]naphthyridin-2-yl)ethyl)phenol (from Example 167) following the procedure described for Example 135, but using ethyl carbonochloridate. LRMS [M+H]=402.2

Example 155 methyl 4-(4-(2-(5-amino-8-methylbenzo[f][1,7]naphthyridin-2-yl)ethyl)phenoxy)butanoate

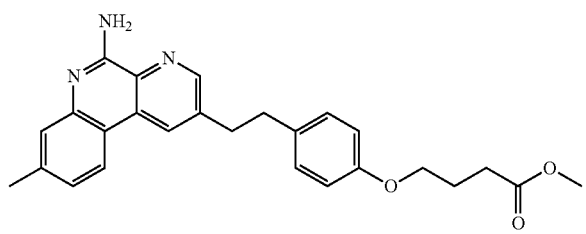

Methyl 4-(4-(2-(5-amino-8-methylbenzo[f][1,7]naphthyridin-2-yl)ethyl)phenoxy)butanoate was prepared from 4-(2-(5-amino-8-methylbenzo[f][1,7]naphthyridin-2-yl)ethyl)phenol (from Example 167) following the procedure described for the preparation of Example 136, but using methyl 4-bromobutanoate. $^1$H NMR (Acetone-d$_6$): δ 8.74 (s, 1H), 8.67 (s, 1H), 8.24 (d, 1H), 7.39 (s, 1H), 7.09-7.19 (m, 3H), 6.82 (d, 2H), 6.53 (br, 2H), 3.97 (t, 2H), 3.60 (s, 3H), 3.19 (t, 2H), 3.04 (t, 2H), 2.48 (t, 2H), 2.44 (s, 3H), 0.84-0.91 (m, 2H). LRMS [M+H]=430.2.

Example 156

4-(4-(2-(5-amino-8-methylbenzo[f][1,7]naphthyridin-2-yl)ethyl)phenoxy)butanoic acid

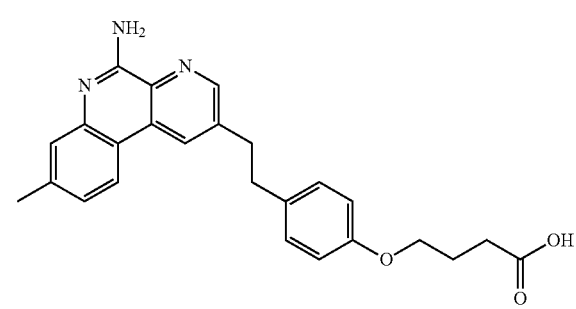 [SMILES: Cc1ccc2c(c1)nc(N)c1ncc(CCc3ccc(OCCCC(=O)O)cc3)cc12]

4-(4-(2-(5-Amino-8-methylbenzo[f][1,7]naphthyridin-2-yl)ethyl)phenoxy)butanoic acid was prepared from methyl 4-(4-(2-(5-amino-8-methylbenzo[f][1,7]naphthyridin-2-yl)ethyl)phenoxy)butanoate (from the previous step) following the procedure described for Example 141. $^1$H NMR (Acetone-d$_6$): δ 7.47 (s, 1H), 7.41 (s, 1H), 7.09 (d, 1H), 6.21 (s, 1H), 6.18 (d, 1H), 5.82 (d, 2H), 5.52 (d, 2H), 2.66 (t, 2H), 1.99 (t, 2H), 1.77 (t, 2H), 1.28 (s, 3H), 1.17 (t, 2H), 0.70-0.79 (m, 2H). LRMS [M+H]=416.2.

Example 157

4-(4-(2-(5-amino-8-methylbenzo[f][1,7]naphthyridin-2-yl)ethyl)-3-methylphenoxy)butanoic acid

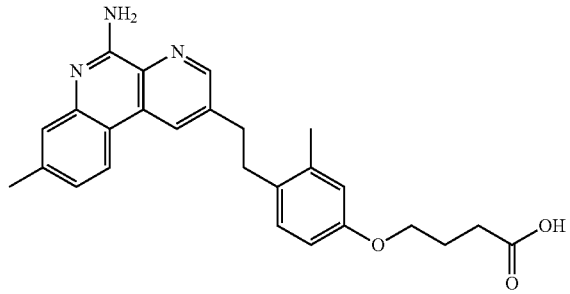 [SMILES: Cc1ccc2c(c1)nc(N)c1ncc(CCc3ccc(OCCCC(=O)O)cc3C)cc12]

Step 1: methyl 4-(4-(2-(5-amino-8-methylbenzo[f][1,7]naphthyridin-2-yl)ethyl)-3-methylphenoxy)butanoate Methyl 4-(4-(2-(5-amino-8-methylbenzo[f][1,7]naphthyridin-2-yl)ethyl)-3-methylphenoxy)butanoate was prepared following the same procedure described for the preparation of Example 155, but using 4-(2-(5-amino-8-methylbenzo[f][1,7]naphthyridin-2-yl)ethyl)-3-methylphenol (from Example 47).

Step 2: 4-(4-(2-(5-Amino-8-methylbenzo[f][1,7]naphthyridin-2-yl)ethyl)-3-methylphenoxy)butanoic acid 4-(4-(2-(5-Amino-8-methylbenzo[f][1,7]naphthyridin-2-yl)ethyl)-3-methylphenoxy)butanoic acid was prepared from methyl 4-(4-(2-(5-amino-8-methylbenzo[f][1,7]naphthyridin-2-yl)ethyl)-3-methylphenoxy)butanoate (from the previous step) following the procedure described for Example 141. $^1$H NMR (Acetone-$d_6$): δ 8.38 (s, 1H), 8.24 (s, 1H), 7.90 (d, 1H), 6.90 (s, 1H), 6.68 (d, 1H), 6.54-6.63 (m, 2H), 6.27 (d, 1H), 6.20 (d, 1H), 3.40 (t, 2H), 2.62 (t, 2H), 2.47 (t, 2H), 1.99 (s, 3H), 1.80 (s, 2H), 1.45 (t, 2H), 1.27-1.39 (m, 2H). LRMS [M+H]=430.2.

Example 158

2-(4-(isopentyloxy)-2-methylphenethyl)-8-methylbenzo[f][1,7]naphthyridin-5-amine

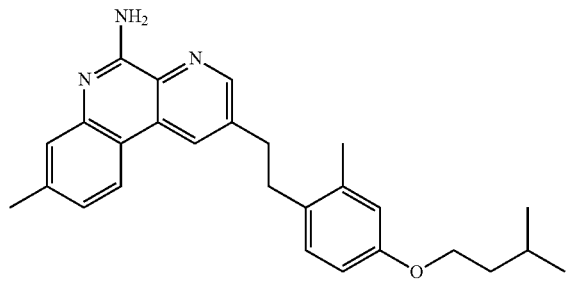 [SMILES: Cc1ccc2c(c1)nc(N)c1ncc(CCc3ccc(OCCC(C)C)cc3C)cc12]

2-(4-(Isopentyloxy)-2-methylphenethyl)-8-methylbenzo[f][1,7]naphthyridin-5-amine was prepared from 4-(2-(5-amino-8-methylbenzo[f][1,7]naphthyridin-2-yl)ethyl)-3-methylphenol (from Example 47) following the procedure described for Example 133, but using 1-bromo-3-methylbutane. $^1$H NMR (Acetone-$d_6$): δ 8.75 (s, 1H), 8.72 (s, 1H), 8.29 (d, 1H), 7.43 (s, 1H), 7.17 (D, 1H), 7.10 (d, 1H), 6.76 (d, 1H), 6.68 (d, 1H), 6.56 (br, 2H), 4.00 (t, 2H), 3.17 (t, 2H), 3.07 (t, 2H), 2.48 (s, 3H), 1.76-1.91 (m, 1H), 1.60-1.71 (m, 2H), 0.96 (s, 6H). LRMS [M+H]=414.2.

Example 159

4-(2-(5-amino-8-methylbenzo[f][1,7]naphthyridin-2-yl)ethyl)phenyl hexyl carbonate

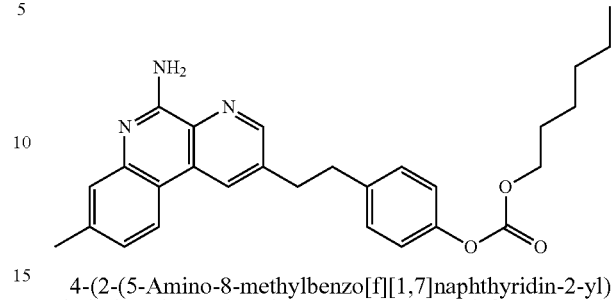

4-(2-(5-Amino-8-methylbenzo[f][1,7]naphthyridin-2-yl)ethyl)phenyl hexyl carbonate was prepared from 4-(2-(5-amino-8-methylbenzo[f][1,7]naphthyridin-2-yl)ethyl)phenol (from Example 167) following the procedures described for Example 135, but using hexyl carbonochloridate. LRMS [M+H]=458.2.

Example 160

2-(2,4,6-trimethylphenethyl)benzo[f][1,7]naphthyridin-5-amine

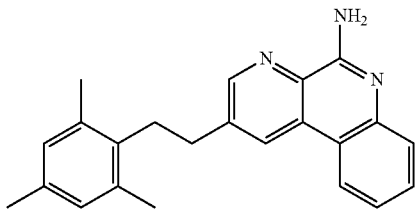 [SMILES: Cc1cc(C)c(CCc2cnc3c(N)nc4ccccc4c3c2)c(C)c1]

Step 1: 2-(mesitylethynyl)benzo[f][1,7]naphthyridin-5-amine 2-(Mesitylethynyl)benzo[f][1,7]naphthyridin-5-amine was prepared from 3-chloro-5-(mesitylethynyl)picolinonitrile (Example 74/Step 1) and tert-butyl 2-(4,4,5,5-tetramethyl-1,3,2-dioxaborolan-2-yl)phenylcarbamate (commercially available) following the procedures described for Example 42/Step 1.

Step 2: 2-(2,4,6-Trimethylphenethyl)benzo[f][1,7]naphthyridin-5-amine 2-(2,4,6-Trimethylphenethyl)benzo[f][1,7]naphthyridin-5-amine was prepared from 2-(mesitylethynyl)benzo[f][1,7]naphthyridin-5-amine (from the previous step) following the procedures described for Example 42/Step 2 to 3. $^1$H NMR (Acetone-$d_6$): δ 8.80 (s, 2H), 8.38 (d, 1H), 7.60 (d, 2H), 7.54 (d, 2H), 7.31 (t, 1H), 6.84 (s, 2H), 6.61 (br, 2H), 3.08 (s, 2H), 2.30 (s, 6H), 2.23 (s, 3H). LRMS [M+H]=342.2.

Example 161

(5-amino-2-(2,4-dimethylphenethyl)benzo[f][1,7]naphthyridin-8-yl)methanol

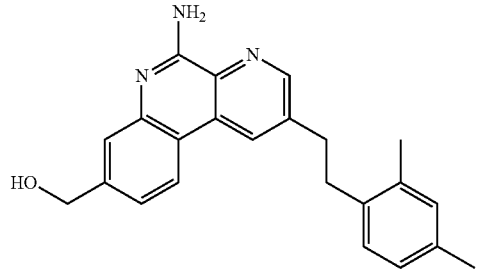 [SMILES: Cc1ccc(CCc2cnc3c(N)nc4cc(CO)ccc4c3c2)c(C)c1]

Step 1: methyl 5-amino-2-((2,4-dimethylphenyl)ethynyl)benzo[f][1,7]naphthyridine-8-carboxylate Methyl 5-amino-2-((2,4-dimethylphenyl)ethynyl)benzo[f][1,7]naphthyridine-8-carboxylate was prepared from 3-chloro-5-((2,4-d methylphenyl)ethynyl)picolinonitrile (from Example 44/Step 3) and 2-(tert-butoxycarbonylamino)-4-(methoxycarbonyl)phenylboronic acid (from Example 82/Step 1) following the procedures described in Example 92/step 1.

Step 2: methyl 5-amino-2-(2,4-dimethylphenethyl)benzo[f][1,7]naphthyridine-8-carboxylate Methyl 5-amino-2-(2,4-dimethylphenethyl)benzo[f][1,7]naphthyridine-8-carboxylate was prepared from methyl 5-amino-2-((2,4-dimethylphenyl)ethynyl)benzo[f][1,7]naphthyridine-8-carboxylate (from the previous step) following the procedures described in Example 41/Step 5.

Step 3: (5-amino-2-(2,4-dimethylphenethyl)benzo[f][1,7]naphthyridin-8-yl)methanol (5-Amino-2-(2,4-dimethylphenethyl)benzo[f][1,7]naphthyridin-8-yl)methanol was prepared from methyl 5-amino-2-(2,4-dimethylphenethyl)benzo[f][1,7]naphthyridine-8-carboxylate (from the previous step) following the procedures described in Example 92/Step 2. $^1$H NMR (Acetone-$d_6$): δ 8.79 (s, 1H), 8.73 (s, 1H), 8.35 (d, 1H), 7.61 (s, 1H), 7.34 (d, 1H), 7.08 (d, 1H), 6.97 (s, 1H), 6.91 (d, 1H), 6.51 (br. 2H), 4.77 (s, 2H), 3.16-3.20 (m, 2H), 3.04-3.10 (m, 2H), 2.28 (s, 3H), 2.25 (s, 3H). LRMS [M+H]=358.2.

Example 162 diethyl 3-(2-(4-(2-(5-amino-8-methylbenzo[f][1,7]naphthyridin-2-yl)ethyl)-3-methylphenoxy)ethoxy)propylphosphonate

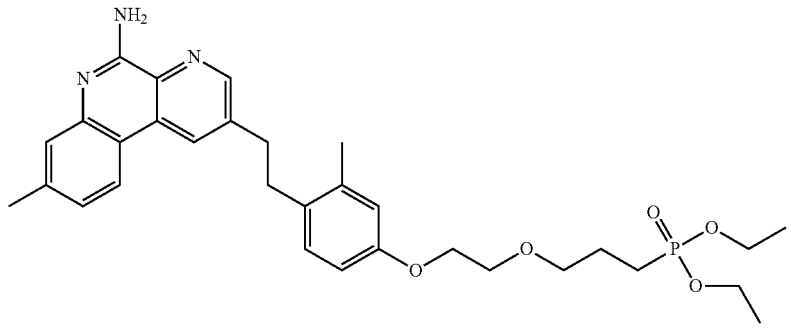 [SMILES: CCOP(=O)(CCCOCCOc1ccc(CCc2cnc3c(N)nc4cc(C)ccc4c3c2)c(C)c1)OCC]

Diethyl 3-(2-(4-(2-(5-amino-8-methylbenzo[f][1,7]naphthyridin-2-yl)ethyl)-3-methylphenoxy)ethoxy)propylphosphonate was prepared following the procedure described for Example 136, but using 4-(2-(5-amino-8-methylbenzo[f][1,7]naphthyridin-2-yl)ethyl)-3-methylphenol (from Example 153) and diethyl 3-(2-bromoethoxy)propylphosphonate. LRMS [M+H]=566.3.

Example 163 diethyl 3-(2-(2-(4-(2-(5-amino-8-methylbenzo[f][1,7]naphthyridin-2-yl)ethyl)-3-methylphenoxy)ethoxy)ethoxy)propylphosphonate

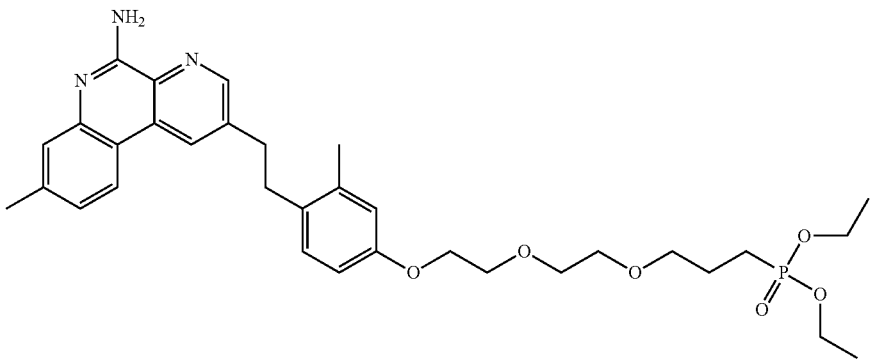 [SMILES: CCOP(=O)(CCCOCCOCCOc1ccc(CCc2cnc3c(N)nc4cc(C)ccc4c3c2)c(C)c1)OCC]

Diethyl 3-(2-(2-(4-(2-(5-amino-8-methylbenzo[f][1,7]naphthyridin-2-yl)ethyl)-3-methylphenoxy)ethoxy)ethoxy)propylphosphonate was prepared from following the procedure described for Example 136, but using 4-(2-(5-amino-8-methylbenzo[f][1,7]naphthyridin-2-yl)ethyl)-3-methylphenol (from Example 145) and diethyl 3-(2-(2-bromoethoxy)ethoxy)propylphosphonate. $^1$H NMR (Acetone-d$_6$): δ 8.75 (s, 1H), 8.70 (s, 1H), 8.26 (d, 1H), 7.42 (s, 1H), 7.16 (d, 1H), 7.09 (d, 1H), 6.77 (s, 1H), 6.71 (d, 1H), 6.58 (br, 2H), 3.95-4.11 (m, 6H), 3.76-3.80 (m, 2H), 3.63-3.67 (m, 2H), 3.55-3.58 (m, 2H), 3.57-3.51 (m, 2H), 3.14-3.18 (m, 2H), 3.04-3.05 (m, 2H), 2.46 (s, 3H), 2.29 (s, 3H), 1.71-1.87 (m, 4H), 1.22-1.29 (m, 8H). LRMS [M+H]=610.3.

Example 164

4-(2-(5-amino-8-methylbenzo[f][1,7]naphthyridin-2-yl)ethyl)-3-methylphenyl dimethylsulfamate

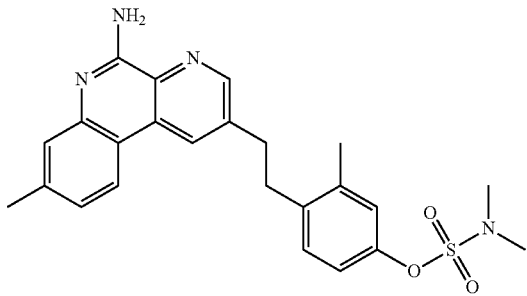

4-(2-(5-Amino-8-methylbenzo[f][1,7]naphthyridin-2-yl)ethyl)-3-methylphenyl dimethylsulfamate was prepared from 4-(2-(5-amino-8-methylbenzo[f][1,7]naphthyridin-2-yl)ethyl)-3-methylphenol (from Example 47) following the procedure described for Example 135, but using dimethylsulfamoyl chloride. $^1$H NMR (Acetone-d$_6$): δ 8.79 (s, 1H), 8.72 (s, 1H), 8.28 (d, 1H), 7.42 (s, 1H), 7.27 (d, 1H), 7.17 (s, 1H), 7.14 (t, 1H), 7.05-7.10 (d, 1H), 3.19-3.25 (m, 2H), 3.11-3.17 (m, 2H), 2.92 (s, 6H), 2.46 (s, 3H), 2.37 (s, 3H). LRMS [M+H]=451.2.

Example 165

(5-amino-2-(4-(dimethylamino)phenethyl)benzo[f][1,7]naphthyridin-8-yl)methanol

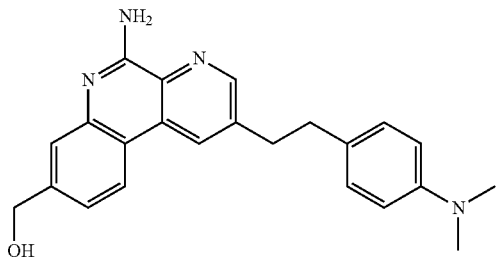 [SMILES: CN(C)c1ccc(CCc2cnc3c(N)nc4cc(CO)ccc4c3c2)cc1]

(5-Amino-2-(4-(dimethylamino)phenethyl)benzo[f][1,7]naphthyridin-8-yl)methanol was prepared from tert-butyl 5-((tert-butyldimethylsilyloxy)methyl)-2-(4,4,5,5-tetramethyl-1,3,2-dioxaborolan-2-yl)phenylcarbamate (from Example 96/step 1) and 4-ethynyl-N,N-dimethylaniline (commercially available) following the procedures described in Example 42/Step 1 to 4 followed by deprotection of TBS group as in Example 96/Step 3. $^1$H NMR (Acetone-d$_6$): δ 8.78 (s, 1H), 8.73 (s, 1H), 8.35 (d, 1H), 7.61 (s, 1H), 7.31-7.35 (d, 1H), 7.08 (d, 1H), 6.68 (d, 2H), 6.50 (br, 2H), 4.78 (s, 2H), 4.34 (s, 1H), 3.16-3.20 (m, 2H), 3.03-3.10 (m, 2H), 2.83 (s, 3H), 2.80 (s, 3H). LRMS [M+H]=373.2.

Example 166

2-(4-(dimethylamino)phenethyl)-8-methylbenzo[f][1,7]naphthyridin-5-amine

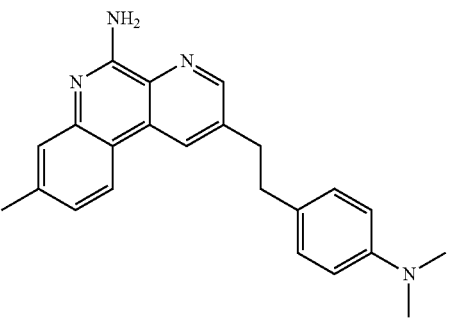

2-(4-(Dimethylamino)phenethyl)-8-methylbenzo[f][1,7]naphthyridin-5-amine was prepared following the procedures described for Example 42/Steps 1 to 3, but using 4-ethynyl-N,N-dimethylaniline in step 1. $^1$H NMR (Acetone-d$_6$) Free base: δ 8.60 (s, 1H), 8.55 (s, 1H), 8.15 (d, 1H), 7.28 (s, 1H), 7.03 (d, 1H), 6.96 (d, 2H), 6.56 (d, 2H), 6.55 (br s, 2H), 3.05 (t, 2H), 2.88 (t, 2H), 2.75 (s, 6H), 2.33 (s, 3H). LRMS [M+H]=357.2

Example 167

4-(2-(5-amino-8-methylbenzo[f][1,7]naphthyridin-2-yl)ethyl)phenol

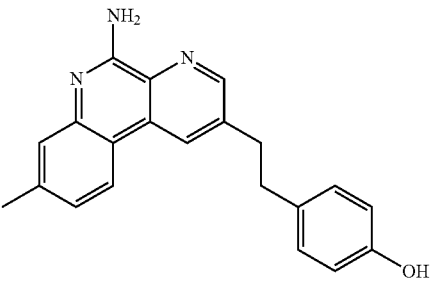 [SMILES: Cc1ccc2c(c1)nc(N)c1ncc(CCc3ccc(O)cc3)cc12]

Step 1: 2-(4-methoxyphenethyl)-8-methylbenzo[f][1,7]naphthyridin-5-amine 2-(4-methoxyphenethyl)-8-methylbenzo[f][1,7]naphthyridin-5-amine was prepared following the procedures described for Example 76/Steps 1 to 3, but using 1-ethynyl-4-methoxybenzene in Step 1.

Step 2: 4-(2-(5-Amino-8-methylbenzo[f][1,7]naphthyridin-2-yl)ethyl)phenol 4-(2-(5-Amino-8-methylbenzo[f][1,7]naphthyridin-2-yl)ethyl)phenol was prepared from 2-(4-methoxyphenethyl)-8- methylbenzo[f][1,7]naphthyridin-5-amine (from the previous step) following the procedure described for Example 47. ¹H NMR (Methanol-d₄): δ 8.59

Example 168

1-(4-(2-(5-amino-8-methylbenzo[f][1,7]naphthyridin-2-yl)ethyl)phenyl)ethanone

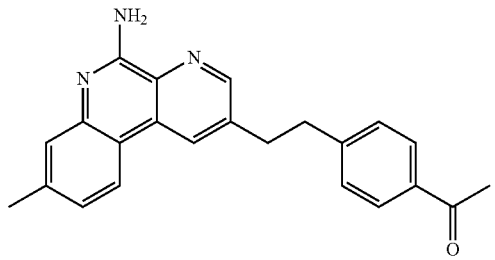 [SMILES: CC(=O)c1ccc(CCc2cnc3c(N)nc4cc(C)ccc4c3c2)cc1]

Step 1: 5-((4-acetylphenyl)ethynyl)-3-chloropicolinonitrile

To a solution of 1-(4-ethynylphenyl)ethanone (commercially available) (1 eq) 3,5-dichloropicolinonitrile (1 eq), dichlorobis(triphenylphosphine)-palladium (II) (20 mol %), copper iodide (10 mol %) and DMF:Triethylamine (10:1) (0.13 M) was stirred at ambient temperature overnight. The reaction mixture was then diluted with ethyl acetate and sodium bi-carbonate solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 5-((4-acetylphenyl)ethynyl)-3-chloropicolinonitrile was isolated as a yellow solid Step 2: 5-(4-acetylphenethyl)-3-chloropicolinonitrile To a solution of 5-((4-acetylphenyl)ethynyl)-3-chloropicolinonitrile (from the previous step) (1 eq) in ethanol (0.1 M) was added Platinum Oxide (30 mol %). Hydrogen gas was introduced via a balloon, and the reaction was stirred for 0.5 hour. The mixture was filtered through a pad of celite, washing with dichloromethane. The filtrate was concentrated en vaccuo and purified by flash chromatography on a COMBIFLASH® system (ISCO) using 0-100% ethyl acetate in hexane to give 5-(4-acetylphenethyl)-3-chloropicolinonitrile as an off-white solid.

Step 3: 1-(4-(2-(5-amino-8-methylbenzo[f][1,7] naphthyridin-2-yl)ethyl)phenyl)ethanone To a solution of 5-(4-acetylphenethyl)-3-chloropicolinonitrile (from the previous step) (1 eq) and tert-butyl 5-methyl-2-(4,4,5,5-tetramethyl-1,3,2-dioxaborolan-2-yl) phenylcarbamate (1.0 eq.), tetrakis(triphenyl-phosphine) palladium (10 mol %), and 2N aqueous sodium carbonate solution (2.0 eq.) in toluene/ethanol (1:1, 0.09 M) was heated under microwave condition using a BIOTAGE INITIATOR 2.0 at 150° C. for 20 minutes. After cooling to ambient temperature, the reaction mixture was diluted with ethanol/water. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 1-(4-(2-(5-amino-8-methylbenzo [f][1,7]naphthyridin-2-yl)ethyl)phenyl)ethanone as a yellow solid. ¹H NMR (Methanol-d₄) TFA Salt: δ 8.69 (d, 2H), 8.30 (d, 1H), 7.80 (d, 2H), 7.38 (s, 1H), 7.36 (d, 1H), 7.28 (d, 2H), 3.25 (t, 2H), 3.13 (t, 2H), 2.47 (s, 3H), 2.45 (s, 3H). LRMS [M+H]=356.2

Example 169

2-(4-((dimethylamino)methyl)phenethyl)-8-methyl-benzo[f][1,7]naphthyridin-5-amine

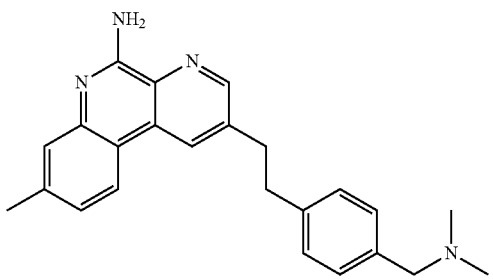

Step 1: 4-(2-(5-amino-8-methylbenzo[f][1,7]naphthyridin-2-yl)ethyl)benzaldehyde 4-(2-(5-Amino-8-methylbenzo[f][1,7]naphthyridin-2-yl) ethyl)benzaldehyde was prepared from 4-ethynylbenzaldehyde (commercially available) following the procedures described for Example 168/Steps 1 to 3.

Step 2: 2-(4-((dimethylamino)methyl)phenethyl)-8-methylbenzo[f][1,7]naphthyridin-5-amine A solution of 4-(2-(5-amino-8-methylbenzo[f][1,7]naphthyridin-2-yl)ethyl)benzaldehyde (from the previous step) (1 eq), sodium acetate (3.5 eq) and N,N'-dimethyl amine hydrochloride (3.5 eq) dissolved in 1-2, dichloroethane (0.04 M) was heated at 80° C. for 2 hours in a sealed vial. After cooling to ambient temperature, the reaction mixture was further cooled down to 0° C. and sodium tri-acetoxy borohydride (1.25 eq) was added. The reaction mixture was stirred at room temperature for one hour. The mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by preparative HPLC using 10-90% acetonitrile/water as the gradient and 2-(4-((dimethylamino)methyl)phenethyl)-8-methylbenzo[f] [1,7]naphthyridin-5-amine was isolated as a off-white powder as a TFA salt. ¹H NMR (Methanol-d₄) TFA Salt: δ 8.83 (s, 1H), 8.81 (s, 1H), 8.41 (d, 1H), 7.52 (s, 1H), 7.45 (d, 1H), 7.43 (s, 1H), 7.40 (m, 3H), 4.29 (s, 2H), 3.30-3.24 (m, 4H), 2.79 (s, 6H), 2.60 (s, 3H). LRMS [M+H]=371.2

Example 170

2-(4-(1-(dimethylamino)ethyl)phenethyl)-8-methyl-benzo[f][1,7]naphthyridin-5-amine

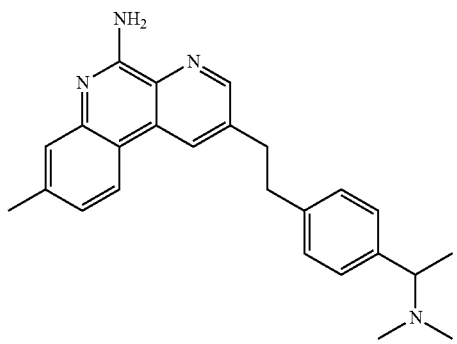

2-(4-(1-(Dimethylamino)ethyl)phenethyl)-8-methyl-benzo[f][1,7]naphthyridin-5-amine was prepared from 1-(4-(2-(5-amino-8-methylbenzo[f][1,7]naphthyridin-2-yl)ethyl)phenyl)ethanone (from Example 168) following the procedures described for Example 169/Step 2. $^1$H NMR (Methanol-d$_4$) TFA Salt: δ 8.84 (s, 1H), 8.79 (s, 1H), 8.40 (d, 1H), 7.52 (s, 1H), 7.44-7.46 (m, 2H), 7.38-7.42 (m, 3H), 4.45 (m, 1H), 3.31 (t, 2H), 3.19 (t, 2H), 2.83 (s, 3H), 2.66 (s, 3H), 2.56 (s, 3H), 1.70 (d, 3H). LRMS [M+H]=385.2

Example 171

1-(4-(2-(5-amino-8-methylbenzo[f][1,7]naphthyridin-2-yl)ethyl)phenyl)ethanone oxime

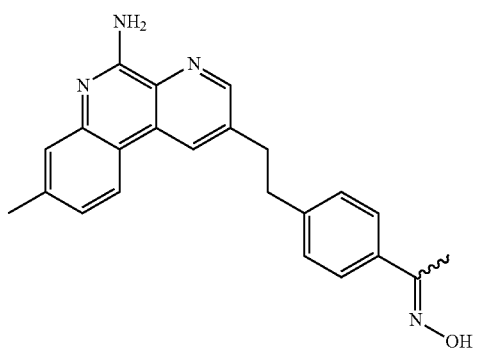

A solution of 1-(4-(2-(5-amino-8-methylbenzo[f][1,7]naphthyridin-2-yl)ethyl)phenyl)ethanone (from Example 168) (1 eq), hydroxylamine hydrochloride (2 eq) and 1 drop of HOAc, dissolved in absolute ethanol (0.028M) was stirred at room temperature for 1.5 hours. The mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 10-80% ethyl acetate in hexane to give 1-(4-(2-(5-amino-8-methylbenzo[f][1,7]naphthyridin-2-yl)ethyl)phenyl)ethanone oxime as a white solid. $^1$H NMR (Methanol-d$_4$): δ 8.56 (s, 1H), 8.52 (s, 1H), 8.12 (d, 1H), 7.45 (d, 2H), 7.31 (s, 1H), 7.12 (m, 3H), 4.51 (s, OH), 3.15 (t, 2H), 3.01 (t, 2H), 2.39 (s, 3H), 2.09 (s, 3H). LRMS [M+H]=371.2

Example 172

8-methyl-2-(4-((methylamino)methyl)phenethyl)benzo[f][1,7]naphthyridin-5-amine

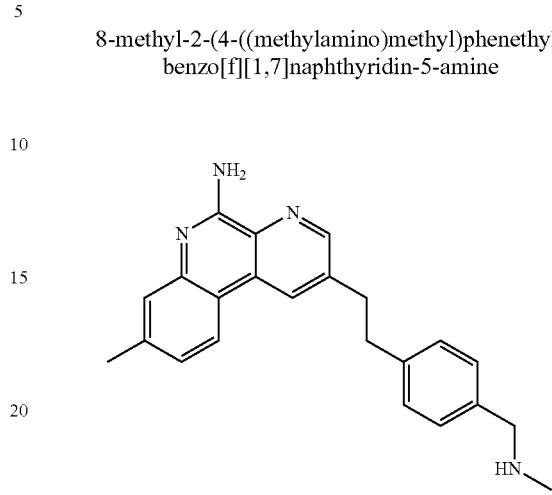

8-Methyl-2-(4-((methylamino)methyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 169/Step 1) and methylamine following the procedures described for Example 169, step 2. $^1$H NMR (Acetone-d$_6$) TFA Salt: δ 8.95 (s, 1H), 8.88 (s, 1H), 8.43 (d, 1H), 7.58 (s, 1H), 7.54 (d, 2H), 7.42 (d, 1H), 7.37 (d, 2H), 4.30 (s, 2H), 3.32-3.37 (m, 4H), 2.75 (s, 3H), 2.55 (s, 3H). LRMS [M+H]=357.2

Example 173

(4-(2-(5-amino-8-methylbenzo[f][1,7]naphthyridin-2-yl)ethyl)benzylamino)ethanol

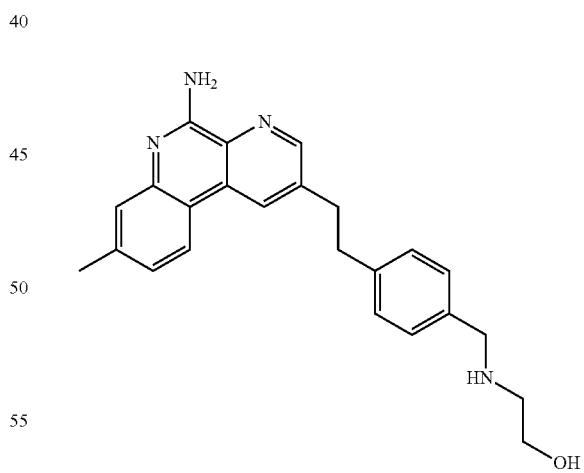

A solution of 4-(2-(5-amino-8-methylbenzo[f][1,7]naphthyridin-2-yl)ethyl)benzaldehyde (from Example 169/Step 1) (1 eq), ethanol amine (8 eq) and 1 drop of HOAc, dissolved in absolute ethanol (0.018M) was stirred at 80° C. for 2 hours. The mixture was cooled down to 0° C. and NaBH$_4$ (3.5 eq) was added and the reaction mixture was stirred for another one hour at room temperature. The mixture was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give a light yellow solid as a TFA salt. $^1$H NMR (Acetone-$d_6$) TFA Salt: δ 8.82 (s, 1H), 8.75 (s, 1H), 8.30 (d, 1H), 7.44 (m, 3H), 7.28 (d, 1H), 7.21 (d, 2H), 4.22 (s, 2H), 3.72 (t, 2H), 3.22 (t, 2H), 3.09 (m, 2H), 3.07 (t, 2H), 3.01 (bs, OH), 2.41 (s, 3H), LRMS [M+H]=387.2

Example 174

8-methyl-2-(4-(pyrrolidin-1-ylmethyl)phenethyl)benzo[f][1,7]naphthyridin-5-amine

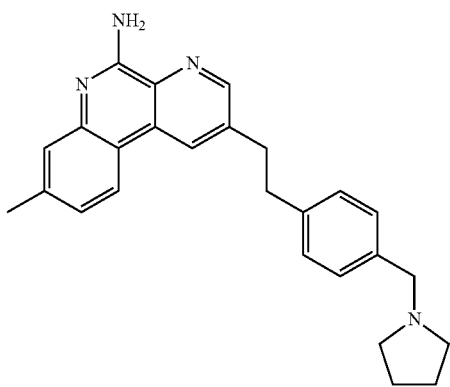 [SMILES: Cc1ccc2c(c1)nc(N)c1ncc(CCc3ccc(CN4CCCC4)cc3)cc12]

8-Methyl-2-(4-(pyrrolidin-1-ylmethyl)phenethyl)benzo[f][1,7]naphthyridin-5-amine was prepared from 4-(2-(5-Amino-8-methylbenzo[f][1,7]naphthyridin-2-yl)ethyl)benzaldehyde (from Example 169/Step 1) and pyrrolidine following the procedures described for Example 169, step 2. $^1$H NMR (Acetone-$d_6$) TFA Salt: δ 8.88 (s, 1H), 8.82 (s, 1H), 8.82 (s, 1H), 8.43 (d, 1H), 8.38 (d, 1H), 7.58 (s, 1H), 7.51 (m, 1H), 7.33 (d, 2H), 4.16 (s, 2H), 3.32-3.38 (m, 4H), 2.55 (s, 3H), 2.20-2.32 (m, 4H), 1.90-1.99 (m, 4H). LRMS [M+H]=397.2

Example 175

2-(3,4-dimethoxyphenethyl)-8-methylbenzo[f][1,7]naphthyridin-5-amine

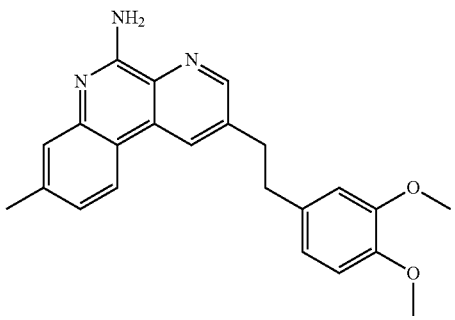

2-(3,4-Dimethoxyphenethyl)-8-methylbenzo[f][1,7]naphthyridin-5-amine was prepared from 4-ethynyl-1,2-dimethoxybenzene (commercially available) following the procedures described for Example 42/Steps 1 to 3. $^1$H NMR (Acetone-$d_6$): δ 8.64 (s, 1H), 8.56 (s, 1H), 8.14 (d, 1H), 7.29 (s, 1H), 7.03 (d, 1H), 6.77 (s, 1H), 6.71 (s, 1H), 6.62 (d, 1H), 6.45 (bs, 2H), 3.62 (s, 6H), 3.12 (t, 2H), 2.94 (t, 2H), 2.33 (s, 3H). LRMS [M+H]=374.2

Example 176

2-(1-(4-(2-(5-amino-8-methylbenzo[f][1,7]naphthyridin-2-yl)ethyl)phenyl)ethylamino)ethanol

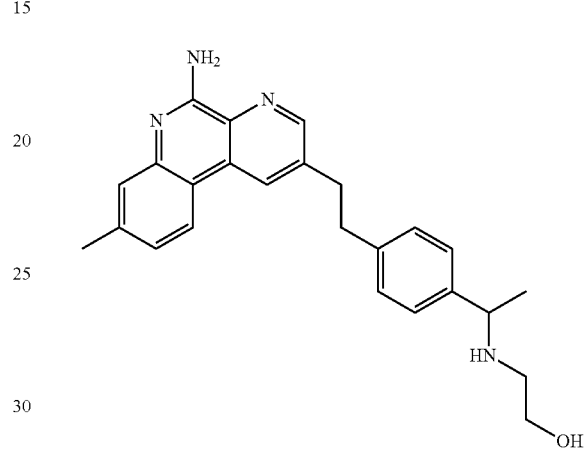

2-(1-(4-(2-(5-Amino-8-methylbenzo[f][1,7]naphthyridin-2-yl)ethyl)phenyl)ethylamino)ethanol (from Example 168) was prepared from 1-(4-(2-(5-amino-8-methylbenzo[f][1,7]naphthyridin-2-yl)ethyl)phenyl)ethanone and ethanol amine (commercially available) following the procedures described for Example 173. $^1$H NMR (Acetone-$d_6$) of TFA Salt: δ 8.78 (d, 1H), 8.29 (d, 1H), 7.83 (s, 1H), 7.45 (m, 3H), 7.28 (m, 3H), 4.22 (m, 1H), 3.52 (m, 2H), 3.23 (t, 2H), 3.09 (t, 2H), 2.85 (m, 1H), 2.65 (m, 1H), 2.41 (s, 3H), 1.61 (d, 3H). LRMS [M+H]=401.2

Example 177

1-(4-(2-(5-amino-8-methylbenzo[f][1,7]naphthyridin-2-yl)ethyl)phenyl)ethanol

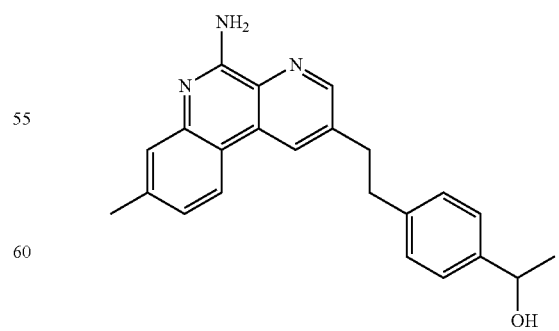

1-(4-(2-(5-Amino-8-methylbenzo[f][1,7]naphthyridin-2-yl)ethyl)phenyl)ethanol (from Example 168) was isolated as a side product during the reductive amination as shown in Example 170. ¹H NMR (Acetone-d₆) of TFA Salt: δ 8.90 (s, 1H), 8.88 (s, 1H), 8.42 (d, 1H), 7.57 (s, 1H), 7.43 (d, 1H), 7.33 (d, 2H), 7.26 (d, 2H), 4.82 (q, 1H), 3.32 (t, 2H), 3.17 (t, 2H), 3.01 2.55 (s, 3H), 1.41 (s, 3H). LRMS [M+H]=358.2

Example 178

8-methyl-2-(4-(oxazol-5-yl)phenethyl)benzo[f][1,7]naphthyridin-5-amine

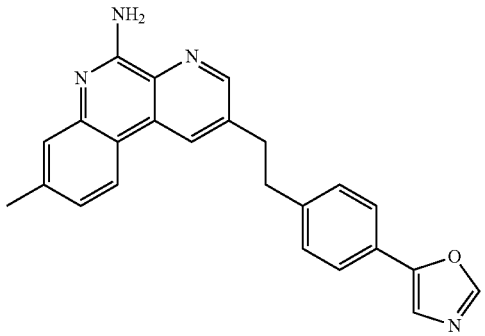 [SMILES: Cc1ccc2c(c1)nc(N)c1ncc(CCc3ccc(-c4cnco4)cc3)cc12]

8-Methyl-2-(4-(oxazol-5-yl)phenethyl)benzo[f][1,7]naphthyridin-5-amine was prepared from 5-(4-ethynylphenyl)oxazole (commercially available) following the procedures described for Example 42/Steps 1 to 3. ¹H NMR (Acetone-d₆) of TFA Salt: 8.69 (s, 1H), 8.59 (s, 1H), 8.16 (d, 1H), 8.04 (s, 1H), 7.55 (m, 2H), 7.38 (s, 1H), 7.28 (m, 2H), 7.01 (m, 2H), 3.16 (t, 2H), 3.07 (t, 2H), 2.33 (s, 3H). LRMS [M+H]=381.2

Example 179

3-(1-(4-(2-(5-amino-8-methylbenzo[f][1,7]naphthyridin-2-yl)ethyl)phenyl)ethylamino)propanenitrile

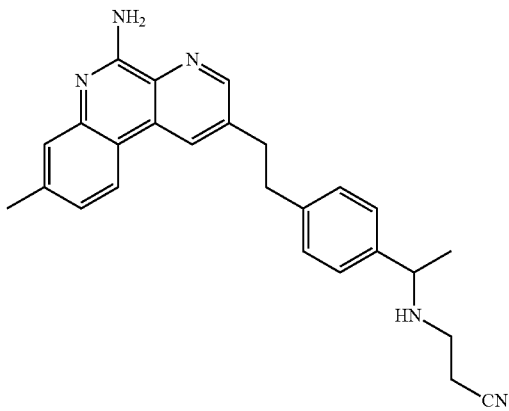 [SMILES: Cc1ccc2c(c1)nc(N)c1ncc(CCc3ccc(C(C)NCCC#N)cc3)cc12]

A solution of 1-(4-(2-(5-amino-8-methylbenzo[f][1,7]naphthyridin-2-yl)ethyl)phenyl)ethanone (from Example 168) (1 eq), 3-aminopropane nitrile (commercially available) (2.5 eq) dissolved in absolute ethanol (0.014M) was stirred at 80° C. for 2 hours. The mixture was cooled to 0° C. and NaCNBH₃ (2 eq) was added and the reaction mixture was stirred for another hour at room temperature. The mixture was diluted with ethyl acetate and ammonium chloride. The two phases were separated, and the aqueous layer was extracted twice with ethyl acetate. The combined organic layers were washed with brine, dried over anhydrous MgSO₄, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanenitrile as a light yellow solid as a TFA salt. ¹H NMR (Acetone-d₆): δ 8.60 (s, 1H), 8.59 (s, 1H), 8.11 (d, 1H), 7.29 (s, 1H), 7.16 (d, 2H), 7.09 (d, 2H), 7.03 (d, 1H), 6.43 (bs, 2H), 3.65 (m, 1H), 3.12 (t, 2H), 2.99 (t, 2H), 2.56 (m, 2H), 2.35 (m, 2H), 2.32 (s, 3H), 1.16 (d, 3H). LRMS [M+H]=410.2

Example 180

(2R)-2-(1-(4-(2-(5-amino-8-methylbenzo[f][1,7]naphthyridin-2-yl)ethyl)phenyl)ethylamino)propan-1-ol

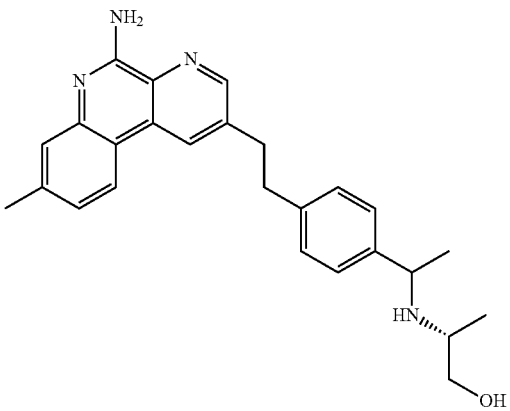 [SMILES: Cc1ccc2c(c1)nc(N)c1ncc(CCc3ccc(C(C)N[C@H](C)CO)cc3)cc12]

(2R)-2-(1-(4-(2-(5-amino-8-methylbenzo[f][1,7]naphthyridin-2-yl)ethyl)phenyl)ethylamino)propan-1-ol was prepared from 1-(4-(2-(5-amino-8-methylbenzo[f][1,7]naphthyridin-2-yl)ethyl)phenyl)ethanone (from Example 168) and (R)-2-aminopropan-1-ol (commercially available) following the procedures described for Example 179. ¹H NMR (Acetone-d₆): δ: 8.94 (m, 2H), 8.45 (m, 1H), 7.64 (d, 2H), 7.59 (s, 1H), 7.55 (br s, 2H), 7.41 (m, 3H), 4.65 (m, 1H), 3.81 (m, 1H), 3.35 (t, 2H), 3.25 (t, 2H), 2.56 (s, 3H), 1.73 (m, 3H), 1.29 (d, 3H), 1.23 (d, 3H). LRMS [M+H]=415.2

Example 181

8-methyl-2-(4-(1-(piperazin-1-yl)ethyl)phenethyl)benzo[f][1,7]naphthyridin-5-amine

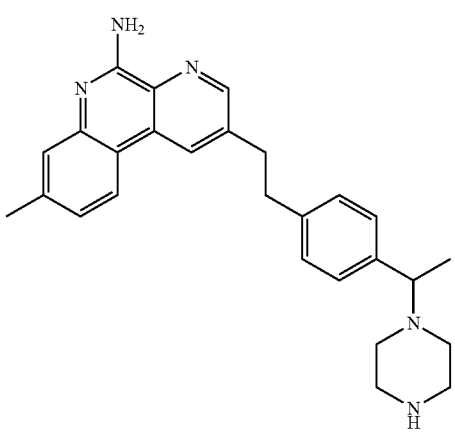 [SMILES: Cc1ccc2c(c1)nc(N)c1ncc(CCc3ccc(C(C)N4CCNCC4)cc3)cc12]

8-Methyl-2-(4-(1-(piperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 168) and piperazine (commercially available) following the procedures described for Example 179. $^1$H NMR (Methanol-$d_4$) TFA Salt: δ 8.83 (s, 1H), 8.75 (s, 1H), 8.39 (d, 1H), 7.51 (s, 1H), 7.46 (d, 1H), 7.26 (m, 4H), 3.62 (m, 1H), 3.25 (t, 2H), 3.12 (t, 2H), 2.80 (m, 4H), 2.69 (m, 4H), 2.56 (s, 3H), 1.42 (d, 3H). LRMS [M+H]=426.2

Example 182

((2S)-1-(1-(4-(2-(5-amino-8-methylbenzo[f][1,7]naphthyridin-2-yl)ethyl)phenyl)ethyl)pyrrolidin-2-yl)methanol

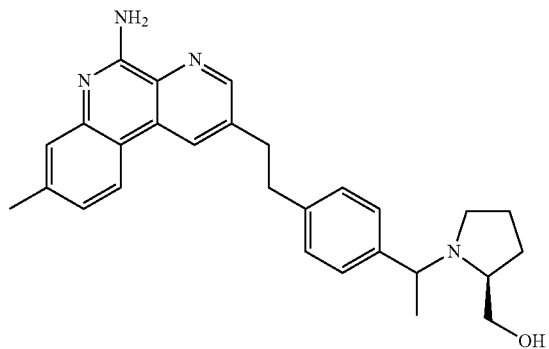 [SMILES: Cc1ccc2c(c1)nc(N)c1ncc(CCc3ccc(C(C)N4CCC[C@H]4CO)cc3)cc12]

((2S)-1-(1-(4-(2-(5-Amino-8-methylbenzo[f][1,7]naphthyridin-2-yl)ethyl)phenyl)ethyl)pyrrolidin-2-yl)methanol was prepared from 1-(4-(2-(5-amino-8-methylbenzo[f][1,7]naphthyridin-2-yl)ethyl)phenyl)ethanone (from Example 168) and (S)-pyrrolidin-2-ylmethanol (commercially available) following the procedures described for Example 179. $^1$H NMR (Acetone-$d_6$) TFA Salt: δ 8.83 (s, 1H), 8.80 (s, 1H), 8.43 (d, 1H), 7.36-7.53 (m, 6H), 4.68 (m, 1H), 3.69 (m, 2H), 3.19-3.21 (m, 4H), 2.55 (m, 4H), 1.75-1.78 (m, 6H), 1.74 (d, 3H). LRMS [M+H]=441.2

Example 183

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine

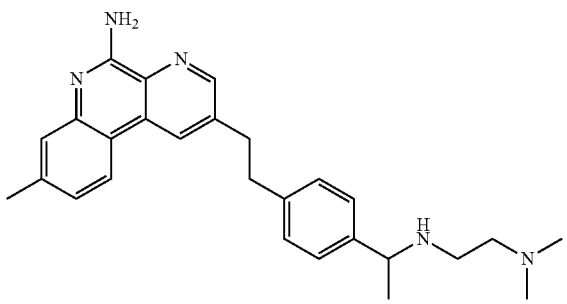

$N^1$-(1-(4-(2-(5-amino-8-methylbenzo[f][1,7]naphthyridin-2-yl)ethyl)phenyl)ethyl)-$N^2$,$N^2$-dimethylethane-1,2-diamine was prepared from 1-(4-(2-(5-amino-8-methylbenzo[f][1,7]naphthyridin-2-yl)ethyl)phenyl)ethanone (from Example 168) and $N^1$,$N^1$-dimethylethane-1,2-diamine (commercially available) following the procedures described for Example 179. $^1$H NMR (Acetone-$d_6$) TFA Salt: δ 8.85 (m, 2H), 8.43 (d, 1H), 7.52 (s, 1H), 7.48 (m, 2H), 7.40 (m, 2H), 6.69 (m, 1H), 4.39 (m, 1H), 3.42 (m, 2H), 3.18-3.25 (m, 6H), 2.87 (s, 6H), 2.56 (s, 3H), 1.69 (d, 3H). LRMS [M+H]=428.2

Example 184

3-(1-(4-(2-(5-amino-8-methylbenzo[f][1,7]naphthyridin-2-yl)ethyl)phenyl)ethylamino)propanoic acid

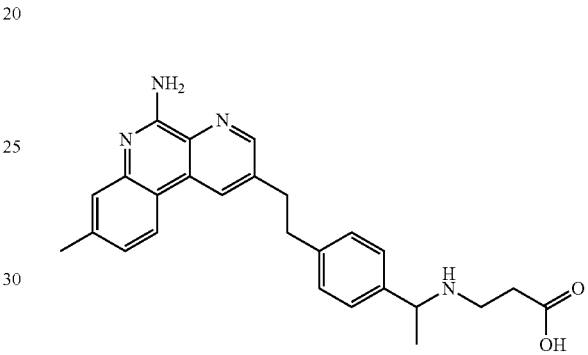

A solution of 1-(4-(2-(5-amino-8-methylbenzo[f][1,7]naphthyridin-2-yl)ethyl)phenyl)ethanone (from Example 168) (1 eq), 3-aminopropanoic acid (commercially available) (5 eq), triethylamine (3 eq) dissolved in absolute ethanol (0.042M) was stirred at 50° C. for 3 hours. The mixture was cooled to 0° C. and NaCNBH$_3$ (1 eq) was added and the reaction mixture was stirred for another six hours at room temperature. Then another equivalent of NaCNBH$_3$ was added and the reaction mixture was stirred at 50° C. for another hour. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous MgSO$_4$, and concentrated en vaccuo. The crude material was purified by Preparative HPLC on a 19×50 mm ATLANTIS® 10 micron C18 (Waters Corp.) system using 10-90% Acetonitrile (0.035% TFA) in Water (0.05% TFA) to give 3-(1-(4-(2-(5-amino-8-methylbenzo[f][1,7]naphthyridin-2-yl)ethyl)phenyl)ethylamino)propanoic acid a white solid as a TFA salt. $^1$H NMR (Methanol-$d_4$) TFA Salt: δ 8.74 (s, 1H), 8.42 (d, 1H), 7.66 (m, 2H), 7.50 (m, 1H), 7.31 (d, 2H), 7.23 (m, 2H), 4.24 (m, 1H), 3.21 (t, 2H), 3.14 (t, 2H), 2.75-3.10 (m, 2H), 2.51 (t, 2H), 2.10 (s, 3H), 1.55 (d, 3H). LRMS [M+H]=429.2

Example 185

8-methyl-2-(4-(1-(4-methylpiperazin-1-yl)ethyl)phenethyl)benzo[f][1,7]naphthyridin-5-amine

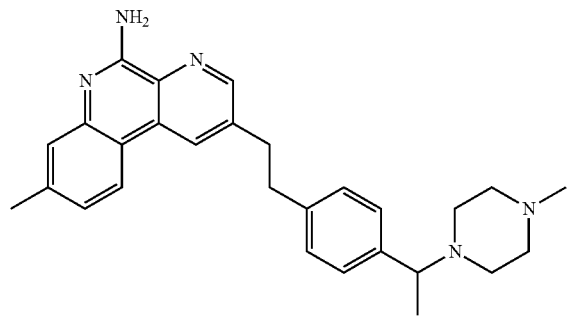

8-Methyl-2-(4-(1-(4-methylpiperazin-1-yl)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 168) and 1-methylpiperazine (commercially available) following the procedures described for Example 179. $^1$H NMR (Acetone-d$_6$) TFA Salt: δ 8.84 (s, 1H), 8.80 (s, 1H), 8.41 (d, 1H), 7.52 (s, 1H), 7.42-7.46 (m, 3H), 7.36-7.38 (m, 2H), 3.53 (m, 1H), 3.18 (m, 2H), 3.12 (m, 2H), 2.92 (s, 2H), 2.66 (s, 2H), 2.56 (s, 2H), 2.16 (s, 3H), 1.99 (m, 2H), 1.69 (d, 3H), 1.30 (s, 3H). LRMS [M+H]=440.2

Example 186

N$^2$-(1-(4-(2-(5-amino-8-methylbenzo[f][1,7]naphthyridin-2-yl)ethyl)phenyl)ethyl)-N$^1$,N$^1$-dimethylpropane-1,2-diamine

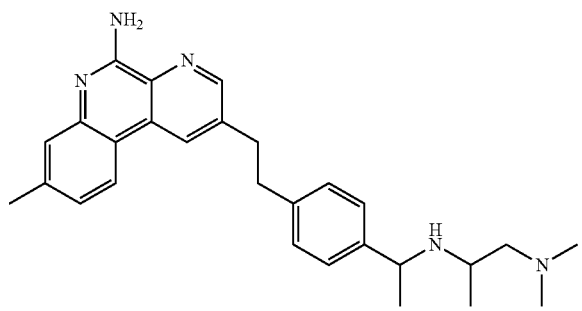

N$^2$-(1-(4-(2-(5-amino-8-methylbenzo[f][1,7]naphthyridin-2-yl)ethyl)phenyl)ethyl)-N$^1$,N$^1$-dimethylpropane-1,2-diamine was prepared from 1-(4-(2-(5-amino-8-methylbenzo[f][1,7]naphthyridin-2-yl)ethyl)phenyl)ethanone (from Example 168) and N$^1$,N$^1$-dimethylpropane-1,2-diamine (commercially available) following the procedures described for Example 179. $^1$H NMR (Acetone-d$_6$) TFA Salt: δ 8.83 (m, 2H), 8.40 (d, 1H), 7.46-7.51 (m, 3H), 7.43 (m, 1H), 7.37 (d, 2H), 4.54 (m, 1H), 3.74 (m, 1H), 3.19 (m, 4H), 2.90 (s, 3H), 2.77 (s, 3H), 2.55 (s, 3H), 2.41 (d, 2H), 1.66 (d, 3H), 1.39 (d, 3H). LRMS [M+H]=442.2

Example 187

8-methyl-2-(4-(1-(2-(pyridin-4-yl)ethylamino)ethyl)phenethyl)benzo[f][1,7]naphthyridin-5-amine

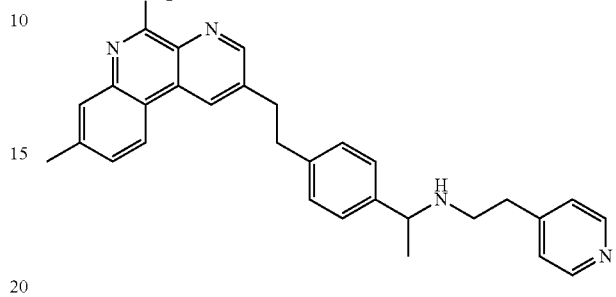

8-Methyl-2-(4-(1-(2-(pyridin-4-yl)ethylamino)ethyl)phenethyl)benzo[f][1,7]naphthyridin-5-amine was prepared from 1-(4-(2-(5-amino-8-methylbenzo[f][1,7]naphthyridin-2-yl)ethyl)phenyl)ethanone (from Example 168) and 2-(pyridin-4-yl)ethanamine (commercially available) following the procedures described for Example 179. $^1$H NMR (Acetone-d$_6$) TFA Salt: δ 8.94 (m, 2H), 8.92 (d, 2H), 8.73 (s, 1H), 8.43 (d, 1H), 7.60 (m, 2H), 7.40 (m, 2H), 7.16-7.26 (m, 3H), 4.55 (m, 1H), 3.55 (m, 4H), 2.56 (m, 4H), 2.12 (s, 3H), 1.73 (d, 3H) LRMS [M+H]=462.2

Example 188

N$^1$-(1-(4-(2-(5-amino-8-methylbenzo[f][1,7]naphthyridin-2-yl)ethyl)phenyl)ethyl)-N$^2$,N$^2$-diethylethane-1,2-diamine

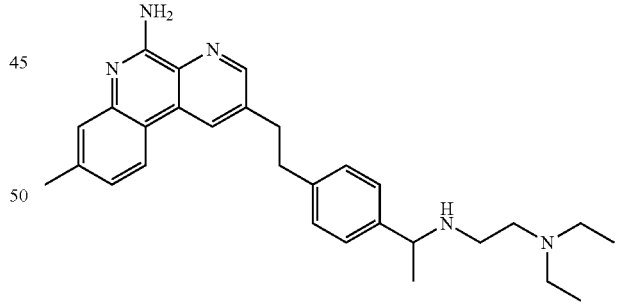

N$^1$-(1-(4-(2-(5-amino-8-methylbenzo[f][1,7]naphthyridin-2-yl)ethyl)phenyl)ethyl)-N$^2$,N$^2$-diethylethane-1,2-diamine was prepared from 1-(4-(2-(5-amino-8-methylbenzo[f][1,7]naphthyridin-2-yl)ethyl)phenyl)ethanone (from Example 168) and N$^1$,N$^1$-diethylethane-1,2-diamine (commercially available) following the procedures described for Example 179. $^1$H NMR (Acetone-d$_6$) TFA Salt: δ: 8.81 (s, 1H), 8.75 (s, 1H), 8.23 (d, 1H), 7.60 (d, 2H), 7.39 (d, 2H), 7.28 (m, 2H), 4.51 (m, 1H), 3.82 (m, 1H), 3.62 (m, 1H), 3.34 (m, 4H), 3.20 (t, 2H), 2.46 (s, 3H), 2.10 (m, 4H), 1.74 (d, 3H), 1.34 (t, 6H). LRMS [M+H]=456.2

Example 189

2-(4-(dimethylamino)-2-methylphenethyl)-8-methyl-benzo[f][1,7]naphthyridin-5-amine

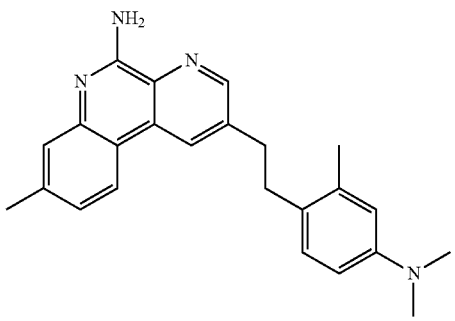

Step 1: 4-iodo-N,N,3-trimethylaniline

To a solution of 4-iodo-3-methylaniline (commercially available) (1 eq), NaHCO₃ (2.5 eq), and iodomethane (2.5 eq), in DMF ((0.2M) was stirred at ambient temperature overnight. The reaction mixture was then diluted with ethyl acetate and water. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-80% ethyl acetate in hexane and 4-iodo-N,N,3-trimethylaniline was isolated as a yellow solid.

Step 2: Synthesis was of: N,N,3-trimethyl-4-((trimethylsilyl)ethynyl)aniline To a solution of 4-iodo-N,N,3-trimethylaniline (from the previous step) (1 eq), ethynyltrimethylsilane (1.5 eq), dichlorobis(triphenylphosphine)-palladium (II) (20 mol %), copper iodide (20 mol %) and triethylamine (0.4 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and N,N,3-trimethyl-4-((trimethylsilyl)ethynyl)aniline was isolated as a yellow solid.

Step 3: 4-ethynyl-N,N, 3-trimethylaniline

To a solution of N,N-3-trimethyl-4-((trimethylsilyl)ethynyl)aniline (from the previous step) (1 eq), K₂CO₃ (2.5 eq), in MeOH ((0.15M) was stirred at ambient temperature for six hours. The solids were filtered out, and the liquid was concentrated en vaccuo. The crude material was purified by flash chromatography on a COMBIFLASH® system (ISCO) using 0-80% ethyl acetate in hexane and 4-ethynyl-N,N-3-trimethylaniline was isolated as a yellow solid.

Step 4: 3-chloro-5-((4-(dimethylamino)-2-methylphenyl)ethynyl) picolinonitrile To a solution of 4-ethynyl-N,N-3-trimethylaniline (from the previous step) (1 eq) 3,5-dichloropicolinonitrile (1.2 eq), dichlorobis(triphenylphosphine)-palladium (II) (10 mol %), copper iodide (10 mol %) and DMF: triethylamine (0.28 M) was stirred at ambient temperature overnight. The reaction mixture was then diluted with ethyl acetate and ammonium chloride solution. The two phases were separated, and the aqueous phase was extracted twice with ethyl acetate. The combined organic layers were washed with brine, dried over sodium sulfate, and concentrated en vaccuo. The crude material was purified by flash chromatography on a COMBIFLASH® system (ISCO) using 0-100% ethyl acetate in hexane and 3-chloro-5-((4-(dimethylamino)-2-methylphenyl)ethynyl)picolinonitrile was isolated as a off-yellow solid.

Step 5: 2((4-(dimethylamino)-2-methylphenyl)ethynyl)-8-methylbenzo[f][1,7]naphthyridin-5-amine A solution of tert-butyl 5-methyl-2-(4,4,5,5-tetramethyl-1,3,2-dioxaborolan-2-yl)phenylcarbamate (1.3 eq.) and 3-chloro-5-((4-(dimethylamino)-2-methylphenyl)ethynyl) picolinonitrile (from the previous step) (1.0 eq.), tetrakis (triphenyl-phosphine)palladium (10 mol %), and 2N aqueous sodium carbonate solution (2.0 eq.) in toluene/ethanol (2:1, 0.17 M) was stirred at 100° C. overnight. After cooling to ambient temperature, the reaction mixture was diluted with methanol. The insoluble solids were filtered off, and the filtrate was concentrated en vaccuo to obtain a crude residue. The crude material was purified by flash chromatography on a COMBIFLASH® system (ISCO) using 0-80% ethyl acetate in hexane to give 2-((4-(dimethylamino)-2-methylphenyl)ethynyl)-8-methylbenzo[f][1,7]naphthyridin-5-amine as a yellow solid.

Step 6: 2-(4-(dimethylamino)-2-methylphenethyl)-8-methylbenzo[f][1,7]naphthyridin-5-amine To a solution of 2-((4-(dimethylamino)-2-methylphenyl)ethynyl)-8-methylbenzo[f][1,7]naphthyridin-5-amine (1 eq), (from the previous step) in ethyl acetate/ethanol (1:5, 0.035 M) was added 10% wt palladium on carbon (0.2 eq.). Hydrogen gas was introduced via a balloon, and the reaction was stirred for 3.5 hours. The mixture was filtered through a pad of celite, washing with dichloromethane. The filtrate was concentrated en vaccuo and purified by preparative HPLC on a 19×50 mm ATLANTIS® 10 micron C18 (Waters Corp.) system using 10-90% Acetonitrile (0.035% TFA) in Water (0.05% TFA) to give 2-(4-(dimethylamino)-2-methylphenethyl)-8-methylbenzo[f][1,7]naphthyridin-5-amine as a white solid as a TFA salt. ¹H NMR (Acetone-d₆) TFA Salt: δ 8.81 (s, 1H), 8.74 (s, 1H), 8.34 (d, 1H), 7.89 (s, 1H), 7.47 (m, 2H), 7.38 (m, 2H), 3.34 (s, 6H), 3.32 (t, 2H), 3.28 (t, 2H), 2.57 (s, 3H), 2.34 (s, 3H). LRMS [M+H]=371.2

Example 190

1-(1-(4-(2-(5-amino-8-methylbenzo[f][1,7]naphthyridin-2-yl)ethyl)phenyl)ethyl)pyrrolidine-3-carboxylic acid

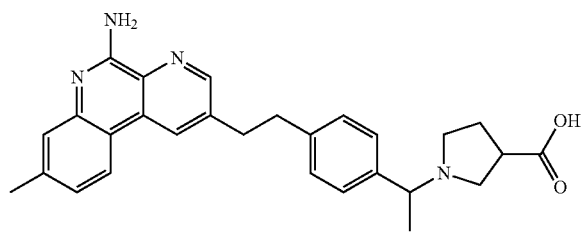 [SMILES: Cc1ccc2c(c1)nc(N)c1ncc(CCc3ccc(C(C)N4CCC(C(=O)O)C4)cc3)cc12]

1-(1-(4-(2-(5-Amino-8-methylbenzo[f][1,7]naphthyridin-2-yl)ethyl)phenyl)ethyl)pyrrolidine-3-carboxylic acid was prepared from 1-(4-(2-(5-amino-8-methylbenzo[f][1,7]naphthyridin-2-yl)ethyl)phenyl)ethanone (from Example 168) and pyrrolidine-3-carboxylic acid (commercially available) following the procedures described for Example 184, except that in this case, acetic acid was used instead of triethylamine (30%). $^1$H NMR (Acetone-$d_6$) TFA Salt: δ 8.81 (s, 1H), 8.75 (s, 1H), 8.70 (s, 1H), 8.28 (d, 1H), 7.59 (d, 2H), 7.37 (m, 3H), 4.46 (m, 1H), 4.21 (m 1H), 3.45 (m, 2H), 3.32 (m, 2H), 3.21 (m, 2H), 3.17 (m, 2H), 2.27 (m, 2H), 2.07 (s, 3H) 1.77 (d, 3H). LRMS [M+H]=455.2

Example 191

4-(1-(4-(2-(5-amino-8-methylbenzo[f][1,7]naphthyridin-2-yl)ethyl)phenyl)ethylamino)phenol

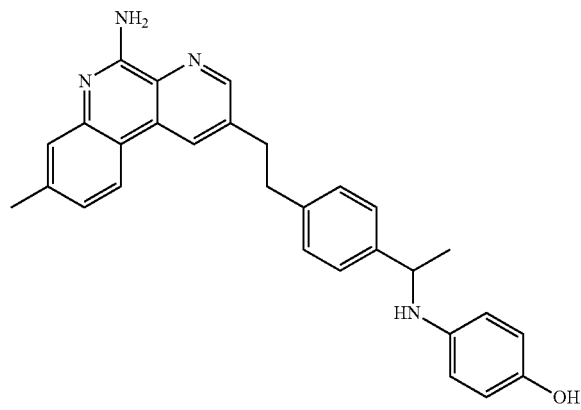 [SMILES: Cc1ccc2c(c1)nc(N)c1ncc(CCc3ccc(C(C)Nc4ccc(O)cc4)cc3)cc12]

4-(1-(4-(2-(5-Amino-8-methylbenzo[f][1,7]naphthyridin-2-yl)ethyl)phenyl)ethylamino)phenol was prepared from 1-(4-(2-(5-amino-8-methylbenzo[f][1,7]naphthyridin-2-yl)ethyl)phenyl)ethanone (from Example 168) and 4-aminophenol following the procedures described for Example 184, except that in this case, acetic acid was used instead of triethylamine (28%). $^1$H NMR (Acetone-$d_6$) TFA Salt: δ 8.83 (s, 1H), 8.73 (s, 1H), 8.33 (d, 1H), 7.44 (s, 1H), 7.40 (d, 2H), 7.36 (d, 1H), 7.24 (d, 2H), 7.10 (d, 2H), 6.76 (d, 2H), 4.72 (m, 1H) 3.27 (t, 2H), 3.12 (t, 2H), 2.50 (s, 3H), 2.06 (d, 3H). LRMS [M+H]=449.2

Example 192

1-(1-(4-(2-(5-amino-8-methylbenzo[f][1,7]naphthyridin-2 yl)ethyl)phenyl)ethyl)pyrrolidin-3-ol

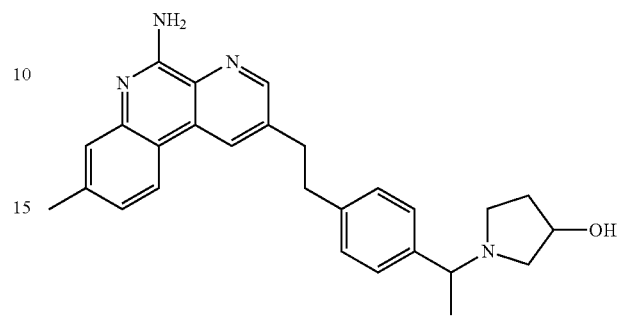

1-(1-(4-(2-(5-Amino-8-methylbenzo[f][1,7]naphthyridin-2yl)ethyl)phenyl)ethyl)pyrrolidin-3-ol was prepared from 1-(4-(2-(5-amino-8-methylbenzo[f][1,7]naphthyridin-2-yl) ethyl)phenyl)ethanone (from Example 168) and pyrrolidin-3-ol following the procedures described for Example 184, except that in this case, acetic acid was used instead of triethylamine (20%). $^1$H NMR (Acetone-$d_6$) TFA Salt: δ 8.83 (s, 1H), 8.76 (s, 1H), 8.72 (s, 1H), 8.29 (d, 1H), 7.57 (s, 1H), 7.42 (s, 1H), 7.33-7.38 (m, 3H), 4.41 (m, 2H), 3.77 (m, 2H), 3.33 (t, 2H), 3.21 (t, 2H), 3.19 (m, 2H), 3.10 (m, 2H), 2.10 (s, 3H), 1.75 (d, 3H). LRMS [M+H]=427.2

Example 193

2-(4-(2-aminopropan-2-yl)phenethyl)-8-methylbenzo[f][1,7]naphthyridin-5-amine

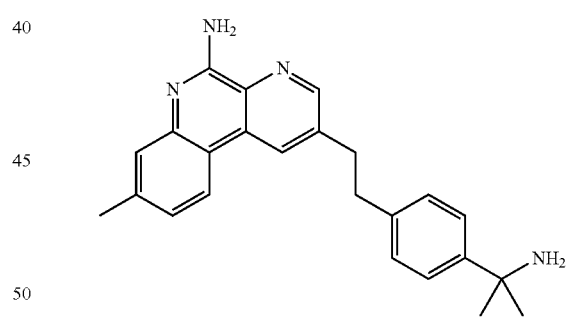

To a solution of 4-(2-(5-amino-8-methylbenzo[f][1,7] naphthyridin-2-yl)ethyl)benzonitrile (from Example 61, step 1) (1 eq), dissolved in dry THF (0.029M) was added very slowly methyl magnesium bromide (6 eq) and the reaction mixture was stirred at room temperature for half hour. Then was added to the reaction flask titanium tetra-isopropoxide (3 eq) over ten minutes. The reaction mixture was refluxed for 16 hours. After cooling to ambient temperature the reaction mixture was diluted with ethyl acetate and saturated ammonium chloride. The two phases were separated, and the aqueous layer was extracted twice with ethyl acetate. The combined organic layers were washed with brine, dried over anhydrous $MgSO_4$, and concentrated en vaccuo. The crude material was purified by Preparative HPLC on a 19×50 mm ATLANTIS® 10 micron C18 (Waters Corp.)

system using 10-90% Acetonitrile (0.035% TFA) in Water (0.05% TFA) to give 2-(4-(2-aminopropan-2-yl)phenethyl)-8-methylbenzo[f][1,7]naphthyridin-5-amine as a white solid of TFA salt. $^1$H NMR (Methanol-$d_4$) TFA Salt δ: 9.01 (s, 2H), 8.92 (s, 1H), 8.42 (s, 1H), 7.65 (d, 2H), 7.56 (s, 1H), 7.39 (m, 2H), 3.19 (m, 4H), 2.54 (s, 3H), 1.82 (6H). LRMS [M+H]=371.2.

Example 194

N-(2-acetamidoethyl)-4-(2-(5-amino-8-methylbenzo[f][1,7]naphthyridin-2-yl)ethyl)-3-methylbenzamide

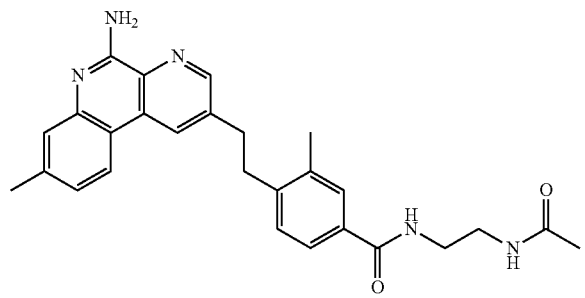 [SMILES: CC(=O)NCCNC(=O)c1ccc(CCc2cnc3c(N)nc4cc(C)ccc4c3c2)c(C)c1]

To a solution of 4-(2-(5-amino-8-methylbenzo[f][1,7]naphthyridin-2-yl)ethyl)-3-methylbenzoyl chloride (Example 113/Step 2) and triethylamine (2.5 eq.) in ether (0.05 M) was added N-(2-aminoethyl)acetamide (5.0 eq.). The reaction mixture was stirred for overnight. Then the reaction mixture was diluted with ethyl acetate and water. The two phases were separated, and the aqueous layer was extracted twice with ethyl acetate. The combined organic layers were washed with brine, dried over anhydrous MgSO$_4$, and concentrated en vaccuo. The crude material was purified by flash chromatography on a COMBIFLASH® system (ISCO) using 0-80% ethyl acetate in hexane to give N-(2-acetamidoethyl)-4-(2-(5-amino-8-methylbenzo[f][1,7]naphthyridin-2-yl)ethyl)-3-methylbenzamide as a white solid. $^1$H NMR (CDCl$_3$): δ 8.61 (s, 1H), 8.38 (s, 1H), 8.07 (d, 1H), 7.65 (s, 1H), 7.51-7.56 (m, 2H), 7.10-7.16 (m, 2H), 6.25 (br, 2H), 3.50-3.59 (m, 4H), 3.08-3.16 (m, 4H), 2.62 (s, 3H), 2.52 (s, 3H), 2.35 (s, 3H). LRMS [M+H]=455.2.

Example 195

Preparation of 4-(2-(5-amino-8-methylbenzo[f][1,7]naphthyridin-2-yl)ethyl)-3-methylphenol

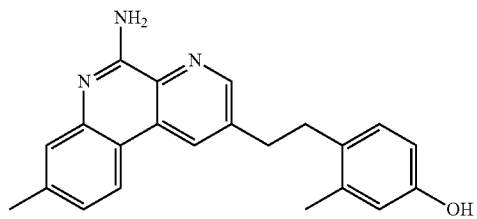 [SMILES: Cc1ccc2c(c1)nc(N)c1ncc(CCc3ccc(O)cc3C)cc12]

Step 1: 3-chloro-5-((4-methoxy-2-methylphenyl)ethynyl)picolinonitrile

To a round bottom flask capped with septa was added 1-ethynyl-4-methoxy-2-methylbenzene (1.1 eq), 3,5-dichloropicolinonitrile (1 eq.), triethylamine (5 eq.), and anhydrous DMF (0.2 M). The mixture was degassed (vacuum) and nitrogen flushed three times. CuI (0.05 eq.) and bis(triphenylphosphine)dichloro-palladium(II) (0.05 eq) were added and the septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-methoxy-2-methylphenyl)ethynyl)picolinonitrile.

Step 2: 2-((4-methoxy-2-methylphenyl)ethynyl)-8-methylbenzo[f][1,7]naphthyridin-5-amine To a round bottom flask with refluxing condenser were added 3-chloro-5-((4-methoxy-2-methylphenyl)ethynyl)picolinonitrile (from the previous step) (1 eq.), tert-butyl 2-(4,4,5,5-tetramethyl-1,3,2-dioxaborolan-2-yl)phenylcarbamate (see Scheme A above) (1.25 eq.), K$_3$PO$_4$ (2 eq.), tris(dibenzylideneacetone)dipalladium(0) (0.05 eq.), and 2-dicyclohexylphosphino-2',6'-dimethoxybiphenyl (Sphos) (0.1 eq.). n-butanol and water (5:2, 0.2 M) were added, and the content was degassed (vacuum followed by nitrogen flush) for three times. The reaction mixture was stirred vigorously under nitrogen at 100° C. overnight in an oil bath. The content was cooled and taken up in 200 mL of water followed by extraction with methylene chloride. Combined organic layers were dried (Na$_2$SO$_4$) and concentrated. Flash chromatography (silica gel, 0-50% EtOAc in CH$_2$Cl$_2$) afforded the product 2-((4-methoxy-2-methylphenyl)ethynyl)-8-methylbenzo[f][1,7]naphthyridin-5-amine Step 3: 2-(4-methoxy-2-methylphenethyl)-8-methylbenzo[f][1,7]naphthyridin-5-amine 2-(4-methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step). To a round bottom flask was added 2-((4-methoxy-2-methylphenyl)ethynyl)-8-methylbenzo[f][1,7]naphthyridin-5-amine (1 eq.) with a stirring bar. Ethanol and methylene chloride (1:2, 0.2 M) were added, followed by palladium in carbon (activated powder, wet, 10% on carbon, 0.1 eq.). The content was degassed (vacuum) followed by hydrogen flush (three times). The reaction mixture was stirred vigorously at room temperature overnight, under a hydrogen balloon. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in CH$_2$Cl$_2$) afforded the product 2-(4-methoxy-2-methylphenethyl)-8-methylbenzo[f][1,7]naphthyridin-5-amine $^1$H NMR (CDCl$_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2.

Step 4: 4-(2-(5-amino-8-methylbenzo[f][1,7]naphthyridin-2-yl)ethyl)-3-methylphenol To a stirred solution of 2-(4-methoxy-2-methylphenethyl)-8-methylbenzo[f][1,7]naphthyridin-5-amine (from the previous step) in methylene chloride (0.2 M) in an ice-water bath was added 1 N solution of BBr$_3$ (2 eq) in CH$_2$Cl$_2$ in a drop-wise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol as a white solid. $^1$H NMR (DMSO-d$_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2.

Tert-butyl 2-(4,4,5,5-tetramethyl-1,3,2-dioxaborolan-2-yl)phenylcarbamate,

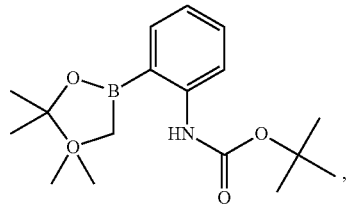

was prepared as follows:

Step 1: tert-butyl 2-bromo-5-methylphenylcarbamate

To a solution of 2-bromo-5-methylaniline (1.0 eq.) in tetrahydrofuran (0.2 M) at 0° C. under N$_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous MgSO$_4$, and concentrated en vacuo. The crude material was purified by flash chromatography on a COMBIFLASH® system (ISCO) using 0-5% ethyl acetate in hexane to give tert-butyl 2-bromo-5-methylphenylcarbamate as a light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from previous step) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under N$_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl)phenylcarbamate.

Example 196

Table A: Compound 6A

Preparation of 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonic acid

Step 1: Synthesis of diethyl 1,1-difluoro-3-(2-(2-iodoethoxy)ethoxy)propylphosphonate To a solution of diethyl difluoromethylphosphonate (1.0 equiv.) in THF (0.8 M) at −78° C. was slowly added a solution of LDA (2 M, 1.1 equiv.) in heptane/THF/ethylbenzene, and the mixture was vigorously stirred for 30 minutes. In a separate reaction flask, a solution of 1,2-bis(2-iodoethoxy)ethane (1.0 equiv.) in THF (0.8M) was cooled to −78° C. To this solution was transferred, by cannula, the freshly prepared alkyl lithium solution and the reaction mixture was allowed to stir for 1 hour at −78° C. At this point, the cooling bath was removed and the reaction mixture was allowed to warm to room temperature. The reaction mixture was then quenched with a 1 M aqueous solution of HCl. The resulting mixture was transferred to a separatory funnel and washed with CH$_2$Cl$_2$ three times. The combined organic layers were dried over anhydrous Na$_2$SO$_4$ and the volatiles were removed in vacuo. The resulting residue was purified by a COMBIFLASH® system (ISCO) using CH$_2$Cl$_2$ to provide diethyl 1,1-difluoro-3-(2-(2-iodoethoxy)ethoxy)propylphosphonate as a yellow oil. $^1$H NMR (CDCl$_3$): δ 4.23-4.31 (m, 4H), 3.75-3.80 (m, 4H), 3.60-3.67 (m, 4H), 3.26 (t, 2H), 2.33-2.50 (m, 2H), 1.38 (t, 6H).

Step 2: Synthesis of diethyl 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonate To a solution of 4-(2-(5-amino-8-methylbenzo[f][1,7]naphthyridin-2-yl)ethyl)-3-methylphenol (4) (1.0 equiv.) in dimethylformamide (0.10 M) at 22° C. was added 60% dispersion of sodium hydride in mineral oil (1.5 equiv.) and the resulting mixture was allowed to stir for 30 minutes. At this point, diethyl 1,1-difluoro-3-(2-(2-iodoethoxy)ethoxy)propylphosphonate (1.2 equiv.) was added to this mixture. The reaction mixture was then allowed to stir for 18 hours, after which it was diluted with ethyl acetate and water. The biphasic layers were separated and the organic layer was washed twice with water. The organic layer was dried over anhydrous Na$_2$SO$_4$ and the volatiles were removed in vacuo. The resulting residue was purified by a COMBIFLASH® system (ISCO) using 0-50% ethyl acetate in hexanes gradient to provide diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate as a solid.

Step 3: Synthesis of 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonic acid To a solution of diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate (1.0 equiv.) in CH$_2$Cl$_2$ (0.10 M) at 0° C. was slowly added trimethylsilyl bromide (10 equiv.). After 1 hour the ice-bath was removed and the reaction mixture was allowed to stir at 22° C. for 18 hours. At this point, the volatiles were removed in vacuo and the resulting residue was purified by Reverse Phase-HPLC using a 20-90% 0.5 mM NH₄OAc (in MeCN) to 10 mM NH₄OAc (in water) gradient to deliver 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid as a solid. $^1$H NMR (Dimethylsulfoxide-d6): δ 8.83 (s, 1H), 8.68 (s, 1H), 8.32 (s, 1H), 7.34 (s, 1H), 7.14 (d, 1H), 7.09 (br, 2H), 7.08 (d, 1H), 6.74 (s, 1H), 6.68 (d, 1H), 4.01 (t, 2H), 3.70 (t, 2H), 3.61 (t, 2H), 3.54-3.59 (m, 2H), 3.48-3.50 (m, 2H), 3.07 (t, 2H), 2.94 (t, 2H), 2.43 (s, 3H), 2.25 (s, 3H), 2.06-2.21 (m, 2H). LRMS [M+H]=590.2

Example 197

Table A: Compound 16A

Preparation of 3-(5-amino-2-(4-(4,4-difluoro-4-phosphonobutoxy)-2-methylphenethyl)benzo[f][1,7]naphthyridin-8-yl)propanoic acid Step 1: (E)-ethyl 3-(3-(tert-butoxycarbonylamino)-4-chlorophenyl)acrylate A solution of tert-butyl 5-bromo-2-chlorophenylcarbamate (1.0 eq.), (E)-ethyl 3-(4,4,5,5-tetramethyl-1,3,2-dioxaborolan-2-yl)acrylate (1.5 eq.), tetrakis(triphenylphosphine)Palladium(0) (10 mol %), and potassium carbonate (2.0 eq.) in toluene/ethanol (10:1, 0.04 M) was stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-80% ethyl acetate in hexane to give the subtitle compound as a white solid.

Step 2: ethyl 3-(3-(tert-butoxycarbonylamino)-4-chlorophenyl)propanoate

To a solution of (E)-ethyl 3-(3-(tert-butoxycarbonylamino)-4-chlorophenyl)acrylate (Step 1) in ethyl acetate/ethanol (1:1, 0.05 M) was added wilkinson's catalyst (0.1 eq.). Hydrogen gas was introduced via a ballon, and the reaction was stirred for 24 hours. The mixture was filtered through a pad of celite, washed with dichloromethane. The filtrate was concentrated en vaccuo and purified by a COMBIFLASH® system (ISCO) using 0-80% ethyl acetate in hexane to give ethyl 3-(3-(tert-butoxycarbonylamino)-4-chlorophenyl)propanoate as a solid.

Step 3: ethyl 3-(3-(tert-butoxycarbonylamino)-4-(4,4,5,5-tetramethyl-1,3,2-dioxaborolan-2-yl)phenyl)propanoate A solution of ethyl 3-(3-(tert-butoxycarbonylamino)-4-chlorophenyl)propanoate (1.0 eq.), 4,4,4',4',5,5,5',5'-octamethyl-2,2'-bi(1,3,2-dioxaborolane) (2.0 eq.), tris(dibenzylideneacetone)dipalladium(0) (5 mol %), 2-dicyclohexylphosphino-2',4',6'-triisopropylbiphenyl (20 mol %), and potassium acetate (2.0 eq.) in 1,4-dioxane (0.04 M) was stirred at 100° C. overnight. After cooling to ambient temperature, the reaction content was concentrated en vaccuo. The crude material was purified by flash chromatography on a COMBIFLASH® system (ISCO) using 0-50% ethyl acetate in hexane to give the subtitle compound as an oil.

Step 4: 1-bromo-4-(methoxymethoxy)-2-methylbenzene

A solution of 4-bromo-3-methylphenol (1.0 eq.), and sodium hydride (1.5 eq.), in DMF (0.04 M) was stirred at room temperature for 30 minutes. Then chloro(methoxy)methane (1.5 eq.) was added slowly and stirred for 4 hours. The reaction content was diluted with ethyl acetate and water. The two phases were separated. The organic layer was washed twice with water, dried over anhydrous MgSO₄, and concentrated en vaccuo. The crude material was purified by flash chromatography on a COMBIFLASH® system (ISCO) using 0-50% ethyl acetate in hexane to give the subtitle compound as a white solid.

Step 5: triethyl((4-(methoxymethoxy)-2-methylphenyl)ethynyl)silane

A solution of 1-bromo-4-(methoxymethoxy)-2-methylbenzene (1.0 eq.), triethyl(ethynyl)silane (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction content was diluted with ethyl acetate and water. The two phases were separated. The organic layer was washed twice with water, dried over anhydrous MgSO₄, and concentrated en vaccuo. The crude material was purified by flash chromatography on a COMBIFLASH® system (ISCO) using 0-50% ethyl acetate in hexane to give the subtitle compound as a white solid.

Step 6: 1-ethynyl-4-(methoxymethoxy)-2-methylbenzene

To a stirred solution of triethyl((4-(methoxymethoxy)-2-methylphenyl)ethynyl)silane (1.0 eq.) in THF (0.2 M) was slowly added TBAF (0.2 eq.) at 0° C. Then the reaction mixture was stirred at 0° C. for 1 hour. After warmed to ambient temperature, the reaction content was diluted with ethyl acetate and water. The two phases were separated, and the aqueous layer was extracted twice with ethyl acetate. The combined organic layers were washed with brine, dried over anhydrous MgSO₄, and concentrated en vaccuo. The crude material was purified by flash chromatography on a COMBIFLASH® system (ISCO) using 0-50% ethyl acetate in hexane to give the subtitle compound as a white solid.

Step 7: 3-chloro-5-((4-(methoxymethoxy)-2-methylphenyl)ethynyl)picolinonitrile

A solution of 3,5-dichloropicolinonitrile (1.0 eq.), 1-ethynyl-4-(methoxymethoxy)-2-methylbenzene (1.0 eq.), bis(triphenyl-phosphine)palladium chloride (10 mol %), copper iodide (10 mol %), and triethylamine (5.0 eq.) in DMF (0.04 M) was stirred at 60° C. for 4 hours. After cooling to ambient temperature, the reaction content was diluted with ethyl acetate and water. The two phases were separated. The organic layer was washed twice with water, dried over anhydrous MgSO₄, and concentrated en vaccuo. The crude material was purified by flash chromatography on a COMBIFLASH® system (ISCO) using 0-80% ethyl acetate in hexane to give the subtitle compound as a white solid.

Step 8: ethyl 3-(5-amino-2-((4-(methoxymethoxy)-2-methylphenyl)ethynyl)-benzo[f][1,7]naphthyridin-8-yl)propanoate A solution of 3-chloro-5-((4-(methoxymethoxy)-2-methylphenyl)ethynyl)picolinonitrile (from step 7, 1.0 eq.), ethyl 3-(3-(tert-butoxycarbonylamino)-4-(4,4,5,5-tetramethyl-1,3,2-dioxaborolan-2-yl)phenyl)propanoate (from step 3, 1.5 eq.), Tris(dibenzylideneacetone)dipalladium(0) (10 mol %), dicyclohexyl(2',6'-dimethoxybiphenyl-2-yl)phosphine (20 mol %), and sodium bicarbonate (2.0 eq.) in n-butanol/$H_2O$ (5:1, 0.04 M) was stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a yellow solid.

Step 9: ethyl 3-(5-amino-2-(4-(methoxymethyl)-2-methylphenethyl)benzo[f][1,7]naphthyridin-8-yl)propanoate To a solution of ethyl 3-(5-amino-2-((4-(methoxymethoxy)-2-methylphenyl)ethynyl)benzo[f][1,7]naphthyridin-8-yl)propanoate (from step 8) in ethyl acetate/ethanol (1:1, 0.05 M) was added 10% wt palladium on carbon (0.2 eq.). Hydrogen gas was introduced via a balloon, and the reaction was stirred for 3 hours. The mixture was filtered through a pad of celite, washed with dichloromethane. The filtrate was concentrated en vaccuo and purified by a COMBIFLASH® system (ISCO) using 0-80% ethyl acetate in hexane to give ethyl 3-(5-amino-2-(4-(methoxymethyl)-2-methylphenethyl)benzo[f][1,7]naphthyridin-8-yl)propanoate as a solid.

Step 10: ethyl 3-(5-amino-2-(4-hydroxy-2-methylphenethyl)benzo[f][1,7]naphthyridin-8-yl)propanoate A solution of ethyl 3-(5-amino-2-(4-(methoxymethyl)-2-methylphenethyl)benzo[f][1,7]naphthyridin-8-yl)propanoate (1.0 eq.), and hydrogen chloride (1.0 eq.) in ethanol (0.04 M) was stirred at ambient temperature for 4 hours. Then the reaction content was diluted with ethyl acetate and water. The two phases were separated, and the aqueous layer was extracted twice with ethyl acetate. The combined organic layers were washed with brine, dried over anhydrous $MgSO_4$, and concentrated en vaccuo. The crude material was purified by flash chromatography on a COMBIFLASH® system (ISCO) using 0-80% ethyl acetate in hexane to give the subtitle compound as a white solid.

Step 11: ethyl 3-(5-amino-2-(4-(4-(diethoxyphosphoryl)-4,4-difluorobutoxy)-2-methylphenethyl)benzo[f][1,7]naphthyridin-8-yl)propanoate A solution of ethyl 3-(5-amino-2-(4-hydroxy-2-methylphenethyl)benzo[f][1,7]naphthyridin-8-yl)propanoate (1.0 eq.), and potassium carbonate (2.0 eq.) in DMF (0.04 M) was stirred for 30 minutes. Then diethyl 4-bromo-1,1-difluorobutylphosphonate (1.5 eq.) was added slowly and the resulting mixture was stirred at 50° C. overnight. After cooling to ambient temperature, the reaction content was diluted with ethyl acetate and water. The two phases were separated. The organic layer was washed twice with water, dried over anhydrous $MgSO_4$, and concentrated en vaccuo. The crude material was carried on to the next step without further purification.

Step 12: 4-(4-(2-(5-amino-8-(3-ethoxy-3-oxopropyl)benzo[f][1,7]naphthyridin-2-yl)ethyl)-3-methylphenoxy)-1,1-difluorobutylphosphonic acid A solution of ethyl 3-(5-amino-2-(4-(4-(diethoxyphosphoryl)-4,4-difluorobutoxy)-2-methylphenethyl)benzo[f][1,7]naphthyridin-8-yl)propanoate (from step 11, 1.0 eq.), and bromotrimethylsilane (10.0 eq.), in dichloromethane (0.04 M) was stirred at room temperature overnight. The reaction content was concentrated en vaccuo. The crude material was carried on to the next step without further purification.

Step 13: 3-(5-amino-2-(4-(4,4-difluoro-4-phosphonobutoxy)-2-methylphenethyl)benzo[f][1,7]naphthyridin-8-yl)propanoic acid A solution of 4-(4-(2-(5-amino-8-(3-ethoxy-3-oxopropyl)benzo[f][1,7]naphthyridin-2-yl)ethyl)-3-methylphenoxy)-1,1-difluorobutylphosphonic acid (1.0 eq.) and 1M sodium hydroxide (4 eq.) in ethanol (0.2 M) was stirred at 70° C. for 4 hour. After cooling to ambient temperature, the crude material was purified by reverse phase high performance liquid chromatography (HPLC) to give the subtitle compound as a white solid. $^1H$ NMR ($CD_3OD$): δ 8.68 (s, 1H), 8.44 (s, 1H), 8.22 (d, 1H), 7.53 (s, 1H), 7.45 (d, 1H), 6.88 (d, 1H), 6.69 (s, 1H), 6.60 (d, 1H), 3.95 (t, 2H), 3.10-3.20 (m, 4H), 3.01 (t, 2H), 2.72 (t, 2H), 2.22 (s, 3H), 1.99-2.05 (m, 4H). $^{19}F$ NMR (MeOD): 6-163.70. LRMS [M+H]=574.2

Other compounds for carrying out the present invention include:
2-methylbenzo[f][1,7]naphthyridin-5-amine; 2-propylbenzo[f][1,7]naphthyridin-5-amine; 2-(3-methoxyphenethyl)benzo[f][1,7]naphthyridin-5-amine; 8-methyl-2-phenethylbenzo[f][1,7]naphthyridin-5-amine; methyl-5-aminobenzo[f][1,7]naphthyridine-3-carboxylate; (5-aminobenzo[f][1,7]naphthyridin-3-yl)methanol; 2-(2-methylphenethyl)benzo[f][1,7]naphthyridin-5-amine; 2-(3-methylphenethyl)benzo[f][1,7]naphthyridin-5-amine; 2-(4-methylphenethyl)benzo[f][1,7]naphthyridin-5-amine; 8-methyl-2-(2-(naphthalen-1-yl)ethyl)benzo[f][1,7]naphthyridin-5-amine; 8-methyl-2-(2-(naphthalen-2-yl)ethyl)benzo[f][1,7]naphthyridin-5-amine; 4-(2-(5-amino-8-methylbenzo[f][1,7]naphthyridin-2-yl)ethyl)benzoic acid; 3-(2-(5-amino-8-methylbenzo[f][1,7]naphthyridin-2-yl)ethyl)benzoic acid; 2-(3-chlorophenethyl)-8-methylbenzo[f][1,7]naphthyridin-5-amine; 2-(2-chlorophenethyl)-8-methylbenzo[f][1,7]naphthyridin-5-amine; (3-(2-(5-amino-8-methylbenzo[f][1,7]naphthyridin-2-yl)ethyl)phenyl)methanol; 2-(4-chlorophenethyl)-8-methylbenzo[f][1,7]naphthyridin-5-amine; 2-(4-butylphenethyl)benzo[f][1,7]naphthyridin-5-amine; 2-(4-butylphenethyl)-8-methylbenzo[f][1,7]naphthyridin-5-amine; 2-(4-propylphenethyl)benzo[f][1,7]naphthyridin-5-amine; 2-(4-(trifluoromethyl)phenethyl)benzo[f][1,7]naphthyridin-5-amine; 2-(2,5-dimethylphenethyl)-8-methylbenzo[f][1,7]naphthyridin-5-amine; 8-methyl-2-(4-propylphenethyl)benzo[f][1,7]naphthyridin-5-amine; 8-methyl-2-(2,4,5-trimethylphenethyl)benzo[f][1,7]naphthyridin-5-amine; 2-(2,5-dimethylphenethyl)benzo[f][1,7]naphthyridin-5-amine; 2-(4-isopropylphenethyl)-8-methylbenzo[f][1,7]

naphthyridin-5-amine; 2-(4-heptylphenethyl)-8-methylbenzo[f][1,7]naphthyridin-5-amine; 2-(4-isobutoxyphenethyl)-8-methylbenzo[f][1,7]naphthyridin-5-amine; 2-(4-((2-methoxyethoxy)methoxy)phenethyl)-8-methylbenzo[f][1,7]naphthyridin-5-amine; 8-methyl-2-(4-(2-phenoxyethoxy)phenethyl)benzo[f][1,7]naphthyridin-5-amine; 8-methyl-2-(4-(4-phenylbutoxy)phenethyl)benzo[f][1,7]naphthyridin-5-amine; 2-(4-(allyloxy)phenethyl)-8-methylbenzo[f][1,7]naphthyridin-5-amine; 8-methyl-2-(4-(3-phenylpropoxy)phenethyl)benzo[f][1,7]naphthyridin-5-amine; 2-(4-(heptan-4-yloxy)phenethyl)-8-methylbenzo[f][1,7]naphthyridin-5-amine; 8-methyl-2-(4-(4-methylpent-3-enyloxy)phenethyl)benzo[f][1,7]naphthyridin-5-amine; 2-(4-(2-cyclohexylethoxy)phenethyl)-8-methylbenzo[f][1,7]naphthyridin-5-amine; 2-(4-isopropoxyphenethyl)-8-methylbenzo[f][1,7]naphthyridin-5-amine; 2-(4-(3,3-dimethylbutoxy)phenethyl)-8-methylbenzo[f][1,7]naphthyridin-5-amine; 8-(2-cyclopropylethyl)-2-(4-(dimethylamino)phenethyl)benzo[f][1,7]naphthyridin-5-amine; 8-(2-cyclopropylethyl)-2-(2,4-dimethylphenethyl)benzo[f][1,7]naphthyridin-5-amine; N-(4-(2-(5-aminobenzo[f][1,7]naphthyridin-2-yl)ethyl)phenyl)acetamide; N-(4-(2-(5-amino-8-methylbenzo[f][1,7]naphthyridin-2-yl)ethyl)phenyl)-4-methylbenzenesulfonamide; 3-methyl-9-p-tolyl-9,10-dihydrobenzo[f]furo[2,3-b][1,7]naphthyridin-6-amine; 4-(2-(5-amino-8-methylbenzo[f][1,7]naphthyridin-2-yl)ethyl)-3-methylbenzonitrile; 4-(2-(5-amino-8-methyl-benzo[f][1,7]naphthyridin-2-yl)ethyl)-N-(2-aminoethyl)-3-methylbenzamide; 8-methyl-2-(2-methyl-4-(1H-tetrazol-5-yl)phenethyl)benzo[f][1,7]naphthyridin-5-amine; methyl 2-(4-(2-(5-amino-8-methylbenzo[f][1,7]naphthyridin-2-yl)ethyl)-3-methylbenzamido)-4-methylpentanoate; methyl 2-(4-(2-(5-amino-8-methylbenzo[f][1,7]naphthyridin-2-yl)ethyl)-3-methylbenzamido)acetate; 2-(4-(2-(5-amino-8-methylbenzo[f][1,7]naphthyridin-2-yl)ethyl)-3-methylbenzamido)-4-methylpentanoic acid; 2-(4-(2-(5-amino-8-methylbenzo[f][1,7]naphthyridin-2-yl)ethyl)-3-methylbenzamido)acetic acid; 6-(5-amino-8-methylbenzo[f][1,7]naphthyridin-2-yl)hexan-1-ol; 7-(5-amino-8-methylbenzo[f][1,7]naphthyridin-2-yl)heptanoic acid; 11-(5-amino-8-methylbenzo[f][1,7]naphthyridin-2-yl)undecan-1-ol; ethyl 2-(4-(2-(5-amino-8-methylbenzo[f][1,7]naphthyridin-2-yl)ethyl)-3-methylphenoxy)acetate; 2-(4-(2-(5-amino-8-methylbenzo[f][1,7]naphthyridin-2-yl)ethyl)-3-methylphenoxy)acetic acid; 3-(4-(2-(5-amino-8-methylbenzo[f][1,7]naphthyridin-2-yl)ethyl)-3-methylphenoxy)propanoic acid; 6-(4-(2-(5-amino-8-methylbenzo[f][1,7]naphthyridin-2-yl)ethyl)-3-methylphenoxy)hexanoic acid; 8-methyl-2-(2-methyl-4-(methylthio)phenethyl)benzo[f][1,7]naphthyridin-5-amine; 8-methyl-2-(4-(methylsulfonyl)phenethyl)benzo[f][1,7]naphthyridin-5-amine; 2-(4-(hexyloxy)phenethyl)-8-methylbenzo[f][1,7]naphthyridin-5-amine; 8-methyl-2-(4-phenethoxyphenethyl)benzo[f][1,7]naphthyridin-5-amine; 8-methyl-2-(4-(pentyloxy)phenethyl)benzo[f][1,7]naphthyridin-5-amine; 8-methyl-2-(4-(4-methylpentyloxy)phenethyl)benzo[f][1,7]naphthyridin-5-amine; 2-(2-fluorophenethyl)benzo[f][1,7]naphthyridin-5-amine; 2-(3-fluorophenethyl)benzo[f][1,7]naphthyridin-5-amine; 2-(4-fluorophenethyl)benzo[f][1,7]naphthyridin-5-amine; 2-(2-(thiophen-3-yl)ethyl)benzo[f][1,7]naphthyridin-5-amine; (5-aminobenzo[f][1,7]naphthyridin-2-yl)methanol; 2-(3,4-dimethylphenethyl)benzo[f][1,7]naphthyridin-5-amine; 2-(3,4-dimethylphenethyl)-8-methylbenzo[f][1,7]naphthyridin-5-amine; 2-(3,5-dimethylphenethyl)-8-methylbenzo[f][1,7]naphthyridin-5-amine; 2-(2-(benzofuran-5-yl)ethyl)-8-methylbenzo[f][1,7]naphthyridin-5-amine; 8-methyl-2-(2-nitroethyl)benzo[f][1,7]naphthyridin-5-amine; 2-(aminomethyl)-8-methylbenzo[f][1,7]naphthyridin-5-amine; $N^2$,8-dimethylbenzo[f][1,7]naphthyridine-2,5-diamine; 2-(5-amino-8-methylbenzo[f][1,7]naphthyridin-2-yl)-1-phenylethanol; 2-(5-amino-8-methylbenzo[f][1,7]naphthyridin-2-yl)-1-(4-methoxyphenyl)ethanol; 2-(biphenyl-2-yl)-8-methylbenzo[f][1,7]naphthyridin-5-amine; 2-(2-(2,6-dimethylpyridin-3-yl)ethyl)-8-methylbenzo[f][1,7]naphthyridin-5-amine; 2-(2-(5-methoxypyridin-2-yl)ethyl)-8-methylbenzo[f][1,7]naphthyridin-5-amine; 3-(4-(2-(5-amino-8-methylbenzo[f][1,7]naphthyridin-2-yl)ethyl)phenyl)propanoic acid; 5-(2-(5-amino-8-methylbenzo[f][1,7]naphthyridin-2-yl)ethyl)-4-methylpyridin-2(1H)-one; 6-(2-(5-amino-8-methylbenzo[f][1,7]naphthyridin-2-yl)ethyl)pyridin-3-ol; 8-methyl-2-(4-(trifluoromethoxy)phenethyl)benzo[f][1,7]naphthyridin-5-amine; 2-(2-(2,3-dihydro-1H-inden-5-yl)ethyl)-8-methylbenzo[f][1,7]naphthyridin-5-amine; 2-(2-(2,3-dihydro-1H-inden-5-yl)ethyl)benzo[f][1,7]naphthyridin-5-amine; (E)-3-(4-(2-(5-amino-8-methylbenzo[f][1,7]naphthyridin-2-yl)ethyl)-3-methylphenyl)acrylic acid; (E)-8-(2-cyclopropylvinyl)-2-phenethylbenzo[f][1,7]naphthyridin-5-amine; 8-pentylbenzo[f][1,7]naphthyridin-5-amine; (E)-8-(2-cyclopropylvinyl)benzo[f][1,7]naphthyridin-5-amine; 8-(2-cyclopropylethyl)-2-phenethylbenzo[f][1,7]naphthyridin-5-amine; 3-(2-(5-aminobenzo[f][1,7]naphthyridin-2-yl)ethyl)phenol; 2-(2-methoxyphenethyl)benzo[f][1,7]naphthyridin-5-amine; 2-(4-ethylphenethyl)benzo[f][1,7]naphthyridin-5-amine; 2-(4-ethylphenethyl)-8-methylbenzo[f][1,7]naphthyridin-5-amine; 2-(4-(dimethylamino)phenethyl)benzo[f][1,7]naphthyridin-5-amine; 2-(4-(piperidin-1-yl)phenethyl)benzo[f][1,7]naphthyridin-5-amine; 2-(4-tert-butylphenethyl)-8-methylbenzo[f][1,7]naphthyridin-5-amine; 8-methyl-2-(4-(piperidin-1-yl)phenethyl)benzo[f][1,7]naphthyridin-5-amine; 2-(4-methoxyphenethyl)-8-methylbenzo[f][1,7]naphthyridin-5-amine; 2-(3,5-dimethoxyphenethyl)-8-methylbenzo[f][1,7]naphthyridin-5-amine; 8-methyl-2-(2-(trifluoromethyl)phenethyl)benzo[f][1,7]naphthyridin-5-amine; 4-(2-(5-amino-8-methylbenzo[f][1,7]naphthyridin-2-yl)ethyl)-N-hydroxybenzimidamide; 4-(2-(5-amino-8-methylbenzo[f][1,7]naphthyridin-2-yl)ethyl)benzonitrile; 8-methyl-2-(4-(1-morpholinoethyl)phenethyl)benzo[f][1,7]naphthyridin-5-amine; 2-(4-aminophenethyl)-8-methylbenzo[f][1,7]naphthyridin-5-amine; 1-(4-(2-(5-amino-8-methylbenzo[f][1,7]naphthyridin-2-yl)ethyl)phenyl)guanidine; 8-methyl-2-(4-(1-(phenethylamino)ethyl)phenethyl)benzo[f][1,7]naphthyridin-5-amine; 2-(4-(2-(5-amino-8-methylbenzo[f][1,7]naphthyridin-2-yl)ethyl)phenyl)acetonitrile; 2-(4-(piperidin-1-ylmethyl)phenethyl)benzo[f][1,7]naphthyridin-5-amine; 1-(4-(2-(5-aminobenzo[f][1,7]naphthyridin-2-yl)ethyl)benzyl)piperidin-4-ol; 2-(4-(aminomethyl)phenethyl)benzo[f][1,7]naphthyridin-5-amine; 2-(4-((ethylamino)methyl)phenethyl)benzo[f][1,7]naphthyridin-5-amine; 2-(4-(2-aminopropan-2-yl)phenethyl)benzo[f][1,7]naphthyridin-5-amine; 1-(1-(4-(2-(5-aminobenzo[f][1,7]naphthyridin-2-yl)ethyl)phenyl)ethyl)pyrrolidine-3-carboxylic acid, 8-methyl-2-(4-(1-(phenylamino)ethyl)phenethyl)benzo[f][1,7]naphthyridin-5-amine, 4-(4-(2-(5-amino-8-methylbenzo[f][1,7]naphthyridin-2-yl)ethyl)-3-methylphenoxy)-1,1- difluorobutylphosphonic acid; 3-(5-amino-2-(4-(4,4-difluoro-4-phosphonobutoxy)-2-methylphenethyl)benzo[f][1,7]naphthyridin-8-yl)propanoic acid; 3-(5-amino-2-(4-(2-(3,3-difluoro-3-phosphonopropoxy)ethoxy)-2-methylphenethyl)benzo[f][1,7]naphthyridin-8-yl) propanoic acid; 3-(5-amino-2-(2-methyl-4-(2-(2-(2-phosphonoethoxy)ethoxy)ethoxy)phenethyl)benzo[f][1,7]naphthyridin-8-yl)propanoic acid; 4-(2-(5-amino-8-methylbenzo[f][1,7]naphthyridin-2-yl)ethyl)-3-methylphenyl dihydrogen phosphate; (4-(2-(5-amino-8-methylbenzo[f][1,7]naphthyridin-2-yl)ethyl)-3-methylphenoxy)methylphosphonic acid; 5-(4-(2-(5-amino-8-methylbenzo[f][1,7]naphthyridin-2-yl)ethyl)-3-methylphenoxy)-1,1-difluoropentylphosphonic acid; 4-(4-(2-(5-amino-8-methylbenzo[f][1,7]naphthyridin-2-yl)ethyl)-3-methylphenoxy)-1,1-difluorobutylphosphonic acid; 3-(2-(4-(2-(5-amino-8-methylbenzo[f][1,7]naphthyridin-2-yl)ethyl)-3-methylphenoxy)ethoxy)-1,1-difluoropropylphosphonic acid; 2-(4-((4-(2-(5-amino-8-methylbenzo[f][1,7]naphthyridin-2-yl)ethyl)-3-methylphenoxy)methyl)phenyl)-1,1-difluoroethylphosphonic acid; 2-(5-amino-2-(4-methoxy-2-methylphenethyl)benzo[f][1,7]naphthyridin-8-yl)-1,1-difluoro-2-oxoethylphosphonic acid; (E)-2-(5-amino-2-(4-methoxy-2-methylphenethyl)benzo[f][1,7]naphthyridin-8-yl)vinylphosphonic acid; 2-(5-amino-2-(4-methoxy-2-methylphenethyl)benzo[f][1,7]naphthyridin-8-yl)ethylphosphonic acid; (E)-2-(5-amino-2-(4-methoxy-2-methylphenethyl)benzo[f][1,7]naphthyridin-8-yl)-1-fluorovinylphosphonic acid; 3-((4-(2-(5-amino-8-methylbenzo[f][1,7]naphthyridin-2-yl)ethyl)-3-methylphenoxy)methyl)phenylphosphonic acid; 5-amino-2-(4-methoxy-2-methylphenethyl)benzo[f][1,7]naphthyridine-8-carbonylphosphonic acid; 3-(5-amino-2-(2-methyl-4-(3-phosphonopropoxy)phenethyl)benzo[f][1,7]naphthyridin-8-yl)propanoic acid; (4-(2-(5-amino-8-methylbenzo[f][1,7]naphthyridin-2-yl)ethyl)-3-methylphenyl)(hydroxy)methylenediphosphonic acid; 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid; (5-amino-2-(4-methoxy-2-methylphenethyl)benzo[f][1,7]naphthyridin-8-yl)(hydroxy)methylenediphosphonic acid; 3-(5-amino-2-(2-methyl-4-(2-(2-phosphonoethoxy)ethoxy)phenethyl)benzo[f][1,7]naphthyridin-8-yl)propanoic acid; 2-(4-(2-(5-amino-8-methylbenzo[f][1,7]naphthyridin-2-yl)ethyl)-3-methylphenoxy)ethylphosphonic acid; 6-(4-(2-(5-amino-8-methylbenzo[f][1,7]naphthyridin-2-yl)ethyl)-3-methylphenoxy)hexylphosphonic acid; 6-(4-(2-(5-amino-8-methylbenzo[f][1,7]naphthyridin-2-yl)ethyl)-3-methylphenoxy)-1,1-difluorohexylphosphonic acid; 4-((4-(2-(5-amino-8-methylbenzo[f][1,7]naphthyridin-2-yl)ethyl)-3-methylphenoxy)methyl)benzylphosphonic acid, and 2-(2-(2-(4-(2-(5-amino-8-methylbenzo[f][1,7]naphthyridin-2-yl)ethyl)-3-methylphenoxy)ethoxy)ethoxy)ethylphosphonic acid.

Example 198

Formation and Characterization of PLG Particles (with and without Compound 47)

PLG particles were synthesized using an oil-in-water (o/w) single emulsion technique. Briefly, 4 mL of 15% w/v RG502H PLG (available Boehringer Ingelheim) solution with 6 or 24 mg Compound 47 (see Example 44), for 1% or 4% loading, respectively, relative to PLG, in dichloromethane was added to 33 mL of water containing 6 mg of dioctyl sulfosuccinate (adjusted to pH7.2). The mixture was homogenized for 1 min at 24,000 rpm using IKA Ultra Turrex T-25 homogenizer followed by homogenization for 6 min at 12,900 rpm using Omni Macro homogenizer. The emulsion was shaken for 3-4 hours at 150 rpm in a ventilated chemical fume hood to evaporate dichloromethane. PLG particles without Compound 47 were synthesized as described above, except that no Compound 47 was added during the particle synthesis. All particle suspensions are filtered using a 53 micron filter.

Particle size of the particles within each resulting suspension was measured using a Horiba LA-930 particle sizer. All PLG formulations had a mean size of 0.5-5 μm at this stage (prior to lyophilization).

To determine PLG content, 1 mL of the particle suspension was added to pre-weighed scintillation vials and the vials were lyophilized using Labconco bench lyophilizer. PLG content was calculated as the difference between the lyophilized and empty vials. PLG recovery for all PLG formulations was determined to be >70%.

Compound 47 was analyzed by Reversed Phase High Performance Liquid Chromatography (RP-HPLC) using a Waters Acquity System using C18 XTerra column (Waters Corporation) and a gradient of 90% water+0.1% TFA/10% acetonitrile+0.1% TFA to 100% acetonitrile+0.1% TFA in 6 min. Compound 47 eluted around 4.7 min.

To determine Compound 47 concentration, 100 μL of the particle suspension described above was mixed with 900 μL of DMSO and analyzed by RP-HPLC. Compound 47 recovery determined based on the Compound 47 concentration in the particle suspension was >75%.

To determine encapsulation efficiency, 100 μL of the particle suspension described above was diluted to 1 mL with 10 mM HCl and rocked for 30 min at room temperature. The resulting particle suspension was centrifuged. The pellet was then dissolved in 1 mL DMSO and analyzed on the RP-HPLC system to determine the amount of encapsulated Compound 47. The supernatant was also analyzed on the RP-HPLC system to determine the amount of non-encapsulated Compound 47. The amount of Compound 47 encapsulated in PLG particles was >90%.

Figure 16:
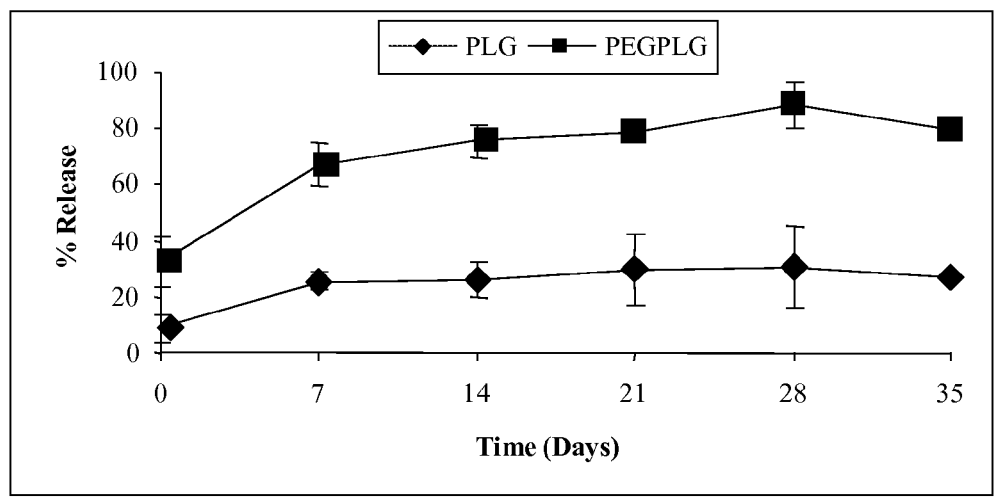
FIG. 16 shows % release of encapsulated Compound 47 from PLG particles and PLG-PEG particles over a period of 35 days in 10 mM HCl.
Figure 17:
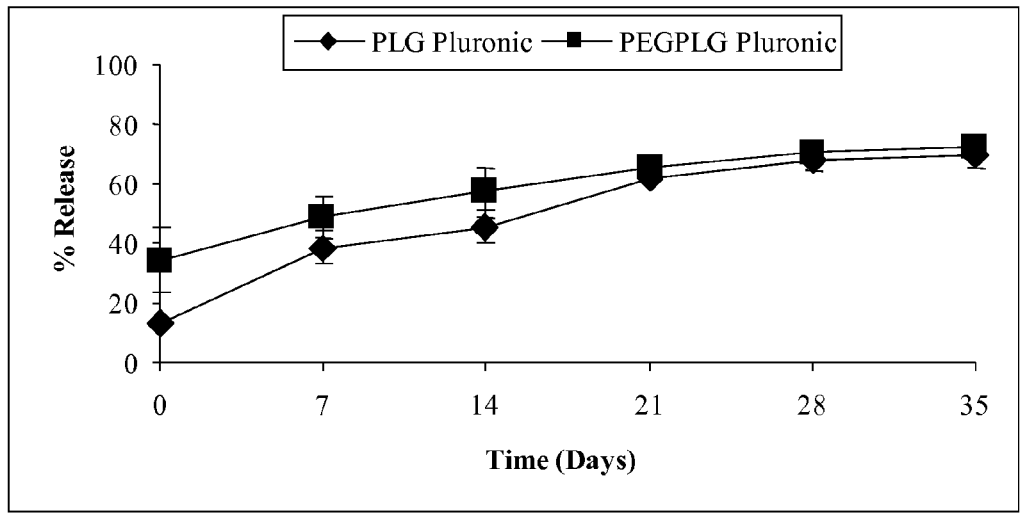
FIG. 17 shows % release of encapsulated Compound 47 from PLG particles and PLG-PEG particles over a period of 35 days in 10 mM HCl with pluronic F-68 as a surfactant.

PLG particles were also synthesized using PEG-PLG diblock copolymer available from Boehringer Ingelheim using the above procedure (24 mg Compound 47, 4% loading). The release characteristics of these particles were compared with those of the PLG particles described above (4% Compound 47 loading). Particles were suspended in vials in 10 mM HCl with target Compound 47 concentration of 15 μg/mL (with or without 1% wt/vol pluronic F-68 as a surfactant). The HCl was provided to solubilize the Compound 47 and allow for its analysis. The vials were maintained at room temperature with stirring at 300 rpm. Samples were collected every 7 days and analyzed using the above-described RP-HPLC assay. The results are presented in FIG. 16 (without surfactant) and FIG. 17 (with surfactant). These results demonstrate that the different PLG copolymers can be used to modulate the release of the SMIP, Compound 47, and that PEG-PLG diblock copolymer resulted in a faster Compound 47 release in the in vitro assay compared to the PLG copolymer.

Example 199

Formation and Characterization of PLG Particles with Adsorbed Antigen

MenB antigens 287-953, 936-741 and 961c, described in WO2004/032958 and Pizza et al., *Science,* 287: 1816-1820

(2000), were adsorbed on the particles at 2-8° C. overnight with 10 mM histidine buffer, pH 5.5, at a 100 µg/mL final concentration of each antigen (which ultimately corresponds to 10 µg of each antigen per dose). MenB adsorption was conducted on the following particle compositions:

Adsorption 1: Compound 47-encapsulated particles with 1% Compound 47 loading relative to PLG were provided in an amount that supplied 250 µg/mL Compound 47 for the particles.

Adsorption 2: Compound 47-encapsulated particles with 4% Compound 47 loading relative to PLG were provided in an amount that supplied 250 µg/mL Compound 47 for the particles.

Adsorption 3: Compound 47-encapsulated particles with 4% Compound 47 loading relative to PLG were provided in an amount that supplied 1000 µg/mL Compound 47.

Adsorption 4: PLG particles without encapsulated Compound 47 were provided in an amount that yielded a PLG content equal to that supplied in Adsorption 3.

MenB adsorption on the particles was characterized by SDS-PAGE followed by coomassie blue staining, and by Experion system (Bio-Rad). See Malyala et al., *J. Pharm. Sci.*, 97:1155-1164 (2008). MenB adsorption was measured to be >70% for 287-953 and 936-741, and >50% for 961c antigens for all PLG formulations.

Lyophilized formulations were then formed in 6 mL borosilicate glass vials as follows:

Vial 1: The particle suspension formed in Adsorption 1 was added to a vial in an amount corresponding to 350 µg Compound 47 (14 doses of 25 µg Compound 47), along with 63 mg Mannitol and 21 mg Sucrose, and lyophilized (using a Virtis shelf lyophilizer). The results associated with Vial 1 are designated in figures to follow as "PLG/3 MB/Compound 471% 25 ug", "1% 25 ug PLG/3MenB/Compound 47", "1% loading 25 ug", "PLG 1%_25 ug", "PLGA_1%_1 mpk" or "1 mpk 1% PLGA".

Vial 2: The particle suspension formed in Adsorption 2 was added to a vial in an amount corresponding to 350 µg Compound 47 (14 doses of 25 µg Compound 47), along with 63 mg Mannitol and 21 mg Sucrose, and lyophilized. The results associated with Vial 2 are designated in figures to follow as "PLG/3 MB/Compound 474% 25 ug", "4% 25 ug PLG/3MenB/Compound 47", "4% loading 25 ug", "PLG 4%_25 ug", "PLGA_4%_1 mpk" or "1 mpk 4% PLGA".

Vial 3: The particle suspension formed in Adsorption 3 was added to a vial in an amount corresponding to 1400 µg Compound 47 (14 doses of 100 µg Compound 47), along with 63 mg Mannitol and 21 mg Sucrose, and lyophilized. The results associated with Vial 3 are designated in figures to follow as "PLG/3 MB/Compound 474% 100 ug", "4% 100 ug PLG/3MenB/Compound 47", "4% loading 100 ug", "PLG 4%_100 ug", "PLGA_4%_4 mpk" or "4 mpk 4% PLGA".

Vial 4: For a first co-lyophilized formulation, the particle suspension formed in Adsorption 4 (PLG without encapsulated Compound 47) was added to a vial in an amount equal to the same PLG content as in Vial 3, along with an Compound 47 suspension (concentration 3.5 mg/mL), prepared using a probe sonicator in 10 mM HCl, in an amount corresponding to 350 µg Compound 47, 63 mg Mannitol and 21 mg Sucrose, and the contents were lyophilized. The results associated with Vial 4 are designated in figures to follow as "PLG/3 MB Co-Lyo Compound 47 25 ug", "PLG/3MenB+Compound 47 25 ug", "PLG Co-lyo 25 ug", "PLG CoLyo_25 ug", "BL_PLGA_1 mpk" or "1 mpk BL PLGA".

Vial 5: For a second co-lyophilized formulation, the particle suspension formed in Adsorption 4 (PLG without encapsulated Compound 47) was added to a vial in an amount equal to the same PLG content as in Vial 3, along with the Compound 47 suspension in an amount corresponding to 1400 µg of Compound 47, 63 mg Mannitol and 21 mg Sucrose, and the contents were lyophilized. The results associated with Vial 5 are designated in figures to follow as "PLG/3 MB Co-Lyo Compound 47 100 ug", "PLG/3MenB+Compound 47 100 ug", "PLG Co-lyo 100 ug", "PLG CoLyo_100 ug", "BL_PLGA_4 mpk" or "4 mpk BL PLGA".

Vial 6: For a control formulation, the particle suspension formed in Adsorption 4 (PLG without encapsulated Compound 47) was added to a vial in an amount equal to the same PLG content as in Vial 3, along with 63 mg Mannitol and 21 mg Sucrose, and the contents were lyophilized. The results associated with Vial 6 are designated in figures to follow as "PLG/3 MB" "PLG/3MenB" or simply "PLG".

Moisture content was determined using the Karl-Fischer titration method and measured to be <5% for all lyophilized formulations.

Endosafe PTS system (Charles River Labs) was used for determining the endotoxin content in the lyophilized formulations. All formulations had endotoxin level of <1 EU/dose or <10 EU/mL (for 100 µL immunization volume).

Example 200

In Vivo Mouse Study

Bactericidal Assay

The PLG formulations described above (Vials 1-6) were reconstituted in 1.4 mL of water for injection with gentle mixing. 100 µL of the formulations were injected per mouse, corresponding to 10 µg of each MenB antigen and in case of formulations containing Compound 47, 25 µg or 100 µg of the adjuvant. Each mouse was immunized intramuscularly (50 µL at two sites) on days 0 and 14, and bled on day 28 and on day 56.

For mice injected with MenB antigen, pooled sera for each group was analyzed for bactericidal assay against the MenB strain NZ98 2 weeks post $2^{nd}$ immunization. The results of this analysis are shown in FIG. 1.

Groups 1, 2 and 3 (from the left) correspond to encapsulated Compound 47 at 1% and 4% loadings that delivered 25 and 100 µg Compound 47 doses (Vials 1-3). Group 4 is the PLG particles without Compound 47 and is a baseline control for the PLG formulations (Vial 6). Groups 5 and 6 refer to the PLG particles initially formed without Compound 47 that were co-lyophilized with Compound 47 suspension (Vials 4 and 5).

For mice injected with MenB antigen, pooled sera for each group was also analyzed for bactericidal assay against the MenB strain NZ98 6 weeks post $2^{nd}$ immunization. The results of this analysis are shown in FIG. 2.

Group 1 is the PLG particles without Compound 47 and is a baseline control for the PLG formulations (Vial 6). Groups 2, 3 and 4 correspond to encapsulated Compound 47 at 1% and 4% loadings that delivered 25 and 100 µg Compound 47 doses (Vials 1-3). Groups 5 and 6 refer to the PLG particles initially formed without Compound 47 that were co-lyophilized with Compound 47 suspension (Vials 4 and 5).

Figure 2:
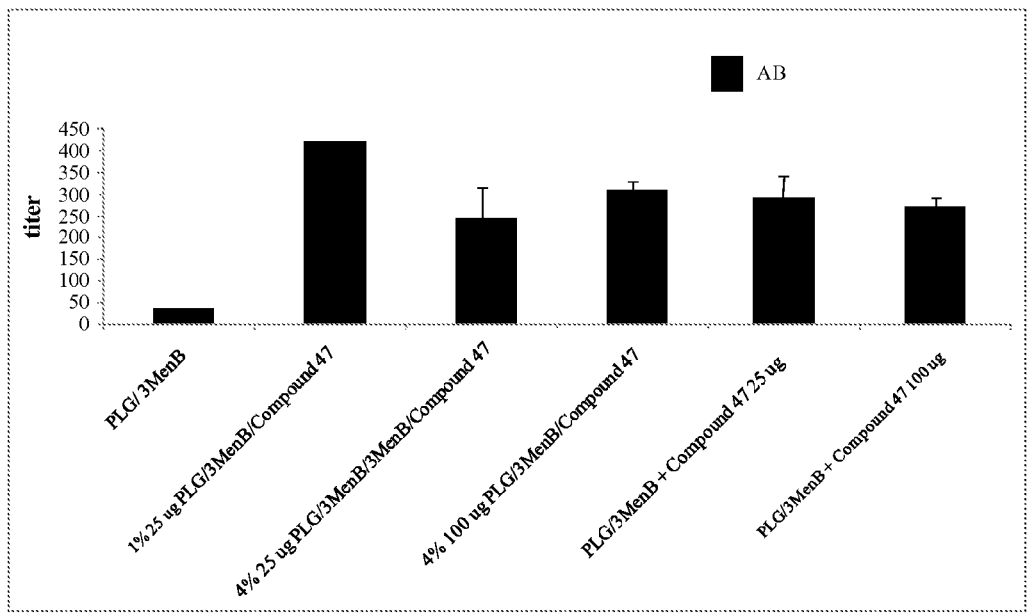

The results of FIGS. 1 and 2 show that Compound 47 delivered with PLG as encapsulated or as co-lyophilized significantly enhances the protection of the immunized mice against the evaluated strain NZ98. The titers were determined with PLG/Compound 47 formulations increased nearly 10-fold or higher compared to the corresponding baseline.

Example 201

In Vivo Mouse Study

Pharmacokinetic Profile

The PLG formulations described above (Vials 1-5) were reconstituted in 1.4 mL of water for injection with gentle mixing. Mice were immunized intramuscularly once, either with 25 µg Compound 47, corresponding to 1 mg/kg (1 mpk) body weight, or with 100 µg Compound 47, corresponding to 4 mg/kg (4 mpk) body weight. Sera, muscle and lymph node (LN) samples were collected, homogenized and analyzed on LC-MS system for Compound 47 to determine the pharmacokinetic profile of the adjuvant.

Figure 3:
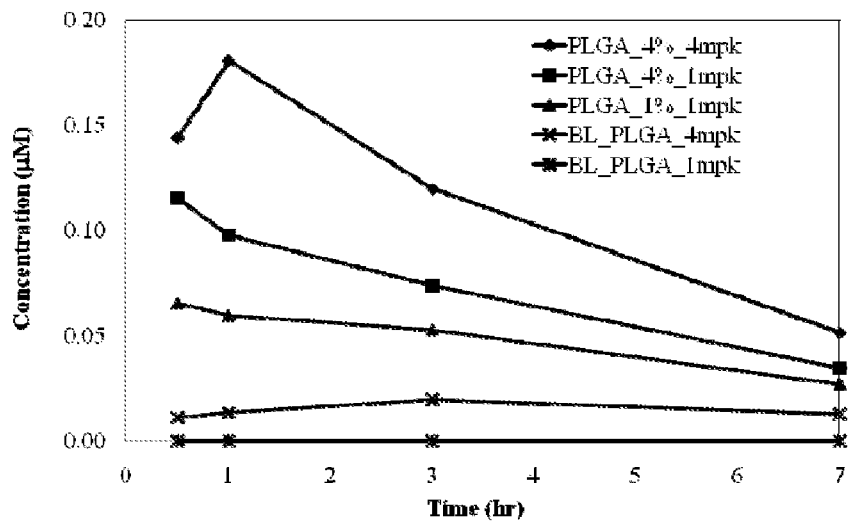
FIGS. 3-5 show serum concentrations of Compound 47 at short duration (up to 7 hours), intermediate duration (up to 2 weeks), and long duration (up to 30 days), respectively, for various formulations in accordance with the invention.
Figure 4:
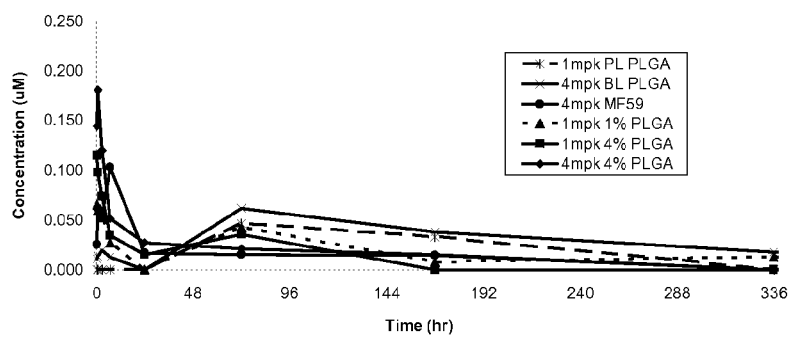
Figure 5:
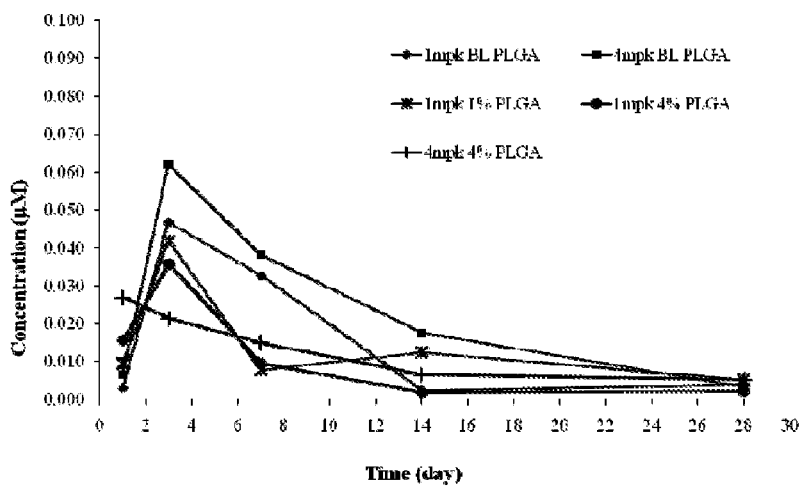

Serum samples were collected from the immunized mice at different time intervals to study the systemic presence of Compound 47 at short duration (up to 7 hours), intermediate duration (up to 2 weeks), and long duration (up to 30 days). FIGS. 3-5 show the Compound 47 levels in sera with PLG formulations containing encapsulated Compound 47 (Vials 1-3) or co-lyophilized Compound 47 (Vials 4-5) over these time periods. As can be seen from FIGS. 3-5, a low level of Compound 47 (<1 uM) was detected with the various PLG formulations in serum. Low systemic exposure to Compound 47 with the PLG formulations is desirable as it suggests low systemic toxicity associated with Compound 47 and correspondingly low system cytokine levels induced by Compound 47.

Figure 6:
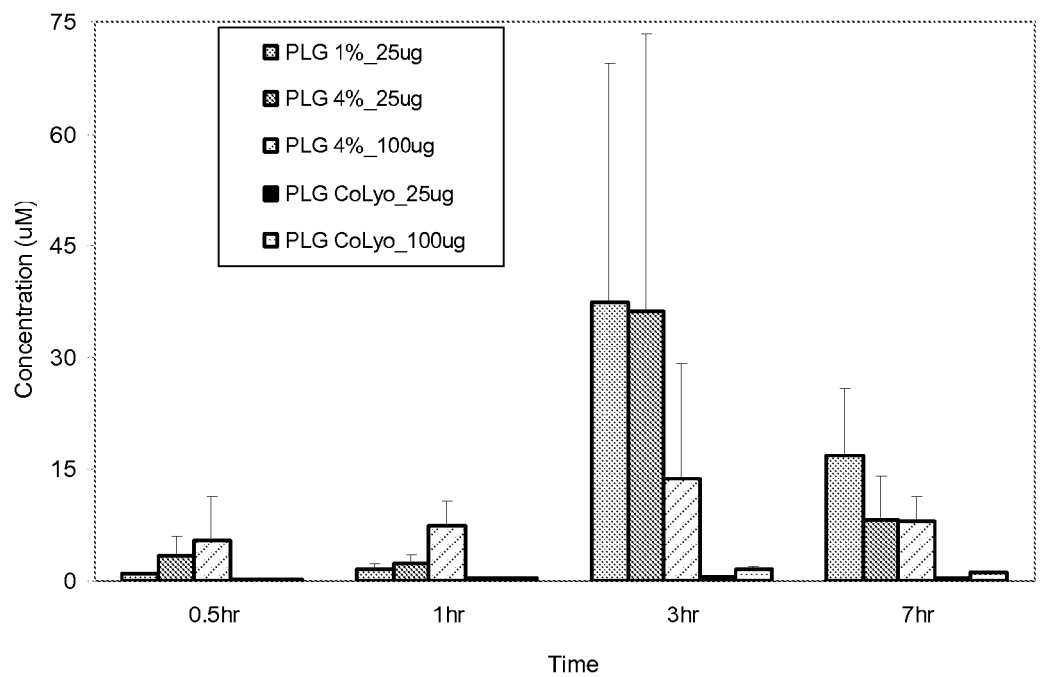
FIG. 6 shows concentrations of Compound 47 in draining lymph nodes for a period of up to 7 hours after administration of various formulations in accordance with the invention.

Draining lymph nodes were collected from the immunized mice at different time intervals (up to 7 hours), homogenized and analyzed using the LC-MS system. The results are shown in FIG. 6. As seen from FIG. 6, PLG formulations with encapsulated Compound 47 (Vials 1-3) resulted in localization of Compound 47 in the draining lymph nodes at a significantly higher concentration than was observed for the co-lyophilized Compound 47 (Vials 4-5). These results demonstrate the ability of PLG formulations with encapsulated Compound 47 to carry the Compound 47 payload to the lymph nodes.

Muscle samples were collected from the immunized mice at different time intervals (up to 4 weeks), homogenized and analyzed using the LC-MS system. Results are shown in FIG. 7.

Figure 7:
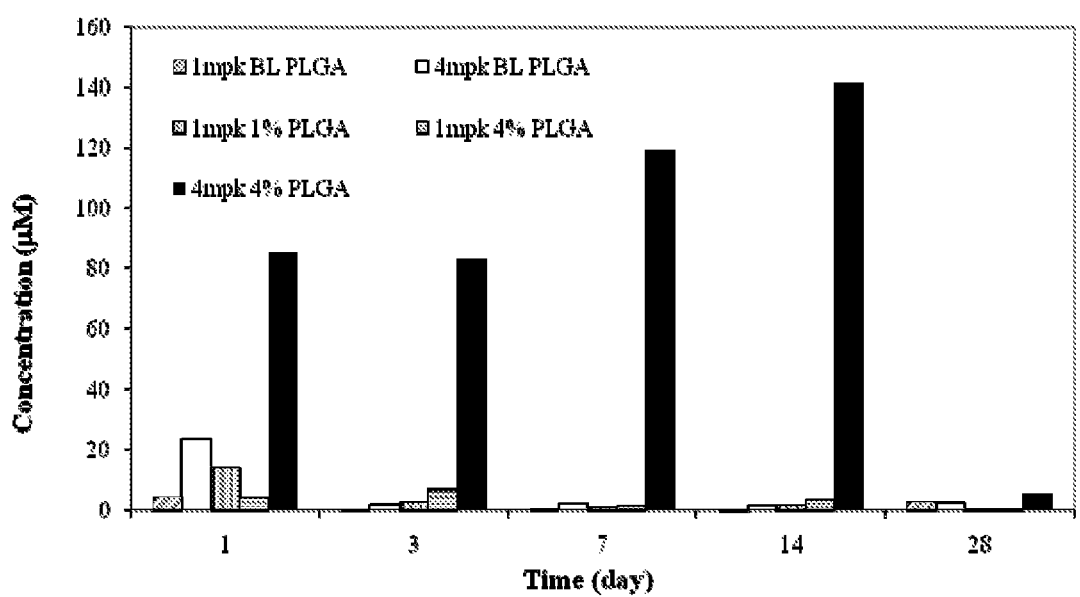
FIG. 7 shows concentrations of Compound 47 in muscle for a period of up to 7 hours after administration of various formulations in accordance with the invention.

As can be seen from FIG. 7, PLG formulations with encapsulated Compound 47 (Vials 1-3) tended to retain the adjuvant at the site of immunization whereas co-lyophilized Compound 47 (Vials 4-5) was not present at significant concentrations after 1 week. These results suggest that the PLG formulations with encapsulated Compound 47 are able to retain the adjuvant at the immunization site for up to 4 weeks, and are effective in reducing the systemic presence of Compound 47.

Figure 8:
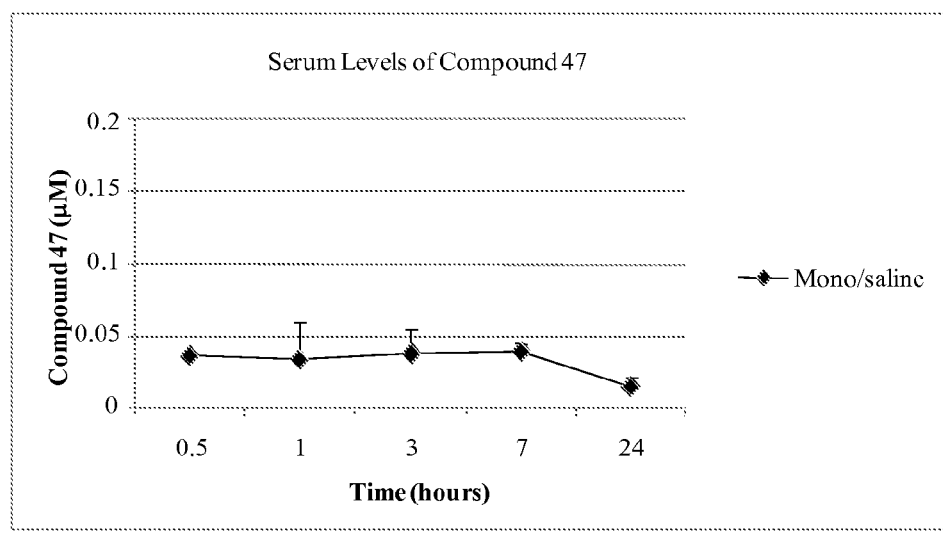
FIG. 8 shows concentrations of Compound 47 in serum for a period of up to 24 hours after administration of a monodispersion of Compound 47.
Figure 9:
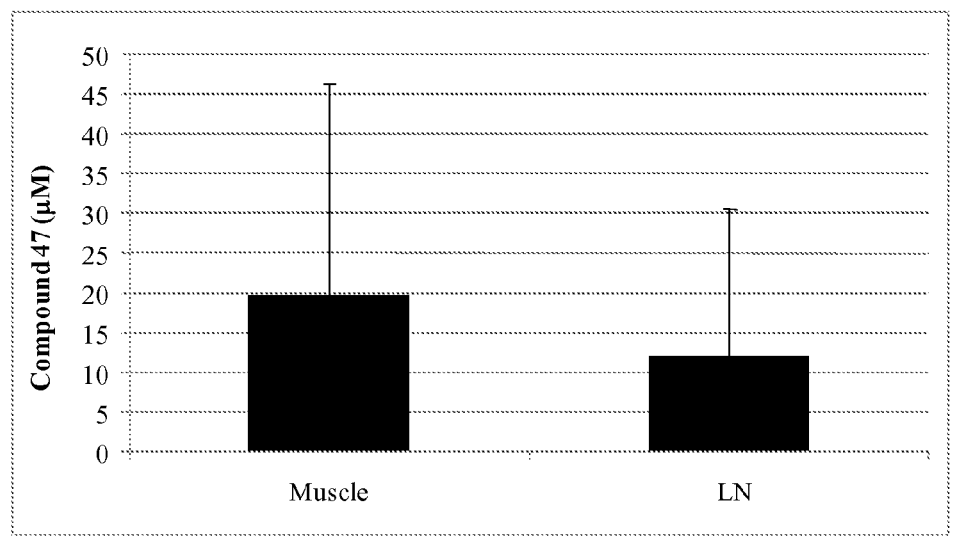
FIG. 9 shows concentrations of Compound 47 in draining lymph nodes and muscle tissue 24 hours after administration of a monodispersion of Compound 47.
Figure 10:
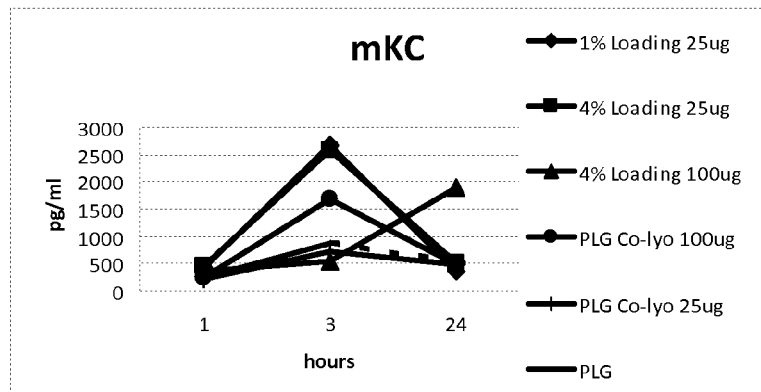
FIGS. 10-15 show serum concentrations of various cytokines (mKC, MCP-1, IL-6, IL-10, IFNg and IL-5) for a period of up to 24 hours after administration of various formulations.
Figure 11:
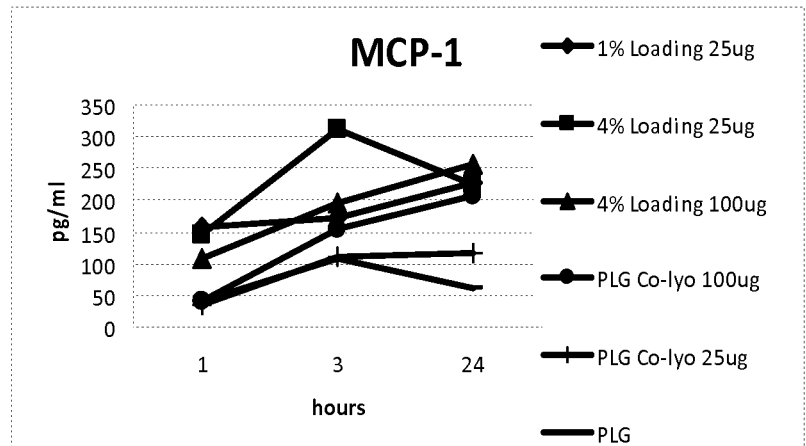
Figure 12:
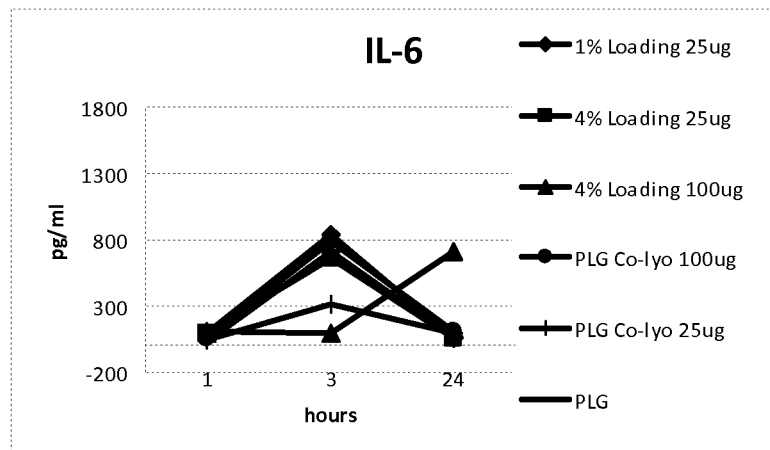
Figure 13:
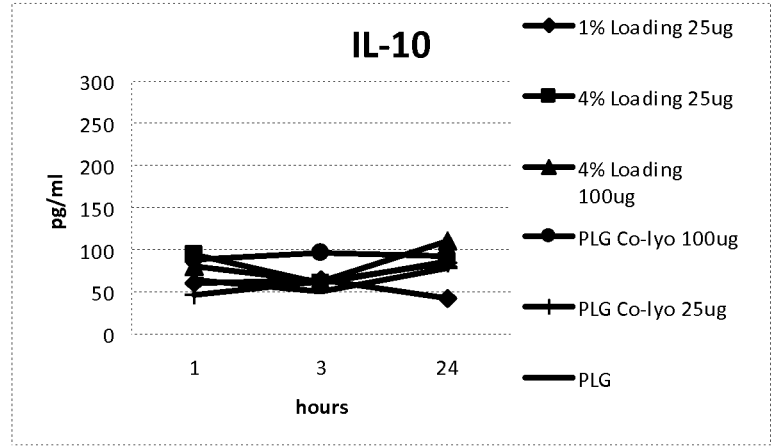
Figure 14:
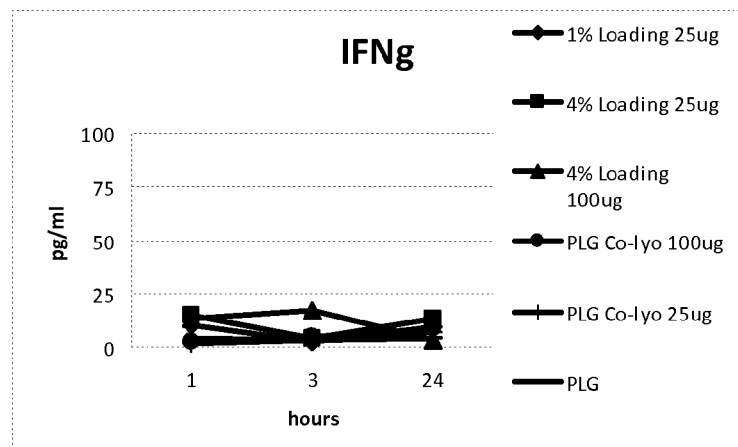
Figure 15:
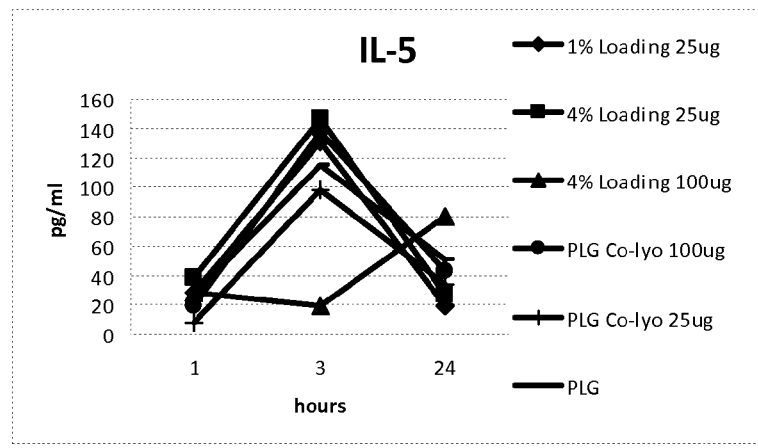

For comparison, a monodispersion of Compound 47 was prepared at 4 mg/mL in a solution of 0.5% w/v Carboxymethyl cellulose/0.5% w/v Tween 80 in sterile water using a high pressure homogenizer (Avestin Emulsiflux C-3). Mice were immunized intramuscularly with 100 µg Compound 47 to determine the pharmacokinetic profile of Compound 47 alone. Serum samples were taken at various times (up to 24 hours) and analyzed as described above. The results are presented in FIG. 8. Draining lymph nodes and muscle samples were also collected at 24 hours and analyzed. The results are presented in FIG. 9. FIGS. 8 and 9 demonstrate Compound 47 delivered as a monodispersion is retained in the muscles and in the lymph nodes, and low systemic exposure to Compound 47 is observed.

The PLG formulations described above (Vials 1-6) were reconstituted in 1.4 mL of water for injection with gentle mixing. 100 µL of the formulations were injected intramuscularly per mouse. Mice were also injected intramuscularly with above-described monodispersion of Compound 47 at a dose of 100 µg Compound 47.

Serum cytokine levels (mKC, MCP-1, IL-6, IL-10, IFNg and IL-5) were measured at 1, 3 and 24 hours using sandwich ELISA. The results are presented in FIGS. 10-15. These data show low serum cytokines and consequently low serum toxicity with Compound 47 formulated in the PLG-based particles.

Thus, novel compositions and methods for using and making the same are disclosed. While the present invention has been described with reference to the specific embodiments thereof, it should be understood by those skilled in the art that various changes may be made and equivalents may be substituted without departing from the true spirit and scope of the invention.

Example 202

Formation and Characterization of PLG Nanoparticles

Procedure 1. PLG microparticles with encapsulated Compound 47 (also referred to herein as CPD47) were synthesized as described in Example 198. For delivering the desired Compound 47 dose, 15 mg of Compound 47 was used corresponding to 2.5% w/w loading of the compound. Following microparticle synthesis, MenB antigen 287-953 (See Example 199) was adsorbed on the surface of the microparticles (to final concentration of ~0.1 mg/mL). Specifically, 1 mL of 0.811 mg/mL 287-953 antigen was added to 6.7 mL of the synthesized microparticles without using Histidine buffer, pH 5.5 overnight at 2-8° C. This formulation is designated "PLG MP/CPD47".

Procedure 2. Blank PLG microparticles for the in vivo evaluation were prepared using water-in-oil-in-water double emulsion technique. M. Singh et al., *J Pharm Sci* 93: 273-82 (2004) and J. Kazzaz et al., *J Control Release* 67: 347-56 (2000). Briefly, 2 mL of PBS was homogenized in 10 mL of 6% w/v RG503 PLG (Boehringer Ingelheim) solution in dichloromethane at 24,000 rpm using IKA T-25 homogenizer. The resulting primary emulsion was homogenized on ice in 48 mL water containing 30 µL of 1% w/v DSS (corresponding to 0.05% w/w DSS relative to PLG) at 16,800 rpm for 10 min. The emulsion was stirred at 1000 rpm for 4 hours in a ventilated chemical fume hood to evaporate dichloromethane. Microparticles were incubated overnight at 2-8° C. with the MenB protein 287-953 (to final concentration of 0.1 mg/mL) using 10 mM Histidine buffer, pH 5.5 to allow protein adsorption. Specifically, to 6.7 ml of the synthesized microparticles were added 0.4 mL of 200 mmol histidine buffer at pH 5.5 and 1 mL 0.811 mg/mL 287-953 antigen. This formulation is designated "PLG MP".

Procedure 3. PLG nanoparticles were prepared by the nanoprecipitation method. Specifically, 400 mg of RG503 PLG and 10 mg of Compound 47 were co-dissolved in 10 mL of dimethyl sulfoxide (DMSO). For blank PLG nanoparticles, no Compound 47 was used. The DMSO mixture was added dropwise to 8 mL water+2 mL of 4% w/v PVA with stirring at 1000 rpm. 12 mL of resulting suspension was dialyzed overnight to remove DMSO at room temperature against 2 L of water using 10 kDa Slide-a-lyzer membrane (Thermo Scientific, Rockford, Ill., USA). Blank PLG nanoparticles and PLG nanoparticles with encapsulated Compound 47 were independently incubated with the MenB 287-953 antigen overnight at 2-8° C. (to final concentration of 0.1 mg/mL) with 10 mM Histidine buffer, pH 5.5 to allow protein adsorption. Specifically, to 6.7 ml of the synthesized microparticles were added 0.4 mL of 200 mmol histidine buffer at pH 5.5 and 1 mL 0.811 mg/mL 287-953 antigen. The formulation containing encapsulated Compound 47 is designated "PLG NP/CPD47". The formulation containing blank nanoparticles is designated "PLG NP".

2 mL of blank PLG microparticles (designated "PLG MP") and blank PLG nanoparticles (designated "PLG NP"), each with adsorbed 287-953 antigen from Procedures 2 and 3 above, were independently spiked with 125 µL of 4 mg/mL Compound 47 monodispersion prepared in 0.5% carboxymethyl cellulose and 0.5% Tween 80 using a high pressure homogenizer. The blank microparticle formulation spiked with Compound 47 is designated "PLG MP+CPD47 MD". The blank nanoparticle formulation spiked with Compound 47 is designated "PLG NP+CPD47 MD".

As a comparative formulation, 2 mL of blank PLG microparticles with adsorbed 287-953 antigen from Procedure 2 above were spiked with 20 µL of 10 mg/mL CpG1826 (CpG oligonucleotide, available from Invivogen, San Diego, Calif., USA) prior to immunization. This formulation is designated "PLG MP+CpG1826".

Another comparative formulation containing 0.1 g/L of the 287-953 antigen (10 µg of the MenB antigen per 100 µL) was also prepared. This formulation is designated "MenB Alone".

A final comparative formulation containing the 287-953 antigen and Compound 47 monodispersion (described above) was prepared. This formulation is designated "CPD47".

Another comparative formulation, a five componenet vaccine against meningococcus B (SCVMB), was prepared as described in S. Jacobsson et al., *Vaccine* 27:1579-1584 (2009) and M. M. Giuliani et al., *Proc. Natl. Acad. Sci. USA* 103(29):10834-10839 (2006), This five-component vaccine contains the New Zealand OMV vaccine (P. Oster et al., Vaccine 23(17-18):2191-2196 (2005)) and a mixture of five genome-derived antigens (GNAs). These GNAs are delived as a fusion between factor H-binding protein (fHbp; GNA1870) variant 1 (v. 1) and GNA2091, a fusion of GNA2132 and GNA1030, and *Neisseria* adhesion A (NadA; GNA1994). This formulation is designated designated "3MenB/Alum/OMV".

All formulations were prepared within two days of immunization and were used without lyophilization. Nanoparticle formulations were characterized as described in Examples 198 and 199 by RP-HPLC for compound content and encapsulation efficiency, particle size (nanoparticles were measured using a Malvern Zetasizer 90ZS, Malvern Instruments, Worcestershire, United Kingdom; microparticles were measured using a Horiba LA-930 particle sizer, Horiba Ltd., Kyoto, Japan), endotoxin content and protein adsorption efficiency (SDS-PAGE). Results are shown in Table 1 to follow.

TABLE 1

| | Endotoxin (EU/mL) | Particle Size (µm) | Compound Content (µg/mL) | Protein Adsorption Efficiency (%) |
|---|---|---|---|---|
| PLG NP | 1.43 | 190.0 nm/ PDI 0.045 | N/A | >70 |
| PLG/ CPD47 NP | 2.41 | 200.1 nm/ PDI 0.215 | 287.2 | >70 |
| PLG MP | 0.942 | D50 0.8030/ D90 1.1675 | N/A | >70 |
| PLG/ CPD47 MP | 1.61 | D50 0.8056/ D90 1.2755 | 316.4 | >70 |

Figure 18:
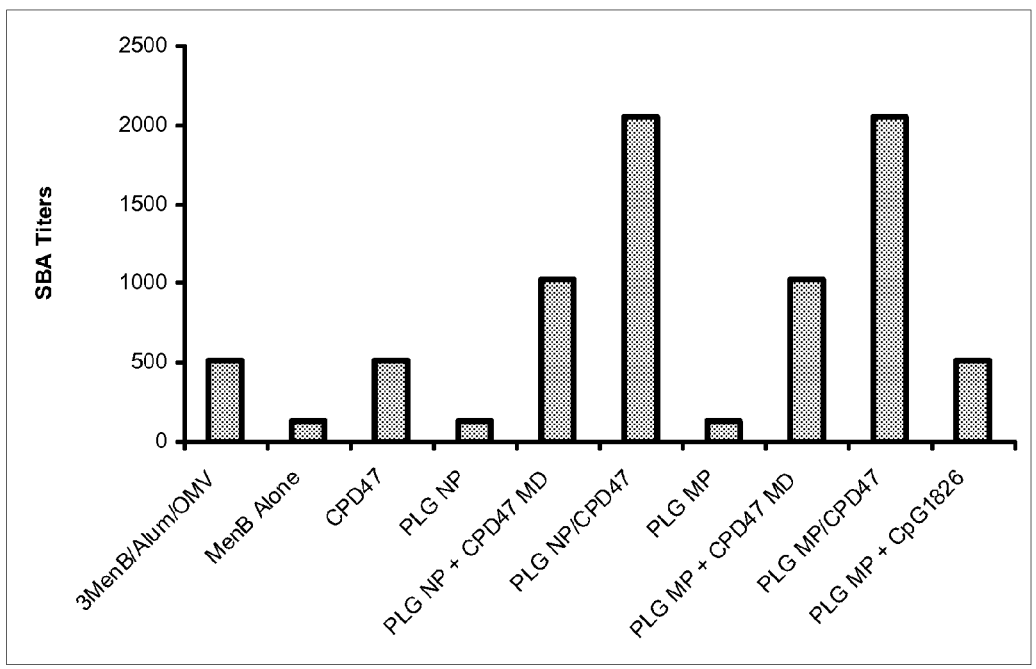
FIG. 18 illustrates titer results of a bactericidal assay against the MenB strain NZ98 at 2 weeks post $2^{nd}$ immunization, for various formulations in accordance with the invention.

Each mouse was immunized intramuscularly with the above formulations (50 µL at two sites, 100 µL total formulation per mouse, corresponding to 10 µg of the MenB antigen) on days 0 and 14 and bled on day 28 as described in Example 200. SBA titers were measured against the *N. meningitidis* strain NZ98. Results are shown in FIG. 18.

Example 203

Formation and Characterization of PLG particles with Compound

Compound 6A (see Example 196), a water soluble benzonaphthyridine compound, was encapsulated at 1% w/w and 4% w/w loading in RG503 PLG microparticles for delivery. (Compound 6A has an aqueous solubility of >4 mg/mL at pH 7 as a sodium salt, and <0.4 mg/mL as base form.) Specifically, 0 mg, 6 mg or 24 mg of the base form of Compound 6A (corresponding to 0%, 1% and 4% Compound 6A loading, respectively, and referred to as the 0% formulation, 1% encapsulated Compound 6A formulation and 4% encapsulated Compound 6A formulation, respectively) were added to 4 mL of dichloromethane. The resulting Compound 6A/dichloromethane suspension was sonicated for 10 min using a bath sonicator to obtain a homogeneous drug suspension (Compound 6A is not soluble in dichloromethane). 600 mg RG503 PLG was dissolved in the Compound 6A/dichloromethane suspension. This organic phase was added to 33 mL of water containing 0.2% w/w DSS (120 µL of 1% w/v DSS) and homogenized for 1 min at 24,000 rpm using IKA T-25 homogenizer. The emulsion was further homogenized on ice using Omni Macro homogenizer at 12,900 rpm for 5 min. The emulsion was shaken at 150 rpm in a ventilated chemical fume hood to evaporate dichloromethane. The particle suspension was filtered through a 40 µm strainer to remove aggregates.

Based on the compound recoveries, each particle suspension was incubated with MenB protein 287-953 to final concentration of 0.1 mg/mL for 2 hours at room temperature to allow protein adsorption. No buffer was used for protein adsorption. Specifics of various formulations follow.

0% formulation (comparative) (10 µg 287-953 protein per dose). 33 ml of the 0% formulation microparticles and 900 microliters of 0.69 mg/mL MenB 287-953 protein were incubated for 2 hours with shaking at 1000 rpm, after which 500 microliters of 4% w/v PVA were added. This composition was spit into 10 vials, and 180 microliters of 15% w/v mannitol and 60 microliters of 15% w/v sucrose were added to each vial, followed by lyophilization. (Result: 6 doses per vial, 10 µg adsorbed 287-953 protein per dose.)

0% formulation with CpG oligonucleotide (comparative) (10 µg 287-953 protein per dose, 25 µg CpG oligonucleotide per dose). 17 ml of the 0% formulation microparticles and 450 microliters of 0.69 mg/mL MenB 287-953 protein were incubated for 2 hours with shaking at 1000 rpm, after which 250 microliters of 4% PVA were added. This composition was spit into 5 vials. Then 15 microliters of 10 mg/ml CpG 1826 (CpG oligonucleotides available from Invivogen), 180 microliters of 15% w/v mannitol and 60 microliters of 15% w/v sucrose were added to each vial, followed by lyophilization. (Result: 6 doses per vial, 10 μg adsorbed 287-953 protein per dose, 25 μg CpG oligonucleotide per dose.)

0% formulation plus colyophilized Compound 6A (10 μg 287-953 protein per dose, 5 μg Compound 6A per dose). 17 ml of the 0% formulation microparticles and 450 microliters of 0.69 mg/mL MenB 287-953 protein were incubated for 2 hours with shaking at 1000 rpm, after which 250 microliters of 4% PVA were added as well as 30 microliters of 5 mg/ml Compound 6A (sodium salt form). This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 5 μg colyophilized Compound 6A per dose.)

0% formulation plus colyophilized Compound 6A (10 μg 287-953 protein per dose, 25 μg Compound 6A per dose). 17 ml of the 0% formulation microparticles and 450 microliters of 0.69 mg/mL MenB 287-953 protein were incubated for 2 hours with shaking at 1000 rpm, after which 250 microliters of 4% PVA were added as well as 150 microliters of 5 mg/ml Compound 6A (sodium salt form). This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 25 μg colyophilized Compound 6A per dose.)

0% formulation plus colyophilized Compound 6A (10 μg 287-953 protein per dose, 100 μg Compound 6A per dose). 33 ml of the 0% formulation microparticles and 900 microliters of 0.69 mg/mL MenB 287-953 protein were incubated for 2 hours with shaking at 1000 rpm, after which 500 microliters of 4% PVA were added as well as 1200 microliters of 5 mg/ml Compound 6A(sodium salt form). This composition was spit into 10 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 100 μg colyophilized Compound 6A per dose.)

1% encapsulated Compound 6A formulation (10 μg 287-953 protein per dose, 5 μg Compound 6A per dose): 3.6 ml of the 1% encapsulated Compound 6A formulation microparticles and 450 microliters of 0.69 mg/mL MenB 287-953 protein were incubated for 2 hours with shaking at 1000 rpm, after which 50 microliters of 4% w/v PVA were added. This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 5 μg encapsulated Compound 6A per dose.)

1% encapsulated Compound 6A formulation (10 μg 287-953 protein per dose, 25 μg Compound 6A per dose). 18 ml of the 1% encapsulated Compound 6A formulation microparticles and 450 microliters of 0.69 mg/mL MenB 287-953 protein were incubated for 2 hours with shaking at 1000 rpm, after which 250 microliters of 4% w/v PVA were added. This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 25 μg encapsulated Compound 6A per dose.)

4% encapsulated Compound 6A formulation (10 μg 287-953 protein per dose, 25 μg Compound 6A per dose): 6 ml of the 4% encapsulated Compound 6A formulation microparticles and 450 microliters of 0.69 mg/mL MenB 287-953 protein were incubated for 2 hours with shaking at 1000 rpm, after which 90 microliters of 4% w/v PVA were added. This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 25 μg encapsulated Compound 6A per dose.)

4% encapsulated Compound 6A formulation (10 μg 287-953 protein per dose, 100 μg Compound 6A per dose): 23 ml of the 4% encapsulated Compound 6A formulation microparticles and 450 microliters of 0.69 mg/mL MenB 287-953 protein were incubated for 2 hours with shaking at 1000 rpm, after which 350 microliters of 4% w/v PVA were added. This composition was spit into 5 vials, and 180 microliters of 15% w/v mannitol and 60 microliters of 15% w/v sucrose were added to each vial, followed by lyophilization. (Result: 6 doses per vial, 10 μg adsorbed 287-953 protein per dose, 100 μg encapsulated Compound 6A per dose.)

Lyophilized particles (0% formulation, 1% encapsulated Compound 6A formulation, and 4% encapsulated Compound 6A formulation) were characterized for particle size using a Horiba LA-930 particle sizer, endotoxin was evaluated using Charles River Laboratories PTS Endosafe System, encapsulation efficiency was evaluated using RP-HPLC (see Example 198) and protein adsorption efficiency based on estimation of density on SDS-PAGE (Example 199). Results are given in Table 2.

TABLE 2

|  | Endotoxin (EU/mL) | Particle Size (μm) D50/D90 | Encapsulation Efficiency (%) | Drug Recovery (%) | Antigen Adsorption (%) |
| --- | --- | --- | --- | --- | --- |
| 0% (Control) | <2.50 | 0.86/1.40 | N/A | N/A | >50 |
| 1% | <2.50 | 0.75/1.62 | 96.9 | 27.7 | >50 |
| 4% | <2.50 | 0.51/14.40 | 97.7 | 14.7 | >50 |

Each of the above vials contains 6 doses and is reconstituted with 0.6 mL water for injection at the time of injection (100 μL per animal).

We claim:

1. An immunogenic composition comprising (a) a first antigen, (b) polymeric particles that comprise a polymer that is at least partially biodegradable wherein said polymer comprises a polymer block selected from a polyester block, a polyorthoester block, and a polyanhydride block, and (c) a benzonaphthyridine compound, wherein the inclusion of the polymeric particles in the composition elicits an enhanced immune response when administered to a vertebrate subject.

2. The immunogenic composition of claim 1, wherein said biodegradable polymer comprises a polyester block that is selected from a poly(lactide) block, a poly(glycolide) block, a poly(lactide-co-glycolide) block and a poly(epsilon-caprolactone) block.

3. The immunogenic composition of claim 1, wherein said biodegradable polymer is a block copolymer that comprises a polyhydroxyacid block and a polymer block that is not a polyhydroxyacid block.

4. The immunogenic composition of claim 1, wherein said biodegradable polymer is a block copolymer that comprises a poly(lactide-co-glycolide) block and a polyethylene glycol block.

5. The immunogenic composition of claim 1, wherein the polymeric particles have a negative charge or a positive charge.

6. The immunogenic composition of claim 1, wherein the polymeric particles are formed by a solvent evaporation process or by a precipitation process.

7. The immunogenic composition of claim 1, wherein the benzonaphthyridine compound is present in an amount that ranges from 0.05% to 25% w/w relative to the polymer content of the polymeric particles.

8. The immunogenic composition of claim 1, wherein said benzonaphthyridine compound is established within said polymeric particles.

9. The immunogenic composition of claim 1, wherein said benzonaphthyridine compound is admixed with said polymeric particles and then co-lyophilized with said polymeric particles.

10. The immunogenic composition of claim 1, wherein the first antigen is present in an amount that ranges from 0.05% to 25% w/w relative to the content of polymeric particles.

11. The immunogenic composition of claim 1, wherein said first antigen is established within said polymeric particles.

12. The immunogenic composition of claim 1, wherein said first antigen is admixed with said polymeric particles and then co-lyophilized with said polymeric particles.

13. The immunogenic composition of claim 1, wherein the first antigen is selected from a polypeptide-containing antigen, a polysaccharide-containing antigen, and a polynucleotide-containing antigen.

14. The immunogenic composition of claim 1, wherein the first antigen is a tumor-cell-derived antigen.

15. The immunogenic composition of claim 1, wherein the first antigen is a pathogenic-organism-derived antigen.

16. The immunogenic composition of claim 15, wherein the pathogenic organism is selected from a virus, a bacterium, a fungus and a parasite.

17. The immunogenic composition of claim 1, wherein the composition comprises a cryoprotective agent.

18. The immunogenic composition of claim 1, wherein the benzonaphthyridine compound is a compound having the structure of Formula (VI), or a pharmaceutically acceptable salt thereof:

Formula (VI)

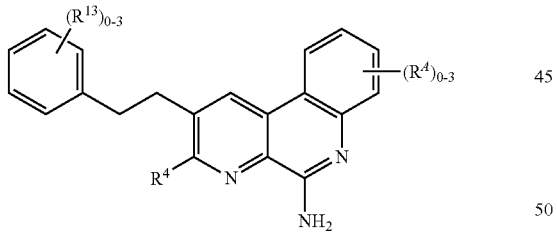

wherein:
$R^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$ alkene, $C_2$-$C_8$ alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$ alkene, $C_2$-$C_8$ alkyne, $C_1$-$C_6$alkoxy, $C_1$-$C_6$haloalkoxy, and $C_3$-$C_8$heterocycloalkyl groups of R$^7$ are each optionally substituted with 1 to 3 R$^{13}$ groups;

each R$^8$ is independently selected from H, —CH(R$^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$ alkyl, $C_2$-$C_8$ alkene, $C_2$-$C_8$ alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)O$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^9$ is independently selected from H, —C(O)R$^8$, —C(O)OR$^8$, —C(O)R$^{10}$, —C(O)OR$^{10}$, —S(O)$_2$R$^{10}$, —C$_1$-$C_6$ alkyl, $C_1$-$C_6$ heteroalkyl and $C_3$-$C_6$ cycloalkyl, or each R$^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of R$^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)$—$CO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH$=$CHCO_2R^8$, —$C(=NH)$—$N(R^9)_2$, and —$(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

19. The immunogenic composition of claim 18, wherein the compound having the structure of Formula (VI) is a compound having the structure of Formula (VII), or a pharmaceutically acceptable salt thereof:

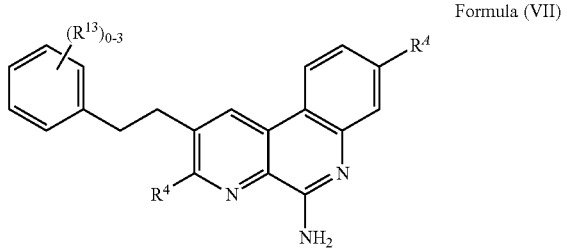

Formula (VII)

wherein:

$R^4$ is selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$ alkene, $C_2$-$C_8$ alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$ alkene, $C_2$-$C_8$ alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$ alkene, $C_2$-$C_8$ alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$ alkyl, $C_2$-$C_8$ alkene, $C_2$-$C_8$ alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)$ OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, $^-$OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;

or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)R$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;

each R$^A$ is independently selected from —R$^8$, —R$^7$, —OW, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC(O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

20. The immunogenic composition of claim 19, wherein each R$^{13}$ is selected from -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)R$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$; and each R$^A$ is independently selected from —R$^7$, —OR$^7$, —R$^8$, —OR$^8$, —R$^{10}$, —OR$^{10}$, —SR$^8$, —N(R$^9$)$_2$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —CH=CHCO$_2$R$^8$, (CH$_2$)$_n$CO$_2$R$^8$, —NR$^9$SO$_2$R$^8$, —P(O)(OR$^8$)$_2$, —OP(O)(OR$^8$)$_2$, —P(O)(OR$^{10}$)$_2$, and —OP(O)(OR$^{10}$)$_2$.

21. The immunogenic composition of claim 20, wherein each L is independently selected from a —(O(CH$_2$)$_m$)$_t$, and C$_1$-C$_6$alkyl, wherein the C$_1$-C$_6$alkyl of L is optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$.

22. The immunogenic composition of claim 21, wherein R$^A$ is H or C$_1$-C$_6$alkyl.

23. The immunogenic composition of claim 19, wherein R$^A$ is H, —CH$_3$ or —CH$_2$CH$_3$; and each R$^{13}$ is independently selected from H, —CH$_3$, —CH$_2$CH$_3$, —CF$_3$, —CH$_2$OH, —OCH$_3$, —COOCH$_3$, —COOCH$_2$CH$_3$, F, Cl, Br, —CH$_2$OCH$_3$, CH$_2$OCH$_2$CH$_3$, —N(CH$_3$)$_2$, —((O(CH$_2$)$_2$)$_{2-4}$OH, —O(CH$_2$)$_{2-4}$—OH, —O(CH$_2$)$_{2-4}$—(PO$_3$H$_2$), —O(CH$_2$)$_{2-4}$—COOH, —O(CH$_2$)$_{2-4}$—CH(CH$_3$)$_2$ and C$_2$-C$_6$ alkyl substituted with 1-3 substituents selected from —OH, —CH$_3$, —COOH, —COOCH$_3$, cyclopropyl, —O(CH$_2$)$_{2-4}$—COOH, —O(CH$_2$)$_{2-4}$(PO$_3$H$_2$), and —COOCH$_2$CH$_3$.

24. The immunogenic composition of claim 19, wherein R$^8$ is H or C$_1$-C$_6$alkyl.

25. The immunogenic composition of claim 19, wherein R$^9$ is H or C$_1$-C$_6$alkyl.

26. The immunogenic composition of claim 19, wherein each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$.

27. The immunogenic composition of claim 19, wherein R$^A$ is H.

28. The immunogenic composition of claim 18, wherein the compound is selected from:

2-(4-(2-(5-amino-8-methylbenzo[f][1,7]naphthyridin-2-yl)ethyl)-3-methylphenyl)propan-2-ol;

2-(4-methoxy-2-methylphenethyl)-8-methylbenzo[f][1,7]naphthyridin-5-amine;

2-(2,4-dimethylphenethyl)benzo[f][1,7]naphthyridin-5-amine;

ethyl 4-(2-(5-amino-8-methylbenzo[f][1,7]naphthyridin-2-yl)ethyl)-3-methylbenzoate;

2-(4-(dimethylamino)phenethyl)-8-methylbenzo[f][1,7]naphthyridin-5-amine, and 2-(4-methoxyphenethyl)-8-methylbenzo[f][1,7]naphthyridin-5-amine.

29. The immunogenic composition of claim 1, wherein the benzonaphthyridine compound is a compound having the structure of Formula (VIII), or a pharmaceutically acceptable salt thereof:

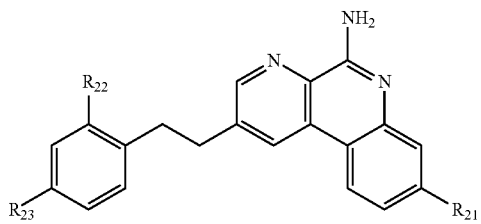

Formula (VIII)

wherein:
R$^{21}$ is H, C$_1$-C$_6$alkyl, —C(R$^{25}$)$_2$OH, -L$^{21}$R$^{25}$, -L$^{21}$R$^{26}$, -L$^{22}$R$^{25}$, -L$^{22}$R$^{26}$, —OL$^{22}$R$^{25}$, or —OL$^{22}$R$^{26}$;
L$^{21}$ is —C(O)— or —O—;
L$^{22}$ is C$_1$-C$_6$alkylene, C$_2$-C$_6$alkenylene, arylene, heteroarylene or —((CR$^{24}$R$^{24}$)$_p$P)$_q$(CH$_2$)$_p$—, wherein the C$_1$-C$_6$alkylene and C$_2$-C$_6$alkenylene of L$^{22}$ are optionally substituted with 1 to 4 fluoro groups;
each L$^{23}$ is independently selected from C$_1$-C$_6$alkylene and —((CR$^{24}$R$^{24}$)$_p$O)$_q$(CH$_2$)$_p$—, wherein the C$_1$-C$_6$alkylene of L$^{23}$ is optionally substituted with 1 to 4 fluoro groups;
L$^{24}$ 1, is arylene or heteroarylene;
R$^{22}$ is H or C$_1$-C$_6$alkyl;
R$^{23}$ is selected from C$_1$-C$_4$alkyl, -L$^{23}$R$^{25}$, -L$^{21}$R$^{25}$, -L$^{23}$R$^{27}$, -L$^{23}$L$^{24}$L$^{23}$R$^{27}$, -L$^{23}$L$^{24}$R$^{25}$, -L$^{23}$L$^{24}$L$^{23}$R$^{25}$, —OL$^{23}$R$^{25}$, —OL$^{23}$R$^{27}$, —OL$^{23}$L$^{24}$R$^{27}$, —OL$^{23}$L$^{24}$L$^{23}$R$^{27}$, —OR$^{28}$, —OL$^{23}$L$^{24}$R$^{25}$, —OL$^{23}$L$^{24}$L$^{23}$R$^{25}$ and —C(R$^{25}$)$_2$OH;
each R$^{24}$ is independently selected from H and fluoro;
R$^{25}$ is —P(O)(OR$^{29}$)$_2$,
R$^{26}$ is —CF$_2$P(O)(OR$^{29}$)$_2$ or —C(O)OR$^{30}$;
R$^{27}$ is —CF$_2$P(O)(OR$^{29}$)$_2$ or —C(O)OR$^{30}$;
R$^{28}$ is H or C$_1$-C$_4$alkyl;
each R$^{29}$ is independently selected from H and C$_1$-C$_6$alkyl;
R$^{30}$ is H or C$_1$-C$_4$alkyl;
each p is independently selected from 1, 2, 3, 4, 5 and 6, and
q is 1, 2, 3 or 4;
with the proviso that when R$^{23}$ is C$_1$-C$_4$ alkyl or —OR$^{28}$, then R$^{21}$ is —C(R$^{25}$)$_2$OH, -L$^{21}$R$^{25}$, -L$^{21}$R$^{26}$, -L$^{22}$R$^{25}$, -L$^{22}$R$^{26}$, —OL$^{22}$R$^{25}$, or —OL$^{22}$R$^{26}$, wherein R$^{26}$ is —CF$_2$P(O)(OR$^{29}$)$_2$ and R$^{27}$ is —CF$_2$P(O)(OR$^{29}$)$_2$.

30. The immunogenic composition of claim 29, wherein the compound is selected from:
4-(4-(2-(5-amino-8-methylbenzo[f][1,7]naphthyridin-2-yl)ethyl)-3-methylphenoxy)-1,1-difluorobutylphosphonic acid;
3-(5-amino-2-(4-(4,4-difluoro-4-phosphonobutoxy)-2-methylphenethyl)benzo[f][1,7]naphthyridin-8-yl)propanoic acid;
3-(5-amino-2-(4-(2-(3,3-difluoro-3-phosphonopropoxy)ethoxy)-2-methylphenethyl)benzo[f][1,7]naphthyridin-8-yl)propanoic acid;
3-(5-amino-2-(2-methyl-4-(2-(2-phosphonoethoxy)ethoxy)ethoxy)phenethyl)benzo[f][1,7]naphthyridin-8-yl)propanoic acid;
4-(2-(5-amino-8-methylbenzo[f][1,7]naphthyridin-2-yl)ethyl)-3-methylphenyl dihydrogen phosphate;
(4-(2-(5-amino-8-methylbenzo[f][1,7]naphthyridin-2-yl)ethyl)-3-methylphenoxy)methylphosphonic acid;
5-(4-(2-(5-amino-8-methylbenzo[f][1,7]naphthyridin-2-yl)ethyl)-3-methylphenoxy)-1,1-difluoropentylphosphonic acid;
4-(4-(2-(5-amino-8-methylbenzo[f][1,7]naphthyridin-2-yl)ethyl)-3-methylphenoxy)-1,1-difluorobutylphosphonic acid;
3-(2-(4-(2-(5-amino-8-methylbenzo[f][1,7]naphthyridin-2-yl)ethyl)-3-methylphenoxy)ethoxy)-1,1-difluoropropylphosphonic acid;
2-(4-((4-(2-(5-amino-8-methylbenzo[f][1,7]naphthyridin-2-yl)ethyl)-3-methylphenoxy)methyl)phenyl)-1,1-difluoroethylphosphonic acid;
2-(5-amino-2-(4-methoxy-2-methylphenethyl)benzo[f][1,7]naphthyridin-8-yl)-1,1-difluoro-2-oxoethylphosphonic acid;
(E)-2-(5-amino-2-(4-methoxy-2-methylphenethyl)benzo[f][1,7]naphthyridin-8-yl)vinylphosphonic acid;
2-(5-amino-2-(4-methoxy-2-methylphenethyl)benzo[f][1,7]naphthyridin-8-yl)ethylphosphonic acid;
(E)-2-(5-amino-2-(4-methoxy-2-methylphenethyl)benzo[f][1,7]naphthyridin-8-yl)-1-fluorovinylphosphonic acid;
3-((4-(2-(5-amino-8-methylbenzo[f][1,7]naphthyridin-2-yl)ethyl)-3-methylphenoxy)methyl)phenylphosphonic acid;
5-amino-2-(4-methoxy-2-methylphenethyl)benzo[f][1,7]naphthyridine-8-carbonylphosphonic acid;
3-(5-amino-2-(2-methyl-4-(3-phosphonopropoxy)phenethyl)benzo[f][1,7]naphthyridin-8-yl)propanoic acid;
(4-(2-(5-amino-8-methylbenzo[f][1,7]naphthyridin-2-yl)ethyl)-3-methylphenyl)(hydroxy)methylenediphosphonic acid;
3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid;
(5-amino-2-(4-methoxy-2-methylphenethyl)benzo[f][1,7]naphthyridin-8-yl)(hydroxy)methylenediphosphonic acid;
3-(5-amino-2-(2-methyl-4-(2-(2-phosphonoethoxy)ethoxy)phenethyl)benzo[f][1,7]naphthyridin-8-yl)propanoic acid;
2-(4-(2-(5-amino-8-methylbenzo[f][1,7]naphthyridin-2-yl)ethyl)-3-methylphenoxy)ethylphosphonic acid;
6-(4-(2-(5-amino-8-methylbenzo[f][1,7]naphthyridin-2-yl)ethyl)-3-methylphenoxy)hexylphosphonic acid;
6-(4-(2-(5-amino-8-methylbenzo[f][1,7]naphthyridin-2-yl)ethyl)-3-methylphenoxy)-1,1-difluorohexylphosphonic acid;
4-((4-(2-(5-amino-8-methylbenzo[f][1,7]naphthyridin-2-yl)ethyl)-3-methylphenoxy)methyl)benzylphosphonic acid;
3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid; and
2-(2-(2-(4-(2-(5-amino-8-methylbenzo[f][1,7]naphthyridin-2-yl)ethyl)-3-methylphenoxy)ethoxy)ethoxy)ethylphosphonic acid.

31. The immunogenic composition of claim 29, further comprising a second antigen distinct from the first antigen.

32. The immunogenic composition of claim 29, wherein the immunogenic composition is an injectable composition.

33. The immunogenic composition of claim 29, wherein said polymer comprises an end group selected from a carboxyl end group, an alkyl ester end group, an amine end group, a hydroxyl end group, a thiol end group, a succinimidyl ester end group, and a maleimide end group.

34. The immunogenic composition of claim 33, wherein said biodegradable polymer comprises a polymer block selected from a polyester block, a polycarbonate block, a polyorthoester block, a polyanhydride block, a polycyanoacrylate block and a polyphosphazine block.

35. The immunogenic composition of claim 33, wherein said biodegradable polymer comprises a polyester block that is selected from a poly(lactide) block, a poly(glycolide) block and a poly(lactide-co-glycolide) block.

36. An immunogenic composition comprising (a) a first antigen, (b) polymeric particles that comprise a polymer that comprises a biodegradable polymer block and a hydrophilic polymer block, and (c) a benzonaphthyridine compound, wherein the inclusion of the polymeric particles in the composition elicits an enhanced immune response when administered to a vertebrate subject.

37. The immunogenic composition of claim 36, wherein said biodegradable polymer block is selected from a polyester block, a polycarbonate block, a polyorthoester block, a polyanhydride block, a polycyanoacrylate block and a polyphosphazine block.

38. The immunogenic composition of claim 36, wherein said hydrophilic polymer block is selected from a polyethylene oxide block, a polypropylene oxide block, a polyvinyl alcohol block, a polyvinylpyrrolidone block, a poly(acrylic acid) block, a poly(methacrylic acid) block and a poly(amino acid) block.

39. The immunogenic composition of claim 36, wherein said hydrophilic polymer block is selected from a positively charged polymer block and a negatively charged polymer block.

40. The immunogenic composition of claim 36, wherein said hydrophilic polymer block is selected from a poly(carboxylic acid) block and a polyamine (block).

41. The immunogenic composition of claim 36, wherein said benzonaphthyridine compound is established within said polymeric particles.

* * * * *

SEQUENCE LISTING

<160> NUMBER OF SEQ ID NOS: 6

<210> SEQ ID NO 1
<211> LENGTH: 248
<212> TYPE: PRT

<213> ORGANISM: N. meningitidis

<400> SEQUENCE: 1

```
Val Ala Ala Asp Ile Gly Ala Gly Leu

```
                100                 105                 110
Ile Asp Ser Leu Ile Asn Gln Arg Ser Phe Leu Val Ser Gly Leu Gly
            115                 120                 125
Gly Glu His Thr Ala Phe Asn Gln Leu Pro Asp Gly Lys Ala Glu Tyr
        130                 135                 140
His Gly Lys Ala Phe Ser Ser Asp Asp Ala Gly Lys Leu Thr Tyr
145                 150                 155                 160
Thr Ile Asp Phe Ala Ala Lys Gln Gly His Gly Lys Ile Glu His Leu
                165                 170                 175
Lys Thr Pro Glu Gln Asn Val Glu Leu Ala Ala Ala Glu Leu Lys Ala
            180                 185                 190
Asp Glu Lys Ser His Ala Val Ile Leu Gly Asp Thr Arg Tyr Gly Ser
        195                 200                 205
Glu Glu Lys Gly Thr Tyr His Leu Ala Leu Phe Gly Asp Arg Ala Gln
    210                 215                 220
Glu Ile Ala Gly Ser Ala Thr Val Lys Ile Gly Glu Lys Val His Glu
225                 230                 235                 240
Ile Gly Ile Ala Gly Lys Gln
                245

<210> SEQ ID NO 3
<211> LENGTH: 250
<212> TYPE: PRT
<213> ORGANISM: N. meningitidis

<400> SEQUENCE: 3

Val Ala Ala Asp Ile Gly Thr Gly Leu Ala Asp Ala Leu Thr Ala Pro
  1               5                  10                  15
Leu Asp His Lys Asp Lys Gly Leu Lys Ser Leu Thr Leu Glu Asp Ser
            20                  25                  30
Ile Pro Gln Asn Gly Thr Leu Thr Leu Ser Ala Gln Gly Ala Glu Lys
        35                  40                  45
Thr Phe Lys Ala Gly Asp Lys Asp Asn Ser Leu Asn Thr Gly Lys Leu
    50                  55                  60
Lys Asn Asp Lys Ile Ser Arg Phe Asp Phe Val Gln Lys Ile Glu Val
65                  70                  75                  80
Asp Gly Gln Thr Ile Thr Leu Ala Ser Gly Glu Phe Gln Ile Tyr Lys
                85                  90                  95
Gln Asn His Ser Ala Val Val Ala Leu Gln Ile Glu Lys Ile Asn Asn
            100                 105                 110
Pro Asp Lys Thr Asp Ser Leu Ile Asn Gln Arg Ser Phe Leu Val Ser
        115                 120                 125
Gly Leu Gly Gly Glu His Thr Ala Phe Asn Gln Leu Pro Gly Gly Lys
    130                 135                 140
Ala Glu Tyr His Gly Lys Ala Phe Ser Ser Asp Asp Pro Asn Gly Arg
145                 150                 155                 160
Leu His Tyr Ser Ile Asp Phe Thr Lys Lys Gln Gly Tyr Gly Arg Ile
                165                 170                 175
Glu His Leu Lys Thr Leu Glu Gln Asn Val Glu Leu Ala Ala Ala Glu
            180                 185                 190
Leu Lys Ala Asp Glu Lys Ser His Ala Val Ile Leu Gly Asp Thr Arg
        195                 200                 205
Tyr Gly Ser Glu Glu Lys Gly Thr Tyr His Leu Ala Leu Phe Gly Asp
    210                 215                 220
```

```
Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 644
<212> TYPE: PRT
<213> ORGANISM: N. meningitidis

<400> SEQUENCE: 4

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350
```

```
Gly Glu Met Leu Ala Gly Thr Ala Val Tyr Asn Gly Glu Val Leu His
            355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
            450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
530                 535                 540

Ala Asp Ile Phe Asp Ala Gln Tyr Pro Asp Ile Arg Phe Val Ser
545                 550                 555                 560

Thr Lys Phe Asn Phe Asn Gly Lys Lys Leu Val Ser Val Asp Gly Asn
            565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: N. meningitidis

<400> SEQUENCE: 5

Met Val Ser Ala Val Ile Gly Ser Ala Ala Val Gly Ala Lys Ser Ala
  1               5                  10                  15

Val Asp Arg Arg Thr Thr Gly Ala Gln Thr Asp Asp Asn Val Met Ala
             20                  25                  30

Leu Arg Ile Glu Thr Thr Ala Arg Ser Tyr Leu Arg Gln Asn Asn Gln
         35                  40                  45

Thr Lys Gly Tyr Thr Pro Gln Ile Ser Val Val Gly Tyr Asn Arg His
     50                  55                  60

Leu Leu Leu Leu Gly Gln Val Ala Thr Glu Gly Glu Lys Gln Phe Val
 65                  70                  75                  80
```

```
Gly Gln Ile Ala Arg Ser Glu Gln Ala Glu Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
        130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
        210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
        290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
        370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: N. meningitidis

<400> SEQUENCE: 6

Ala Thr Asn Asp Asp Val Lys Lys Ala Ala Thr Val Ala Ile Ala
 1               5                  10                  15
```

-continued

```
Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
 50                  55                  60

Lys Val Val Thr Asn Leu Thr Lys Thr Val Asn Glu Asn Lys Gln Asn
 65                  70                  75                  80

Val Asp Ala Lys Val Lys Ala Ala Glu Ser Glu Ile Glu Lys Leu Thr
            85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
            165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
            325
```